(12) United States Patent
Hatakeyama et al.

(10) Patent No.: US 11,998,339 B2
(45) Date of Patent: Jun. 4, 2024

(54) BIO-ELECTRODE COMPOSITION, BIO-ELECTRODE, AND METHOD FOR MANUFACTURING BIO-ELECTRODE

(71) Applicant: SHIN-ETSU CHEMICAL CO., LTD., Tokyo (JP)

(72) Inventors: Jun Hatakeyama, Joetsu (JP); Motoaki Iwabuchi, Joetsu (JP); Joe Ikeda, Joetsu (JP); Koji Hasegawa, Joetsu (JP); Yasuyoshi Kuroda, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 624 days.

(21) Appl. No.: 17/155,845

(22) Filed: Jan. 22, 2021

(65) Prior Publication Data

US 2022/0110569 A1     Apr. 14, 2022

(30) Foreign Application Priority Data

Jan. 22, 2020   (JP) .................. 2020-008032

(51) Int. Cl.
   *A61B 5/268*   (2021.01)
   *A61B 5/26*    (2021.01)
   (Continued)

(52) U.S. Cl.
   CPC ............. *A61B 5/268* (2021.01); *A61B 5/26* (2021.01); *A61B 5/265* (2021.01); *C08G 18/673* (2013.01);
   (Continued)

(58) Field of Classification Search
   CPC ........... A61B 5/268; A61B 5/26; A61B 5/265; C08G 77/20; C08G 77/70
   See application file for complete search history.

(56) References Cited

U.S. PATENT DOCUMENTS

| 5,981,680 A | 11/1999 | Petroff et al. |
| 2002/0188069 A1 | 12/2002 | Sugo et al. |

(Continued)

FOREIGN PATENT DOCUMENTS

| JP | H05-095924 A | 4/1993 |
| JP | 2002-332305 A | 11/2002 |

(Continued)

OTHER PUBLICATIONS

Polyglyceryl-3 Polydimethylsiloxyethyl Dimethicone—Surfactant—SAAPedia—Surfactant Technology Platform, dated Oct. 14, 2012. (Year: 2012).*

(Continued)

*Primary Examiner* — Heidi R Kelley
*Assistant Examiner* — Surbhi M Du
(74) *Attorney, Agent, or Firm* — Oliff PLC

(57) ABSTRACT

A bio-electrode composition contains: (A) a polymer compound containing a repeating unit-a having a structure selected from the group consisting of salts of ammonium, sodium, potassium, and silver formed with any of fluorosulfonic acid, fluorosulfonimide, and N-carbonyl-fluorosulfonamide; and (B) a silicone compound having a polyglycerin structure. This bio-electrode composition is able to form a living body contact layer for a bio-electrode which enable quick signal collection after attachment to skin.

19 Claims, 2 Drawing Sheets

(51) Int. Cl.
*A61B 5/265* (2021.01)
*C08G 18/67* (2006.01)
*C08G 77/00* (2006.01)
*C08G 77/20* (2006.01)

(52) U.S. Cl.
CPC ............ *C08G 77/20* (2013.01); *C08G 77/70* (2013.01); *A61B 2562/0215* (2017.08); *A61B 2562/125* (2013.01)

(56) References Cited

U.S. PATENT DOCUMENTS

| | | |
|---|---|---|
| 2008/0118860 A1 | 5/2008 | Harada et al. |
| 2009/0061358 A1 | 3/2009 | Ohashi et al. |
| 2015/0275060 A1 | 10/2015 | Kuroda et al. |
| 2016/0155530 A1 | 6/2016 | Someya et al. |
| 2017/0275510 A1 | 9/2017 | Quan et al. |
| 2018/0072930 A1 | 3/2018 | Hatakeyama et al. |
| 2018/0085019 A1 | 3/2018 | Hatakeyama et al. |
| 2018/0086948 A1 | 3/2018 | Hatakeyama et al. |
| 2018/0168470 A1 | 6/2018 | Hatakeyama et al. |
| 2018/0215876 A1 | 8/2018 | Hatakeyama et al. |
| 2018/0223133 A1* | 8/2018 | Hatakeyama .......... C09J 183/04 |
| 2018/0229023 A1 | 8/2018 | Hatakeyama et al. |
| 2018/0229024 A1 | 8/2018 | Hatakeyama et al. |
| 2018/0240564 A1* | 8/2018 | Hatakeyama ......... C08F 128/00 |
| 2018/0273811 A1 | 9/2018 | Cura et al. |
| 2019/0106528 A1 | 4/2019 | Hatakeyama et al. |
| 2019/0151648 A1 | 5/2019 | Hatakeyama et al. |
| 2019/0159978 A1 | 5/2019 | Sakuta et al. |
| 2019/0298891 A1 | 10/2019 | Hatakeyama et al. |
| 2020/0275853 A1* | 9/2020 | Futashima ............... C08K 5/14 |

FOREIGN PATENT DOCUMENTS

| | | |
|---|---|---|
| JP | 2003-225217 A | 8/2003 |
| JP | 2004-033468 A | 2/2004 |
| JP | 2005-320418 A | 11/2005 |
| JP | 2008-111103 A | 5/2008 |
| JP | 2009-080474 A | 4/2009 |
| JP | 2011-079946 A | 4/2011 |
| JP | 2012-197270 A | 10/2012 |
| JP | 2015-019806 A | 2/2015 |
| JP | 2015-100673 A | 6/2015 |
| JP | 2015-193803 A | 11/2015 |
| JP | 2016-011338 A | 1/2016 |
| JP | 2016-065238 A | 4/2016 |
| JP | 2017-148452 A | 8/2017 |
| JP | 2018-044147 A | 3/2018 |
| JP | 2018-059050 A | 4/2018 |
| JP | 2018-059052 A | 4/2018 |
| JP | 2018-099504 A | 6/2018 |
| JP | 2018-123304 A | 8/2018 |
| JP | 2018-126496 A | 8/2018 |
| JP | 2018-130533 A | 8/2018 |
| JP | 2018-130534 A | 8/2018 |
| JP | 2019-503406 A | 2/2019 |
| JP | 2019-070109 A | 5/2019 |
| JP | 2019-099469 A | 6/2019 |
| TW | 201927904 A | 7/2019 |
| TW | 201942210 A | 11/2019 |
| WO | 2003/075864 A1 | 9/2003 |
| WO | 2013/039151 A1 | 3/2013 |
| WO | 2019/139164 A1 | 7/2019 |

OTHER PUBLICATIONS

Jun. 21, 2021 Extended Search Report issued in European Patent Application No. 21153053.0.
Dec. 13, 2021 Office Action issued in Taiwan Patent Application No. 110101872.
"Shin-Etsu Personal Care Silicones," https://www.silicone.jp/products/personalcare/products/polyglycerin_modified_silicones.shtml.
"Polyglyceryl-3 dimethicone hydroxyethyl dimethicone," http://www.saapedia.org/cht/surfactant/?type=detail&id=3662.
Jun. 7, 2022 Office Action issued in Korean Patent Application No. 10-2021-0003378.
Dec. 27, 2022 Office Action issued in Korean Patent Application No. 10-2021-0003378.
Aug. 8, 2023 Office Action issued in Japanese Patent Application No. 2020-204524.

* cited by examiner

[FIG. 1]
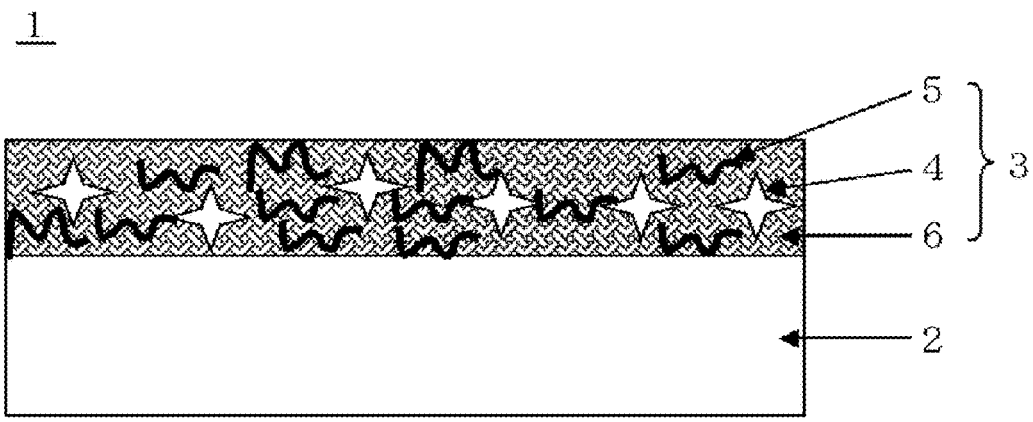
[FIG. 2]
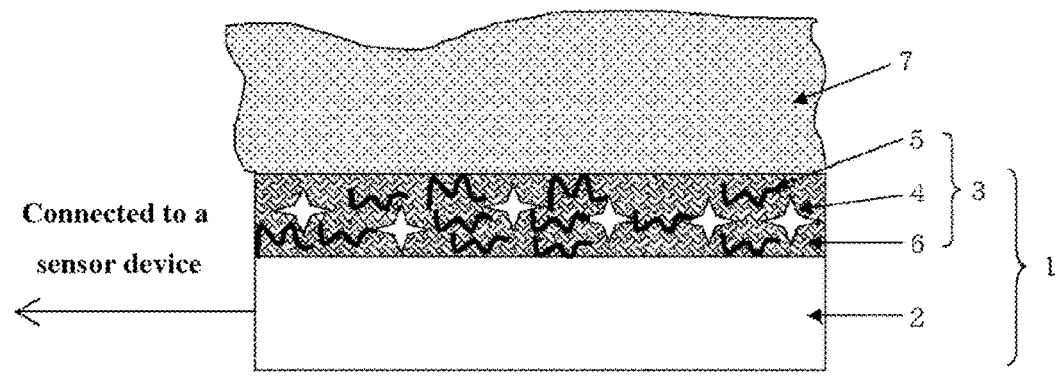
[FIG. 3]
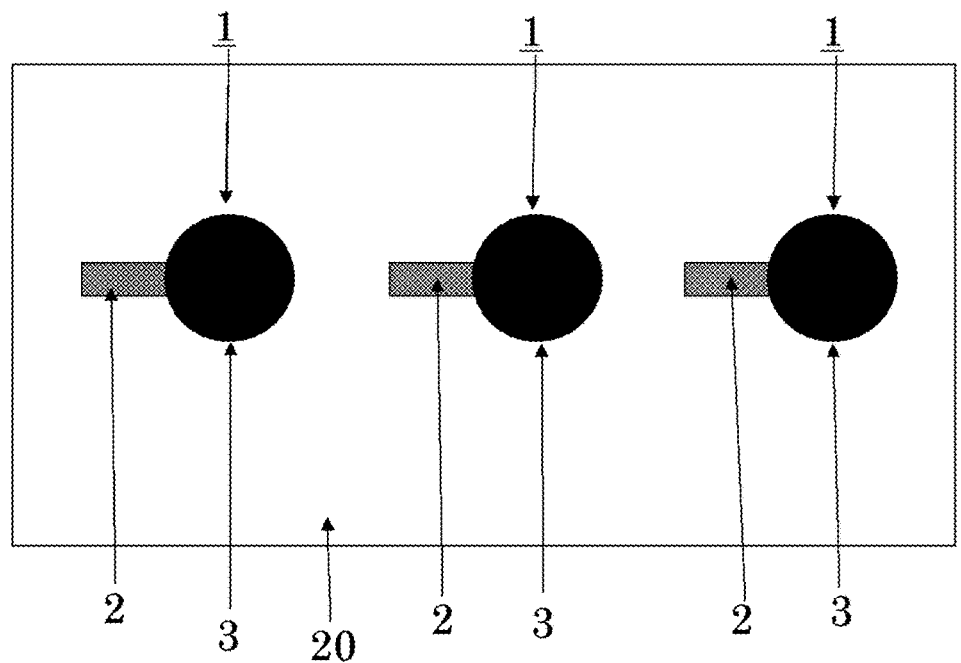

[FIG. 4]
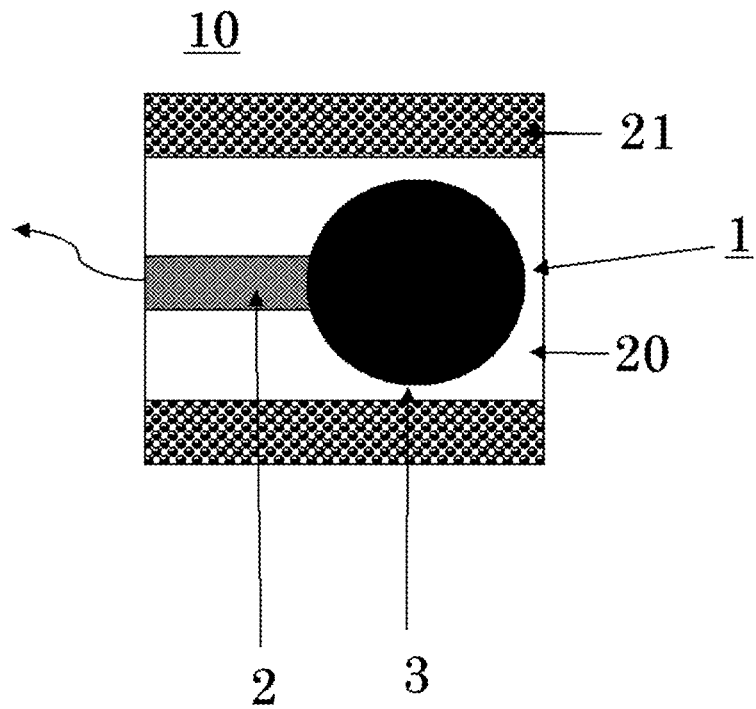
[FIG. 5]
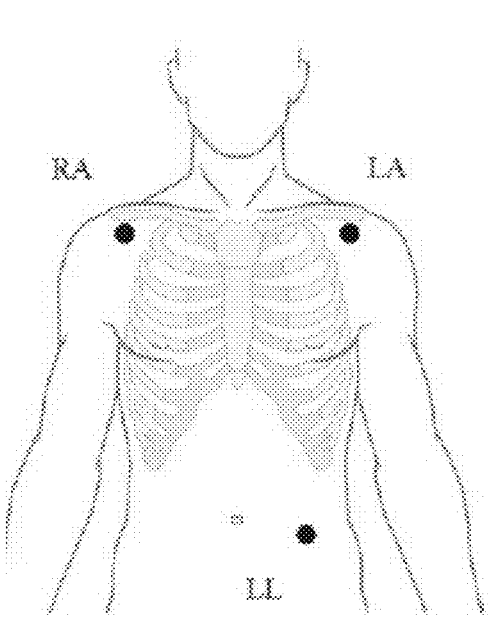
[FIG. 6]
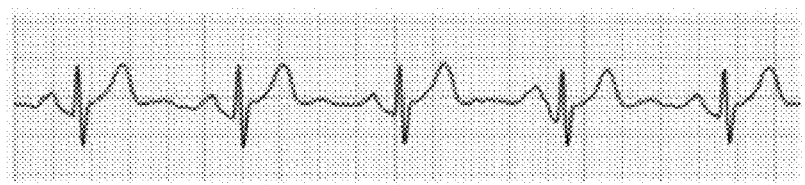

BIO-ELECTRODE COMPOSITION, BIO-ELECTRODE, AND METHOD FOR MANUFACTURING BIO-ELECTRODE

TECHNICAL FIELD

The present invention relates to a bio-electrode that is used in contact with the skin of a living body and capable of detecting physical conditions such as heart rate by an electric signal transmitted from the skin, a method for manufacturing the bio-electrode, and a bio-electrode composition desirably used for a bio-electrode.

BACKGROUND ART

In recent years, as Internet of Things (IoT) becomes more widespread, the development of wearable devices is accelerated. The typical examples thereof include watches and eye-glasses that allow for Internet access. Even in the fields of medicine and sports, wearable devices for constantly monitoring the user's physical state are increasingly demanded, and such technological development is expected to be further encouraged.

In the field of medicine, use of wearable devices has been examined for monitoring the state of human organs by sensing extremely weak current, such as an electrocardiogram which detect an electric signal to measure the motion of the heart. The electrocardiogram measurement is conducted by attaching an electrode coated with an electro-conductive paste to a body, but this is a single (not continuous), short-time measurement. On the other hand, the above medical wearable device is aimed at continuously monitoring the condition of health for a few weeks. Accordingly, a bio-electrode used in a medical wearable device is required to make no changes in electric conductivity even in long-time use and cause no skin allergy. In addition to these, it is required that a bio-electrodes is light-weight and can be produced at low cost.

Medical wearable devices are classified into two types: a type in which a device is directly attached to body and a type in which a device is incorporated into clothes. As the type in which a device is attached to a body, it has been proposed a bio-electrode using water soluble gel containing water and electrolyte, which are materials of the foregoing electro-conductive paste (Patent Document 1). The water soluble gel contains sodium, potassium, or calcium as the electrolyte in a water soluble polymer for retaining water, and converts changes of ion concentration from skin into electricity. On the other hand, as the type in which a device is incorporated into clothes, it has been proposed a means to use cloth in which an electro-conductive polymer such as PEDOT-PSS (poly-3,4-ethylenedioxythiophene-polystyrenesulfonate) or silver paste is incorporated into the fibers for electrodes (Patent Document 2).

However, the use of the hydrophilic gel containing water and electrolytes unfortunately brings about loss of electric conductivity due to water evaporation in drying process. Meanwhile, the use of a higher-ionization-tendency metal such as copper can cause some users to suffer from skin allergy. The use of an electro-conductive polymer such as PEDOT-PSS can also cause skin allergy due to the strong acidity of the electro-conductive polymer, as well as peeling of the electro-conductive polymer from fibers during washing.

By taking advantage of excellent electric conductivity, the use of metal nanowire, carbon black, carbon nanotube, and the like as electrode materials has been examined (Patent Documents 3, 4, and 5). With higher contact probability among metal nanowires, the wires can conduct electricity even when added in small quantities. The metal nanowire, however, can cause skin allergies since they are thin material with sharp tips. The carbon nanotubes can stimulate (irritate) a living body by the same reason. Although the carbon black is not as poisonous as carbon nanotube, it also stimulates the skin to a certain degree. Accordingly, even if these electrode materials themselves cause no allergic reaction, the biocompatibility may be degraded depending on the shape of a material and its inherent stimulation, thereby making it hard to satisfy both electric conductivity and biocompatibility.

Although metal films seem to function as an excellent bio-electrode thanks to extremely high electric conductivity, this is not always the case. Upon heartbeat, the human skin releases not only extremely weak current, but also a sodium ion, a potassium ion, and a calcium ion. It is thus necessary to convert changes in ion concentration into current. Noble metals, however, are difficult to ionize and are inefficient in converting ions from skin to current. Therefore, the resulting bio-electrode using the noble metal is characterized by high impedance and high resistance to the skin during electrical conduction.

There have been proposed bio-electrodes in each of which an ionic polymer is added (Patent Documents 6, 7, 8). A bio-electrode obtained by mixing a silicone adhesive with an ion polymer and a carbon powder added thereto has adhesion and high water repellency so that biological signals can be stably collected even when the bio-electrode is attached to the skin for a long time in a wet state by shower or sweat. Ion polymers do not permeate to the skin and hence do not stimulate the skin, and the biocompatibility is high. From these aspects, the bio-electrode enables long-time attachment.

Although silicones are inherently insulators, the ionic conductivity is improved by the combination with an ion polymer and a carbon powder, and thus the function as a bio-electrode is obtained. Nevertheless, it has been desired to improve the performance by further improving the ionic conductivity.

Patent Documents 6, 7, and 8 mentioned above state that a silicone compound having a polyether chain as an additive is effective to improve the ionic conductivity. Polyether chains are also used to improve the ionic conductivity of lithium ion polymer batteries, and are effective to improve the conductivity of ions. However, the ionic conductivity due to such polyether chain is lower than that in a water-containing gel of a hydrophilic gel, and further improvement of the ionic conductivity is demanded.

Bio-electrodes are required to be able to collect signals immediately after attached to skin. A gel electrode has ion concentrations equivalent to those of skin, and ions move in and out smoothly. In a water-containing gel, ions move so fast that signals can be detected immediately after attachment to the skin. Meanwhile, it takes long time for a dry electrode to detect signals after attachment to skin, presumably for the following reason. Specifically, although ions are released from skin, no signal is found until the dry electrode surface is saturated with the ions.

CITATION LIST

Patent Literature

Patent Document 1: WO 2013-039151 A1
Patent Document 2: JP 2015-100673 A
Patent Document 3: JP H05-095924 A Patent Document 4: JP 2003-225217 A
Patent Document 5: JP 2015-019806 A
Patent Document 6: JP 2018-99504 A
Patent Document 7: JP 2018-126496 A
Patent Document 8: JP 2018-130533 A
Patent Document 9: JP 2019-99469 A
Patent Document 10: WO 2003/075864 A1
Patent Document 11: JP 2012-197270 A

SUMMARY OF INVENTION

Technical Problem

The present invention has been made to solve the problems and has an object to provide: a bio-electrode composition capable of forming a living body contact layer for a bio-electrode to enable quick signal collection after attachment to skin; a bio-electrode including a living body contact layer formed of the bio-electrode composition; and a method for manufacturing the bio-electrode.

Solution to Problem

To achieve the object, the present invention provides a bio-electrode composition, a bio-electrode, and a method for manufacturing the bio-electrode, which are described below.

The present invention provides a bio-electrode composition comprising:
(A) a polymer compound comprising a repeating unit-a having a structure selected from the group consisting of salts of ammonium, sodium, potassium, and silver formed with any of fluorosulfonic acid, fluorosulfonimide, and N-carbonyl-fluorosulfonamide; and
(B) a silicone compound having a polyglycerin structure.

The inventive bio-electrode composition is capable of exhibiting excellent moisture-holding property because the silicone compound (B) having the polyglycerin structure has high hygroscopicity. The polymer compound (A) is capable of exhibiting excellent ionic conductivity, and the presence of the moisture held by the silicone compound (B) enables the polymer compound (A) to demonstrate more excellent ionic conductivity in the co-presence of the silicone compound (B) in the bio-electrode composition according to the present invention. Thus, a living body contact layer formed of a cured material of the inventive bio-electrode composition can exhibit excellent sensitivity to ions released from a living body, specifically, skin. Consequently, the inventive bio-electrode composition is capable of forming a living body contact layer for a bio-electrode to enable quick signal collection after attachment to skin.

Moreover, the polymer compound (A) incorporated in the inventive bio-electrode composition allows electricity to pass therethrough due to the ion conductivity. In other words, the inventive bio-electrode composition can exhibit high ionic conductivity and thus exhibit excellent electric conductivity.

Additionally, the polymer compound (A) incorporated in the inventive bio-electrode composition can exhibit sufficiently low acidity to achieve lower irritation to a body.

Further, even when the cured material of the inventive bio-electrode composition is wetted with water, since the silicone compound (B) is capable of absorbing excessive moisture, it is possible to prevent significant reduction in the electric conductivity (ionic conductivity) of the polymer compound (A). Meanwhile, even when the cured material of the inventive bio-electrode composition is dried, since the silicone compound (B) is capable of retaining moisture, this makes it possible to prevent significant reduction in the electric conductivity (ionic conductivity) of the polymer compound (A).

Further, the use of the inventive bio-electrode composition enables low-cost formation of a living body contact layer for a light-weight bio-electrode.

In sum, the inventive bio-electrode composition is capable of forming a living body contact layer for a bio-electrode that is excellent in electric conductivity and biocompatibility, light-weight, manufacturable at low cost, and capable of preventing significant reduction in the electric conductivity even when wetted with water or dried, and also capable of quick signal collection after attachment to skin.

The repeating unit-a is preferably shown by any of the following general formulae (1)-1 to (1)-4,

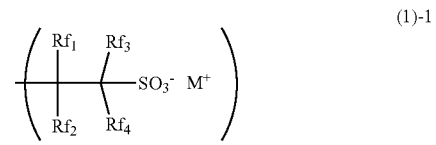

(1)-1

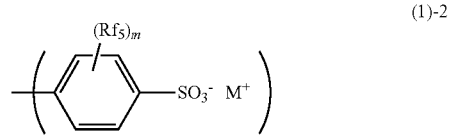

(1)-2

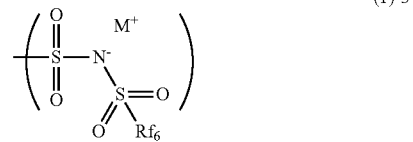

(1)-3

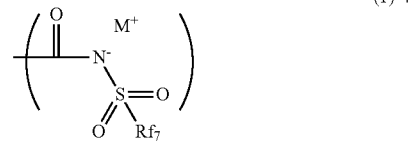

(1)-4 wherein $Rf_1$ and $Rf_2$ each represent a hydrogen atom, a fluorine atom, an oxygen atom, a methyl group, or a trifluoromethyl group, provided that when $Rf_1$ and $Rf_2$ represent an oxygen atom, the single oxygen atom represented by $Rf_1$ and $Rf_2$ bonds to a single carbon atom to form a carbonyl group; and $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group;

$Rf_5$, $Rf_6$, and $Rf_7$ each represent a fluorine atom, or a linear or branched alkyl group having 1 to 4 carbon atoms and at least one or more fluorine atoms;

$M^+$ represents an ion selected from the group consisting of an ammonium ion, a sodium ion, a potassium ion, and a silver ion; and "m" represents an integer of 1 to 4.

The repeating unit-a having such structures enables the bio-electrode composition to form a living body contact layer for a bio-electrode that is more excellent in electric conductivity and biocompatibility.

The repeating unit-a further preferably comprises at least one repeating unit selected from the group consisting of repeating units-a1 to -a7 shown by the following general formula (2), (2)

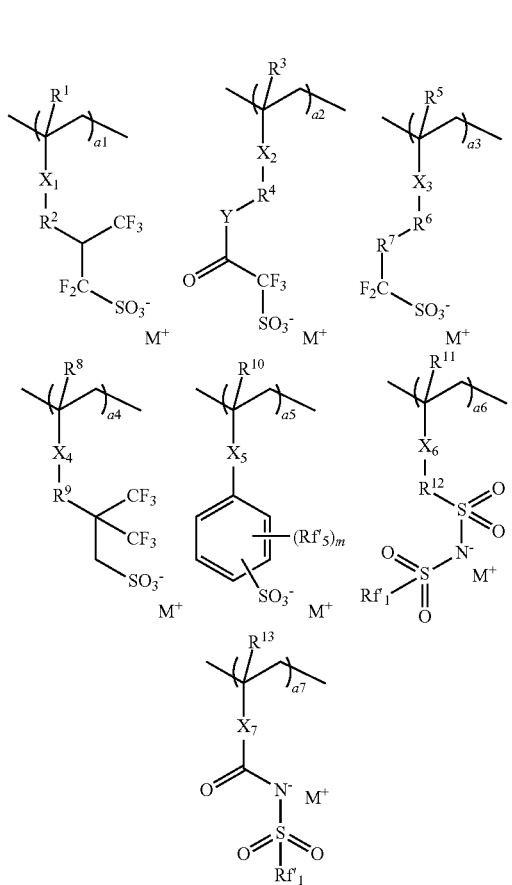

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent a single bond, or a linear, branched, or cyclic hydrocarbon group having 1 to 12 carbon atoms, the hydrocarbon group optionally having either or both of an ester group and an ether group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_5$ represents any of a single bond, an ether group, and an ester group; Y represents an oxygen atom or a —$NR^{19}$— group; $R^{19}$ represents a hydrogen atom, or a linear or branched alkyl group having 1 to 4 carbon atoms; $Rf_1'$ represents a fluorine atom or a trifluoromethyl group; $Rf_5'$ represents a fluorine atom, or a linear or branched alkyl group having 1 to 4 carbon atoms and at least one or more fluorine atoms; "m" represents an integer of 1 to 4; a1, a2, a3, a4, a5, a6, and a7 satisfy $0 \le a1 \le 1.0$, $0 \le a2 \le 1.0$, $0 \le a3 \le 1.0$, $0 \le a4 \le 1.0$, $0 \le a5 \le 1.0$, $0 \le a6 \le 1.0$, $0 \le a7 \le 1.0$, and $0 < a1+a2+a3+a4+a5+a6+a7 \le 1.0$; and $M^+$ represents an ion selected from the group consisting of an ammonium ion, a sodium ion, a potassium ion, and a silver ion.

The repeating unit-a having such structures enables the bio-electrode composition to form a living body contact layer for a bio-electrode that is further excellent in electric conductivity and biocompatibility.

The polymer compound (A) preferably comprises an ammonium ion shown by the following general formula (3) as the $M^+$,

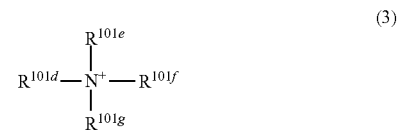

(3)

wherein $R^{101d}$, $R^{101e}$, $R^{101f}$, and $R^{101g}$ each represent a hydrogen atom, a linear, branched, or cyclic alkyl group having 1 to 12 carbon atoms, a linear, branched, or cyclic alkenyl group or alkynyl group having 2 to 12 carbon atoms, or an aromatic group having 4 to 20 carbon atoms, and optionally have one or more selected from the group consisting of an ether group, a carbonyl group, an ester group, a hydroxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the formula (3) within the ring.

The polymer compound (A) containing such an ammonium ion enables the bio-electrode composition to form a living body contact layer for a bio-electrode that is further excellent in electric conductivity and biocompatibility.

The silicone compound (B) having the polyglycerin structure is preferably shown by the following general formula (4) or (5),

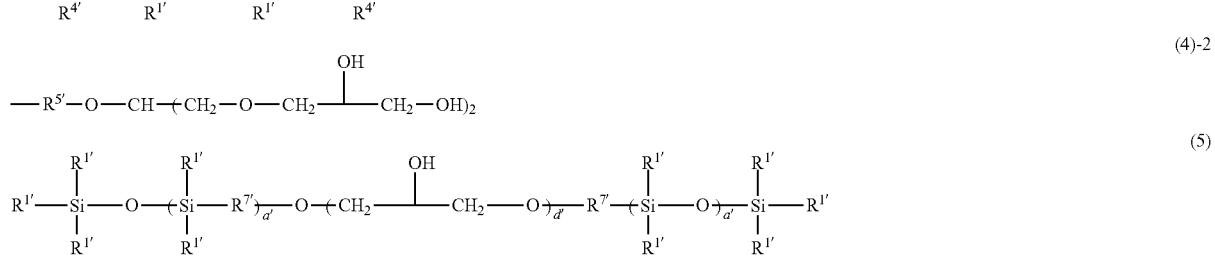

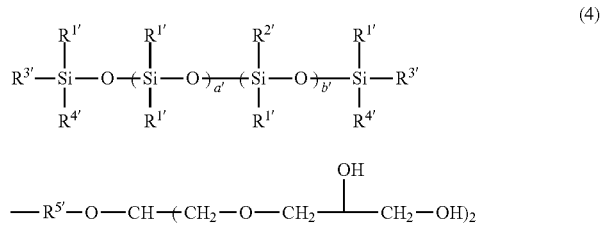

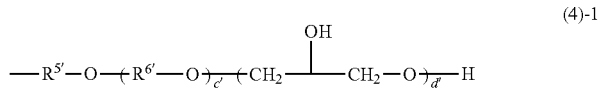

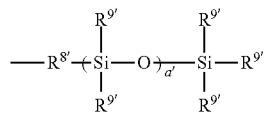

(6)

wherein each $R^{1\prime}$ is identical to or different from each other and independently represents a hydrogen atom, a linear or branched alkyl group having 1 to 50 carbon atoms and optionally containing an ether group, a phenyl group, or a silicone chain shown by a general formula (6); $R^{2\prime}$ represents a group having a polyglycerin group structure shown by a formula (4)-1 or (4)-2; each $R^{3\prime}$ is identical to or different from each other and independently represents the $R^{1\prime}$ group or the $R^{2\prime}$ group; and each $R^{4\prime}$ is identical to or different from each other and independently represents the $R^{1\prime}$ group, the $R^{2\prime}$ group, or an oxygen atom, provided that when $R^{4\prime}$ represents an oxygen atom, the $R^{4\prime}$ moieties bond to each other and optionally constitute an ether group to form a ring together with silicon atoms;

each a' is identical to or different from each other and represents 0 to 100, b' represents 0 to 100, and a'+b' is 0 to 200, provided that when b' is 0, at least one $R^{3\prime}$ is the $R^{2\prime}$ group;

$R^{5\prime}$ represents an alkylene group having 2 to 10 carbon atoms or an aralkylene group having 7 to 10 carbon atoms; c' represents 0 to 20; and d' represents 1 to 20; and $R^{6\prime}$ and $R^{7\prime}$ each represent an alkylene group having 2 to 6 carbon atoms; $R^{8\prime}$ represents an alkylene group having 2 to 6 carbon atoms, or an ether group; and $R^{9\prime}$ represents a hydrogen atom, a linear or branched alkyl group having 1 to 50 carbon atoms and optionally containing an ether group, or a phenyl group.

Incorporating the silicone compound (B) as described above enables the bio-electrode composition to form a living body contact layer that is capable of exhibiting more excellent moisture-holding property, and consequently more excellent sensitivity to ions released from skin.

The inventive bio-electrode composition may further comprise (C) a resin component which is one or more selected from the group consisting of silicone base resins other than the silicone compound (B), acrylic base resins, and urethane base resins.

The resin component (C) to be incorporated into the bio-electrode composition can be selected in accordance with properties to be imparted to the living body contact layer.

The resin component (C) can comprise any of, for example:

a silicone resin having an $SiO_2$ unit and an $R_xSiO_{(4-x)/2}$ unit, wherein R represents a substituted or unsubstituted monovalent hydrocarbon group having 1 to 10 carbon atoms, and "x" is a number in a range of 2.5 to 3.5;

diorganosiloxane having an alkenyl group; and organohydrogenpolysiloxane having an SiH group.

Such a resin component (C) is compatible with the polymer compound (A), thereby making it possible to prevent elution of the salt and to provide the bio-electrode composition with higher adhesion.

The inventive bio-electrode composition may further comprise an organic solvent.

The bio-electrode composition containing an organic solvent can exhibit high coating properties.

The inventive bio-electrode composition may further comprise a carbon powder, a silver powder, a silicon powder, and/or a lithium titanate powder.

A carbon powder and a silver powder function as electric conductivity improvers, and can impart more excellent electric conductivity to the living body contact layer formed from the bio-electrode composition. A silicon powder and a lithium titanate powder can further enhance the ion reception sensitivity of the living body contact layer formed from the bio-electrode composition.

The carbon powder is, for example, one or both of carbon black and carbon nanotube.

Incorporating such a carbon powder can provide higher electric conductivity.

The present invention also provides a bio-electrode comprising:

an electro-conductive base material; and a living body contact layer formed on the electro-conductive base material, the living body contact layer comprises a cured material of the inventive bio-electrode composition.

Since the inventive bio-electrode has the living body contact layer containing the cured material of the above-described bio-electrode composition, the inventive bio-electrode is excellent in electric conductivity and biocompatibility, light-weight, manufacturable at low cost, capable of preventing significant reduction in the electric conductivity even when wetted with water or dried, and capable of quick signal collection after attachment to skin.

The electro-conductive base material can comprise, for example, one or more selected from the group consisting of gold, silver, silver chloride, platinum, aluminum, magnesium, tin, tungsten, iron, copper, nickel, stainless steel, chromium, titanium, and carbon.

The inventive bio-electrode can use various electro-conductive base materials as described above.

The living body contact layer is preferably humidified.

The bio-electrode including such a living body contact layer is capable of more quickly collecting signals when attached to skin.

Further, the present invention provides a method for manufacturing a bio-electrode having an electro-conductive base material and a living body contact layer formed on the electro-conductive base material, comprising:

applying the inventive bio-electrode composition onto the electro-conductive base material; and curing the bio-electrode composition to form the living body contact layer.

Such a manufacturing method makes it possible to manufacture easily at low cost a bio-electrode which is excellent in electric conductivity and biocompatibility, light-weight, and capable of preventing significant reduction in the electric conductivity even when wetted with water or dried, and which enables quick signal collection after attachment to skin.

The electro-conductive base material can comprise, for example, one or more selected from the group consisting of gold, silver, silver chloride, platinum, aluminum, magnesium, tin, tungsten, iron, copper, nickel, stainless steel, chromium, titanium, and carbon.

As described above, the inventive bio-electrode can employ various electro-conductive base materials.

Preferably, in this method, after the living body contact layer is formed, the living body contact layer is immersed in water, or the living body contact layer is humidified.

This allows more effective utilization of the moisture-holding effect of the silicone compound (B) contained in the living body contact layer.

Furthermore, the present invention provides a bio-electrode composition comprising a silicone compound having a polyglycerin structure.

This bio-electrode composition is capable of exhibiting excellent moisture-holding property because the silicone compound having a polyglycerin structure is high in hygroscopicity. Thus, the bio-electrode composition makes it possible to prevent electric conductivity from being significantly reduced, which would otherwise occur by wetting with water or drying. Moreover, this bio-electrode composition can demonstrate excellent ionic conductivity when further containing a material with ionic conductivity. Accordingly, this bio-electrode composition can form a living body contact layer for a bio-electrode, the living body contact layer being capable of preventing significant reduction in electric conductivity regardless of wetting with water or drying, and capable of quickly collecting signals after attachment to skin.

Advantageous Effects of Invention

As described above, the inventive bio-electrode compositions make it possible to form a living body contact layer for a bio-electrode that is excellent in electric conductivity and biocompatibility, light-weight, manufacturable at low cost, and capable of preventing significant reduction in the electric conductivity even when wetted with water or dried, and also capable of quick signal collection after attachment to skin.

BRIEF DESCRIPTION OF DRAWINGS

FIG. 1 is a schematic sectional view showing an example of the inventive bio-electrode;

FIG. 2 is a schematic sectional view showing an example of the inventive bio-electrode worn on a living body;

FIG. 3 is a schematic view of printed bio-electrodes prepared in Examples of the present invention;

FIG. 4 is a schematic view of one of the bio-electrodes prepared in Examples of the present invention, the bio-electrode being cut out and provided with an adhesive layer thereon;

FIG. 5 is a view showing locations where electrodes and earth are attached on a human body in measuring biological signals in Examples of the present invention; and FIG. 6 is one of electrocardiogram waveforms obtained using the bio-electrodes in Examples of the present invention.

DESCRIPTION OF EMBODIMENTS

As described above, it has been desired to develop: a bio-electrode composition capable of forming a living body contact layer for a bio-electrode to enable quick signal collection after attachment to skin; a bio-electrode including a living body contact layer formed of the bio-electrode composition; and a method for manufacturing the bio-electrode.

The surface of skin releases ions of sodium, potassium, and calcium in accordance with heartbeat. A bio-electrode is required to convert the increase and decrease of these ions released from skin to electric signals. Accordingly, a material that is excellent in ionic conductivity to transmit information on the increase and decrease of ions is required.

In neutralized salts formed from highly acidic acids, the ions are strongly polarized, so that the ionic conductivity is improved. This is why lithium salts of bis(trifluoromethanesulfonyl)imidic acid and tris(trifluoromethanesulfonyl)methide acid show high ionic conductivity as electrolytes of a lithium ion battery. On the other hand, there is problem that, before the formation of the neutralized salt, the higher acidity of the acid makes the salt have stronger irritation to a body. That is, ionic conductivity and irritation to a body are in relation of trade-off. In a salt applied to a bio-electrode, however, higher ionic conductivity and lower irritation to a body have to be combined.

There is a tendency that as the molecular weight of ionic compound increases, the permeability decreases, and then the stimulus to skin decreases. Accordingly, the ionic compound is preferably a polymer type with higher molecular weight. Thus, the present inventors have synthesized a polymer obtained by polymerizing an ionic compound having a polymerizable double bond, that is, a polymer compound (A), and have found that adding this polymer enables formation of a bio-electrode sensitive to the increase and decrease of ions released from skin.

Patent Documents 6, 7, and 8 noted above disclose a copolymer of a strong-acidic ionic repeating unit, a repeating unit having a silicone chain, and a hydrophilic repeating unit such as polyether. The ionic repeating unit and the hydrophilic repeating unit are units necessary to exhibit and enhance the ionic conductivity in accordance with the combination. However, these units alone make the hydrophilicity so high that when the resulting bio-electrode film comes into contact with water or sweat, the ion polymer is dissolved in water, and no biological signal is collected in some cases. Accordingly, the ion polymer needs to be insoluble in water. For this reason, the repeating unit having a silicone chain is also copolymerized.

When an ion polymer having an ionic repeating unit, a hydrophilic repeating unit, and a repeating unit with hydrophobic silicone is added to a silicone adhesive, ionic conductivity is exhibited, and biological signals can be obtained. The mechanism of ion conduction in the silicone adhesive, which is inherently an insulator, is conceivably attributable to the microphase separation structure of the ion polymer. Nafion which is excellent in ionic conductivity is described to exhibit high ionic conductivity by microphase separation of a hydrophilic sulfonate moiety and a hydrophobic fluoropolymer moiety thereof.

If an ionic polymer for bio-electrode can be formed to attain more prominent microphase separation, the ionic conductivity will be further improved, and it will be possible to form a dry electrode that can obtain biological signals in higher sensitivity.

In this respect, adding a hygroscopic material is effective to further improve the ionic conductivity. Patent Documents 6, 7, 8 noted above disclose the addition of a polyether-silicone compound. Further, examples of the hygroscopic material include silicone compounds having polyglycerin. Such materials are used as moisturizers of cosmetics (Patent Documents 9, 10, and 11). Polyglycerin having not only a polyether group but also a hydroxy group is high in hygroscopicity, and high ionic conductivity can be obtained by combining an ion polymer with a compound having such polyglycerin bonded to a silicone chain.

Furthermore, the present inventors have found that it is preferable to enhance electron conductivity in addition to ionic conductivity so as to obtain a highly sensitive bio-electrode. Adding a carbon powder, a metal powder, a silicon powder, or a lithium titanate powder is effective to enhance electron conductivity.

Specifically, the present invention is a bio-electrode composition comprising:

(A) a polymer compound comprising a repeating unit-a having a structure selected from the group consisting of salts of ammonium, sodium, potassium, and silver formed with any of fluorosulfonic acid, fluorosulfonimide, and N-carbonyl-fluorosulfonamide; and (B) a silicone compound having a polyglycerin structure.

Hereinafter, the present invention will be described in detail, but the present invention is not limited thereto.

<Bio-Electrode Composition>

The inventive bio-electrode composition contains (A) a polymer compound (polymer) having an ionic repeating unit, and (B) a silicone compound having a polyglycerin structure.

For example, the inventive bio-electrode composition can further contain a resin component (C) other than the polymer compound (A), a metal powder, a carbon powder, a silicon powder, a lithium titanate powder, a tackifier, a crosslinking agent, a crosslinking catalyst, an ionic additive, and/or an organic solvent.

Hereinafter, each component will be further described in detail.

[(A) Polymer Compound]

The polymer compound (A) blended in the inventive bio-electrode composition can be called, for example, ionic material (conductive material). The polymer compound (A) is specifically a polymer compound (polymer) containing a repeating unit-a having a structure selected from the group consisting of salts of ammonium, sodium, potassium, and silver formed with any of fluorosulfonic acid, fluorosulfonimide, and N-carbonyl-fluorosulfonamide. Hence, the polymer compound (A) can also be called salt.

The repeating unit-a is preferably shown by any of the following general formulae (1)-1 to (1)-4.

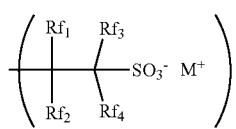

(1)-1

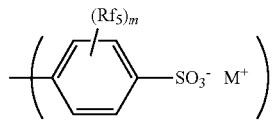

(1)-2

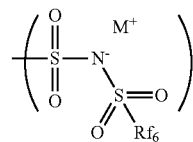

(1)-3

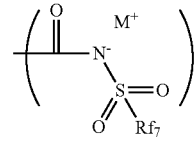

(1)-4

In the formula (1)-1, $Rf_1$ and $Rf_2$ each represent a hydrogen atom, a fluorine atom, an oxygen atom, a methyl group, or a trifluoromethyl group. When $Rf_1$ and $Rf_2$ represent an oxygen atom, the single oxygen atom represented by $Rf_1$ and $Rf_2$ bonds to a single carbon atom to form a carbonyl group. $Rf_3$ and $Rf_4$ each represent a hydrogen atom, a fluorine atom, or a trifluoromethyl group. At least one of $Rf_1$ to $Rf_4$ is a fluorine atom or a trifluoromethyl group.

In the formulae (1)-2, (1)-3, and (1)-4, $Rf_5$, $Rf_6$, and $Rf_7$ each represent a fluorine atom, or a linear or branched alkyl group having 1 to 4 carbon atoms and at least one or more fluorine atoms.

In the formulae (1)-1 to (1)-4, $M^+$ represents an ion selected from the group consisting of an ammonium ion, a sodium ion, a potassium ion, and a silver ion.

In the formula (1)-2, "m" represents an integer of 1 to 4.

When the repeating unit-a has such structures, the resulting bio-electrode composition is capable of forming a living body contact layer for a bio-electrode that is more excellent in electric conductivity and biocompatibility.

The repeating unit-a is further preferably a repeating unit having at least one repeating unit selected from the group consisting of repeating units-a1 to -a7 shown by the following general formula (2).

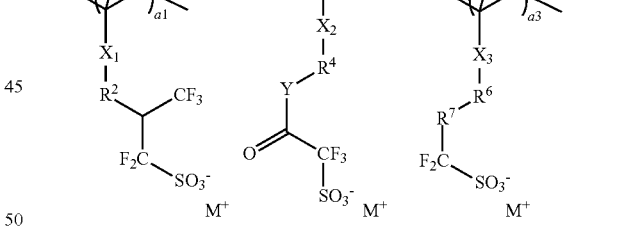

(2)

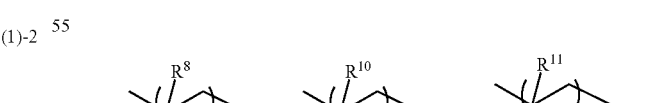

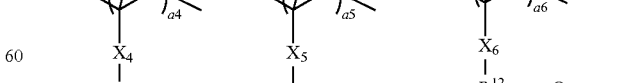

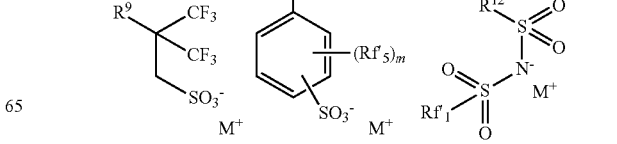

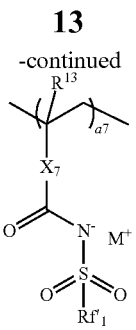

In the formula (2), $R^1$, $R^3$, $R^5$, $R^8$, $R^{10}$, $R^{11}$, and $R^{13}$ each independently represent a hydrogen atom or a methyl group. $R^2$, $R^4$, $R^6$, $R^9$, and $R^{12}$ each independently represent a single bond, or a linear, branched, or cyclic hydrocarbon group having 1 to 12 carbon atoms. The hydrocarbon group optionally has either or both of an ester group and an ether group. $R^7$ represents a linear or branched alkylene group having 1 to 4 carbon atoms, and one or two hydrogen atoms in $R^7$ are optionally substituted with a fluorine atom. $X_1$, $X_2$, $X_3$, $X_4$, $X_6$, and $X_7$ each independently represent any of a single bond, a phenylene group, a naphthylene group, an ether group, an ester group, and an amide group. $X_5$ represents any of a single bond, an ether group, and an ester group. Y represents an oxygen atom or a —$NR^{19}$— group. $R^{19}$ represents a hydrogen atom, or a linear or branched alkyl group having 1 to 4 carbon atoms. $Rf_1'$ represents a fluorine atom or a trifluoromethyl group. $Rf_5'$ represents a fluorine atom, or a linear or branched alkyl group having 1 to 4 carbon atoms and at least one or more fluorine atoms. "m" represents an integer of 1 to 4. a1, a2, a3, a4, a5, a6, and a7 satisfy $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, and $0 < a1+a2+a3+a4+a5+a6+a7 \leq 1.0$. $M^+$ represents an ion selected from the group consisting of an ammonium ion, a sodium ion, a potassium ion, and a silver ion.

When the repeating unit-a has such structures, the resulting bio-electrode composition is capable of forming a living body contact layer for a bio-electrode that is further excellent in electric conductivity and biocompatibility.

Note that a1, a2, a3, a4, a5, a6, and a7 are symbols to identify the respective repeating units, and also represent the proportions of the respective repeating units in the polymer compound (A). The formula (2) specifically illustrates: the repeating units-a1, -a2, -a3, -a4, and -a5 in this order from left to right at the top; and the repeating units-a6 and -a7 in this order from left to right at the bottom.

Among the repeating units-a1 to -a7 shown by the general formula (2), the repeating units-a1 to -a5 can be obtained from fluorosulfonic acid salt monomers specifically exemplified below.

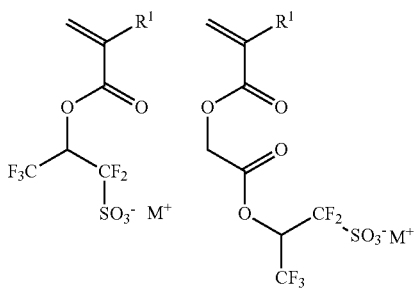

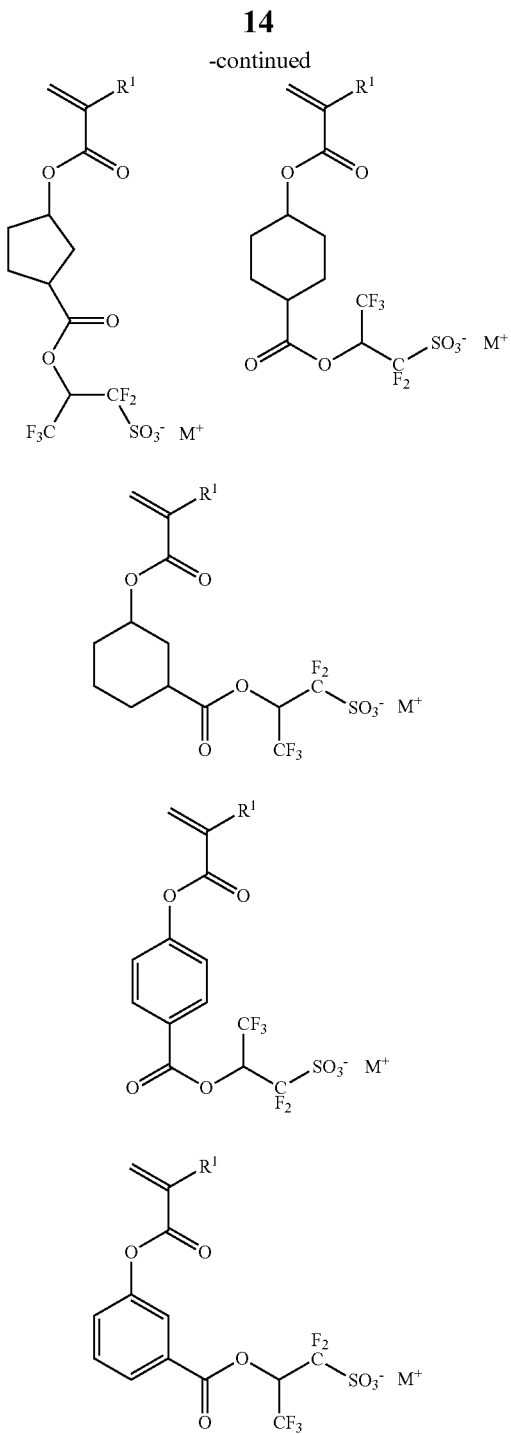

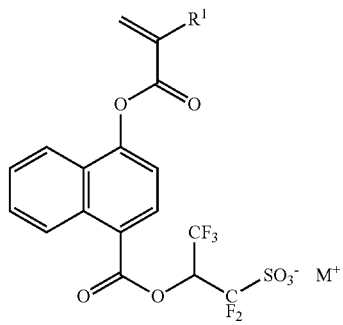

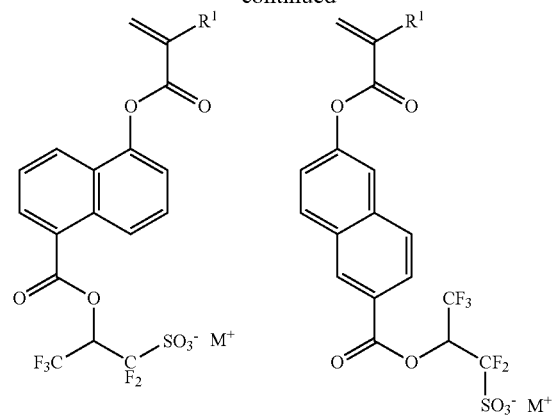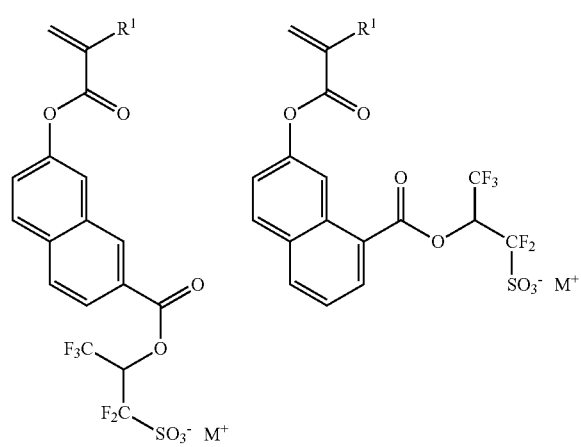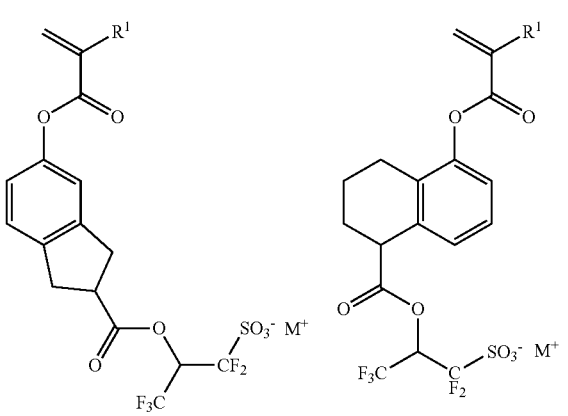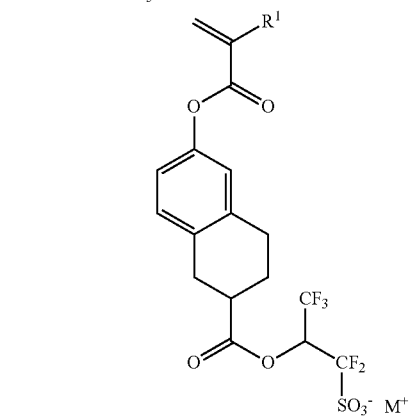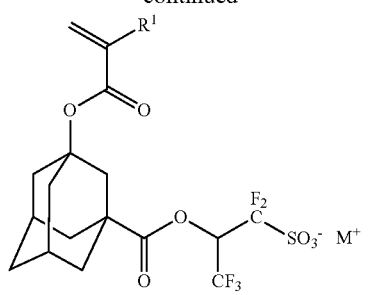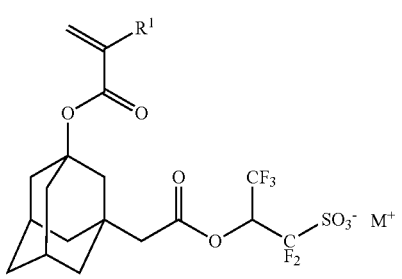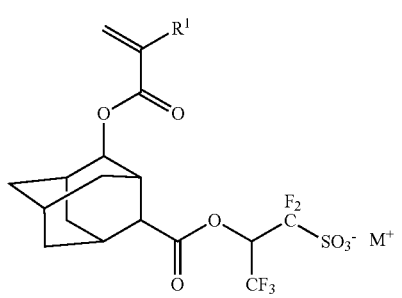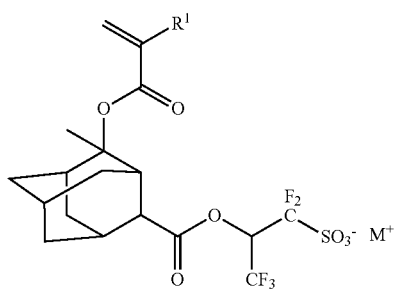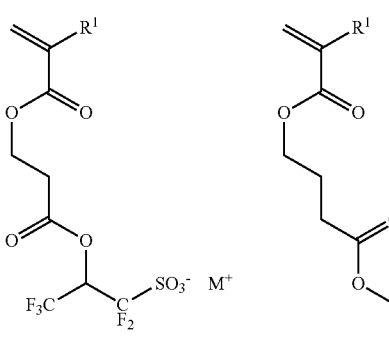

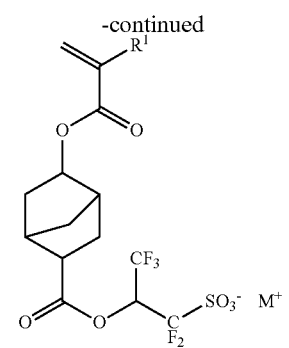
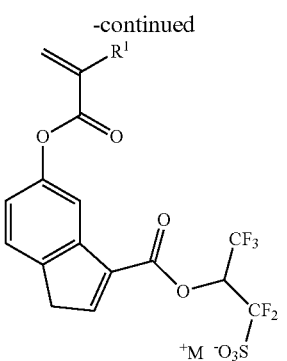
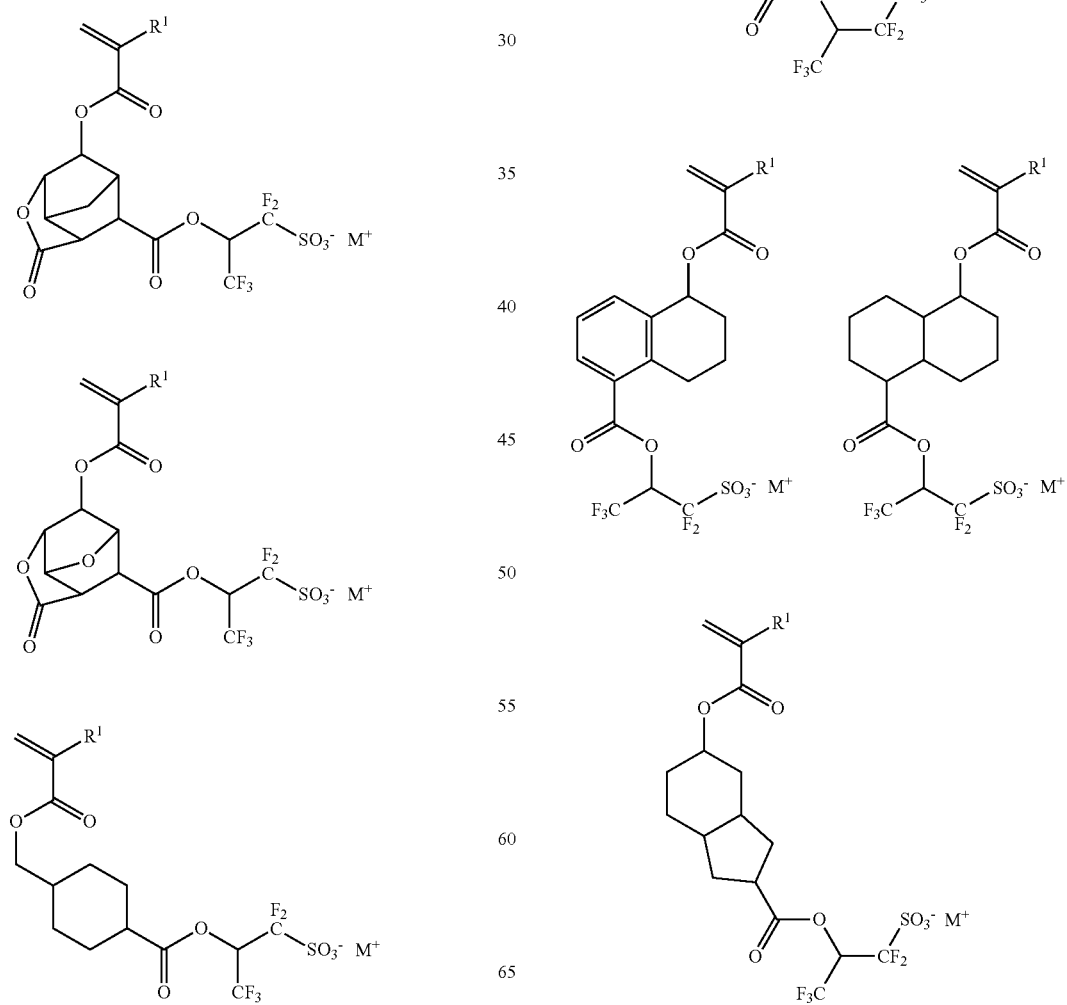

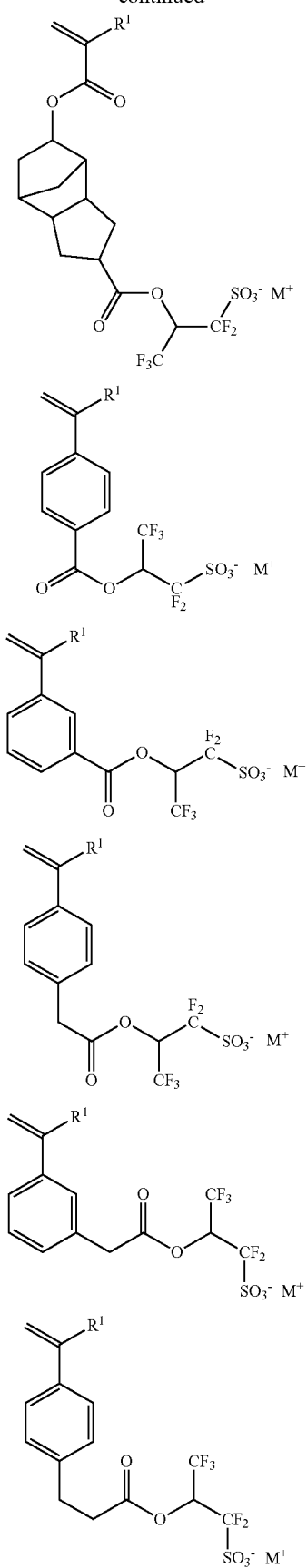
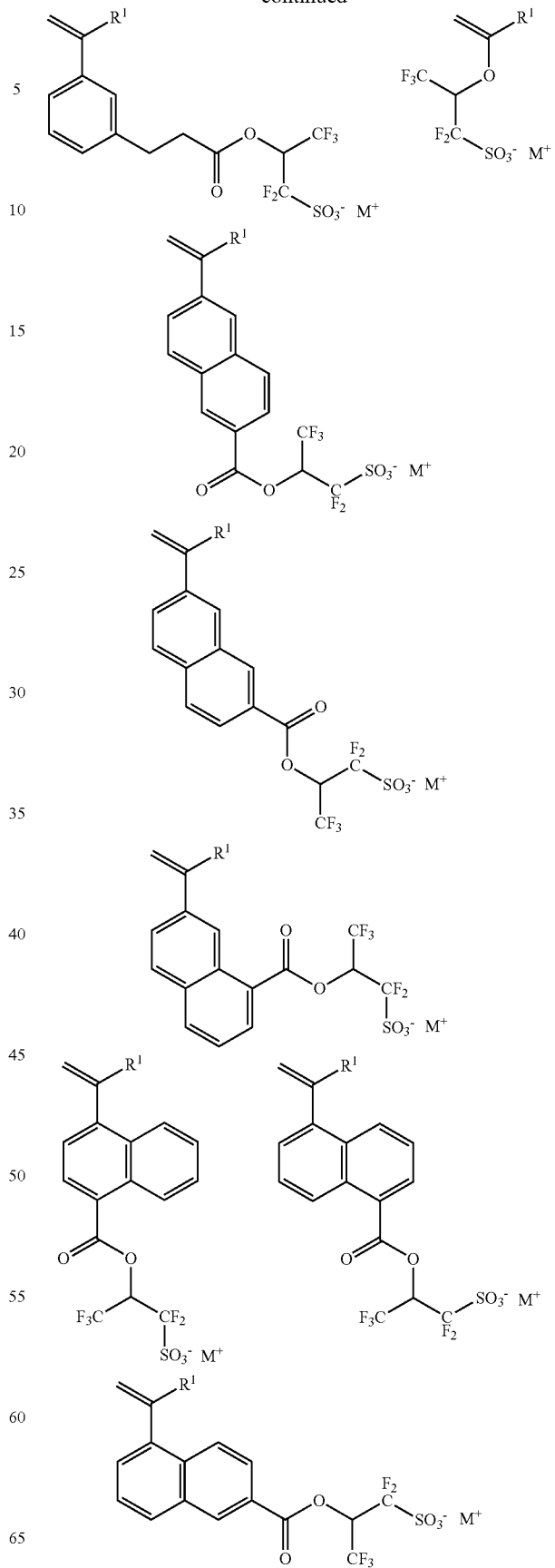

-continued
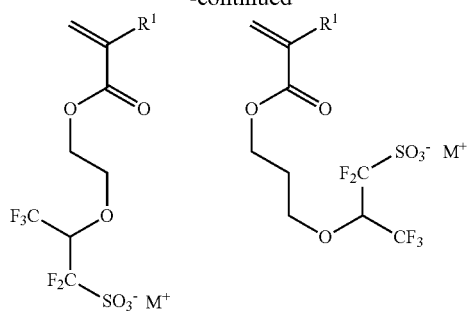
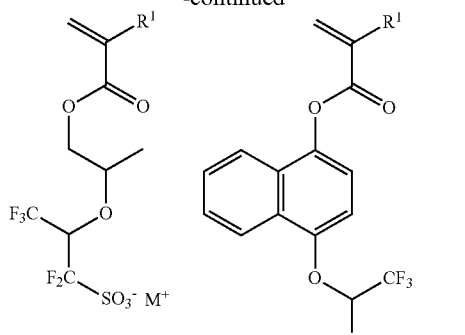
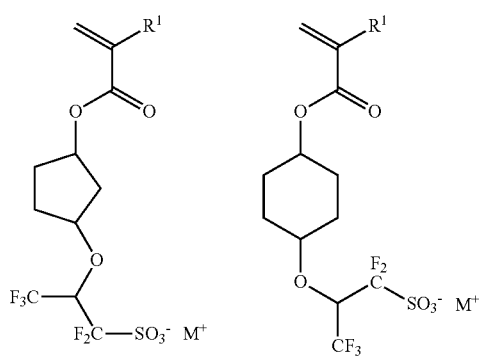
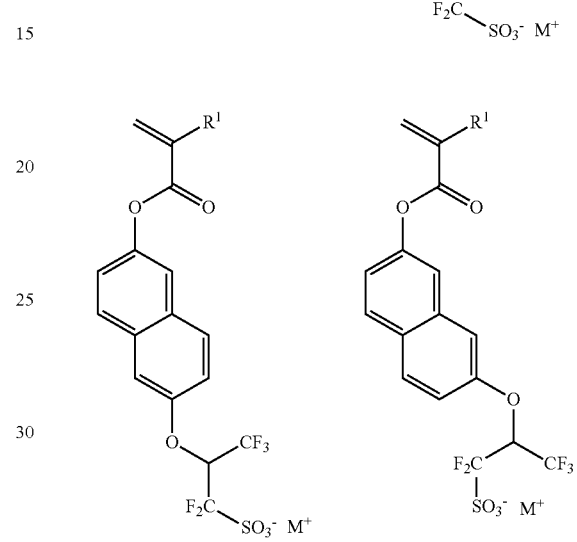
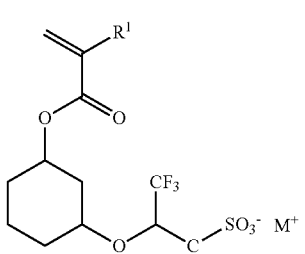
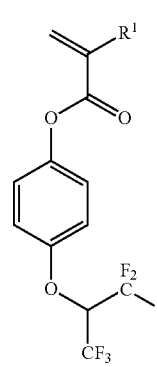
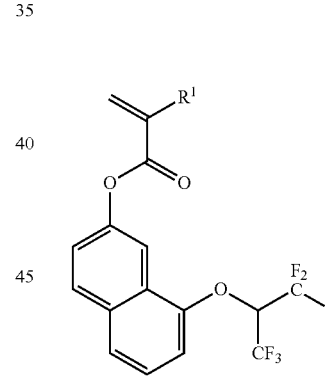
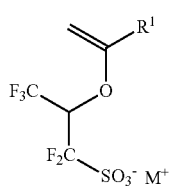
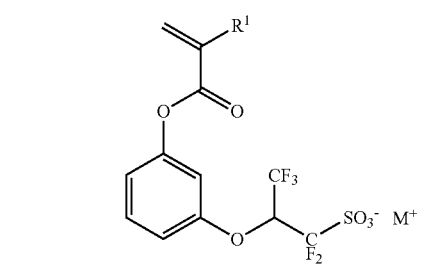
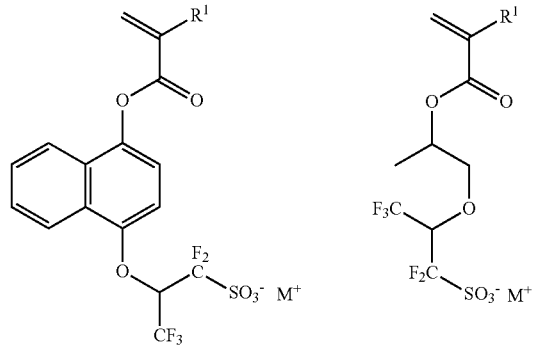
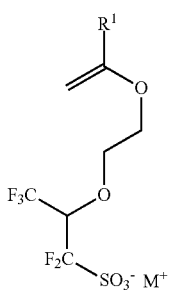
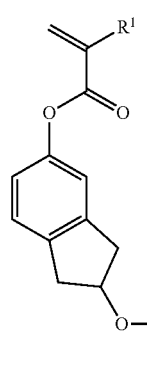

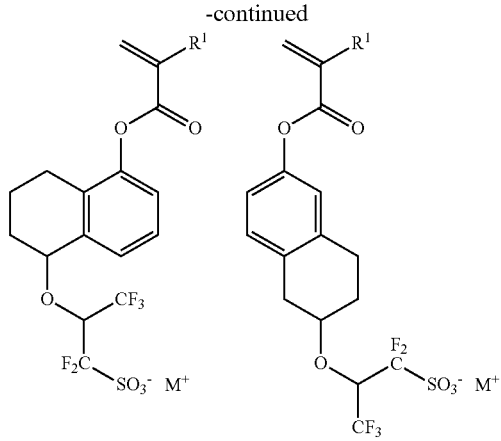
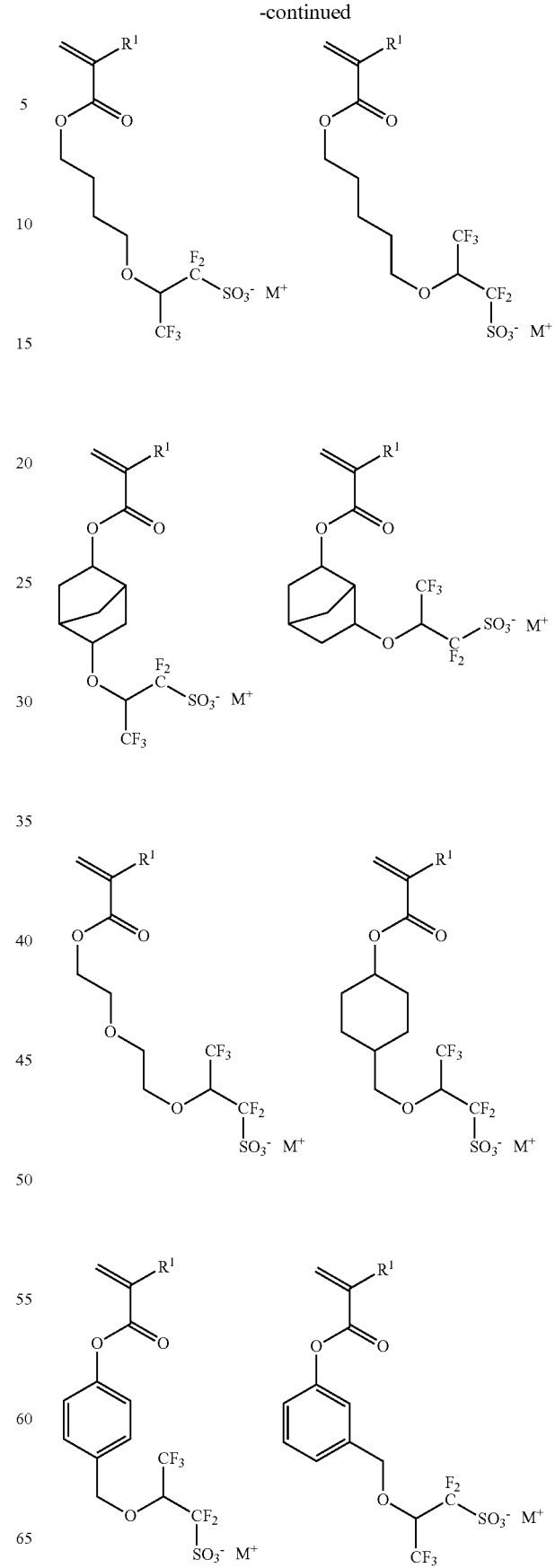

-continued
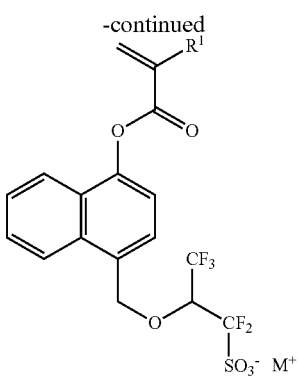
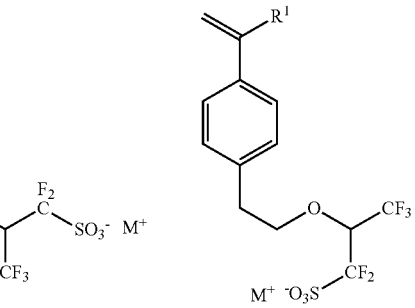
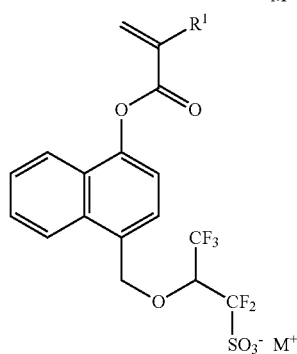
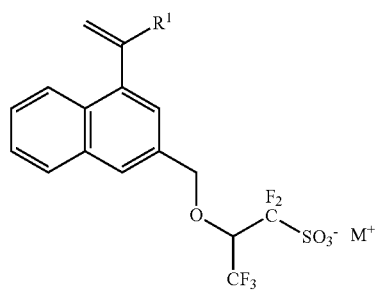
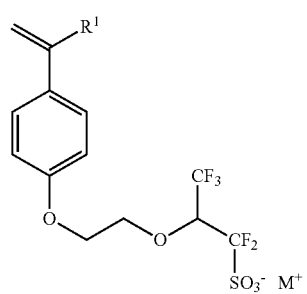
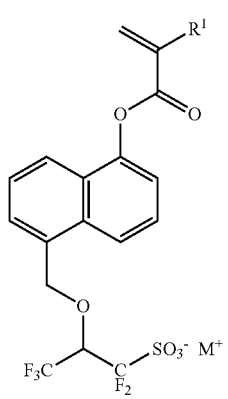
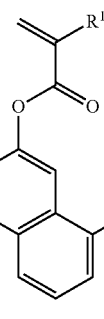
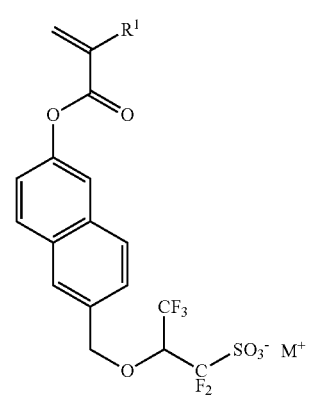
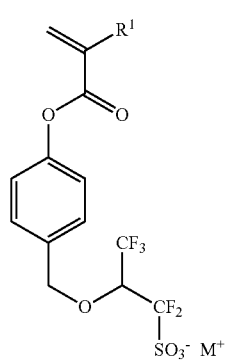
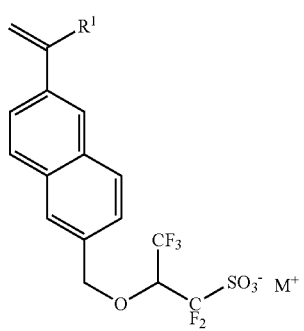

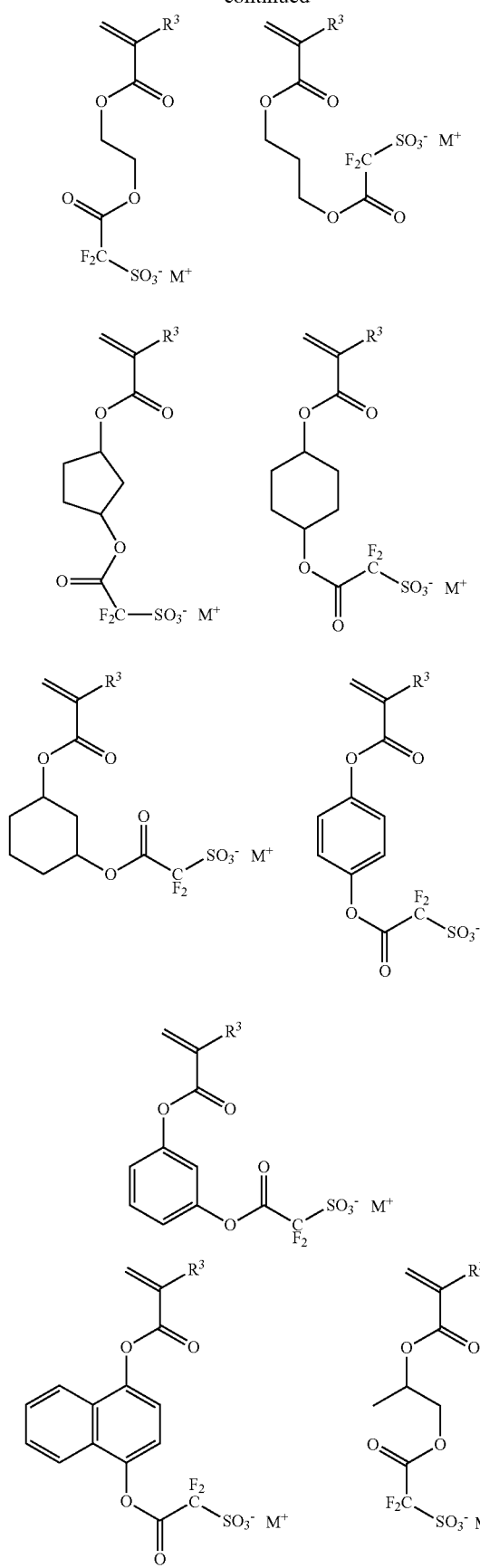

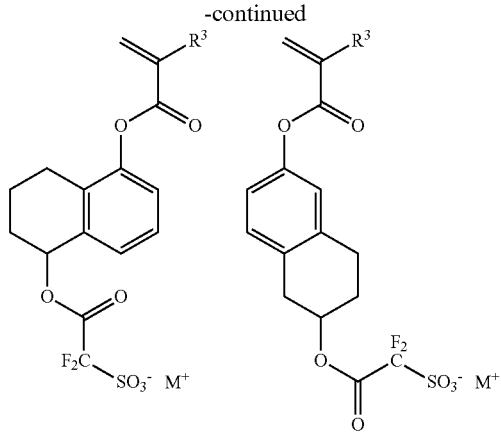
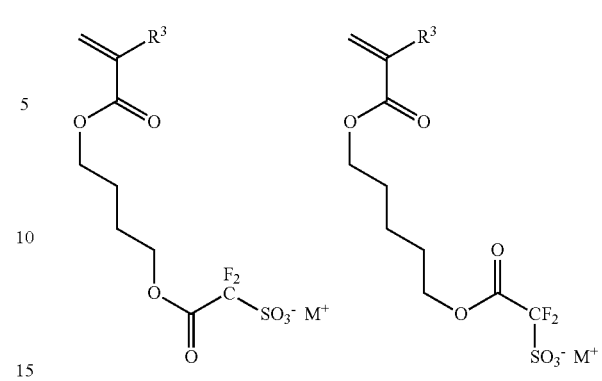
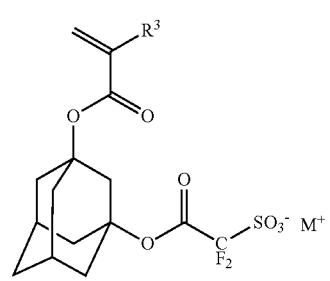
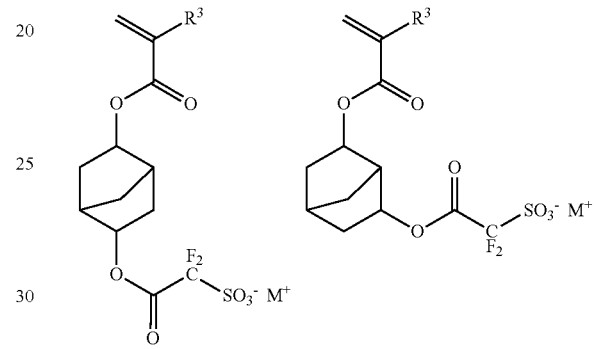
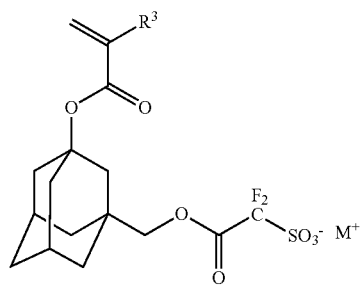
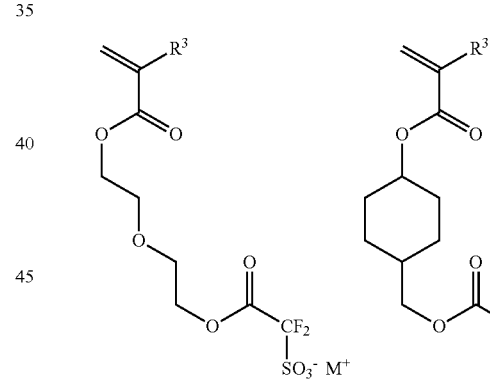
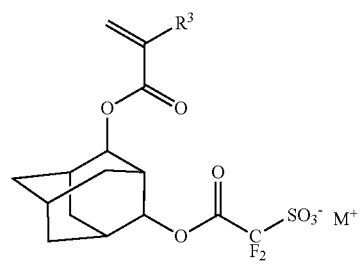
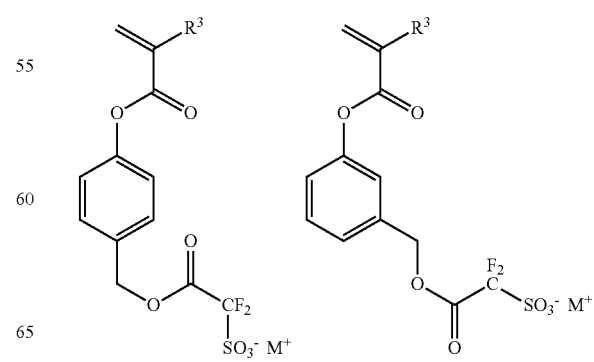

-continued
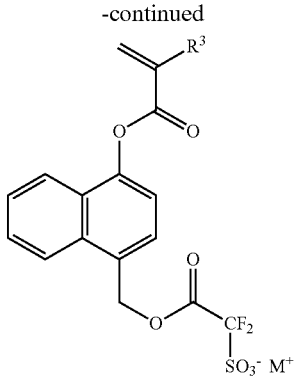
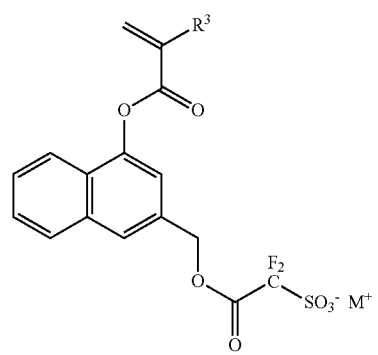
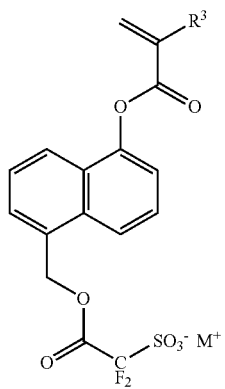
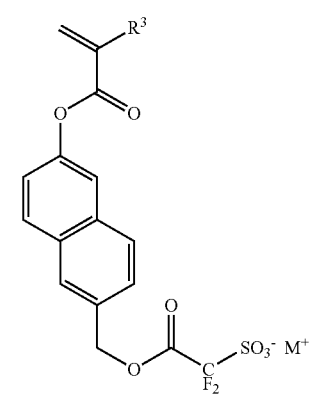
-continued
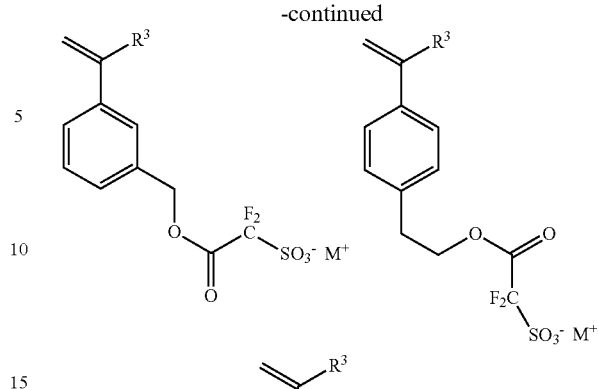
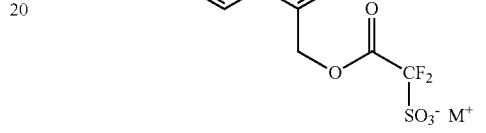
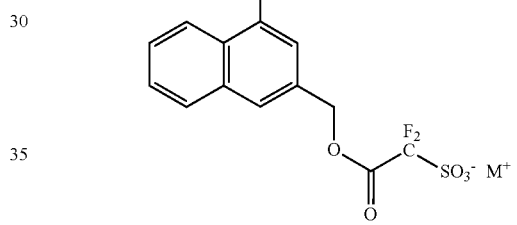
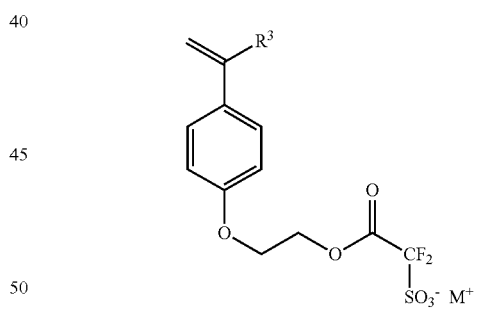
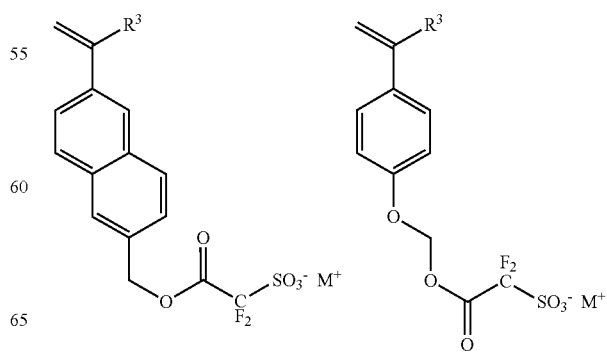

-continued
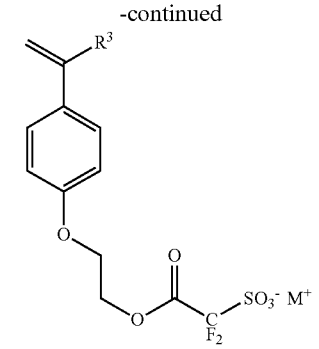
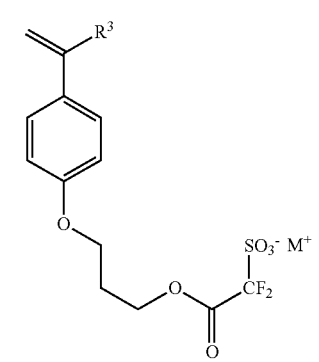
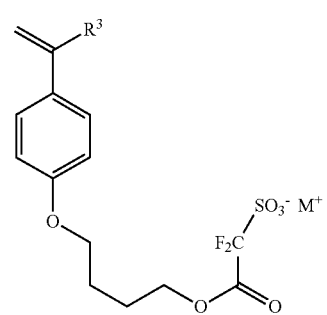
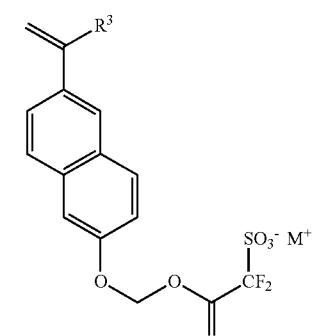
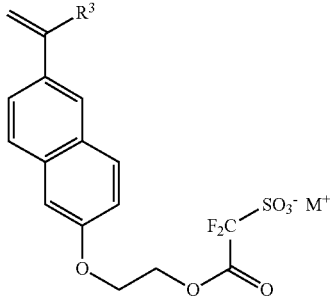
-continued
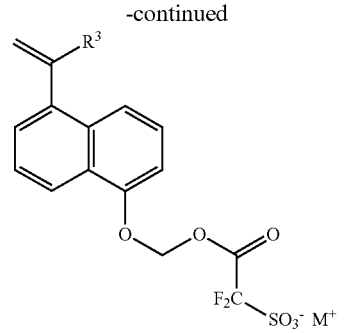
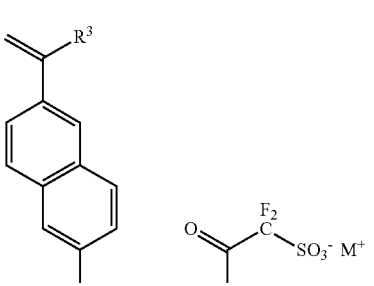
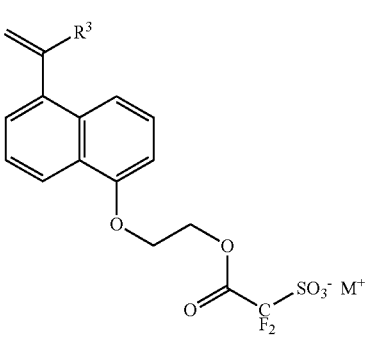
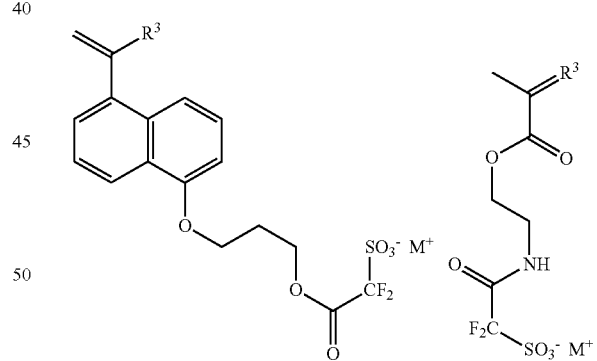
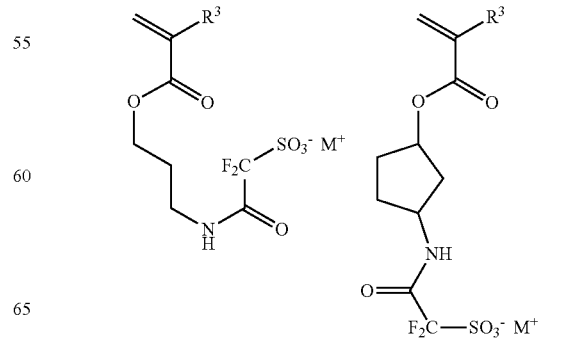

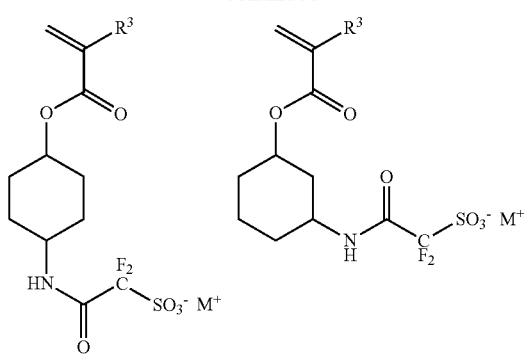
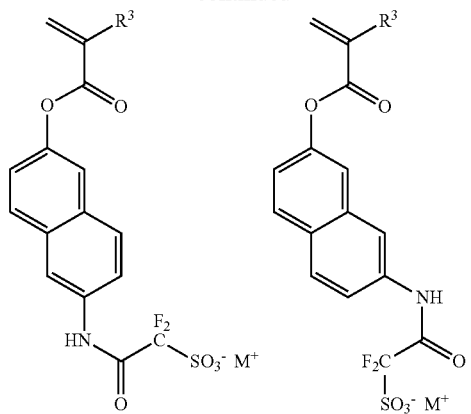
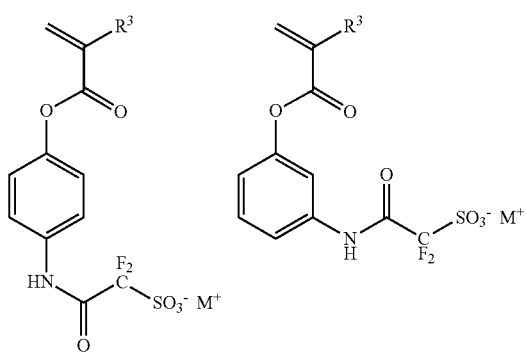
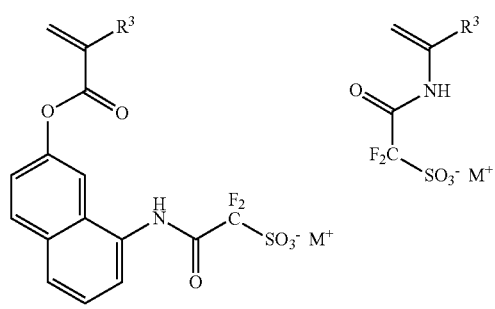
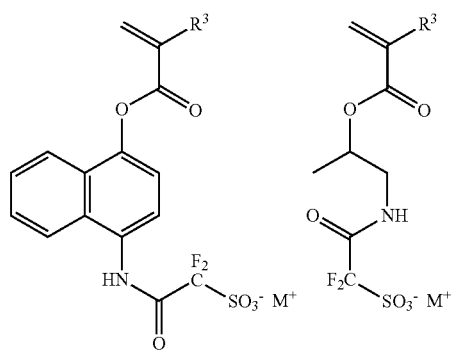
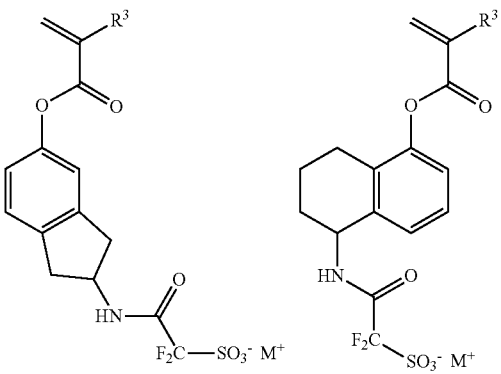
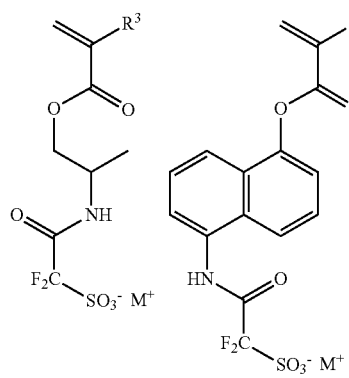
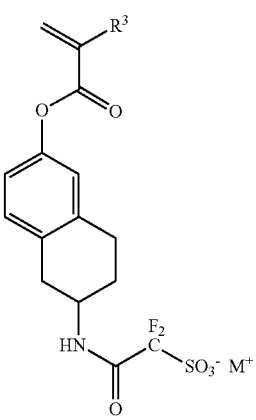

37
-continued
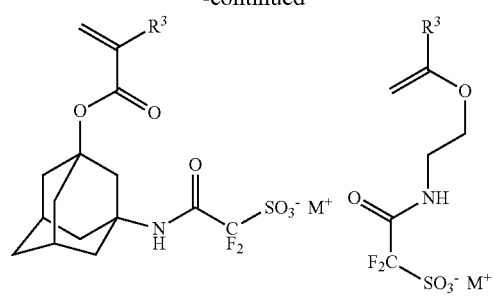
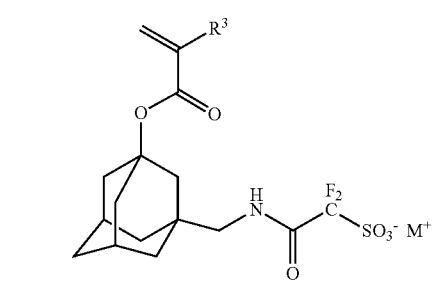
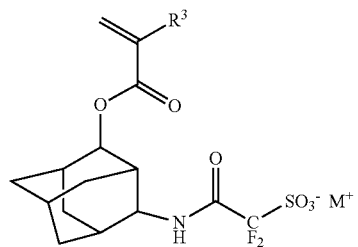
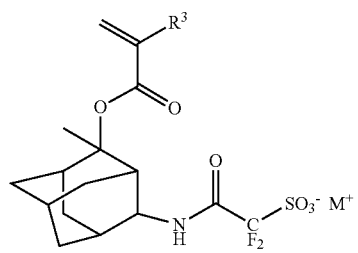
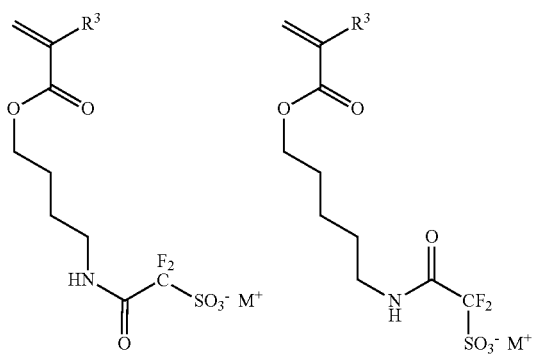
38
-continued
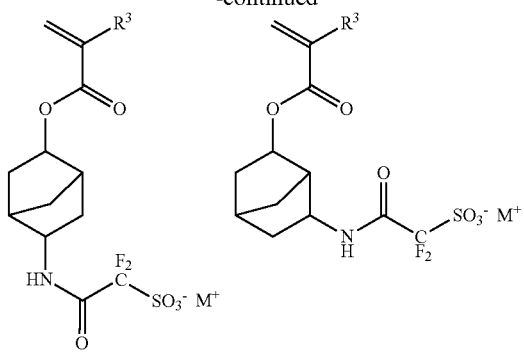
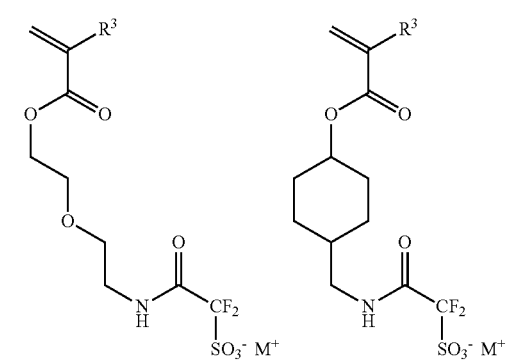
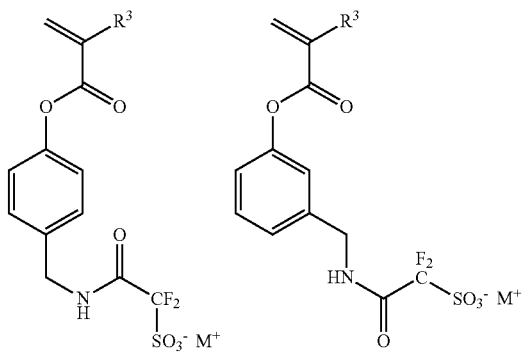
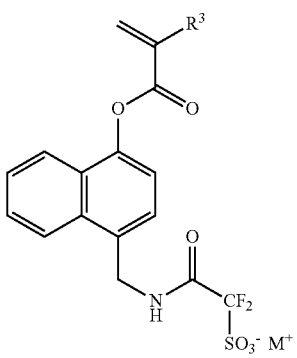

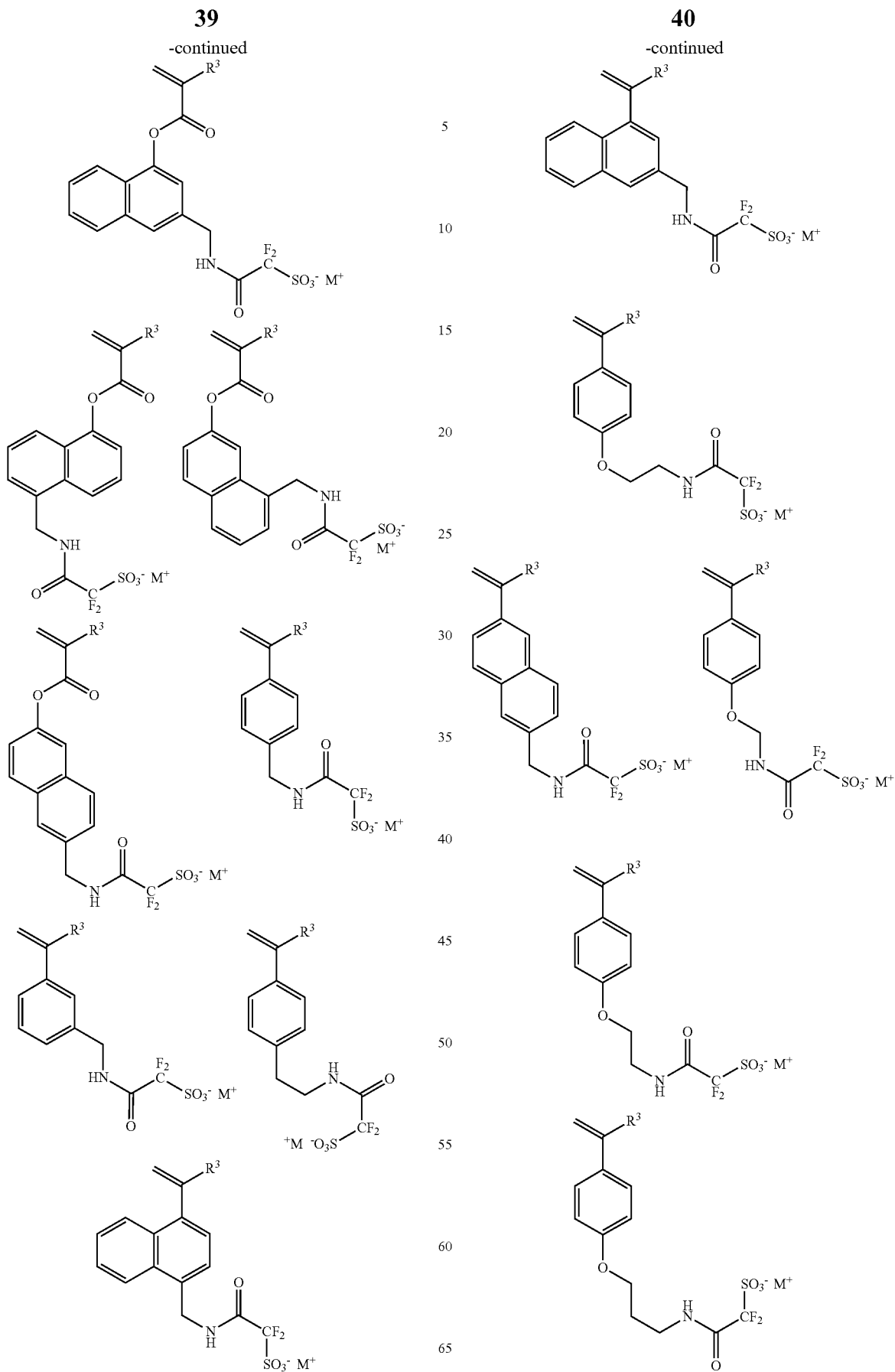

-continued
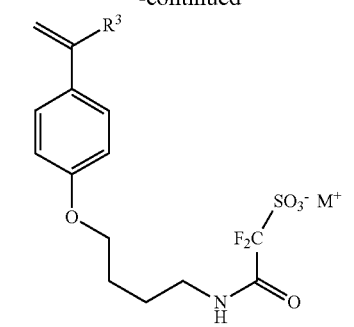
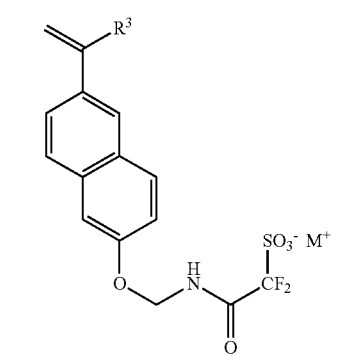
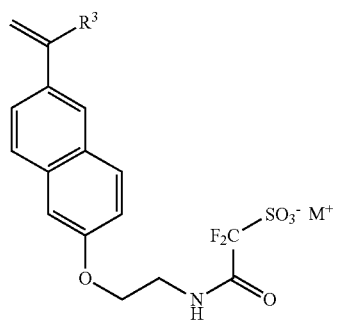
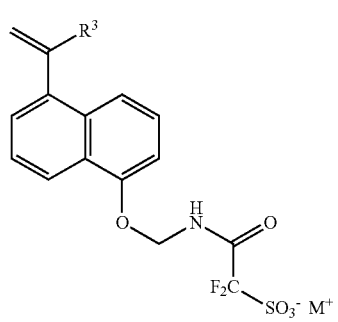
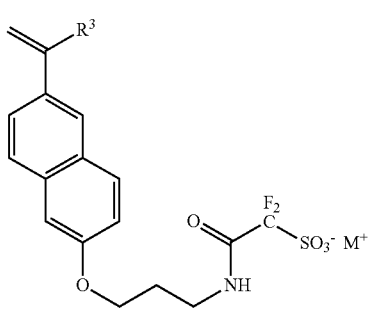
-continued
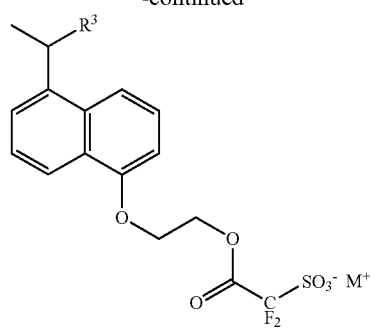
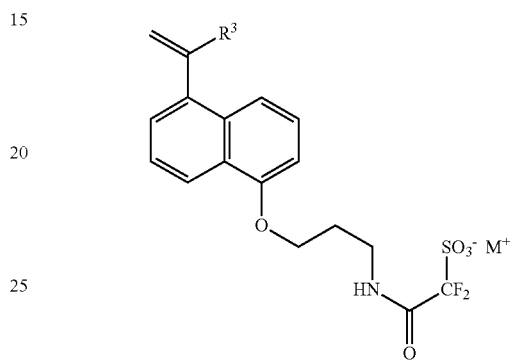
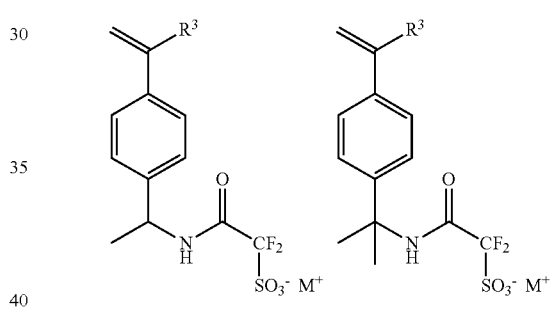
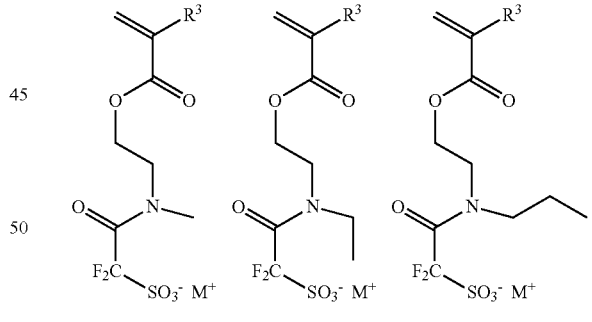
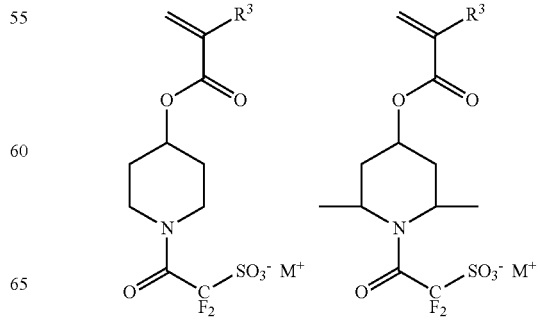

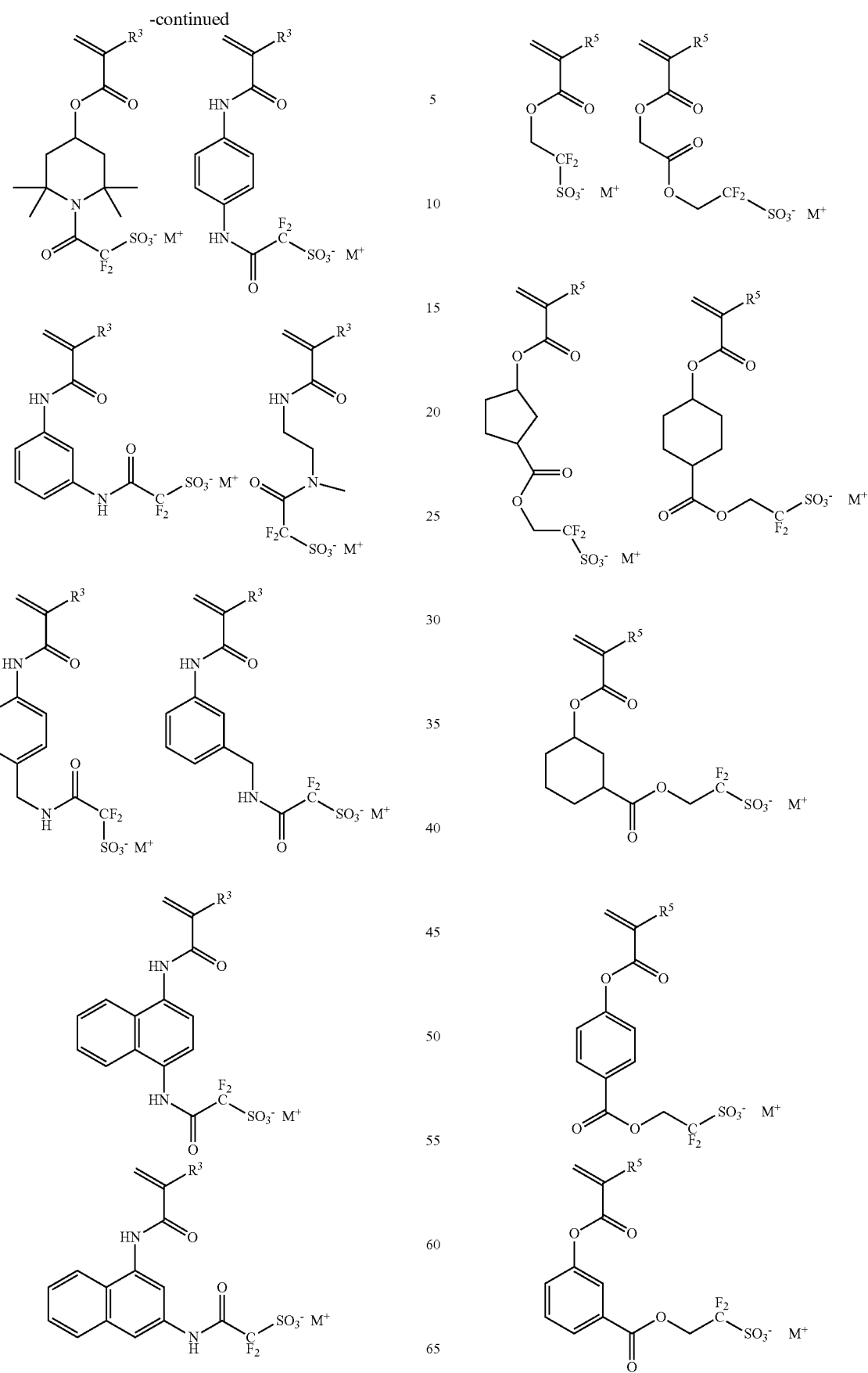

-continued
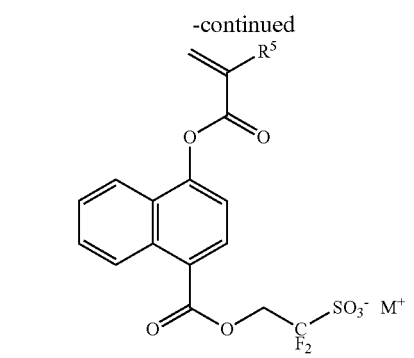
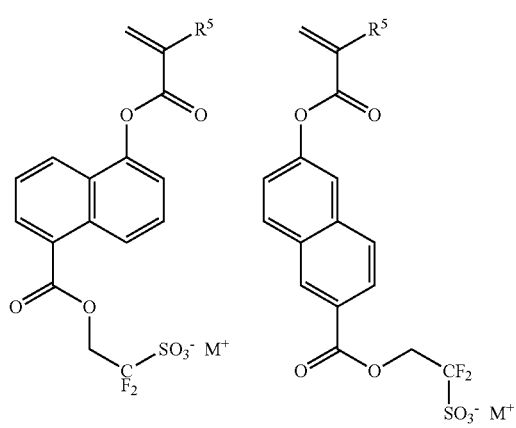
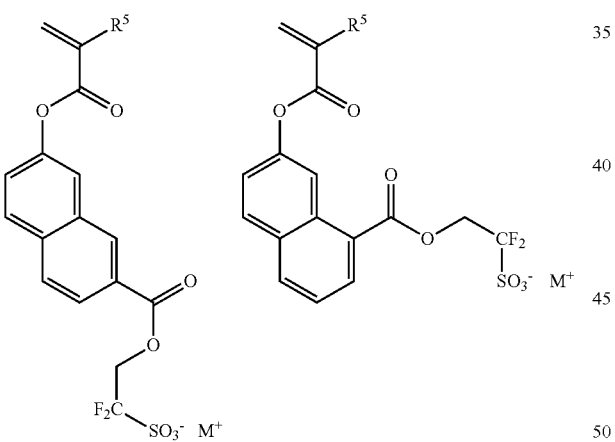
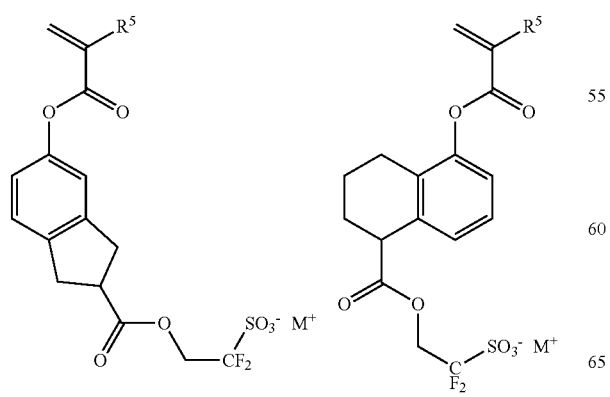
-continued
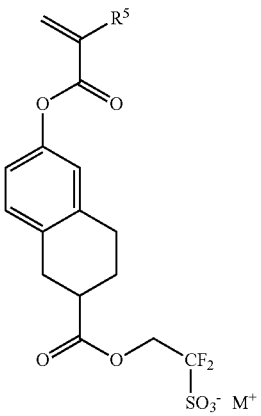
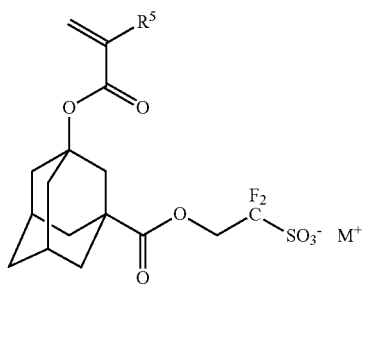
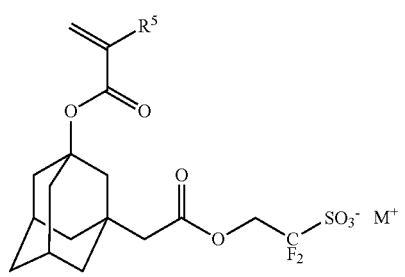
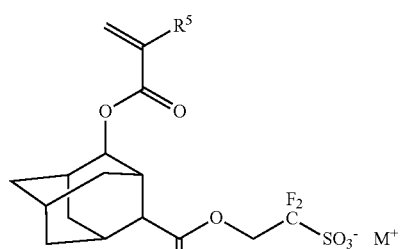
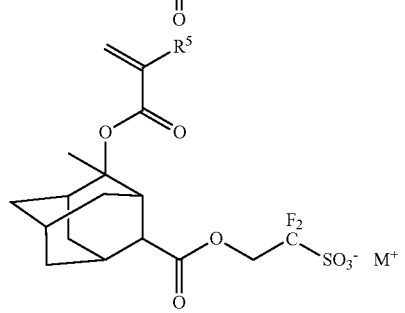

-continued
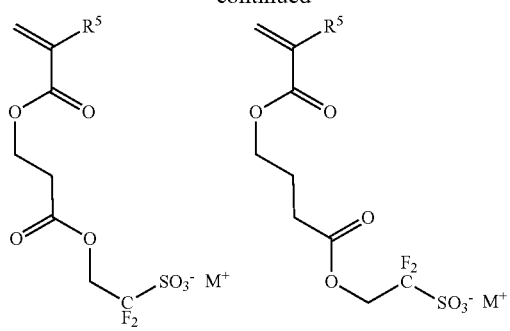
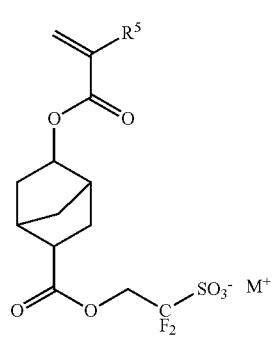
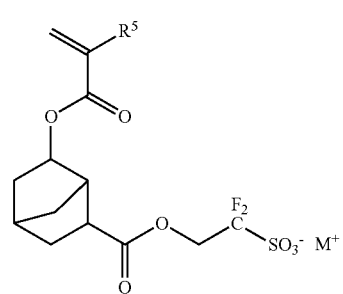
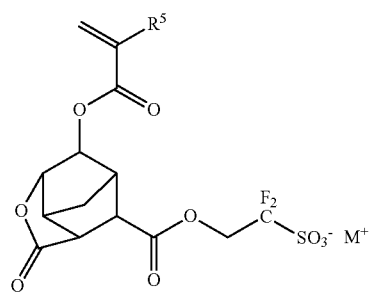
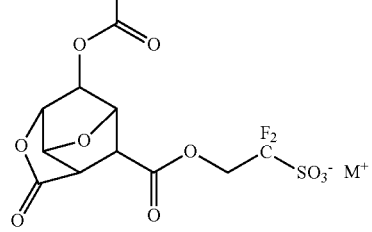
-continued
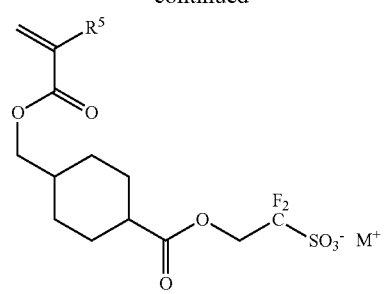
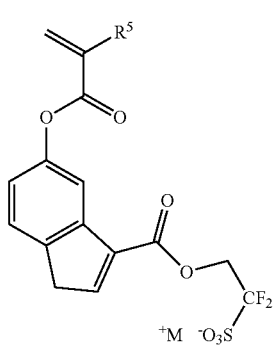
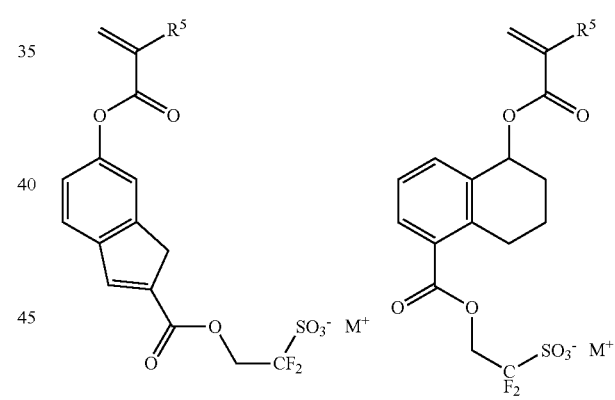
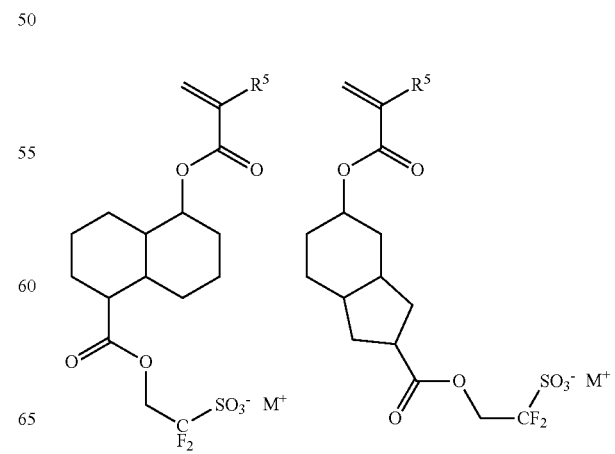

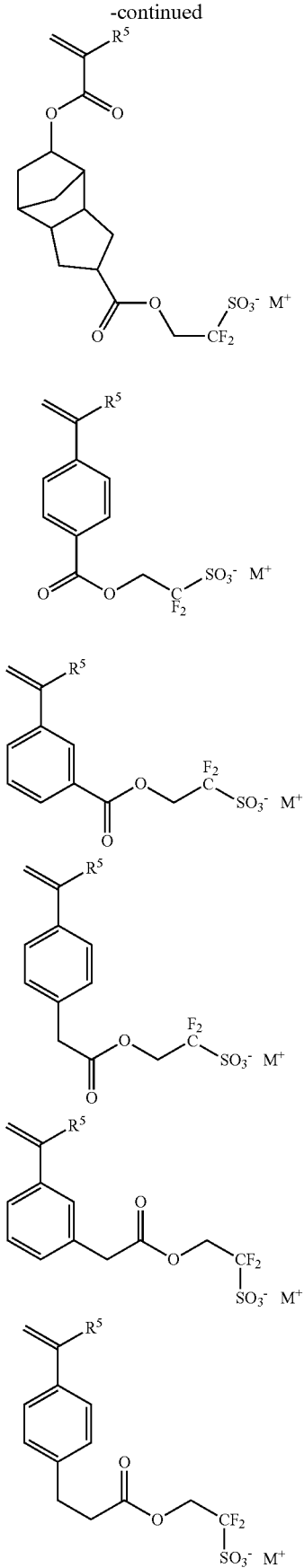

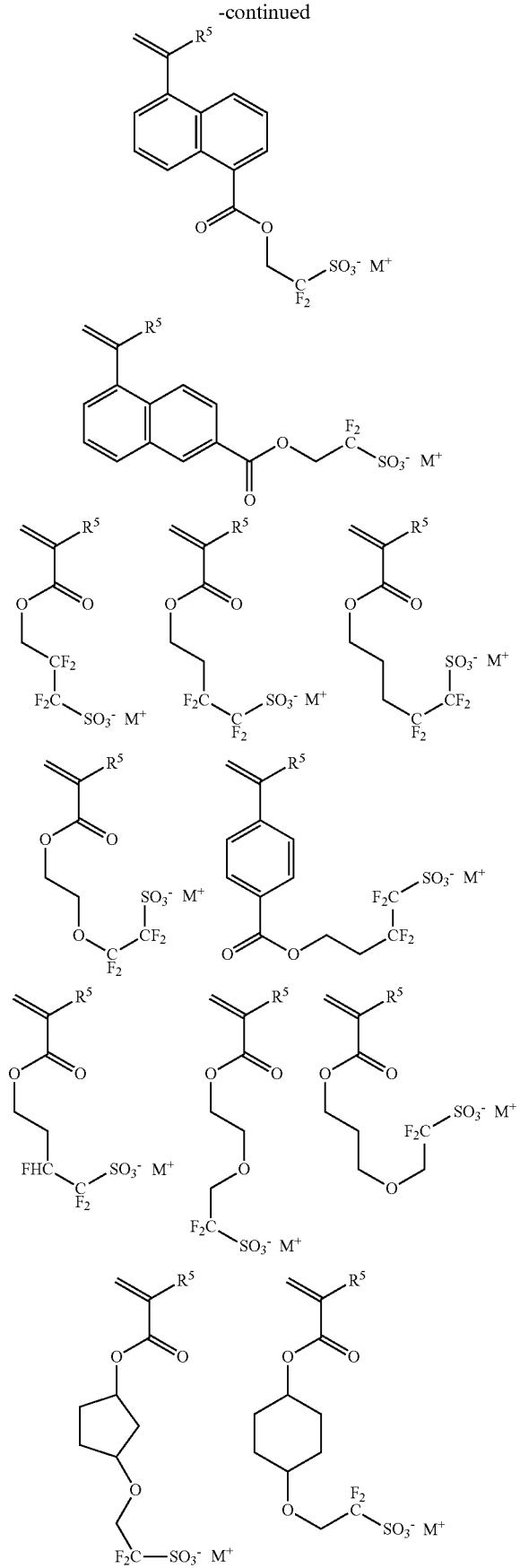
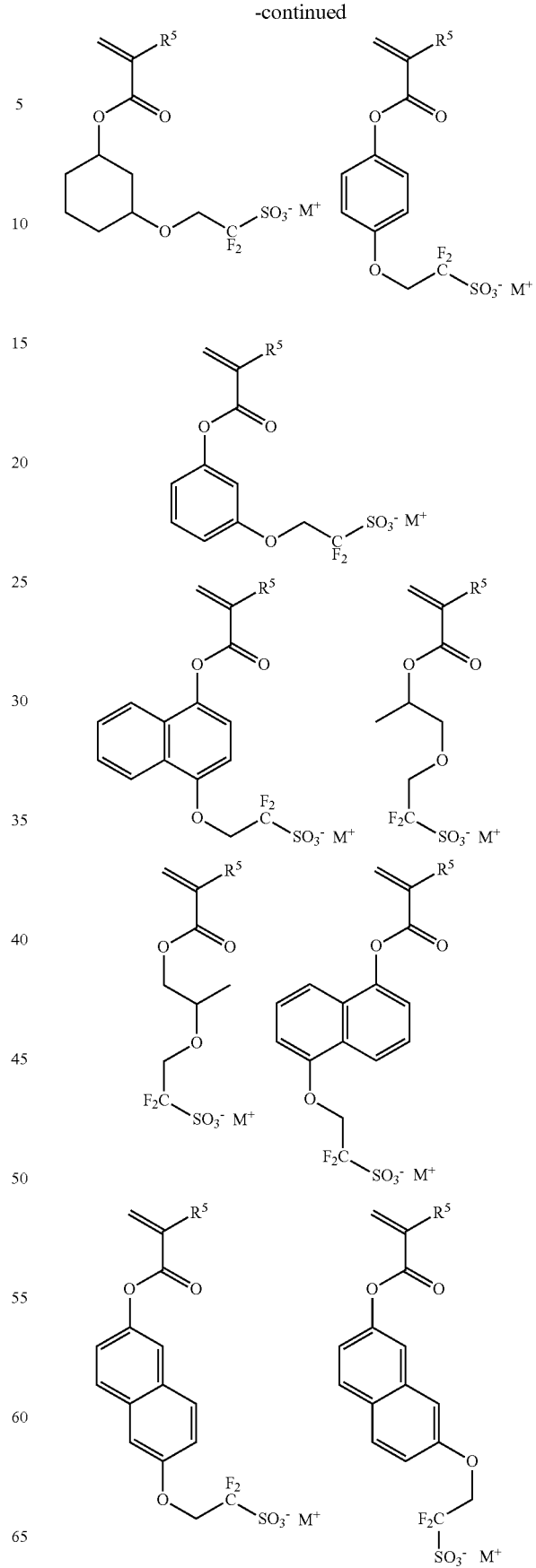

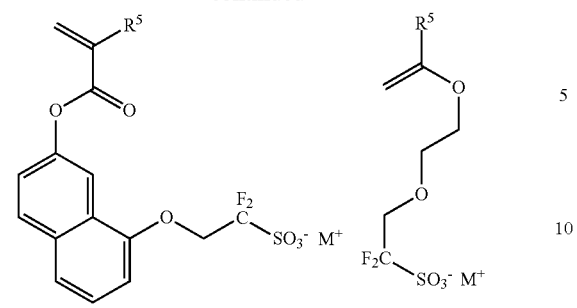
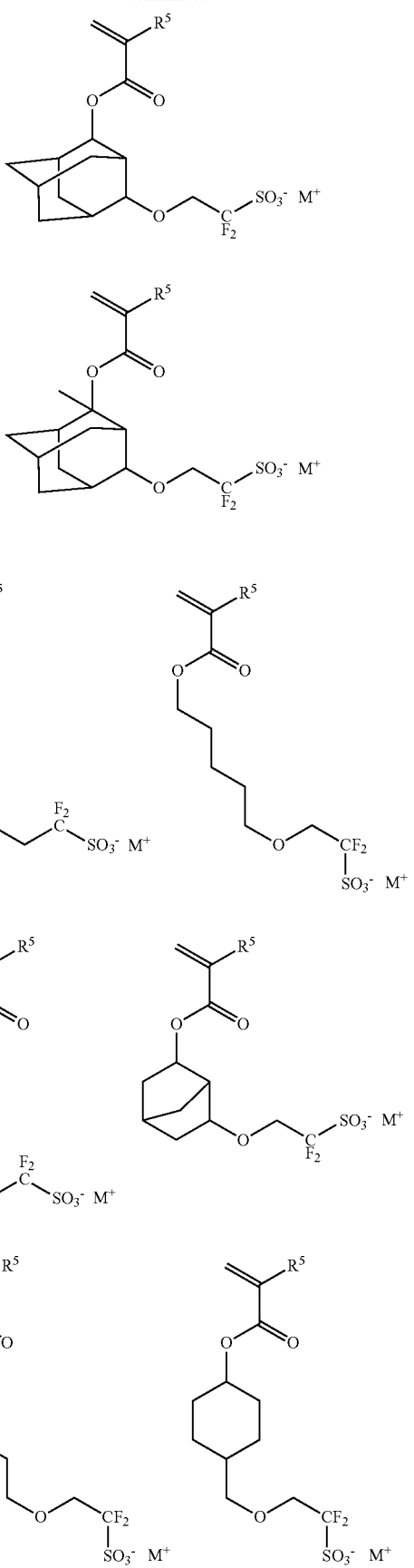

55
-continued
56
-continued
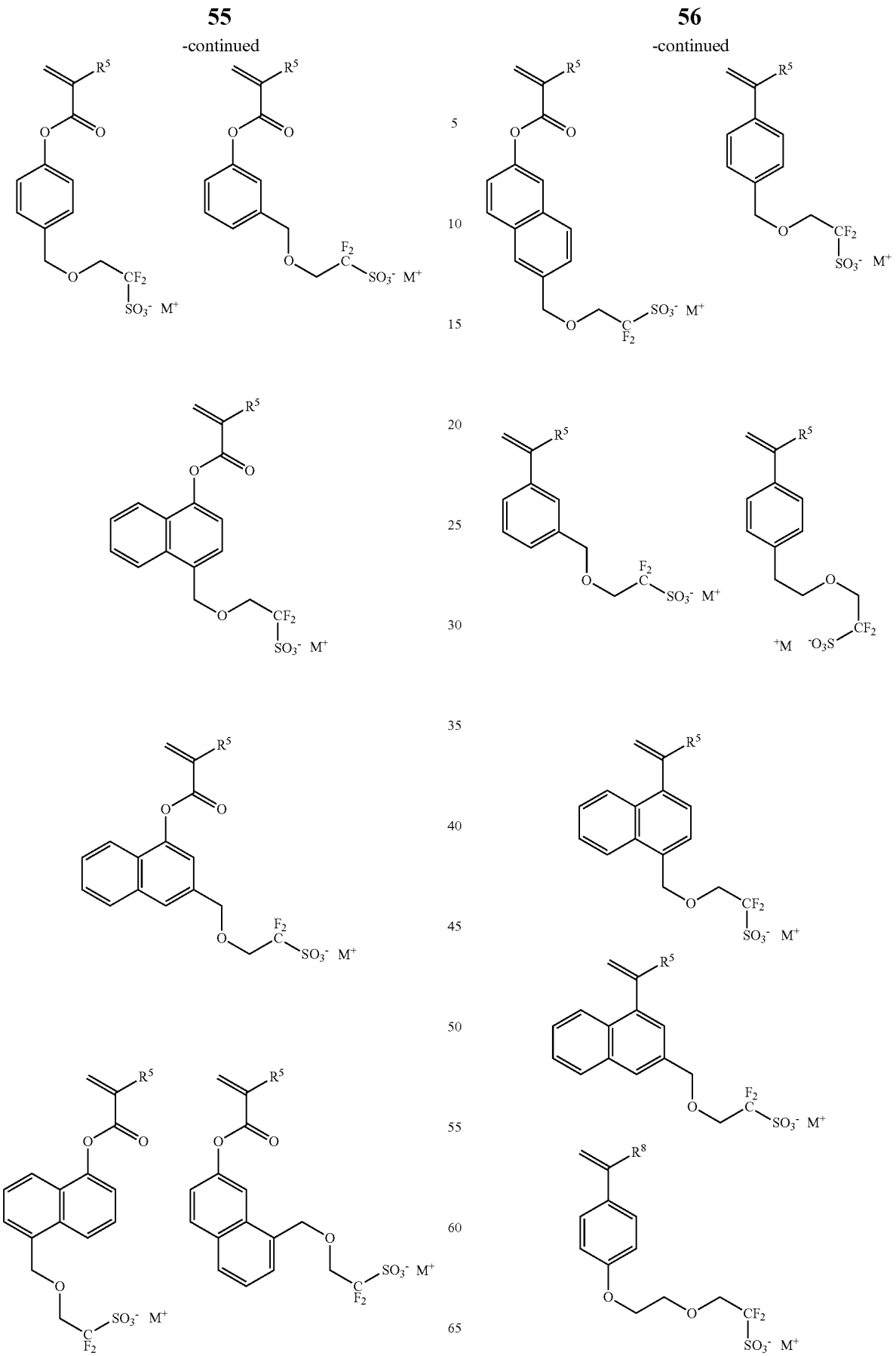

57
-continued
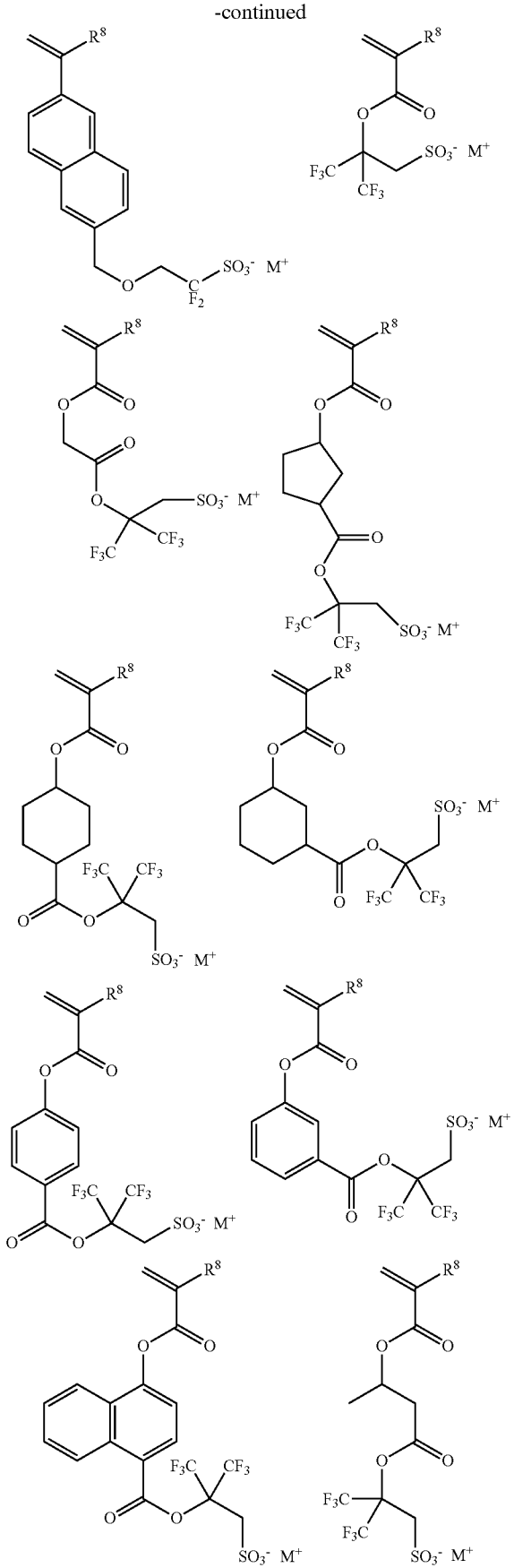
58
-continued
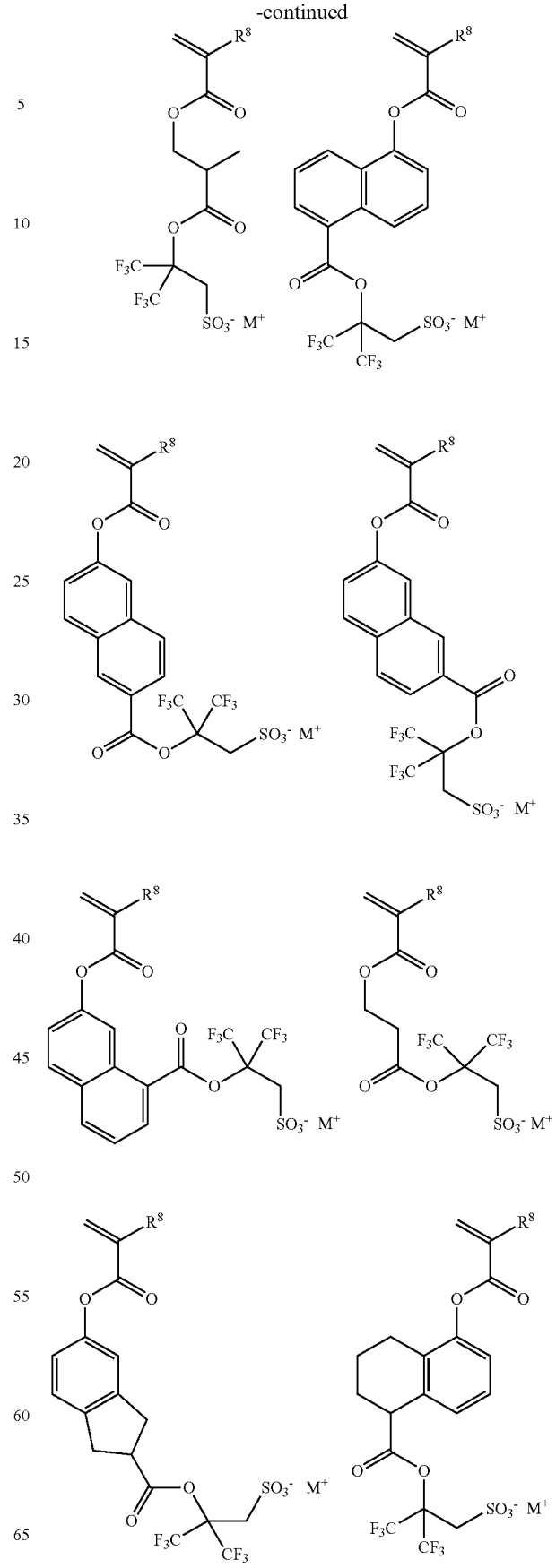

-continued
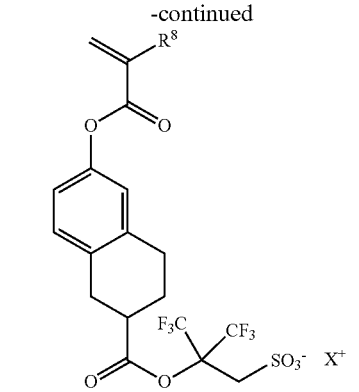
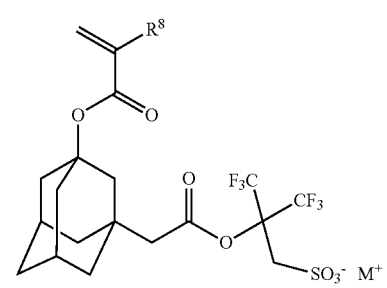
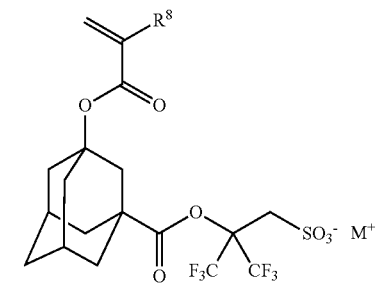
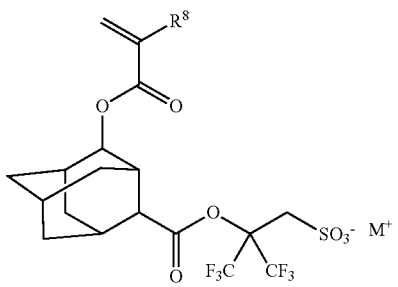
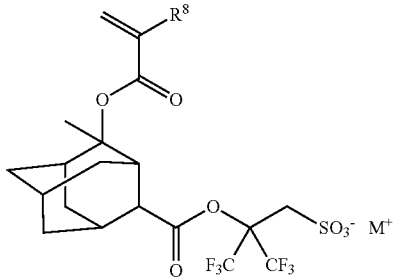
-continued
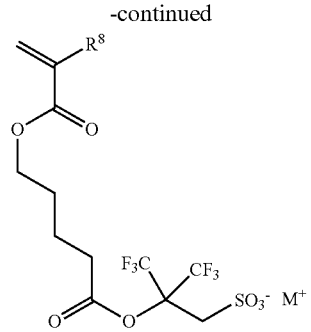
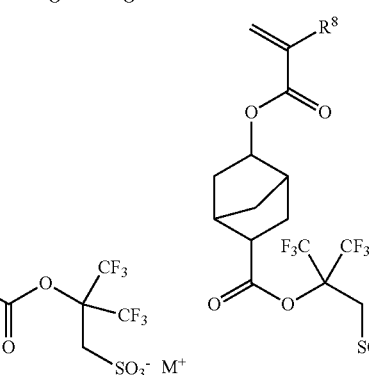
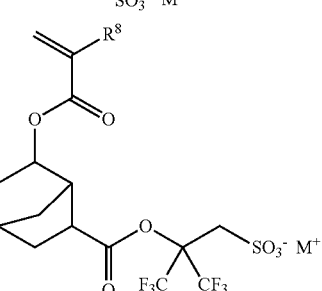
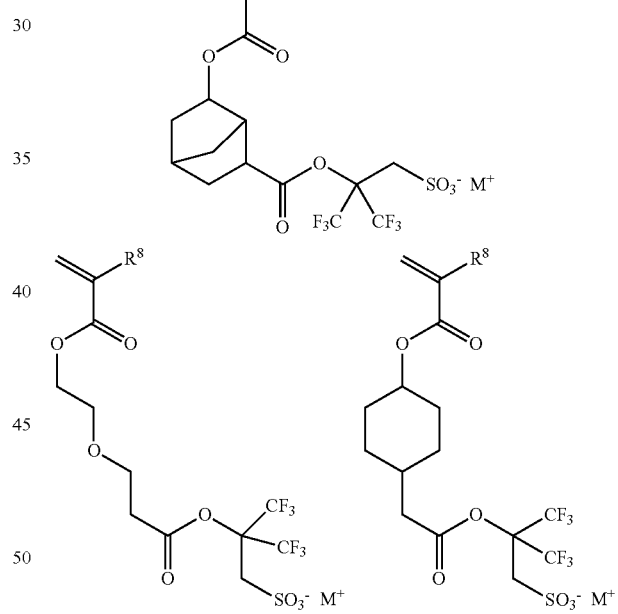
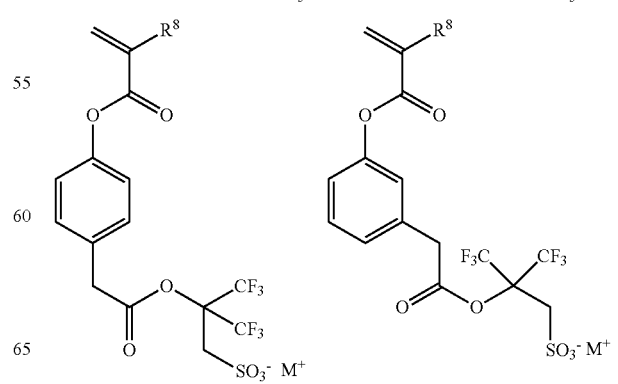

61
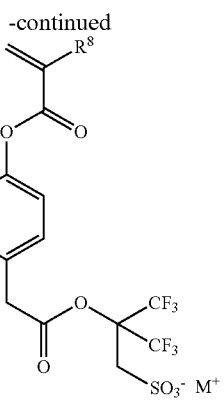
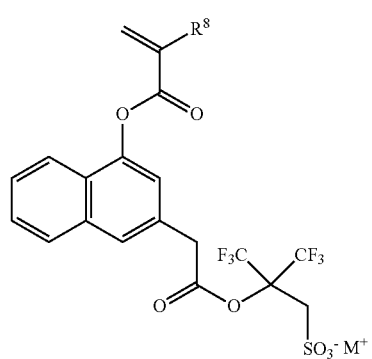
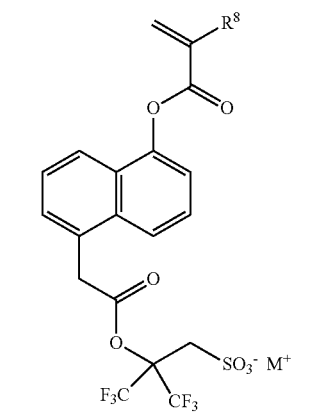
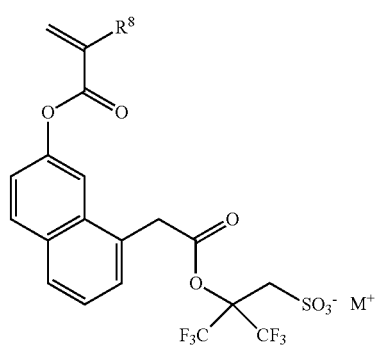
62
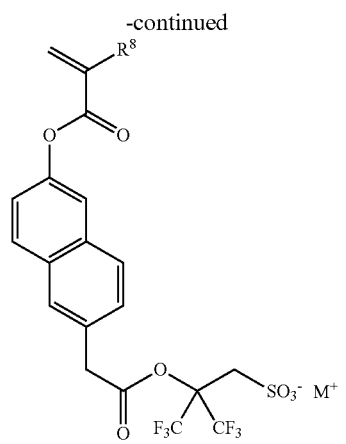
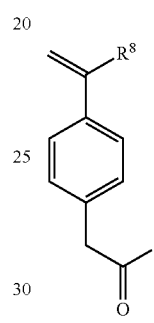 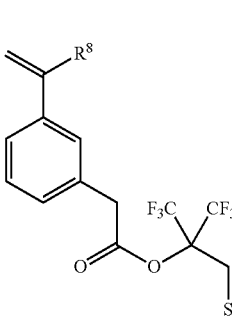
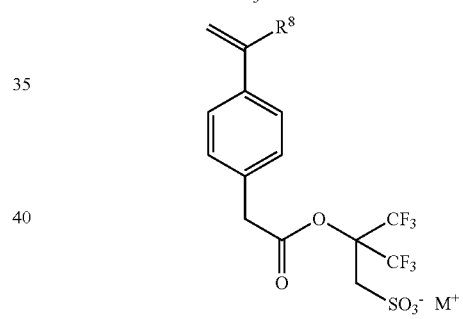
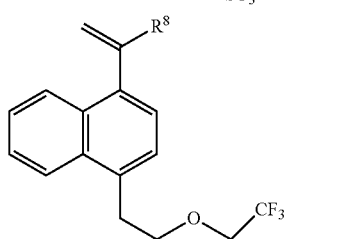
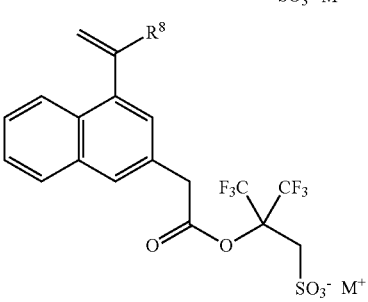

-continued
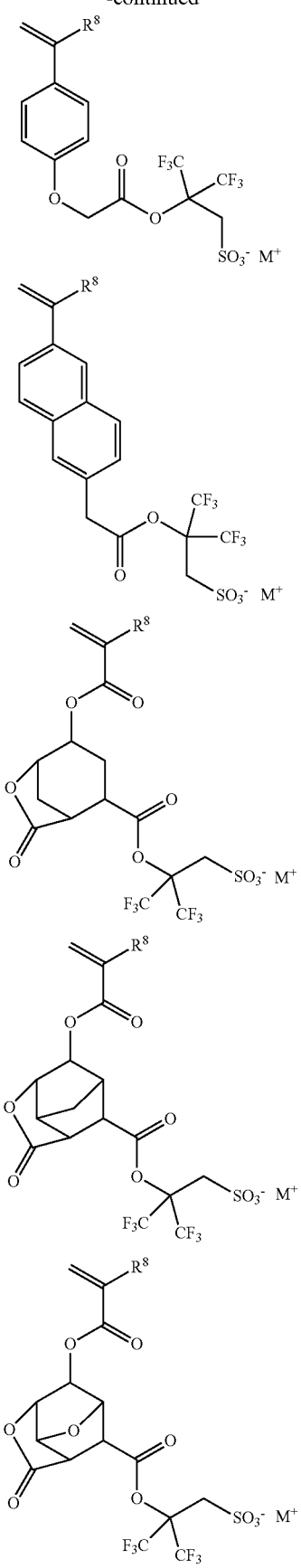
-continued
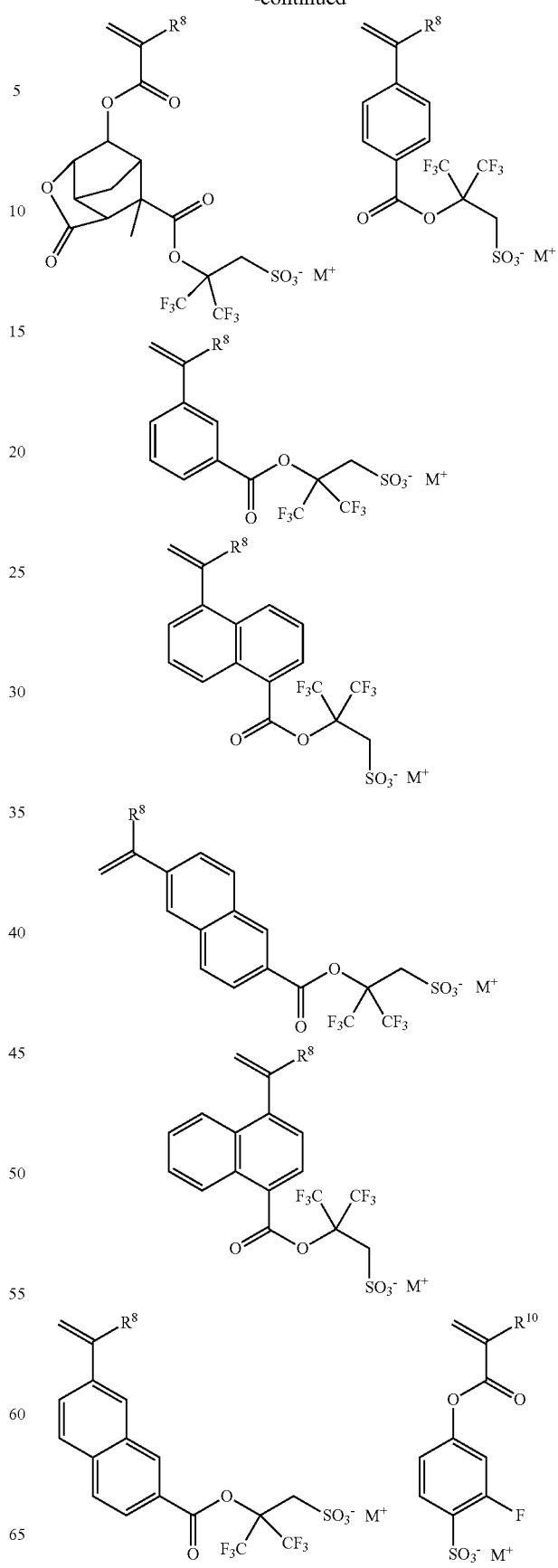

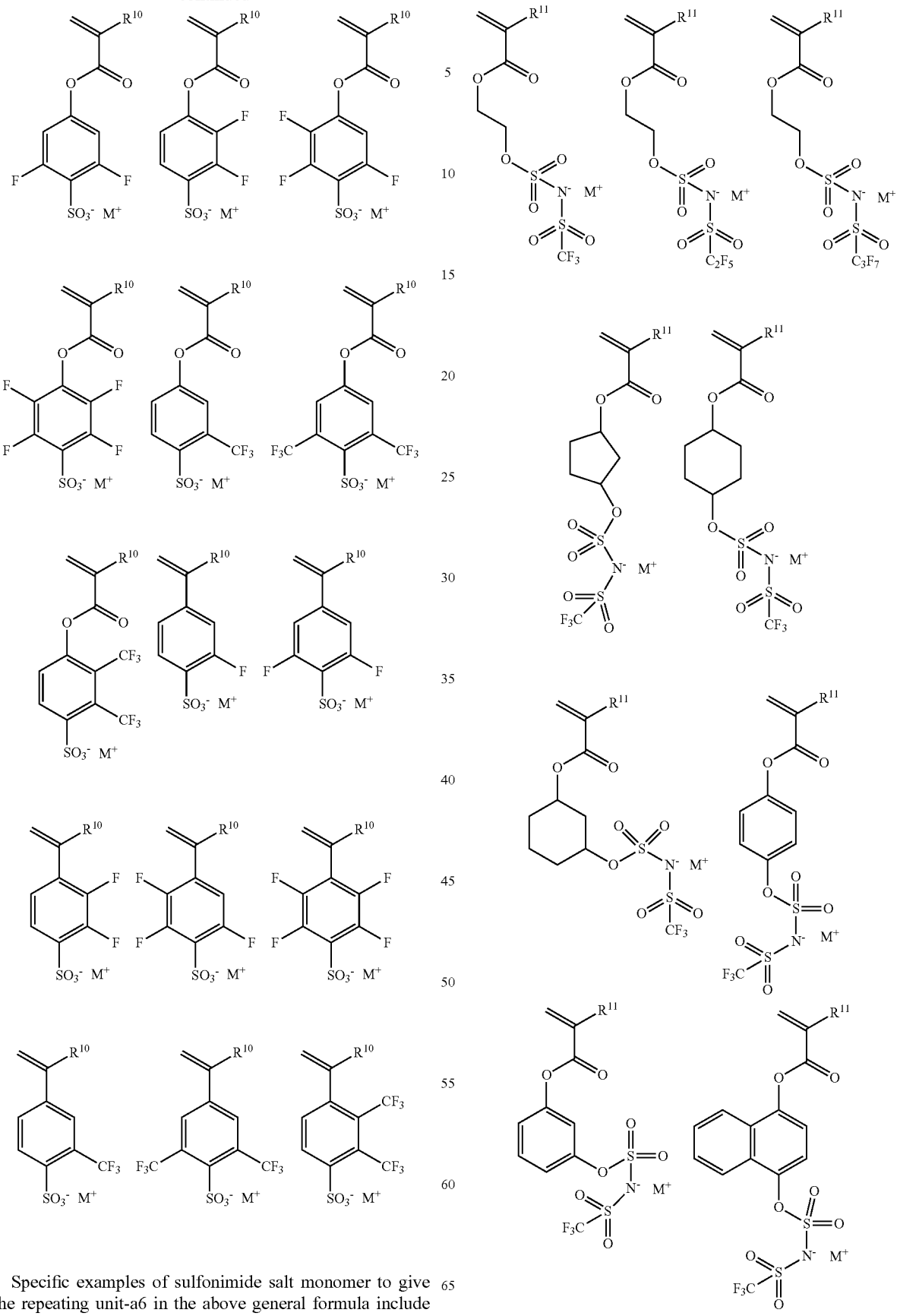
Specific examples of sulfonimide salt monomer to give the repeating unit-a6 in the above general formula include the following.

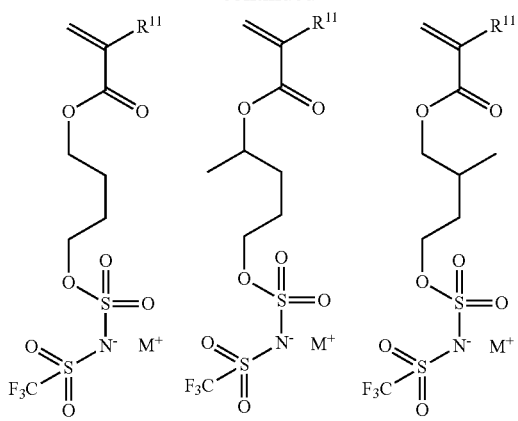
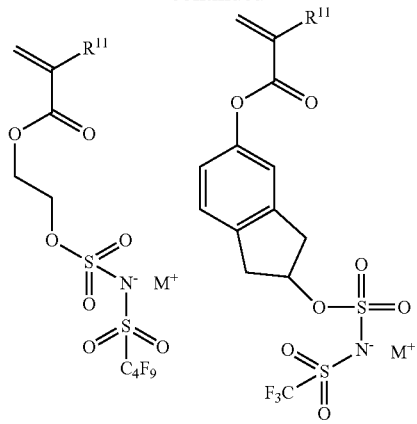
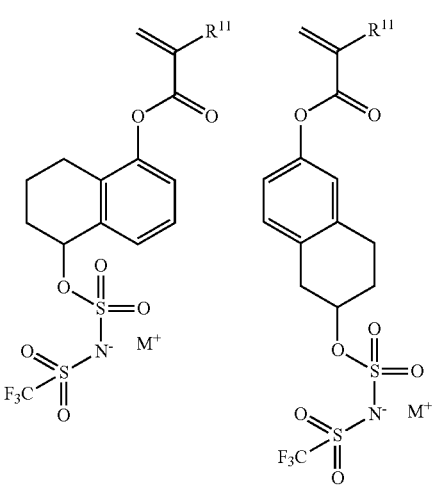
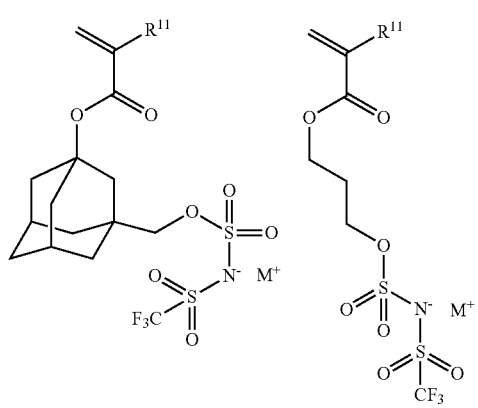
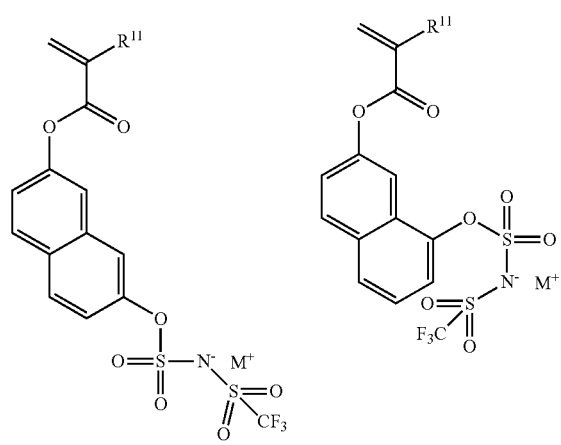

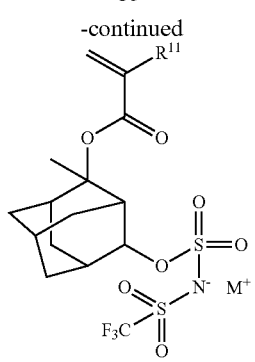
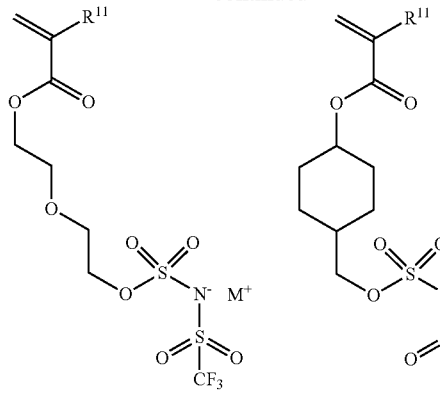
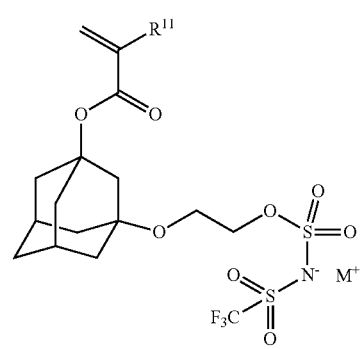
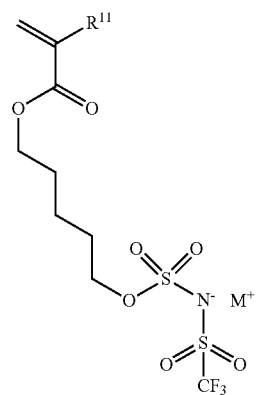

71
-continued
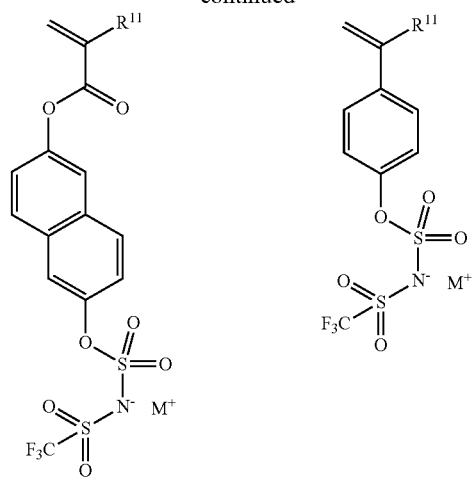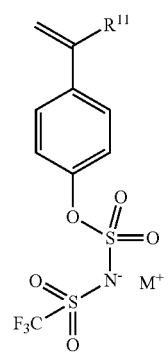
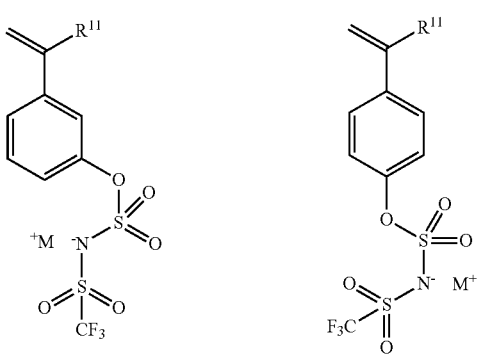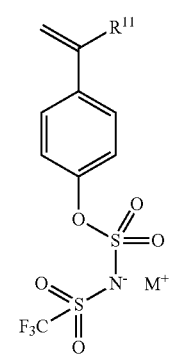
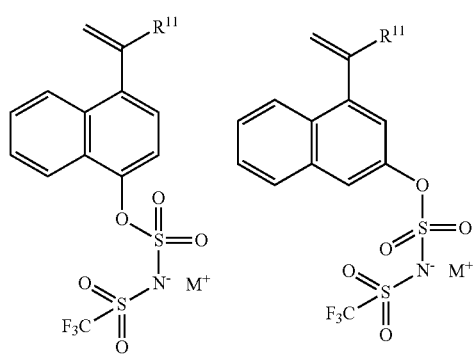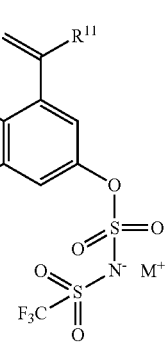
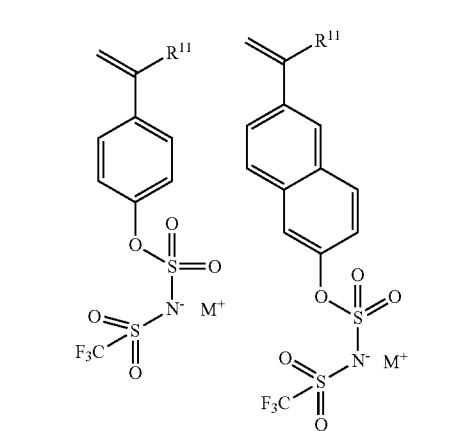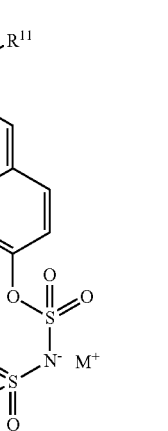
72
-continued
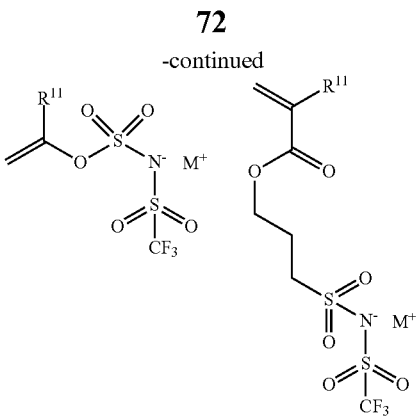
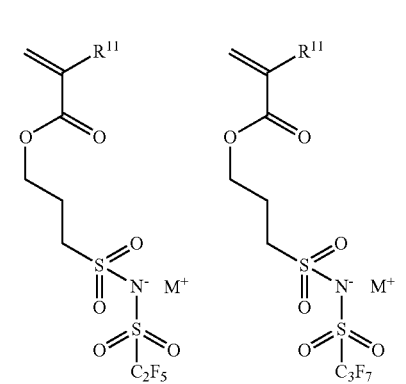
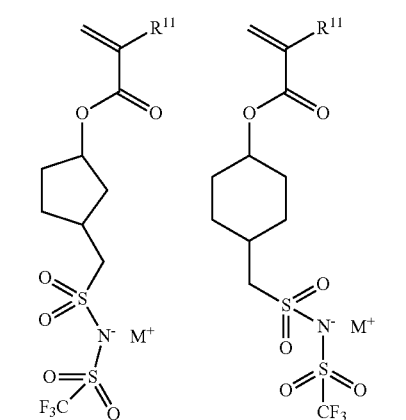
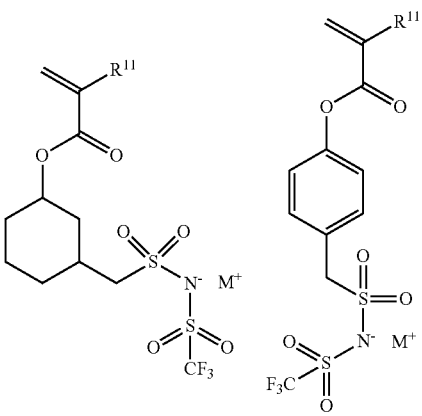

73
-continued
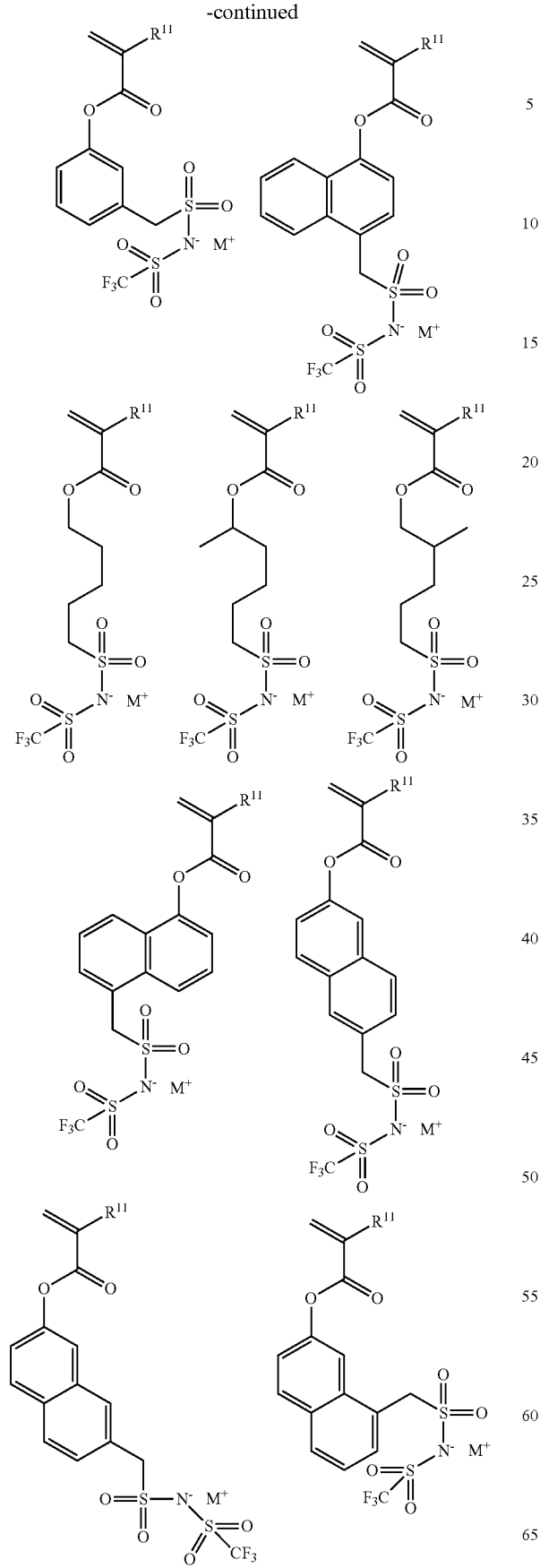
74
-continued
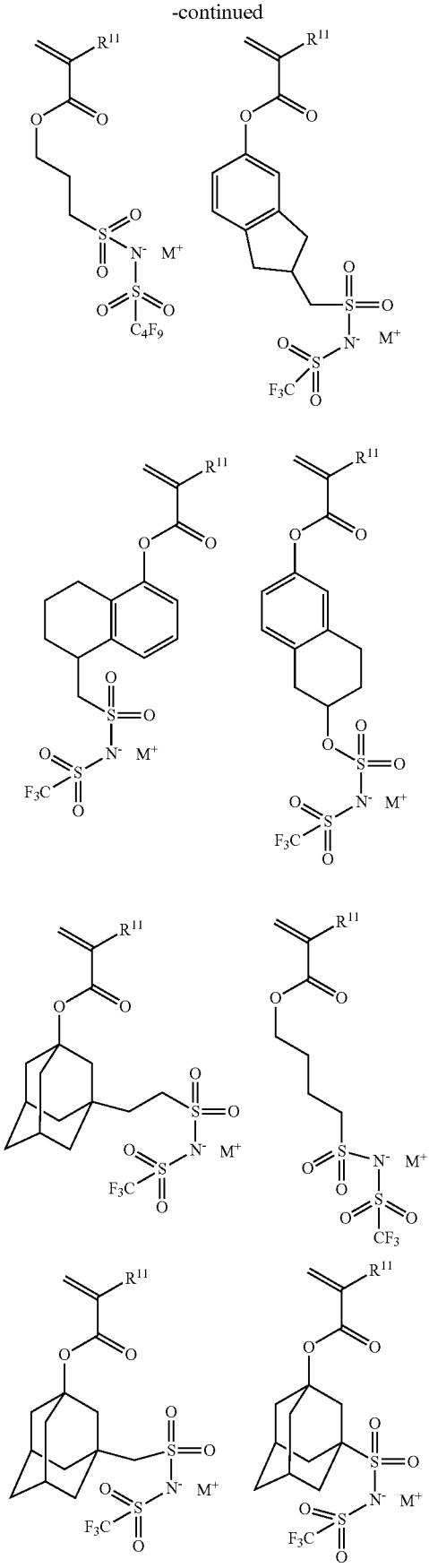

-continued
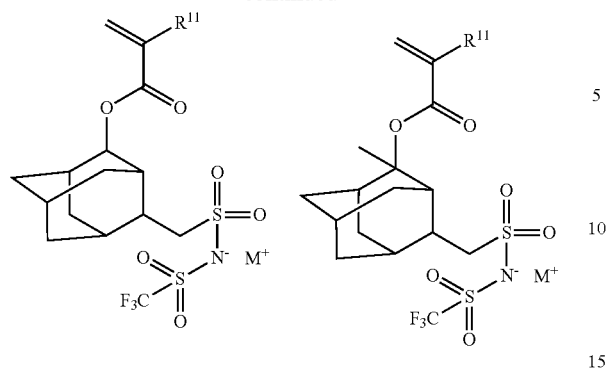
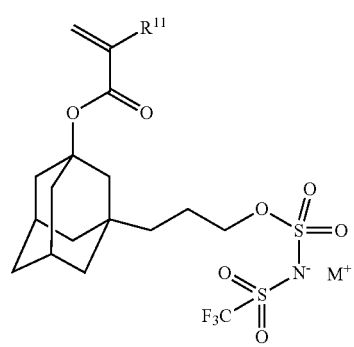
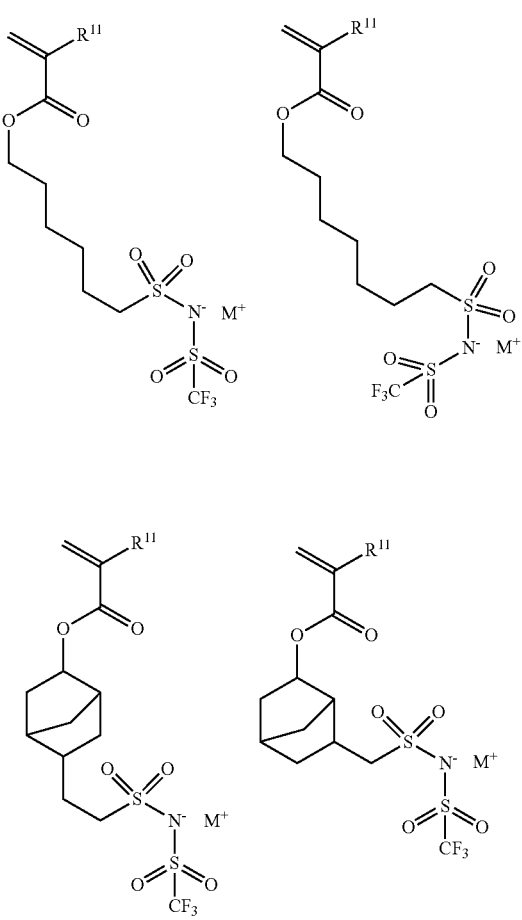
-continued
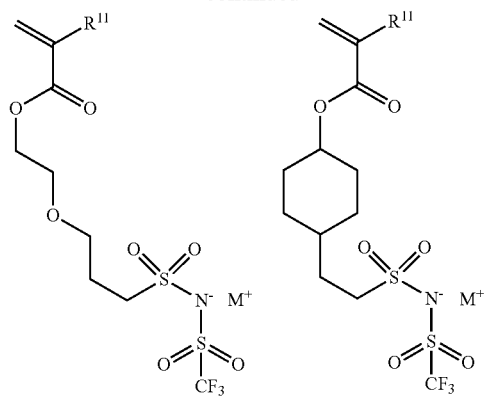
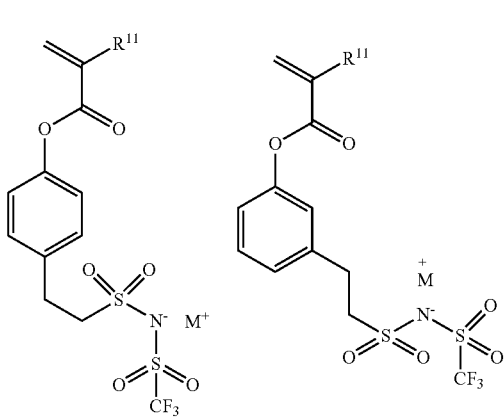
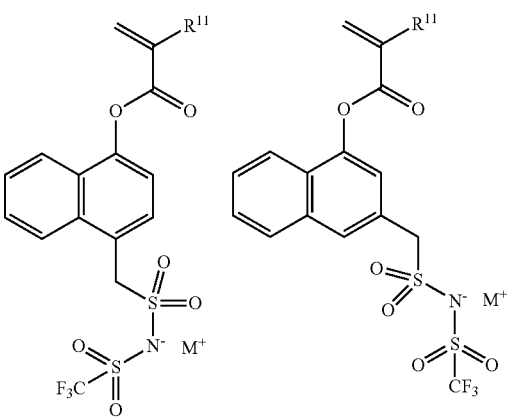

77
-continued
78
-continued
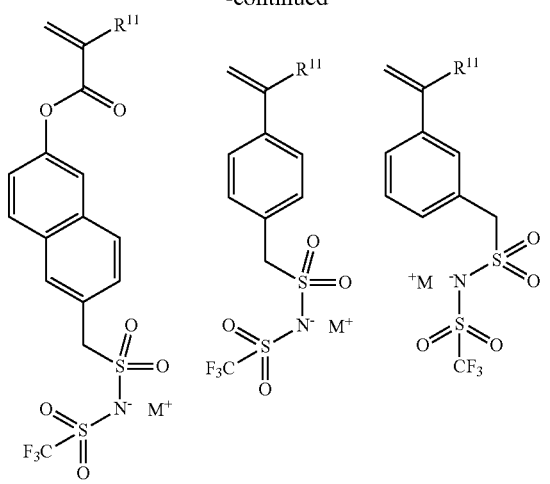
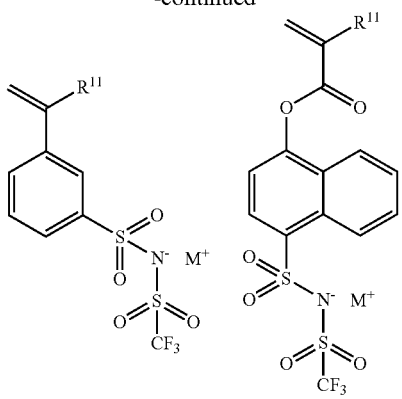

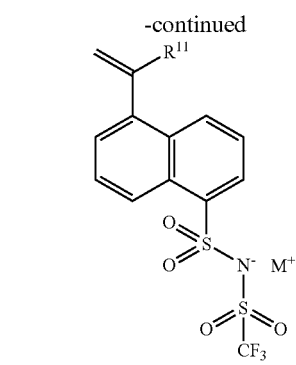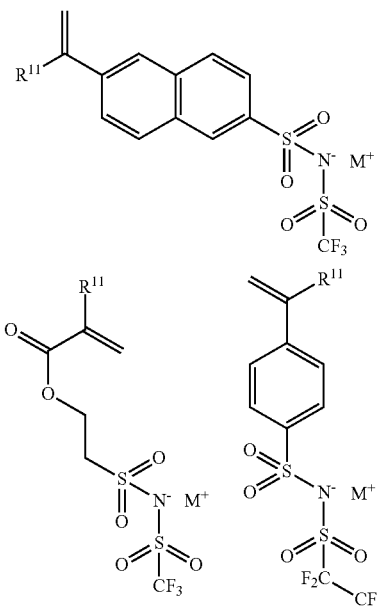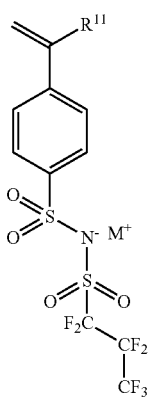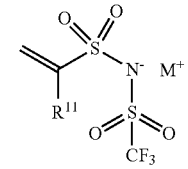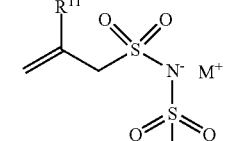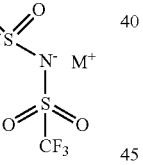
Specific examples of N-carbonylsulfonamide salt monomer to give the repeating unit-a7 in the above general formula include the following.
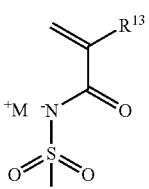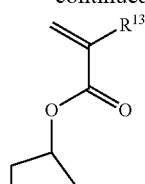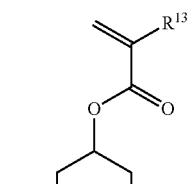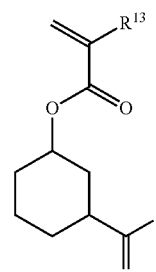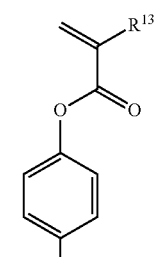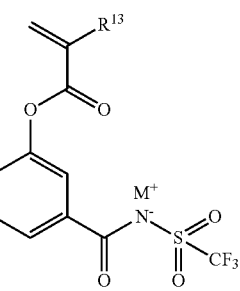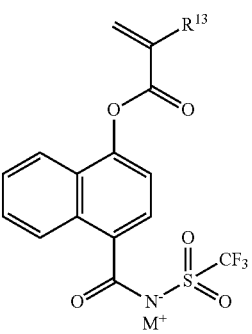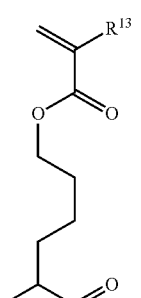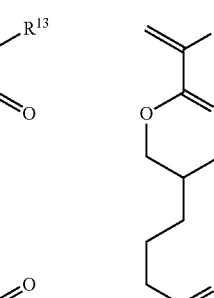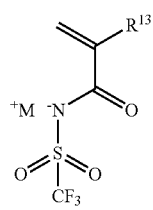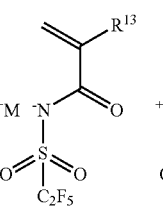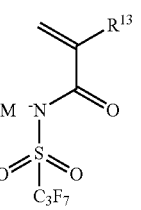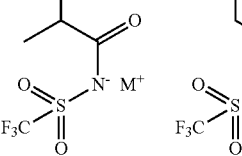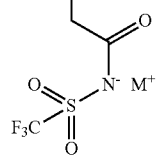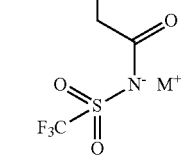

81
-continued
82
-continued
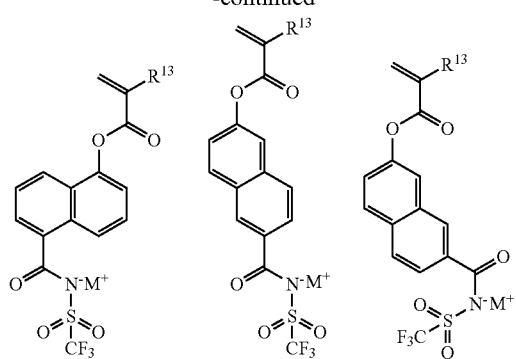
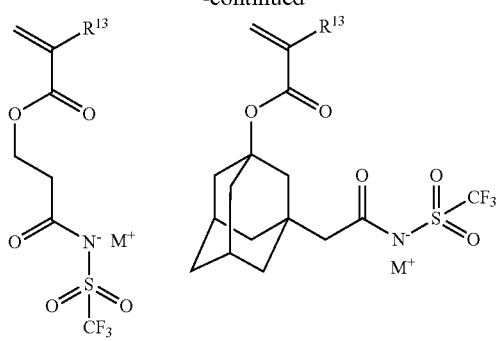
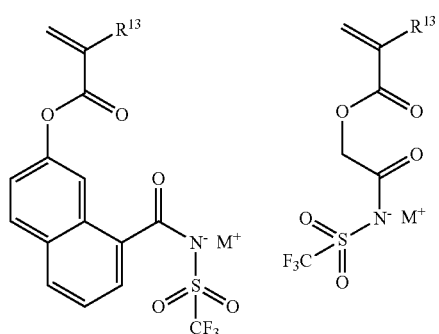
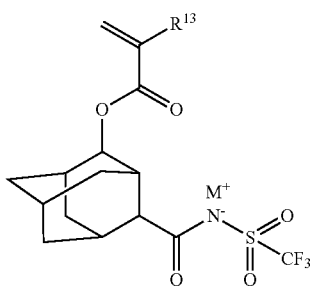
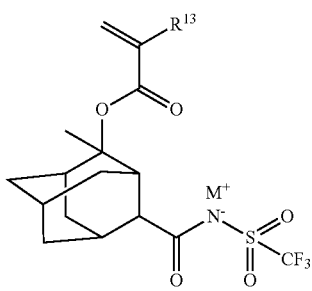
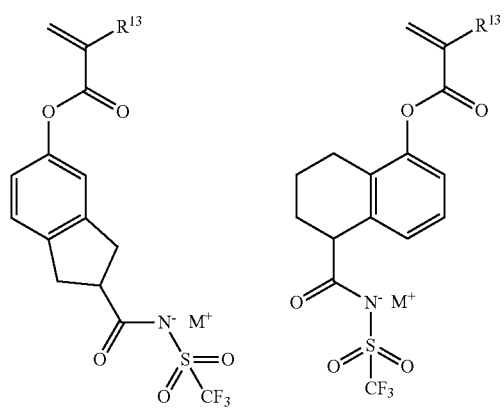
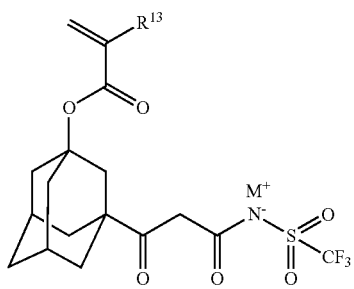
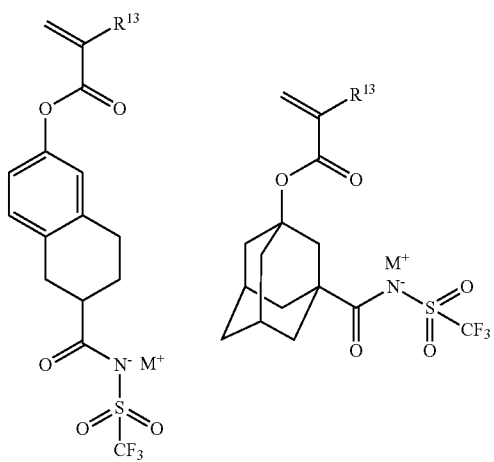
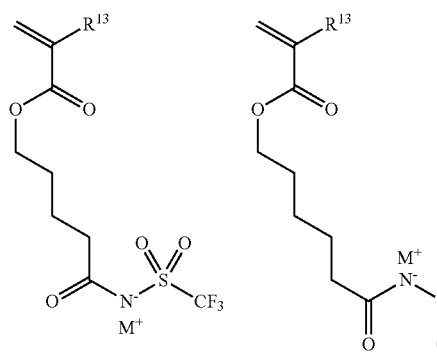

-continued

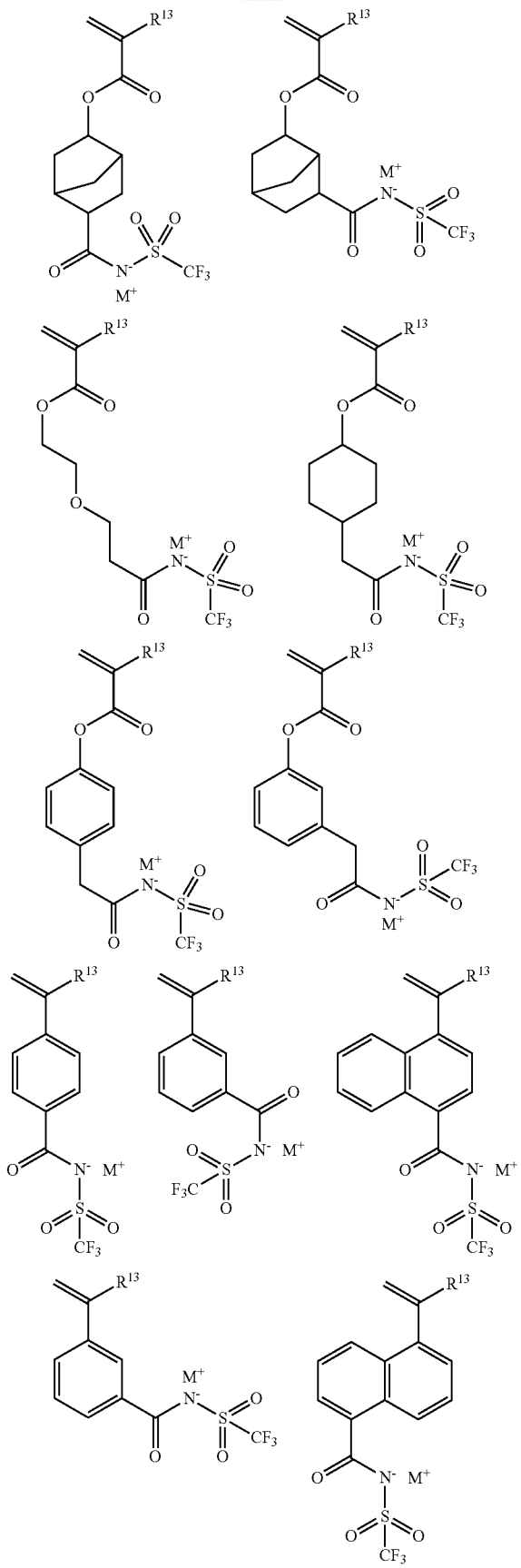

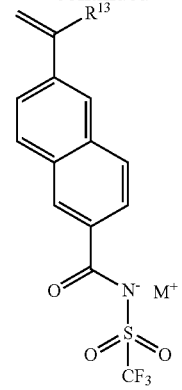

In the formulae, $R^1$, $R^3$, $R^5$, $R^8$, $R^{10}$, $R^{11}$, and $R^{13}$ are as defined above.

The polymer compound (A) (component (A)) preferably contains an ammonium ion (ammonium cation) shown by the following general formula (3) as $M^+$ in the repeating unit-a (e.g., the repeating units-a1 to -a7).

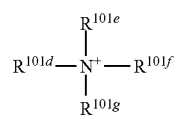
(3)

In the formula, $R^{101d}$, $R^{101e}$, $R^{101f}$, and $R^{101g}$ each represent a hydrogen atom, a linear, branched, or cyclic alkyl group having 1 to 12 carbon atoms, a linear, branched, or cyclic alkenyl group or alkynyl group having 2 to 12 carbon atoms, or an aromatic group having 4 to 20 carbon atoms, and optionally have one or more selected from the group consisting of an ether group, a carbonyl group, an ester group, a hydroxy group, an amino group, a nitro group, a sulfonyl group, a sulfinyl group, a halogen atom, and a sulfur atom. $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the formula (3) within the ring.

Specific examples of the ammonium ion shown by the general formula (3) include the following.

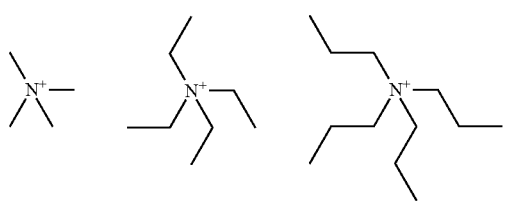

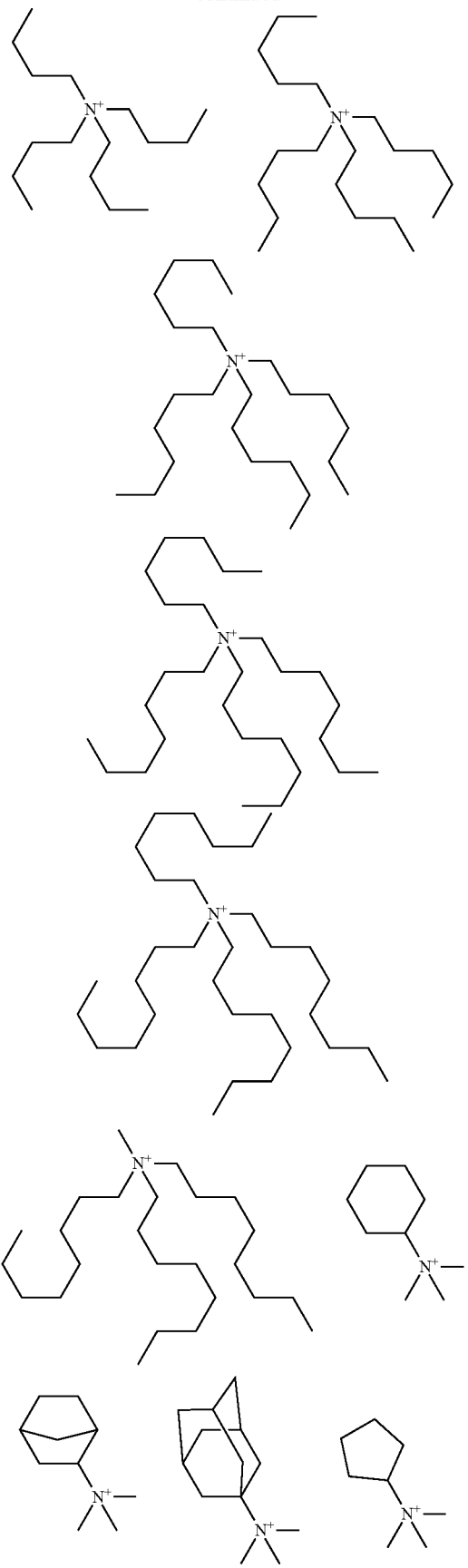
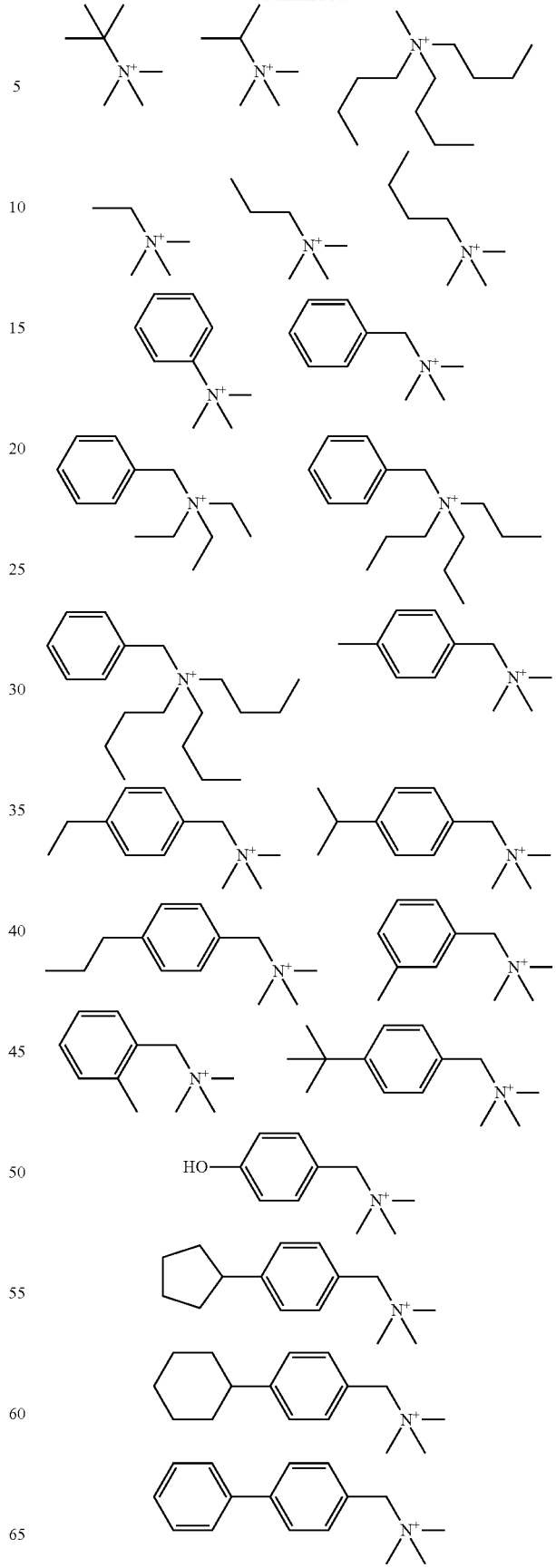

-continued
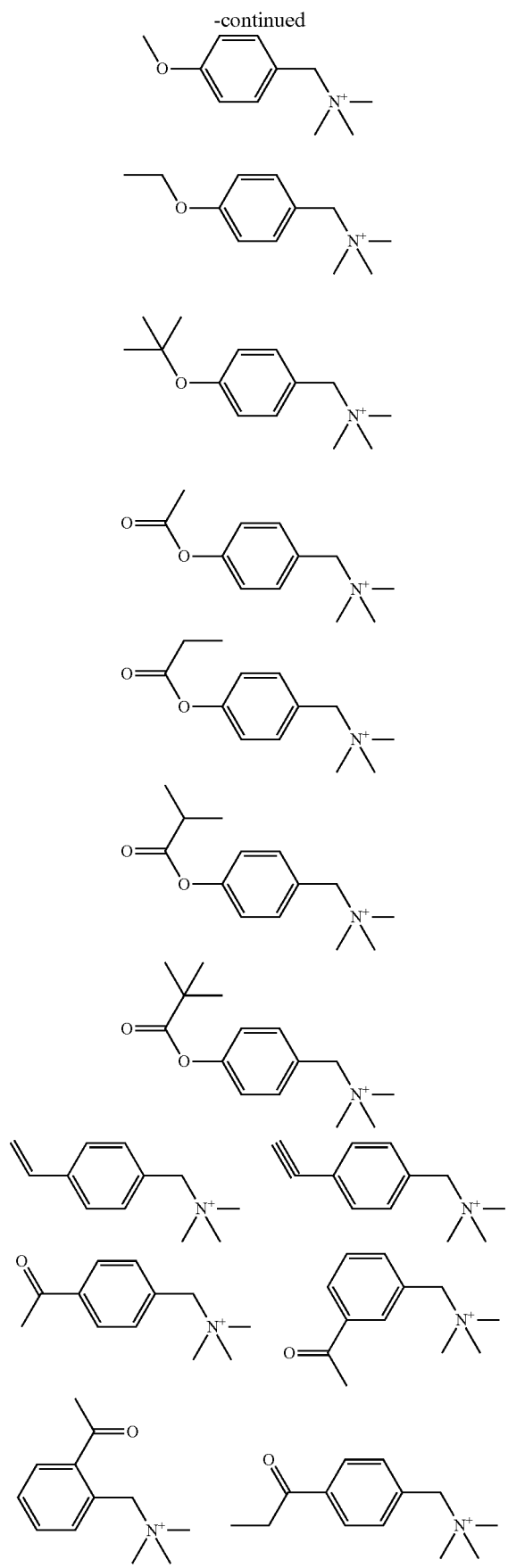
-continued
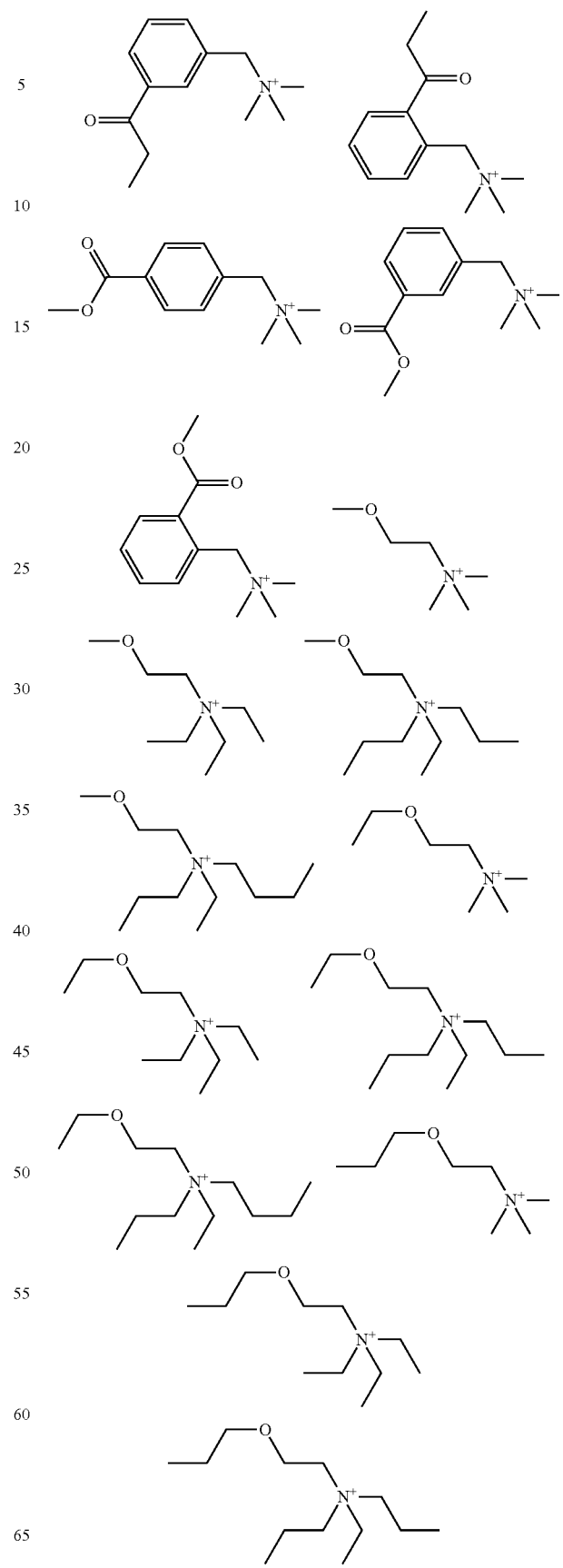

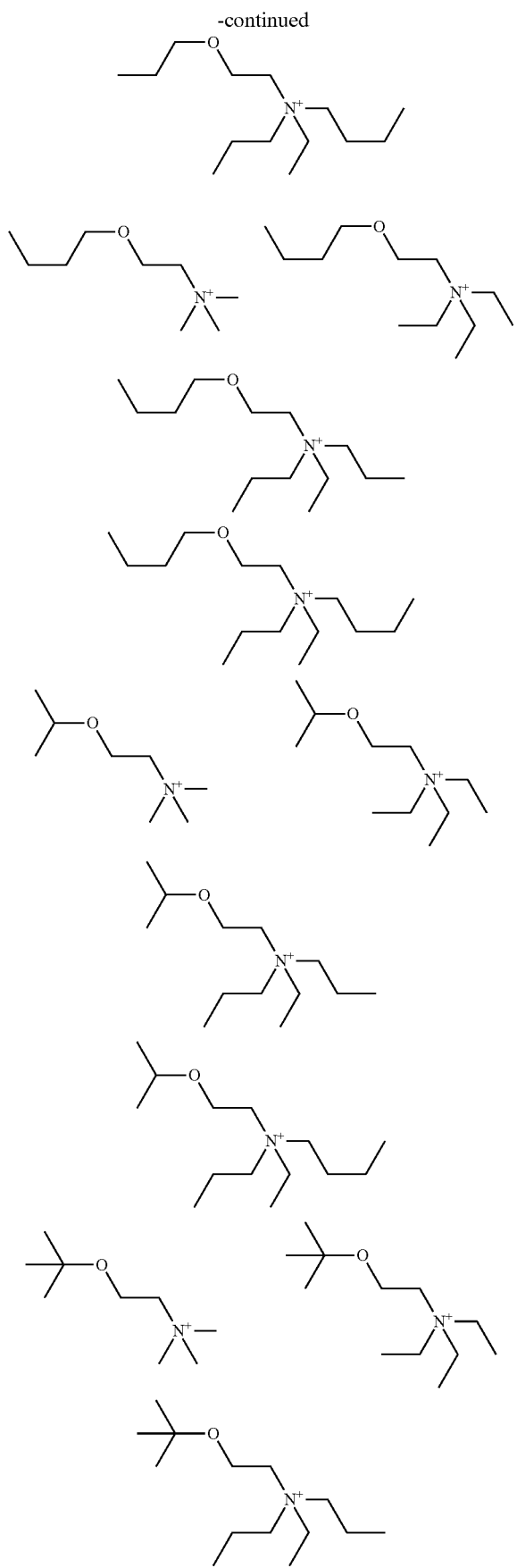
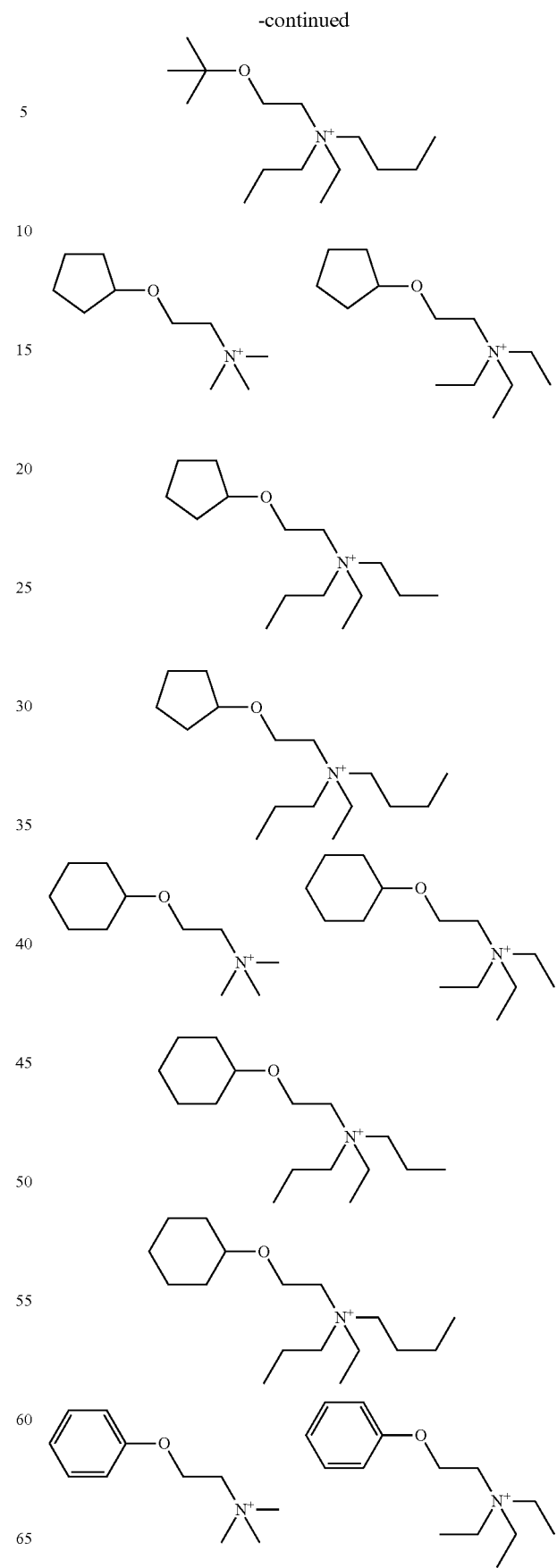

-continued
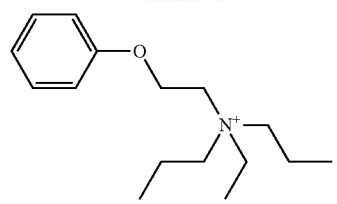
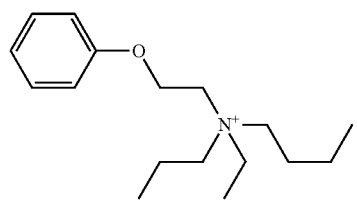
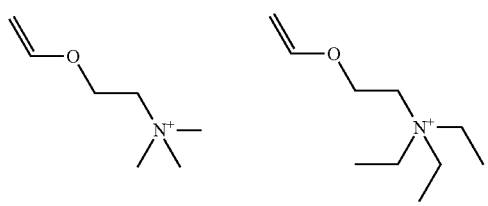
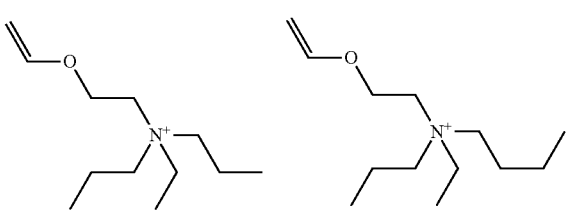
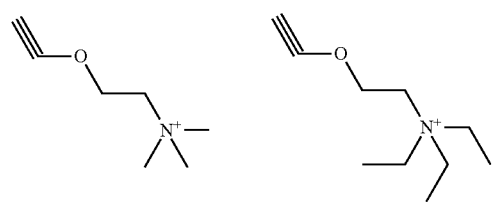
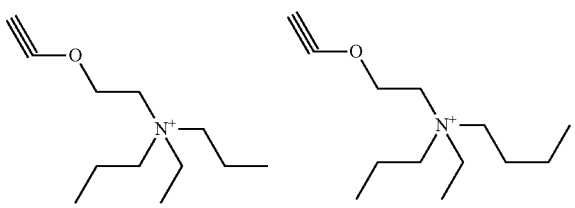
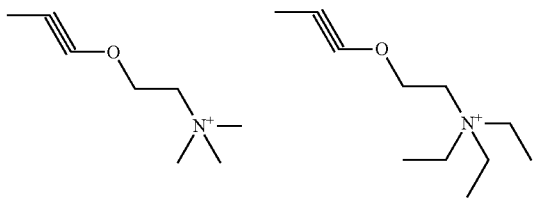
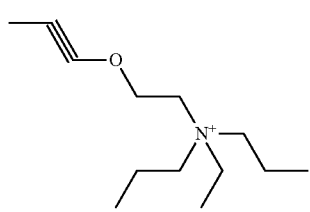
-continued
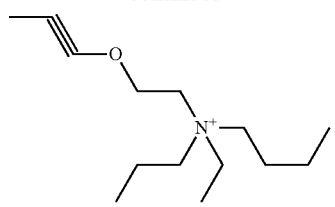
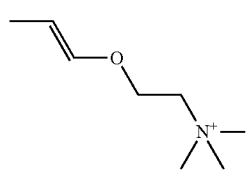
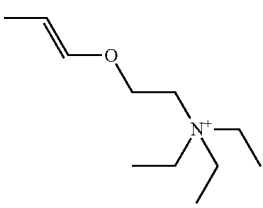
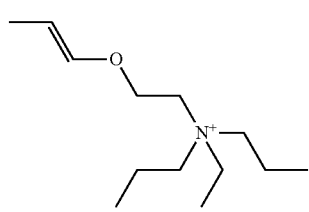
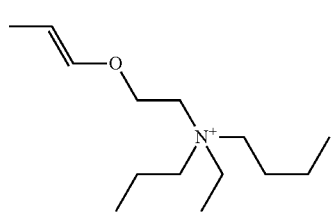
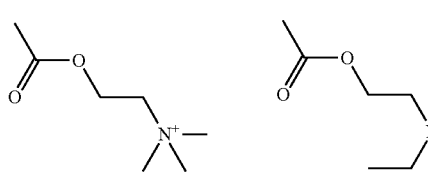
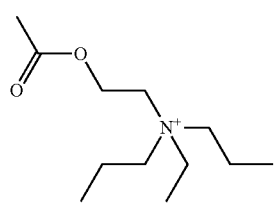
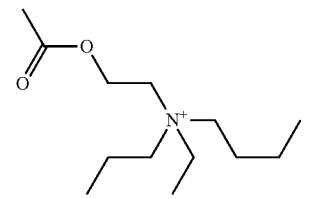
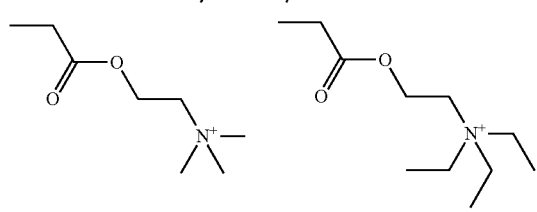

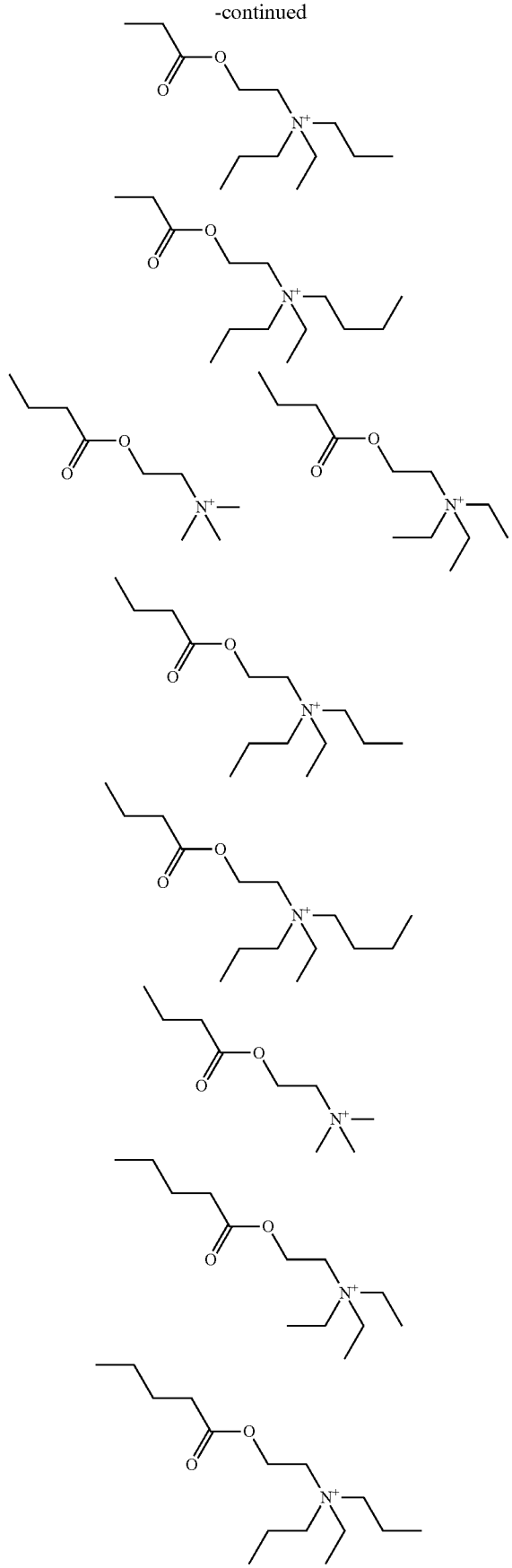
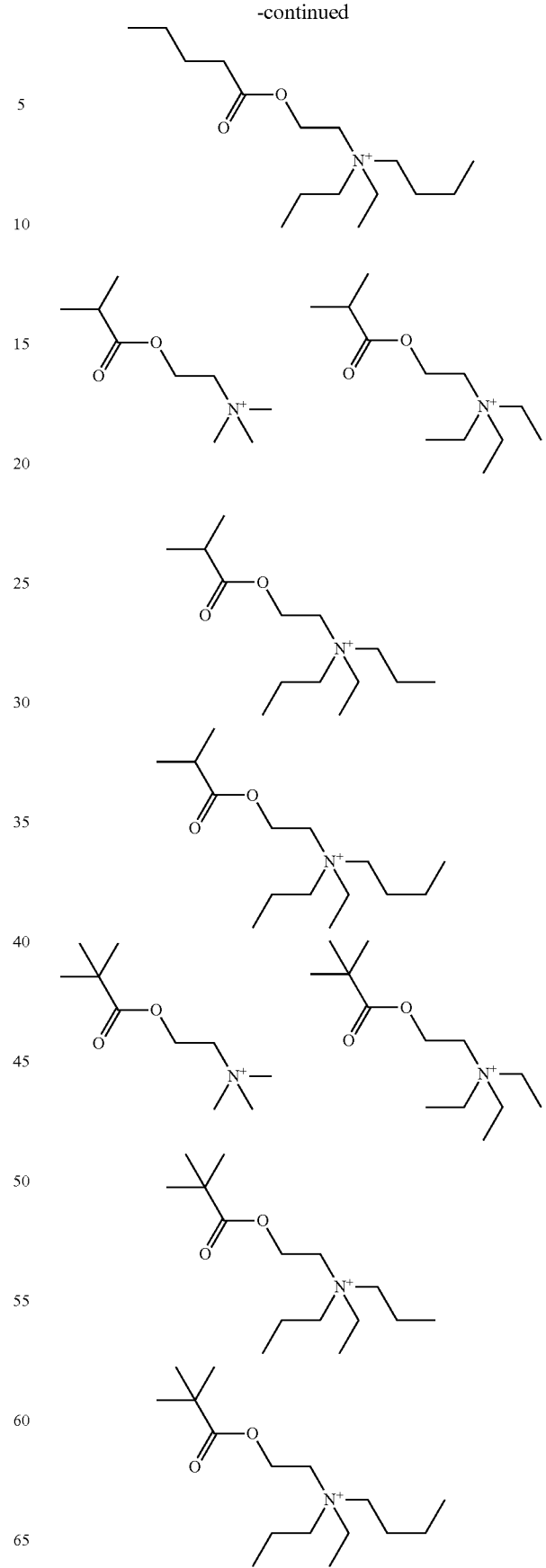

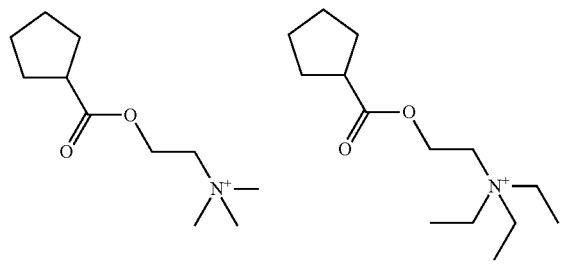
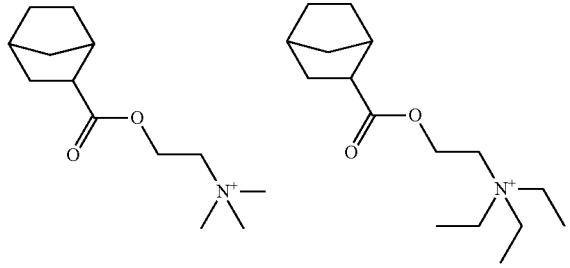
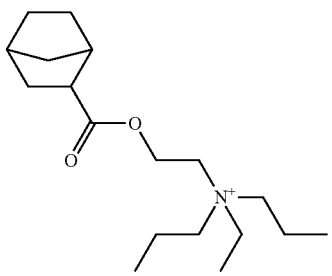
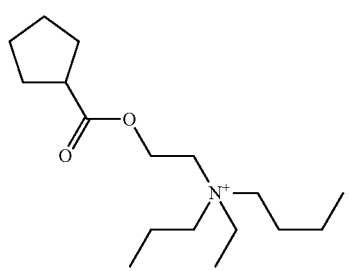
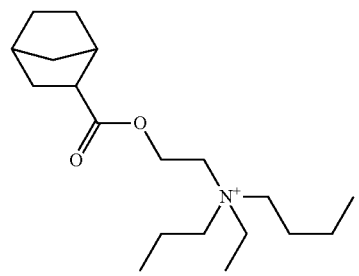
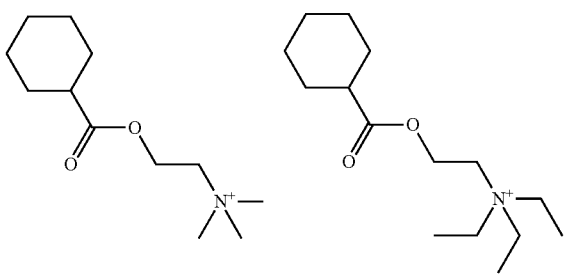
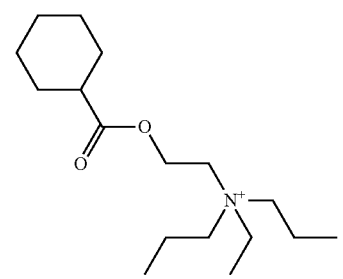
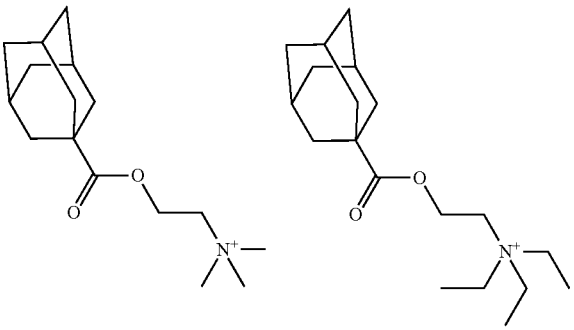
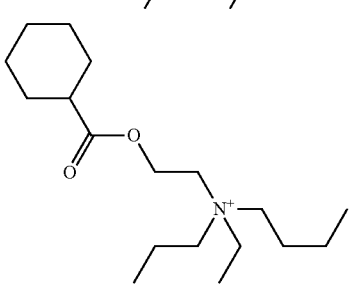
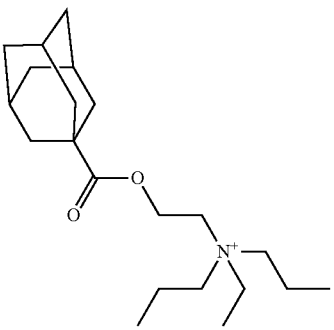

97
-continued
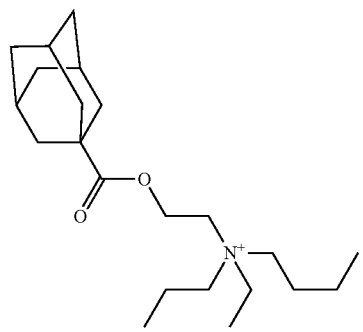
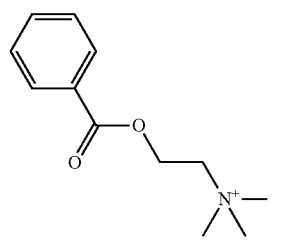 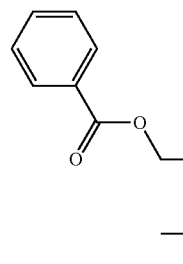
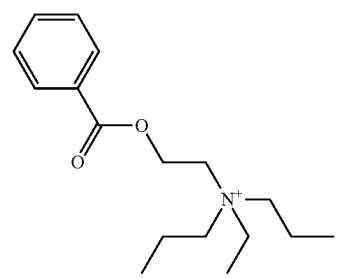
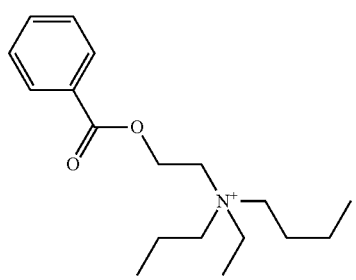
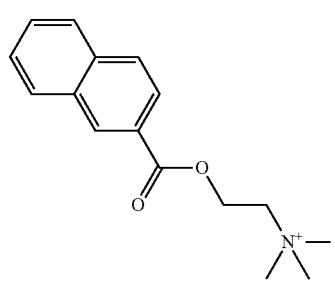
98
-continued
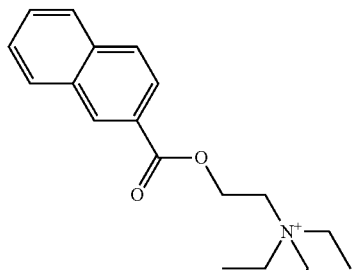
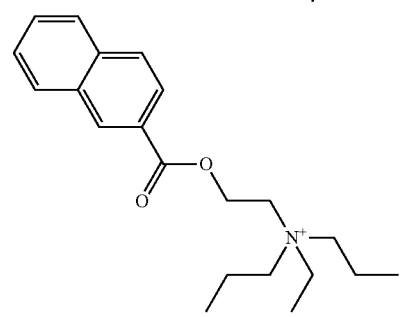
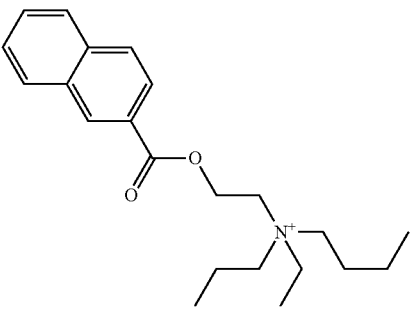
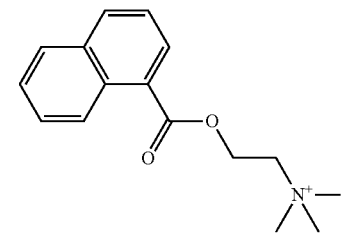
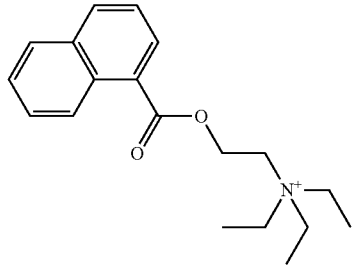
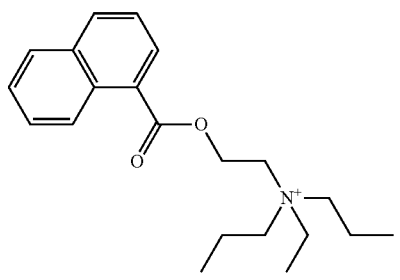

99
-continued
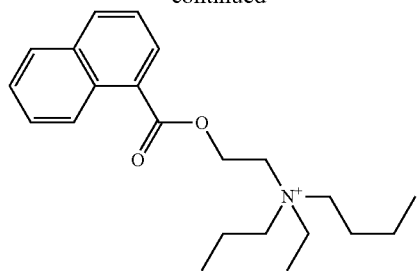
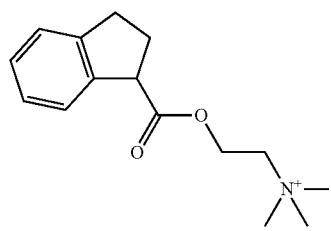
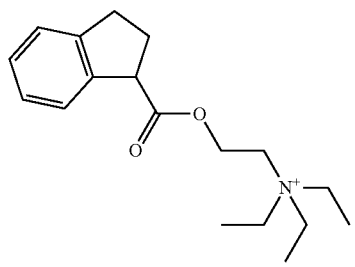
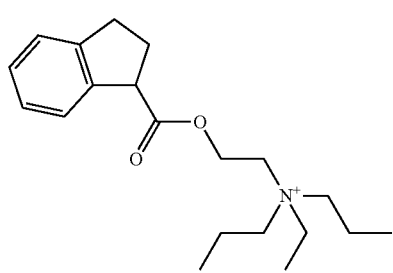
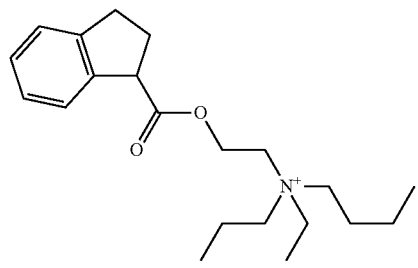
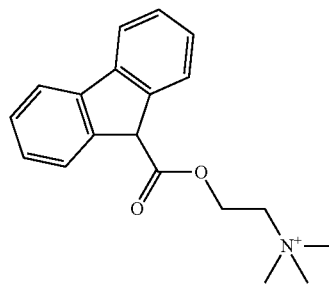
100
-continued
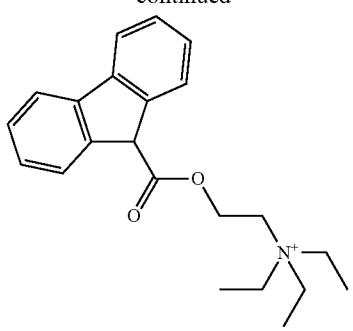
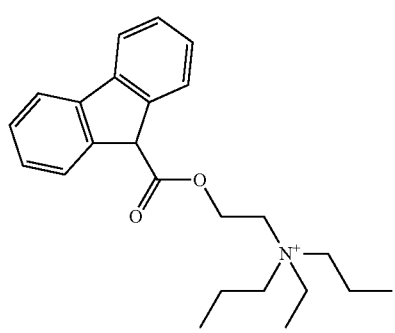
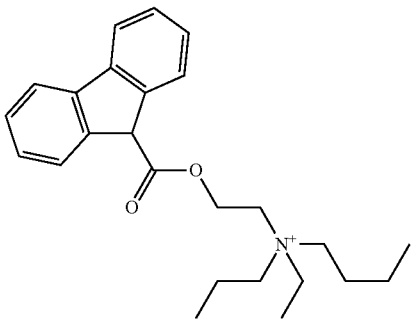
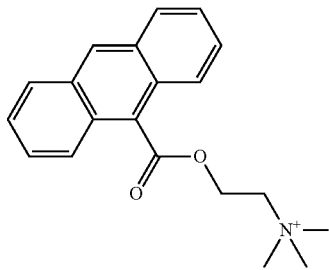
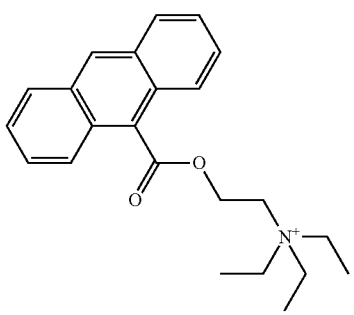

101
-continued
102
-continued
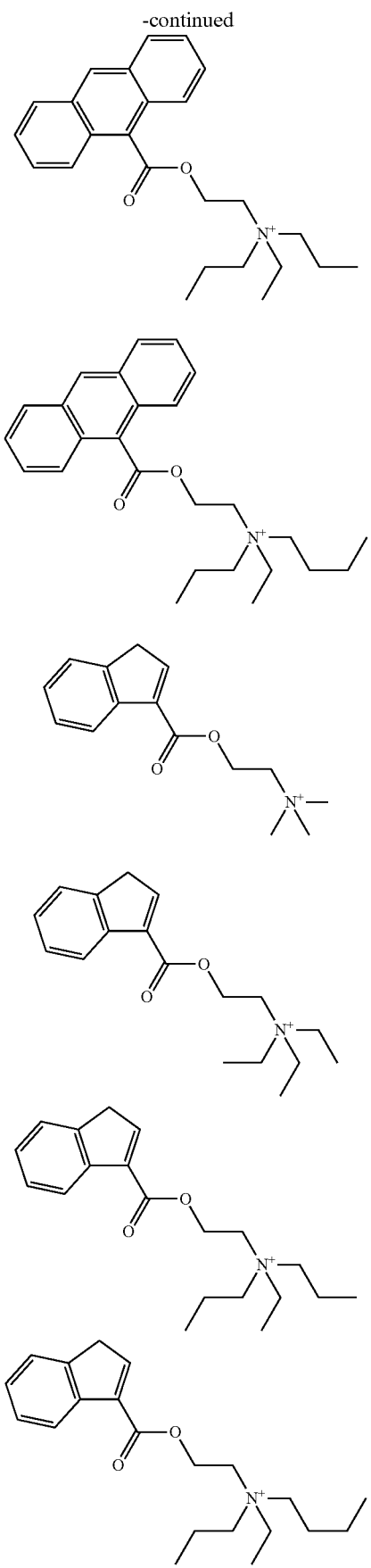
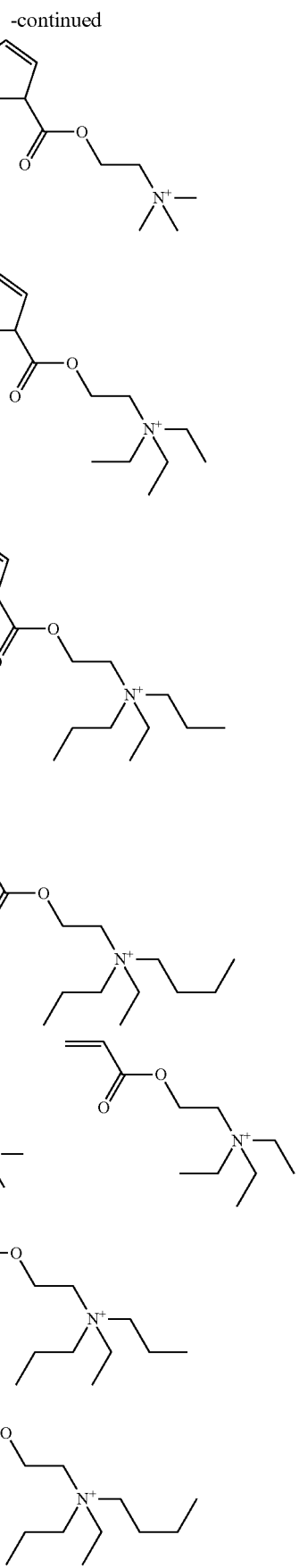

103
-continued
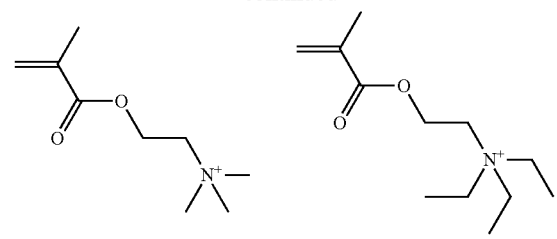
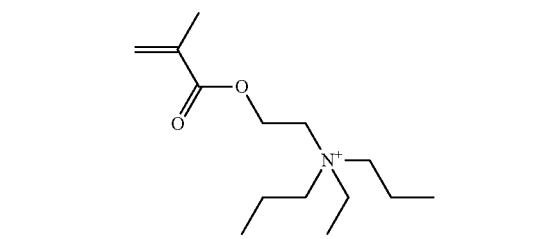
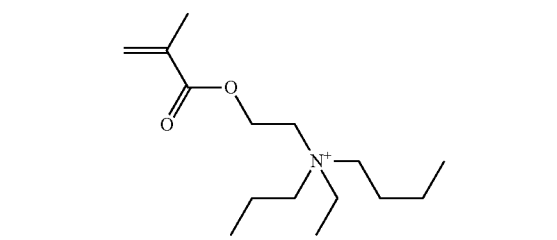
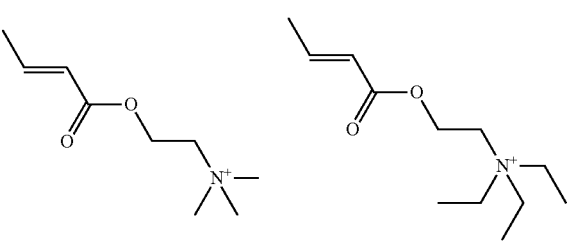
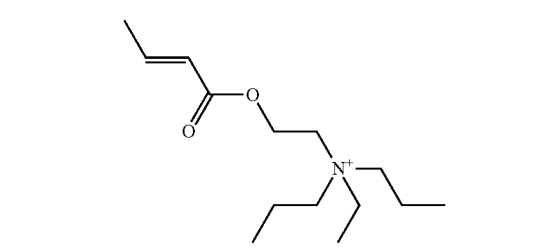
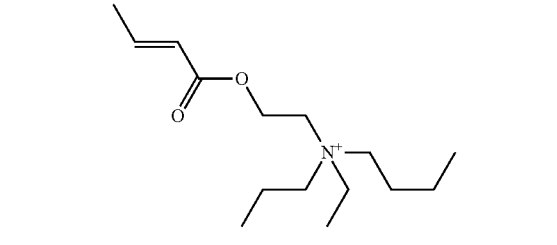
104
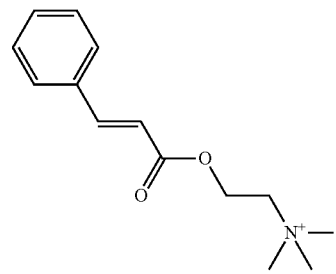
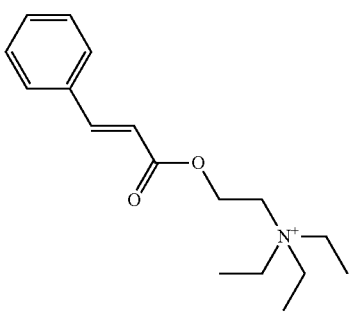
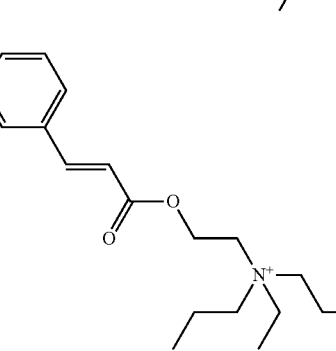
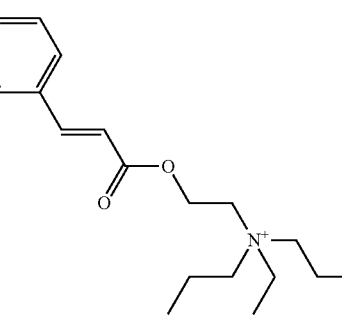
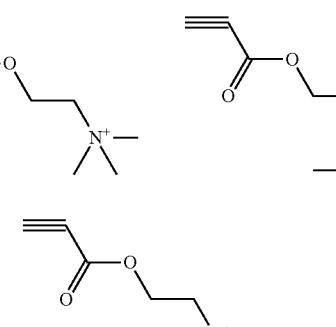
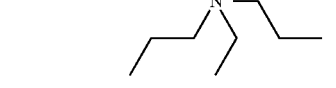

105
-continued
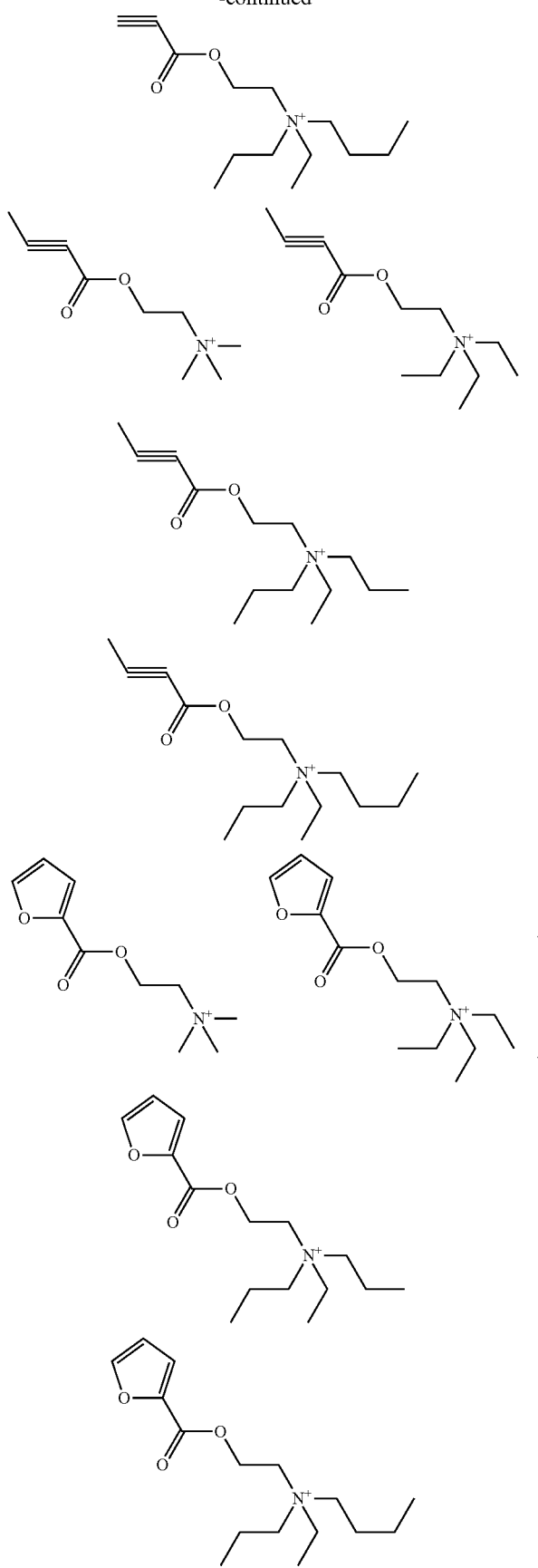
106
-continued
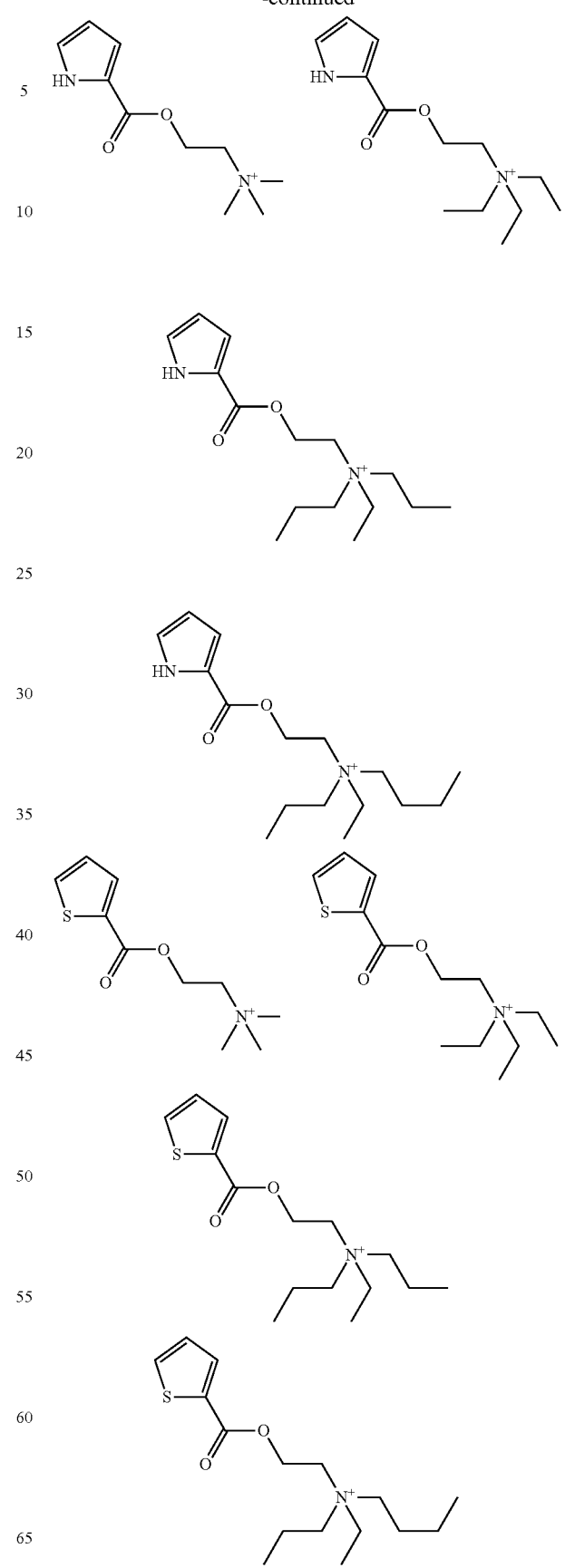

-continued
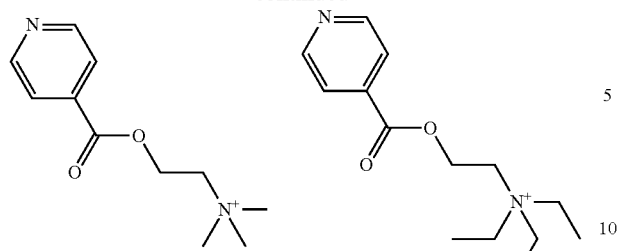
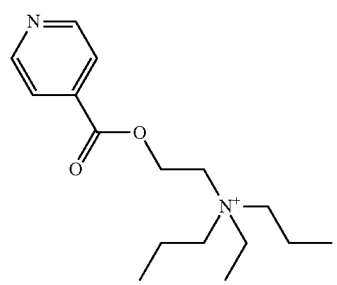
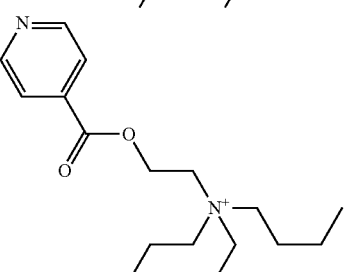
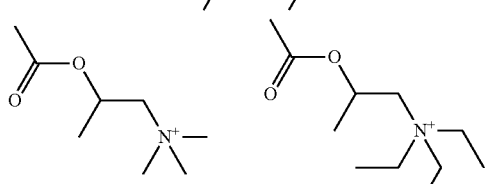
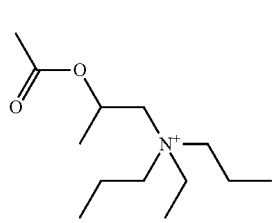
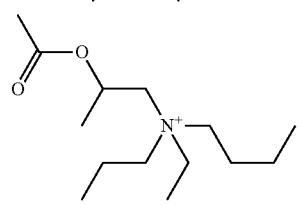
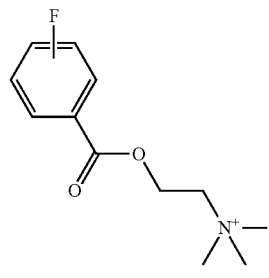
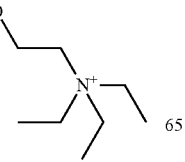
-continued
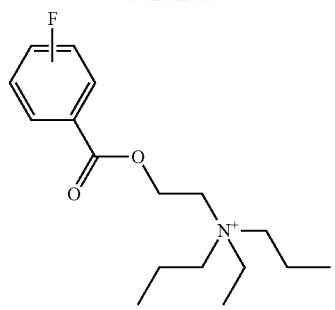
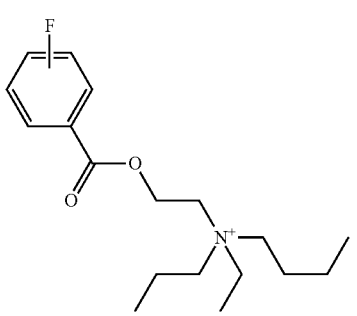
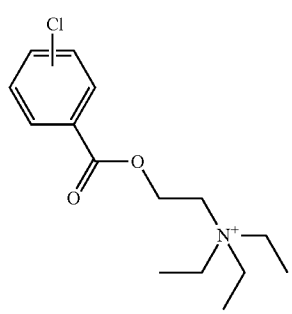
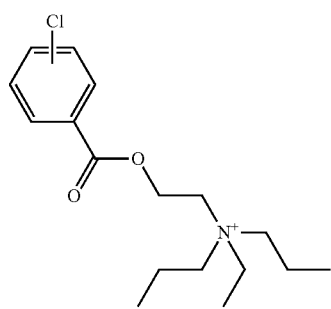
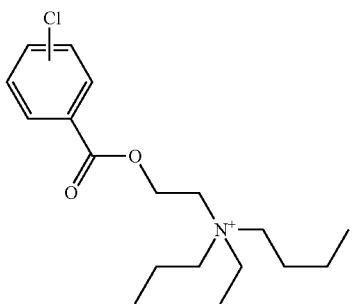

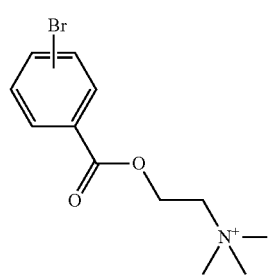
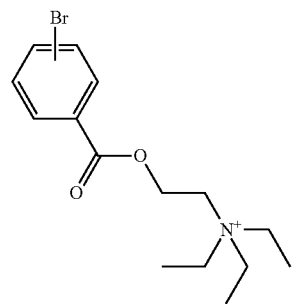
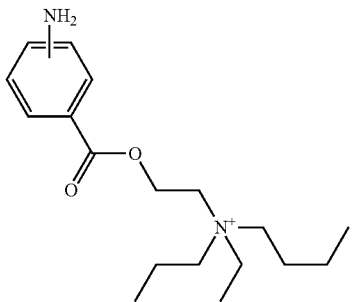
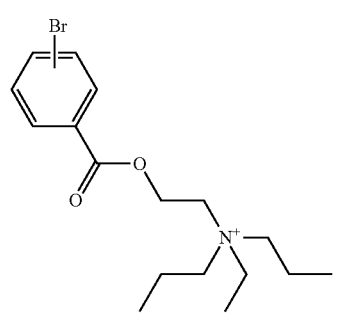
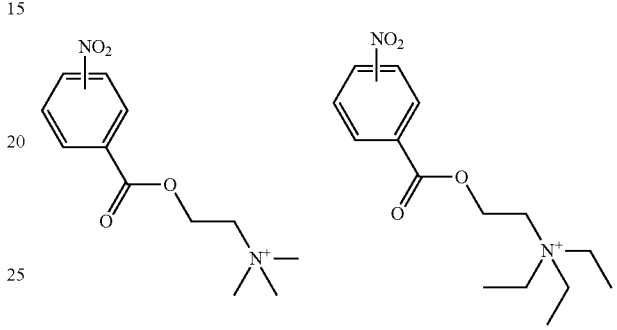
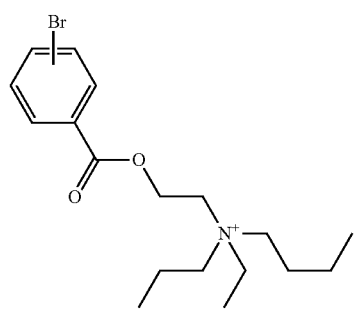
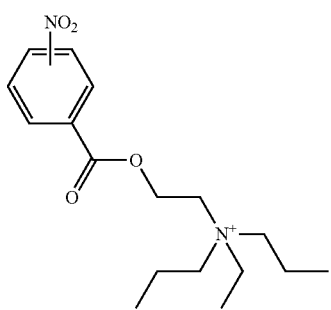
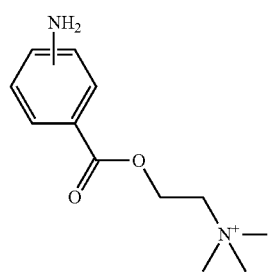
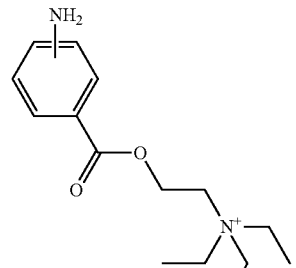
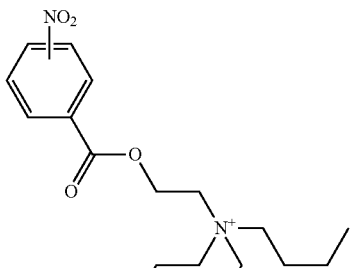
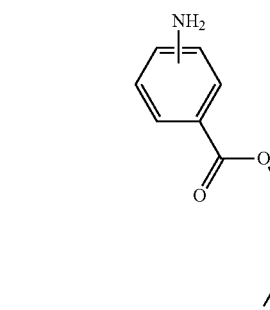
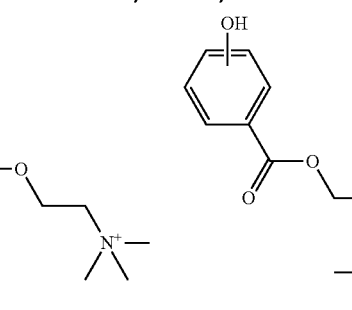

111
-continued
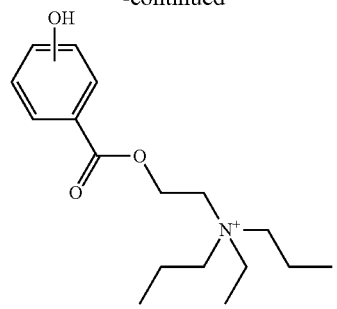
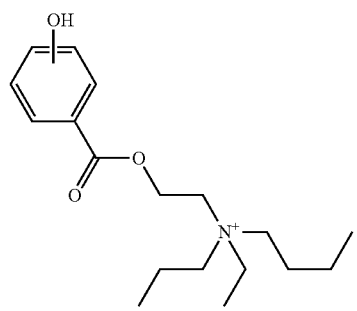
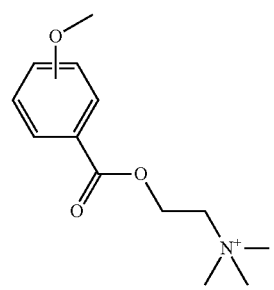
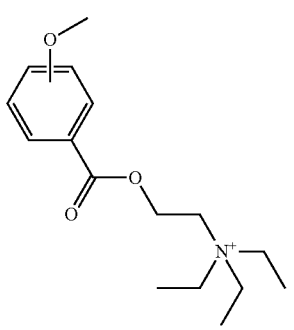
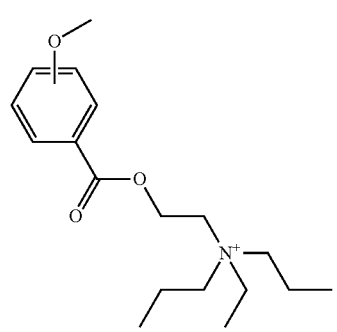
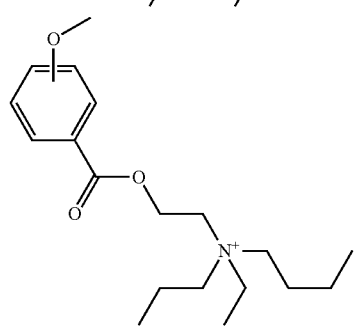
112
-continued
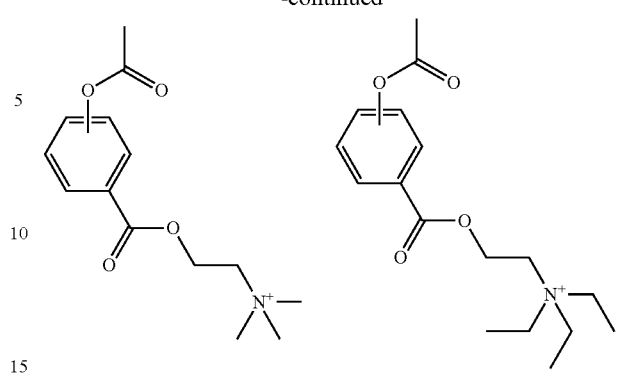
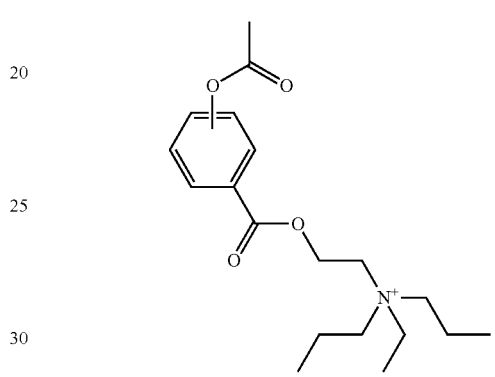
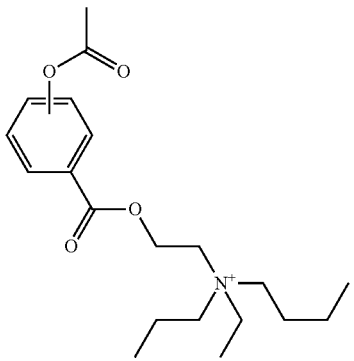
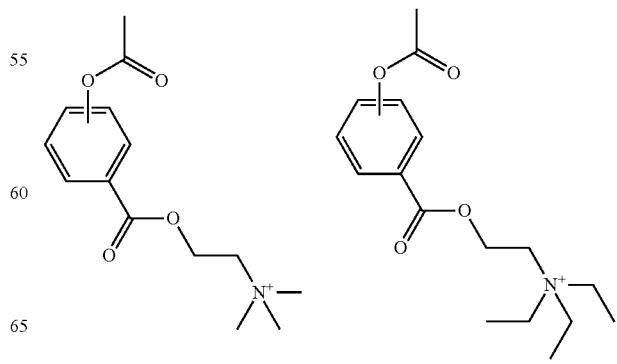

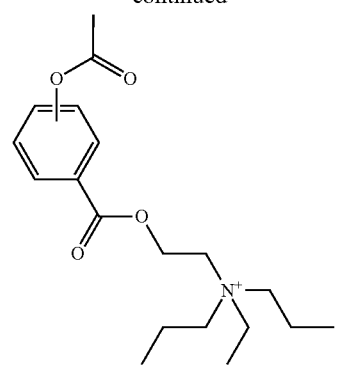
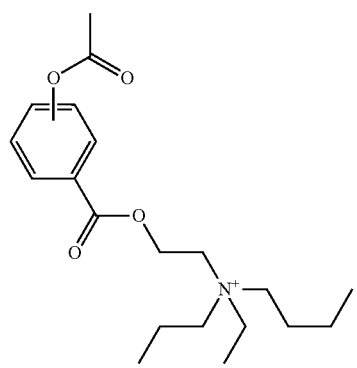
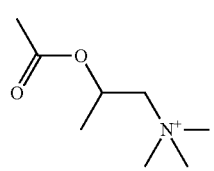
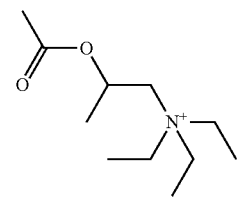
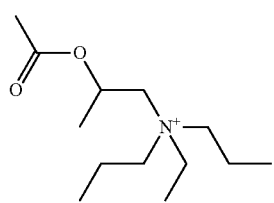
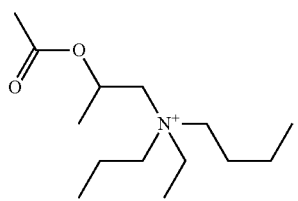
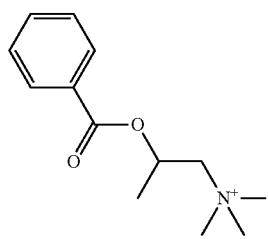
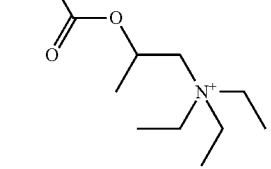
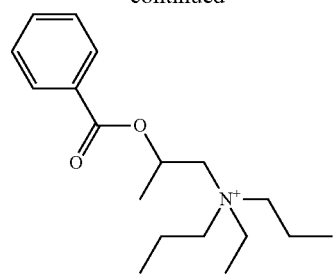
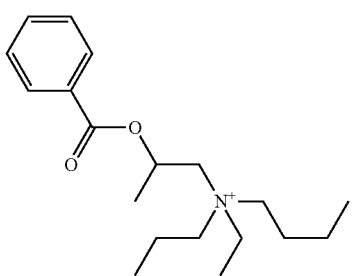
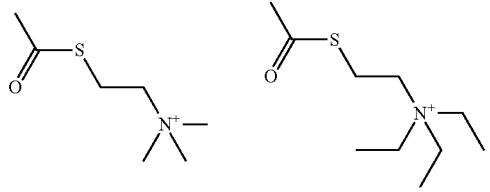
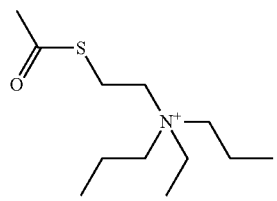
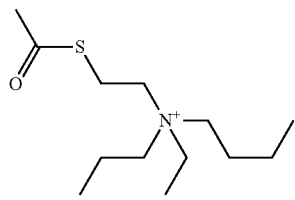
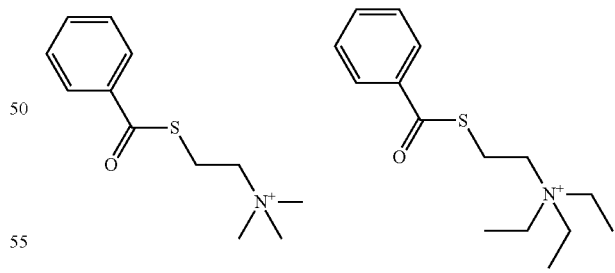
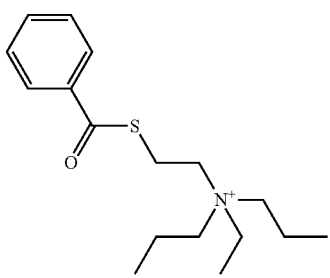

115
-continued
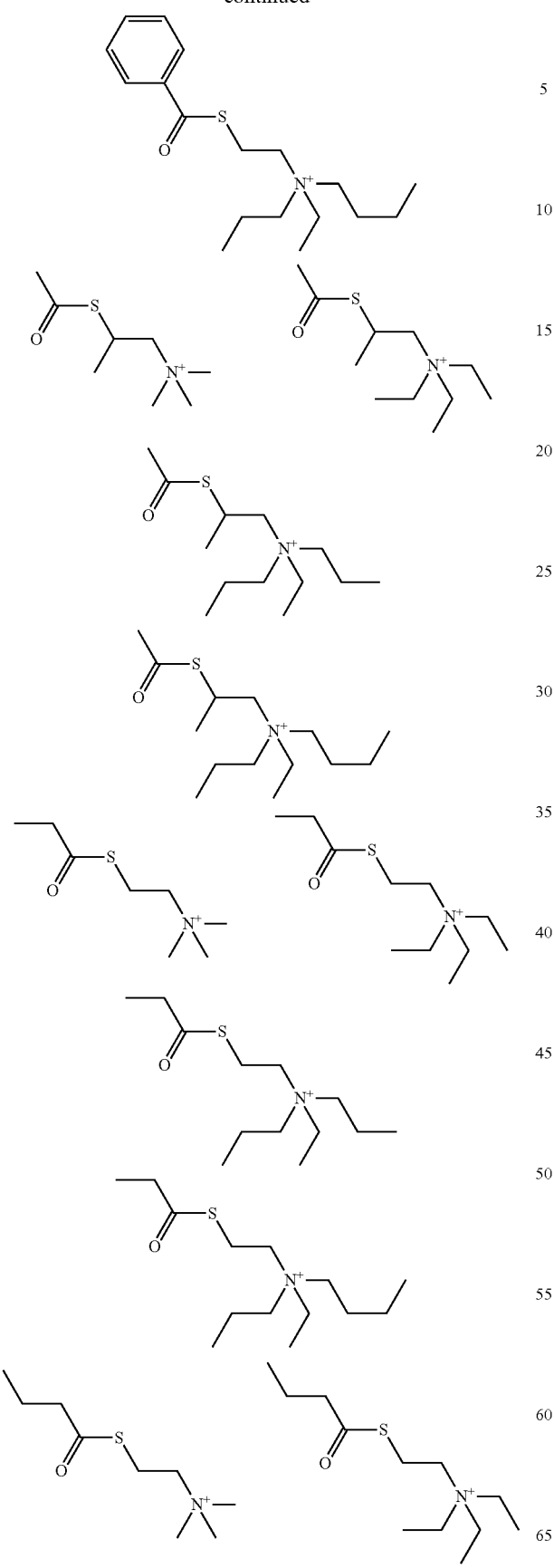
116
-continued
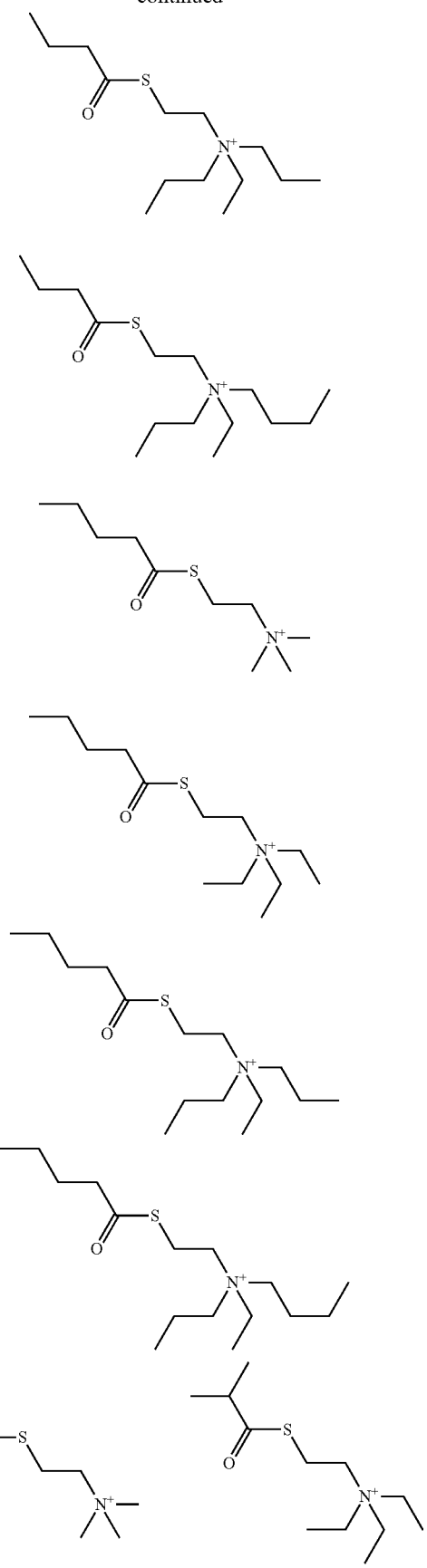

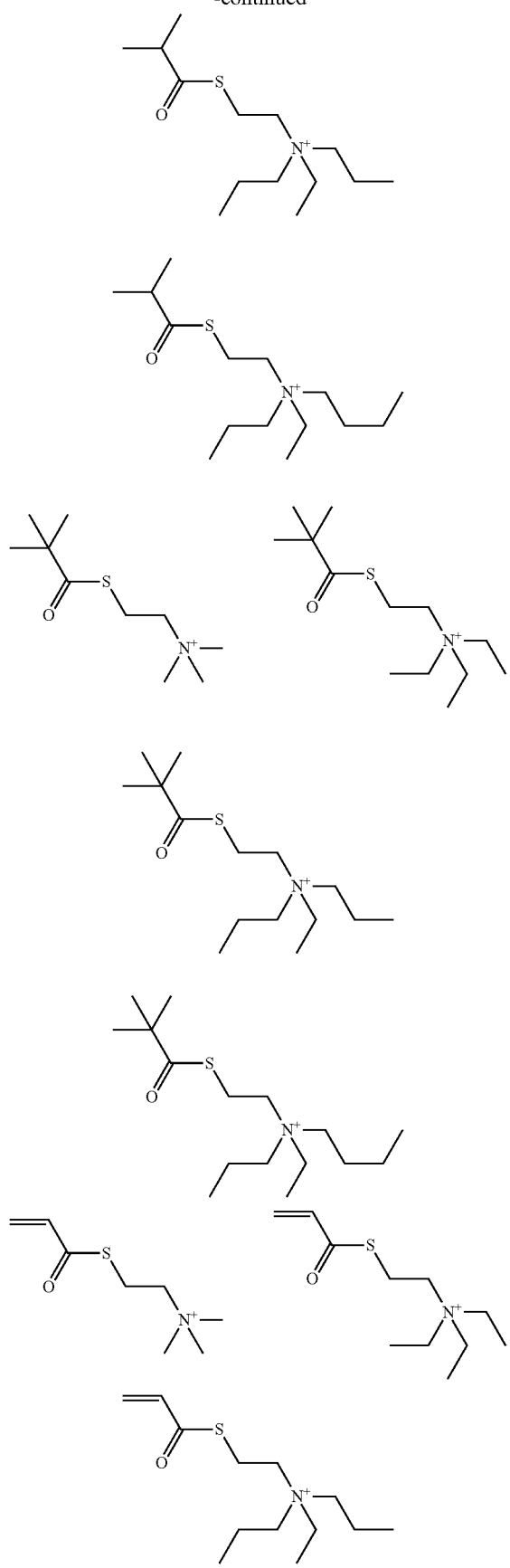
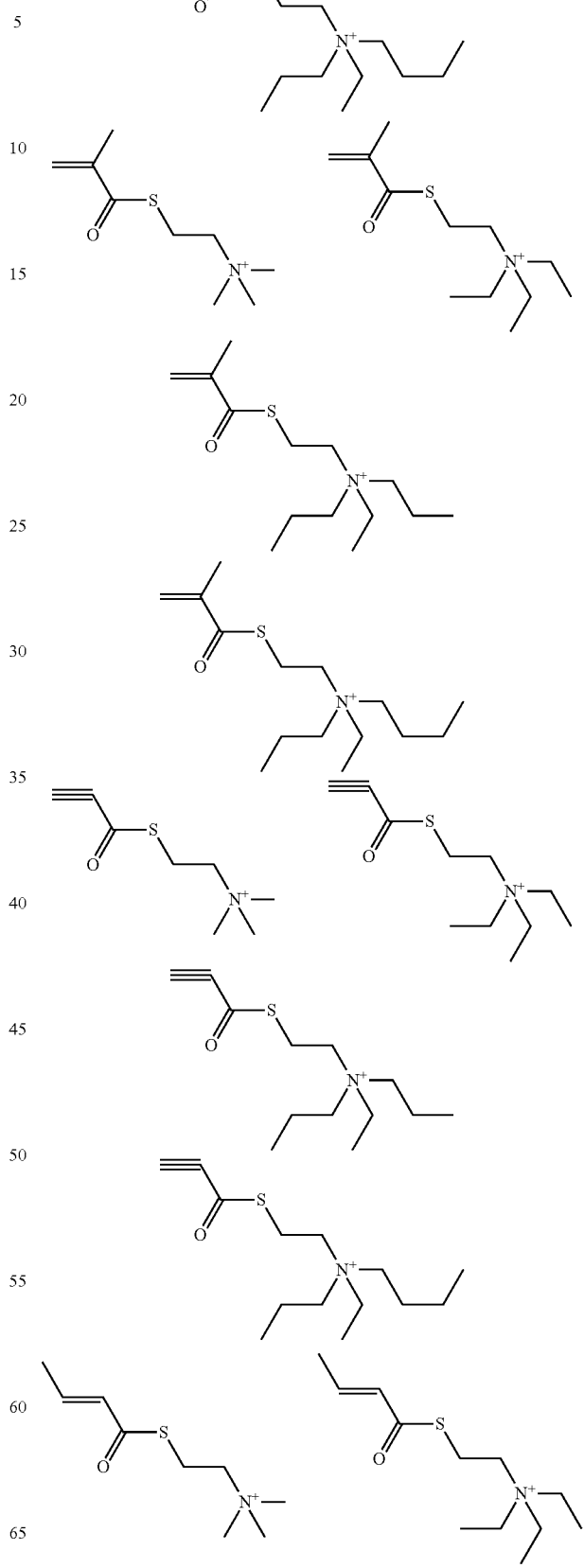

119
-continued
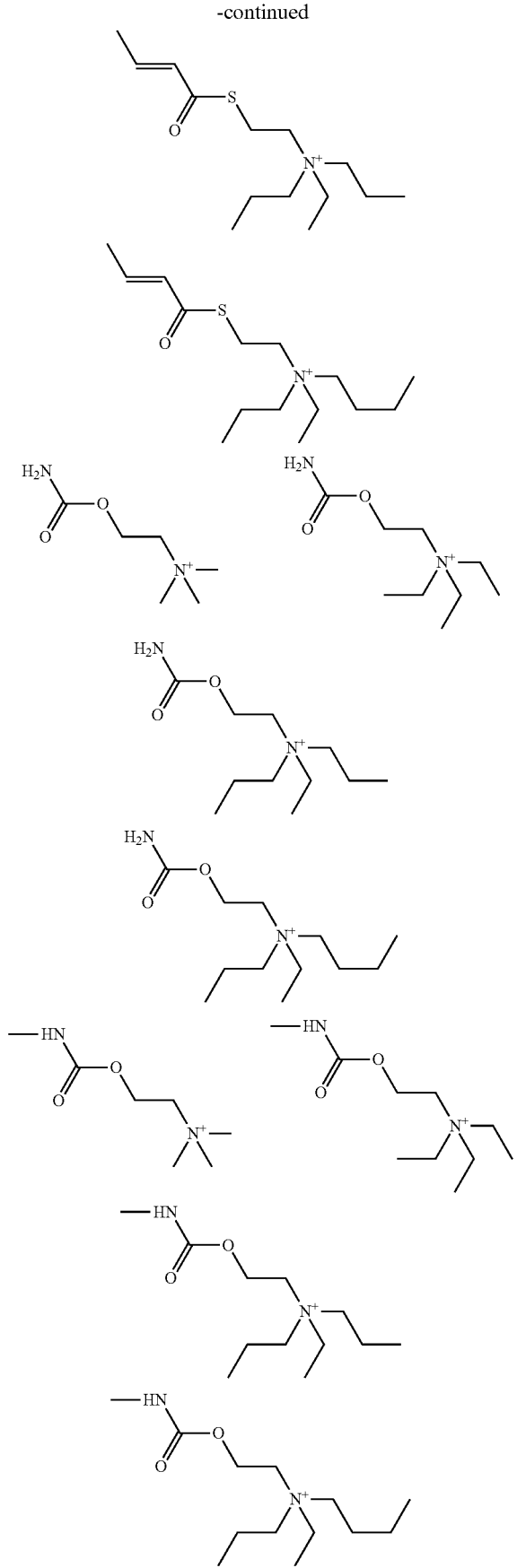
120
-continued
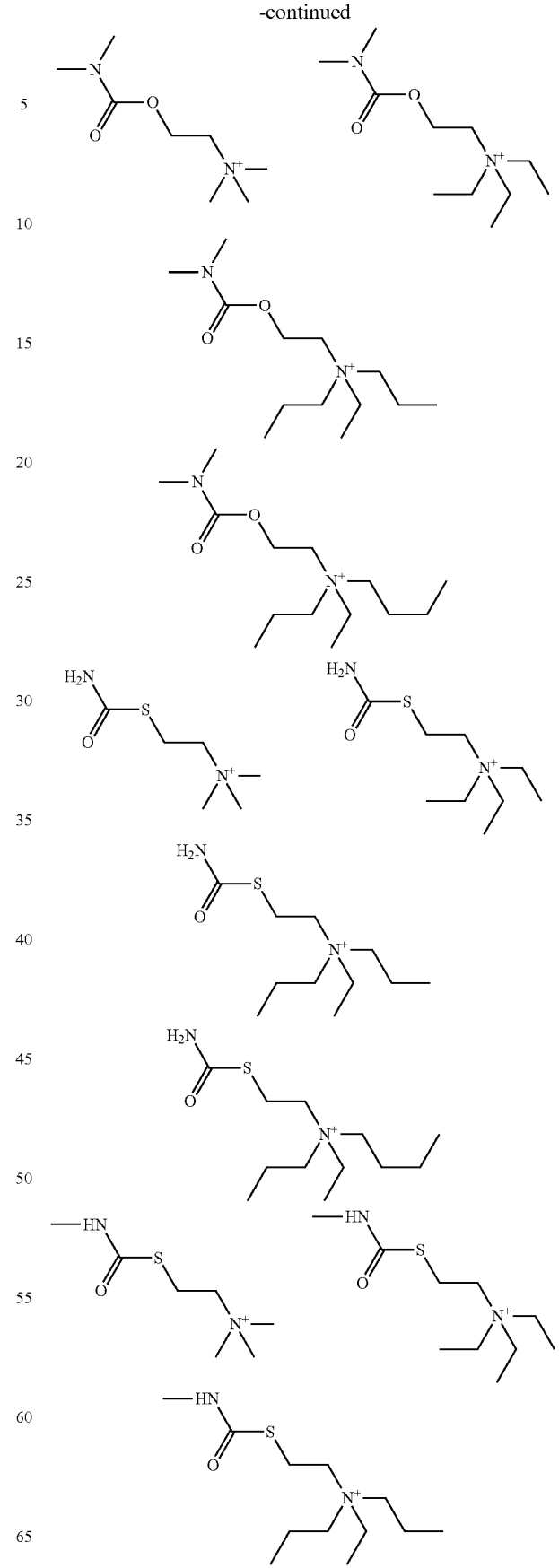

121
-continued
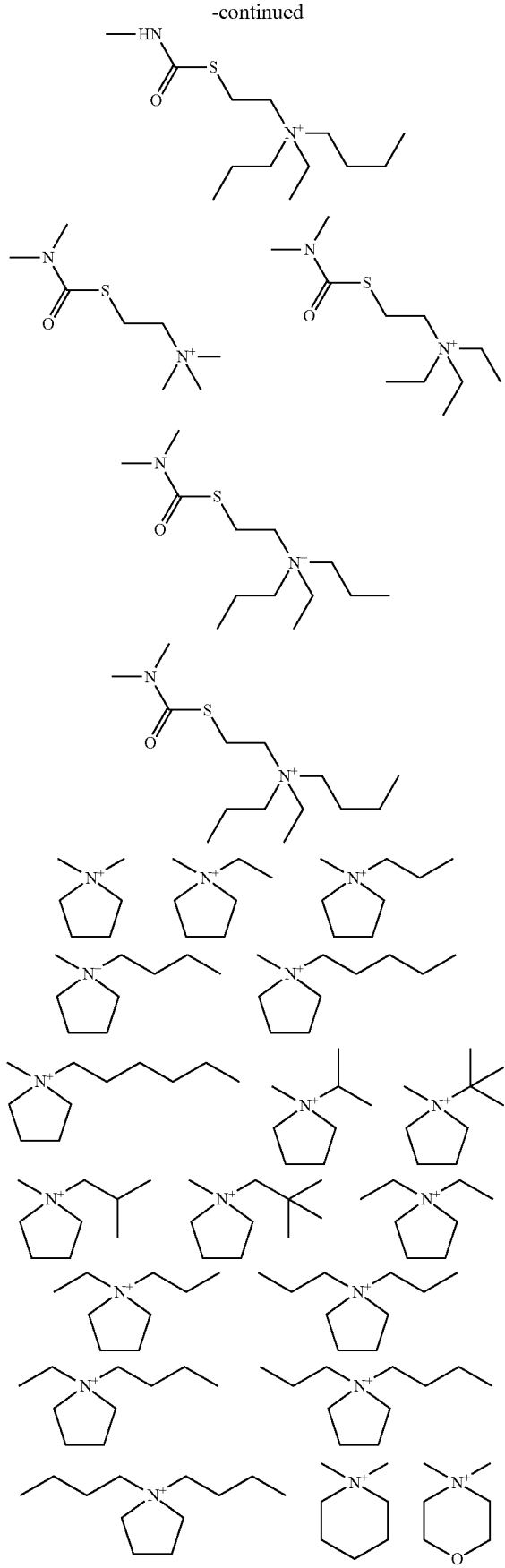
122
-continued
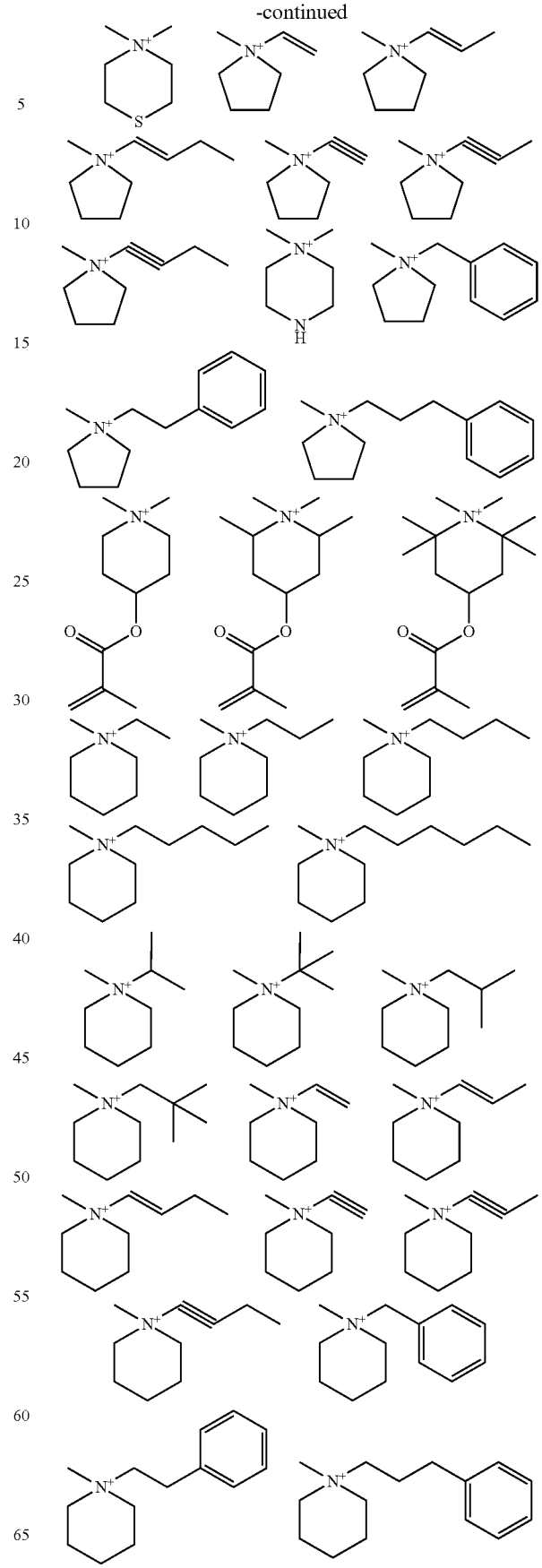

123
-continued
124
-continued
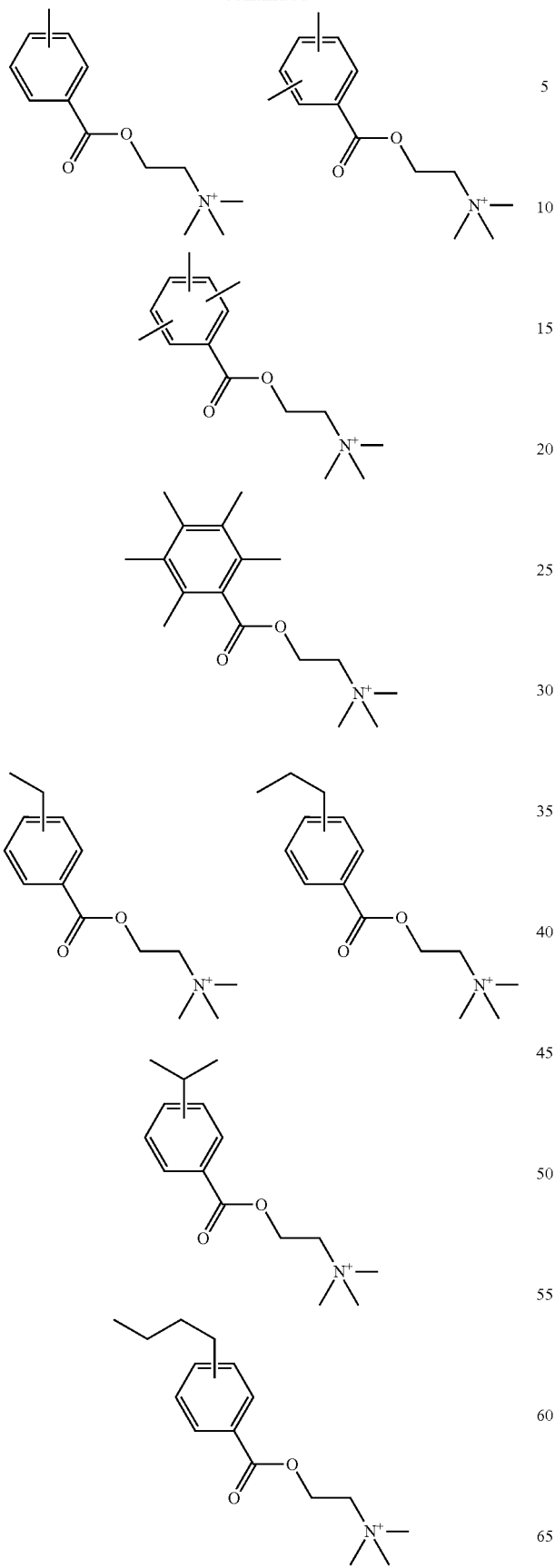
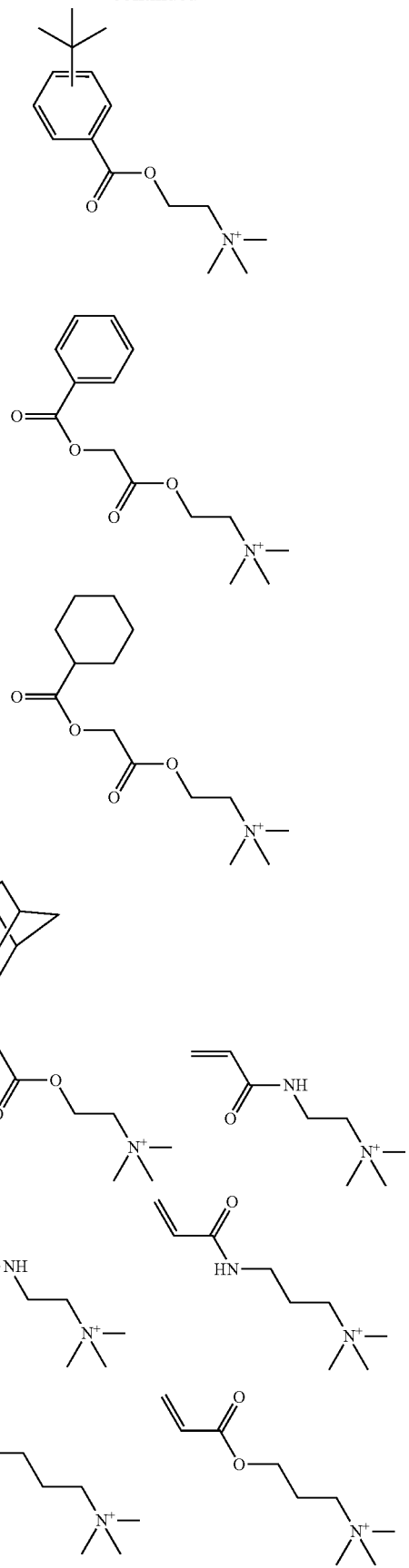

125
-continued
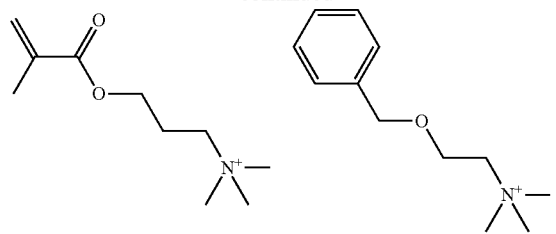
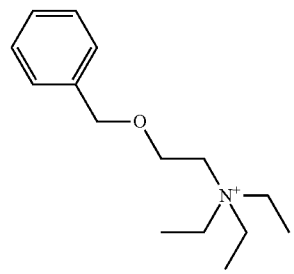
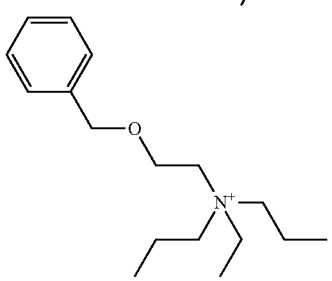
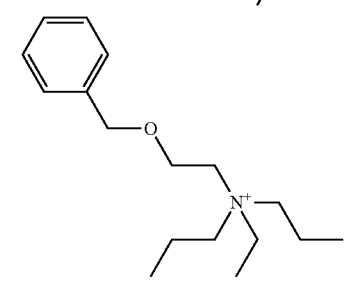
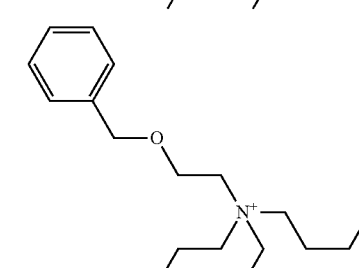
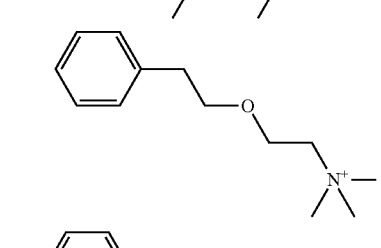
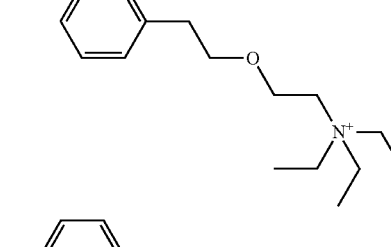
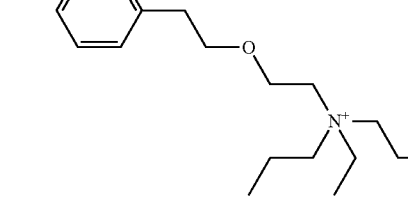
126
-continued
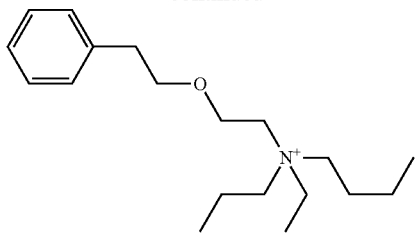
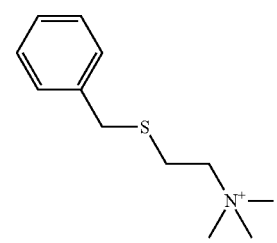
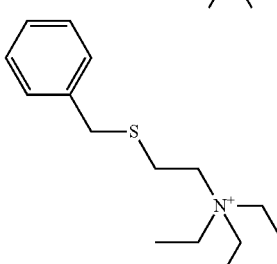
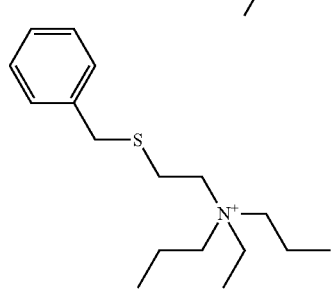
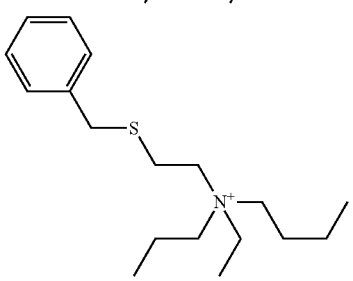
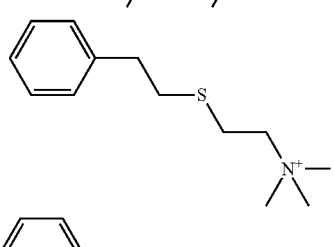
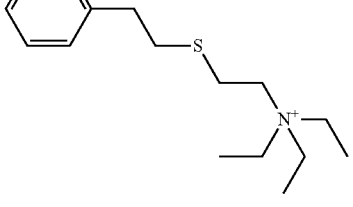

127
-continued
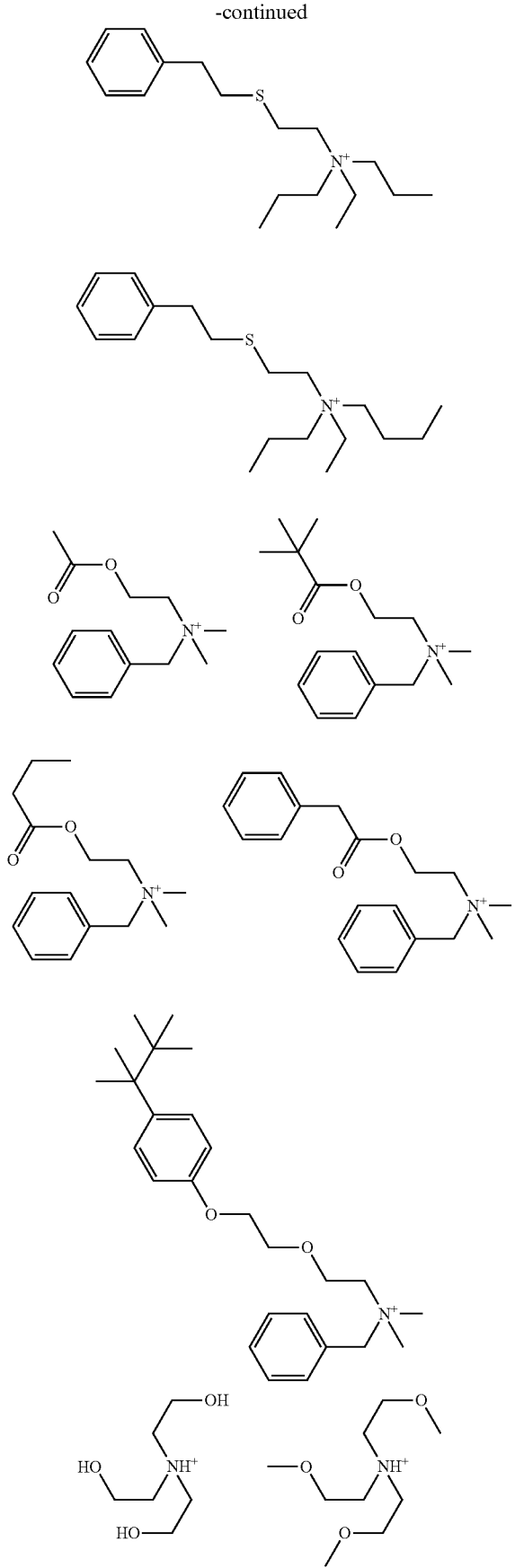
128
-continued
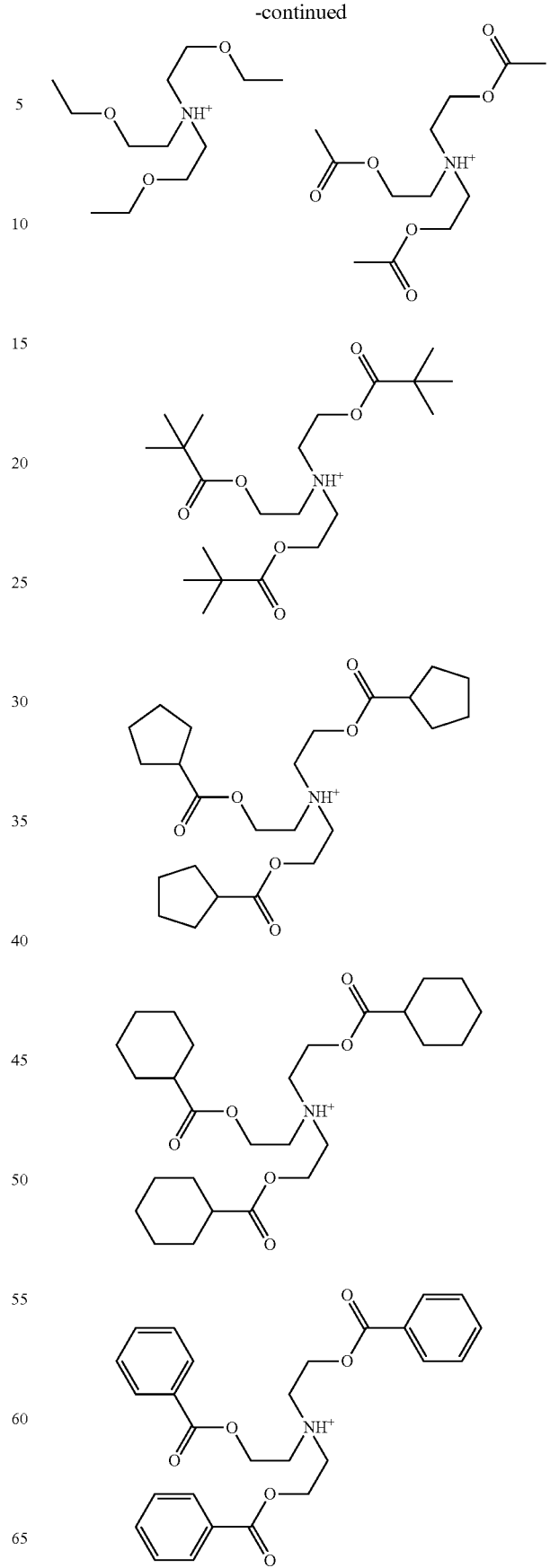

129
-continued
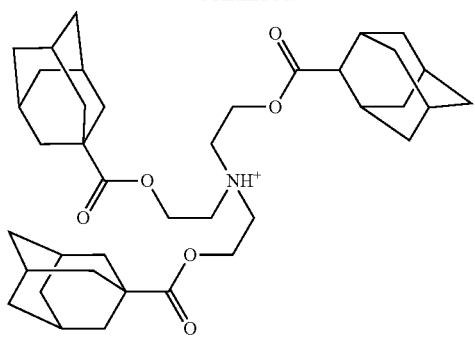
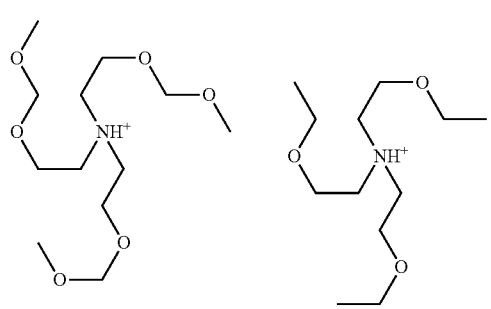
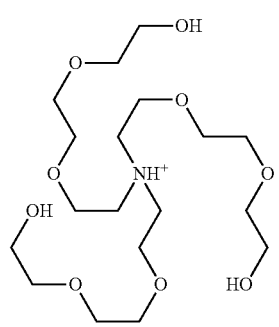
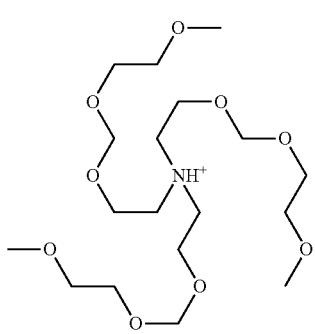
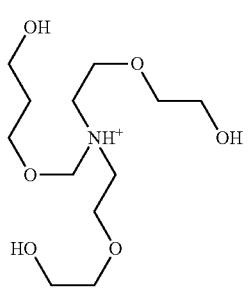
130
-continued
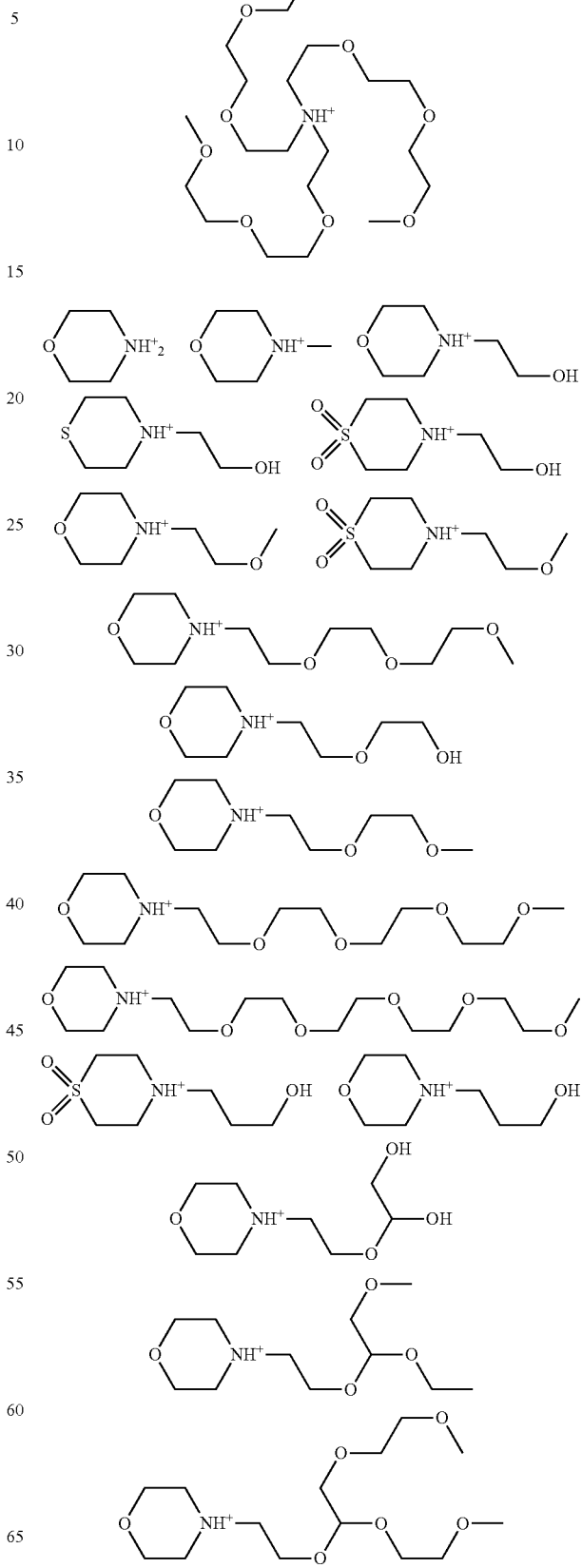

131
-continued

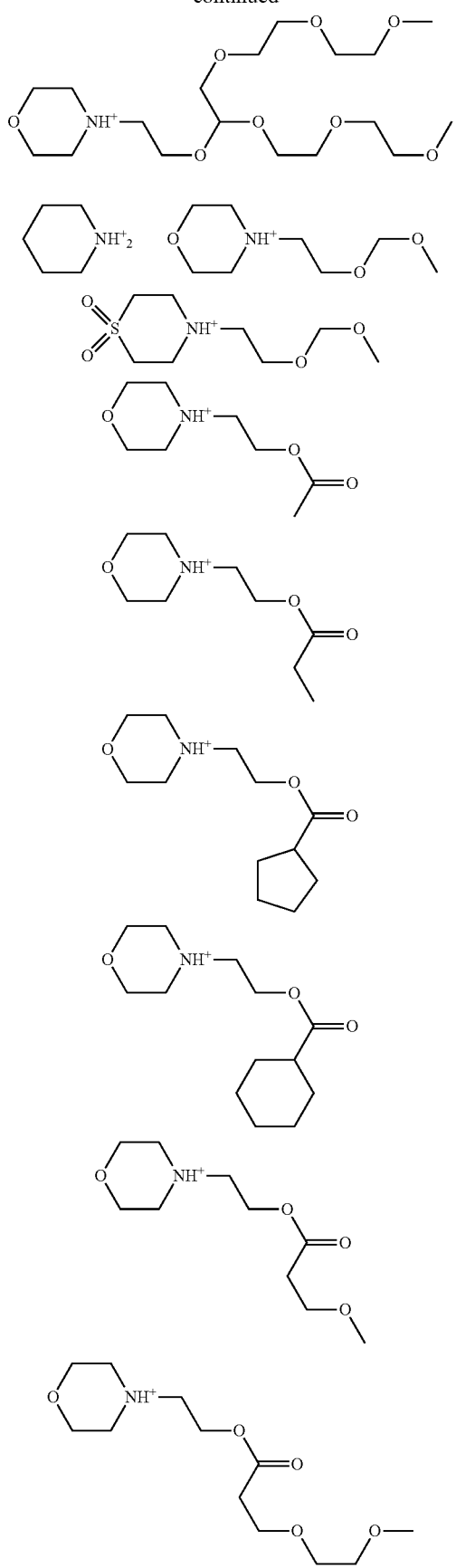

132
-continued

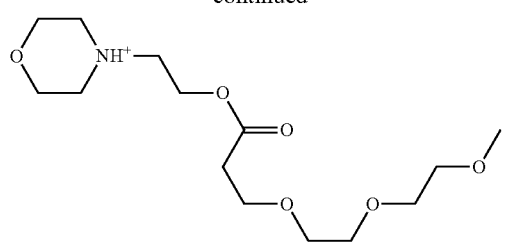

The ammonium ion shown by the general formula (3) is particularly preferably a tertiary or quaternary ammonium ion.

(Repeating Unit-b)

In the polymer compound (A) (component (A)) of the inventive bio-electrode composition, a repeating unit-b having a glyme chain can also be copolymerized in addition to the repeating unit(s)-a1 to -a7 in order to improve the electric conductivity. Specific examples of a monomer to give the repeating unit-b having a glyme chain include the following. The copolymerization with a repeating unit having a glyme chain facilitates the movement of ions released from skin in the living body contact layer (dry electrode film), and thus can increase the sensitivity of the bio-electrode (dry electrode).

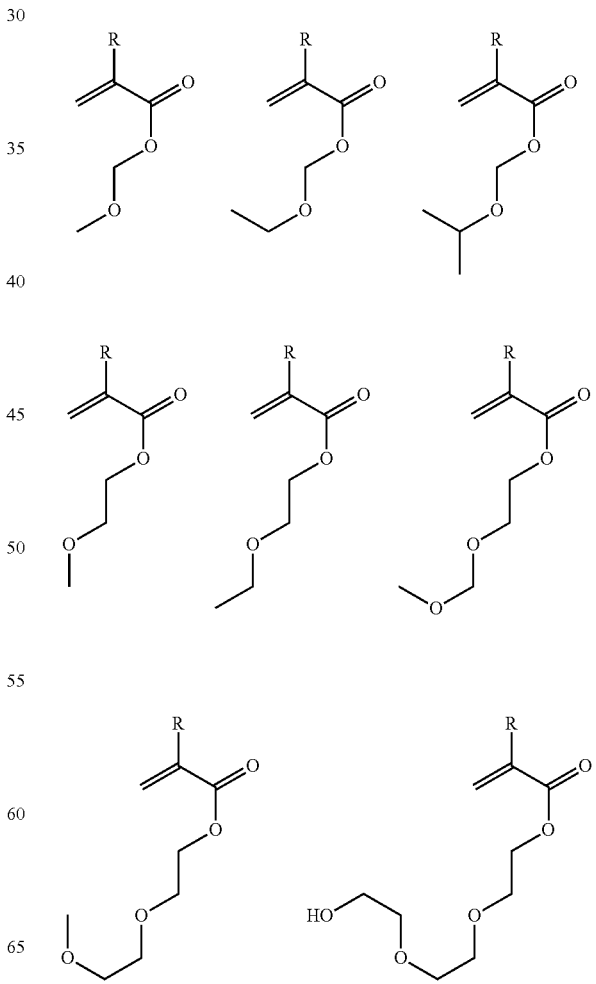

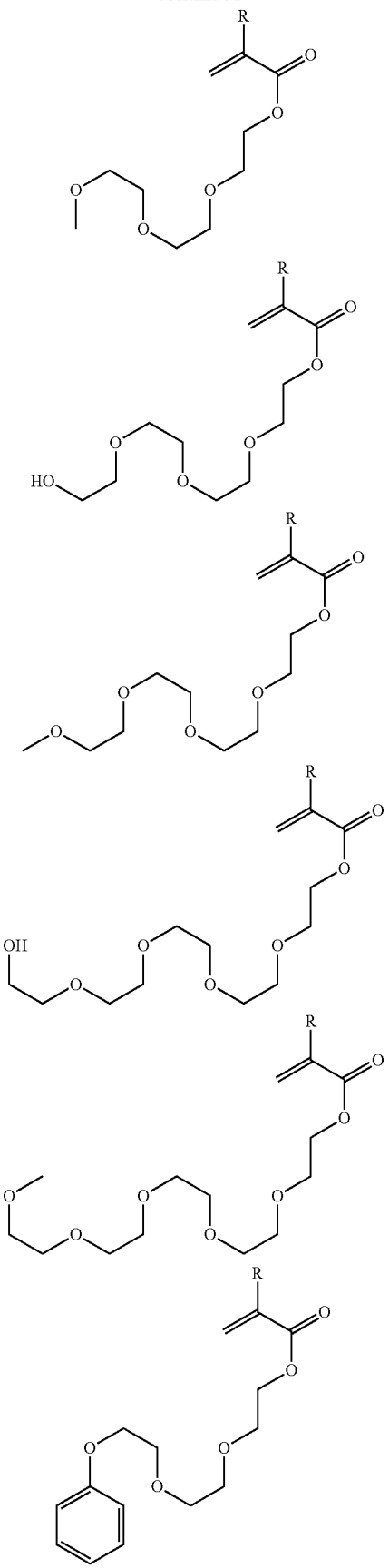
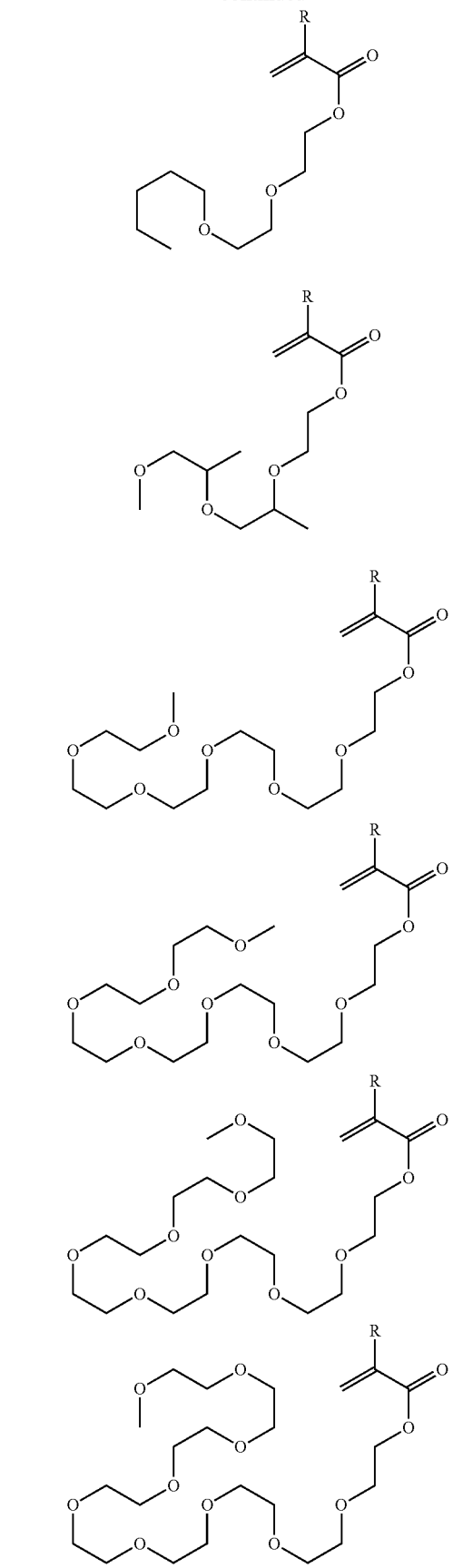

135
-continued
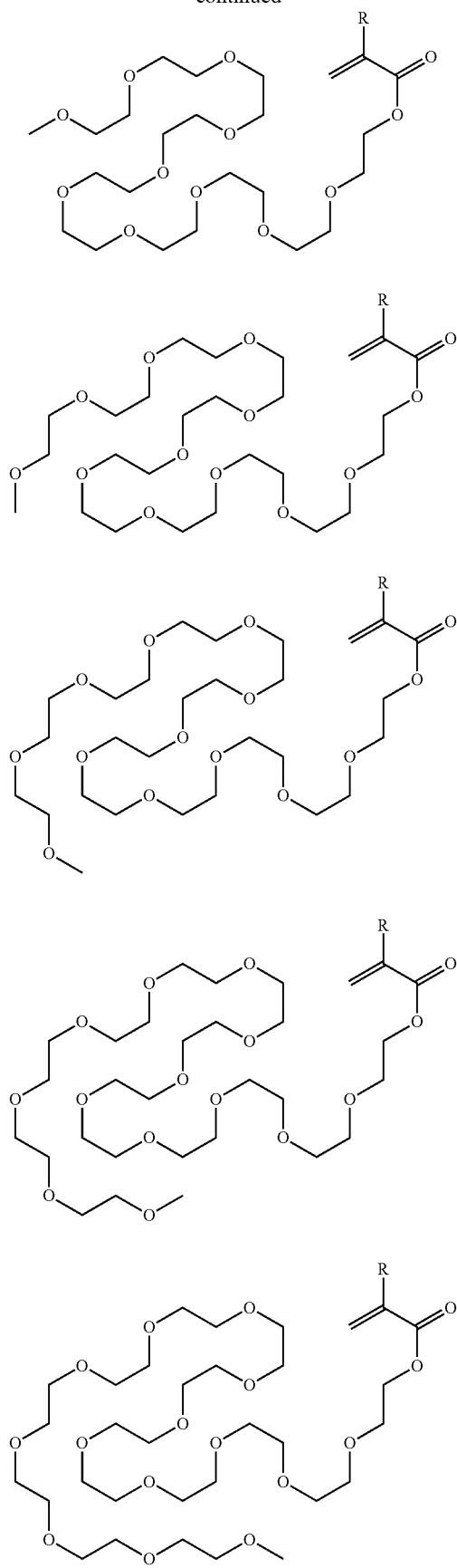
136
-continued
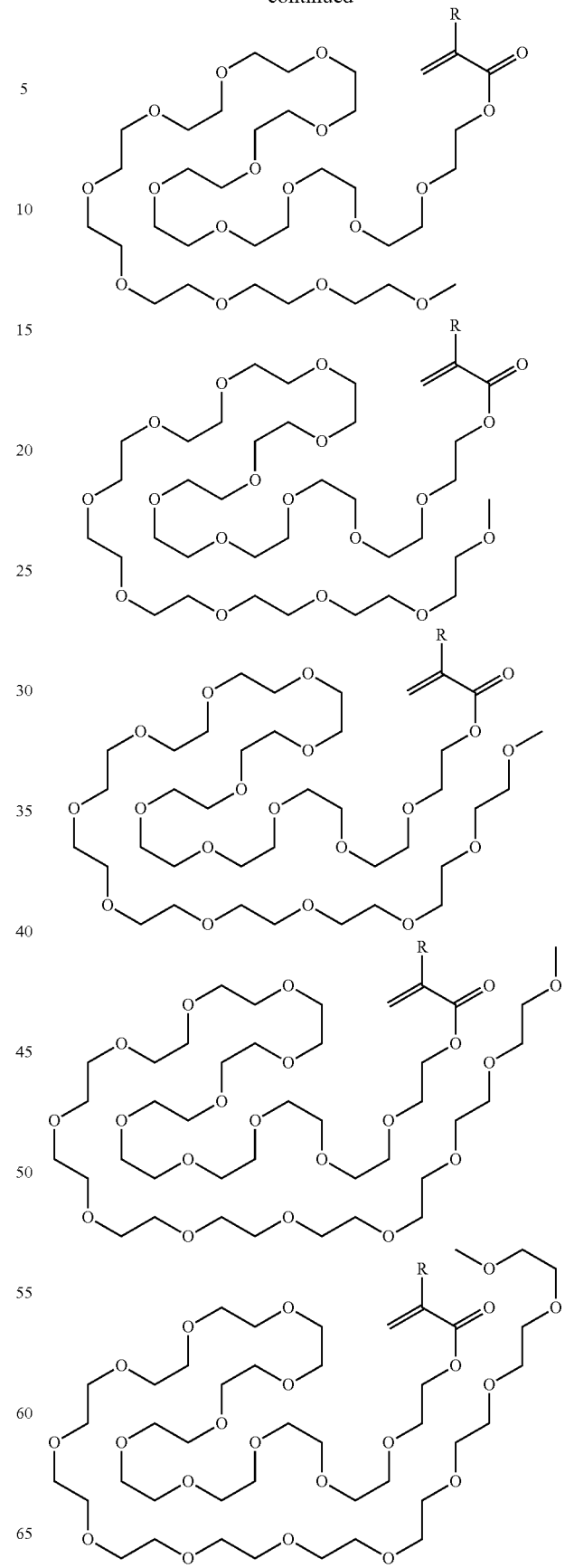

137
-continued
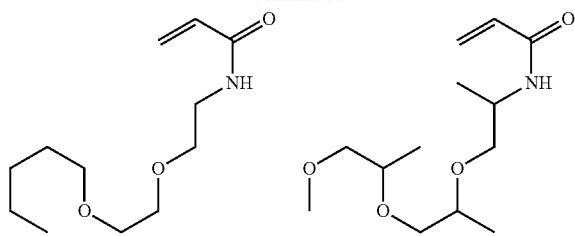
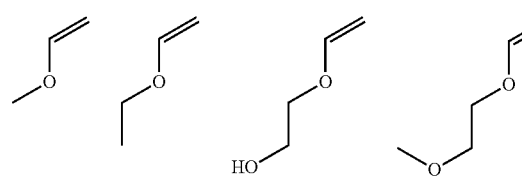
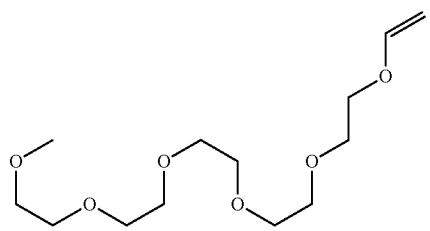
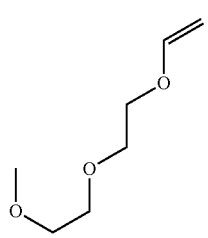
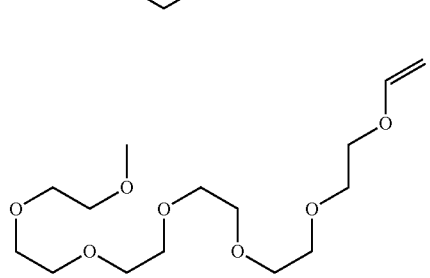
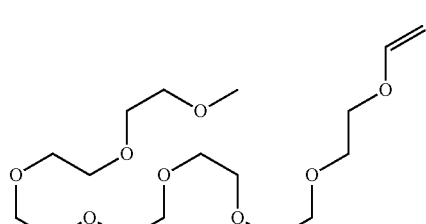
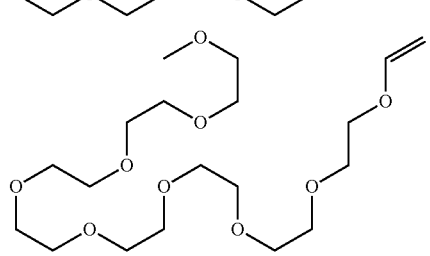
138
-continued
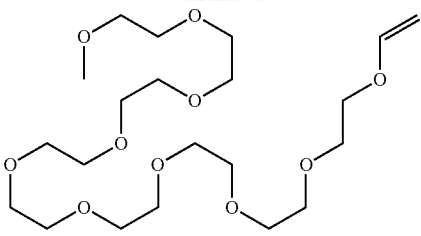
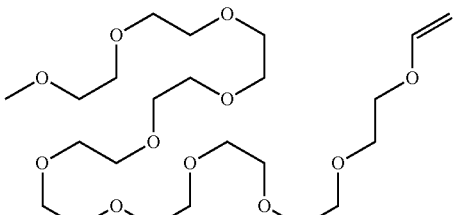
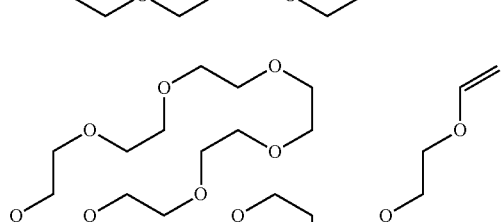
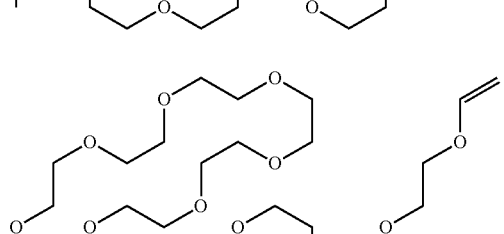
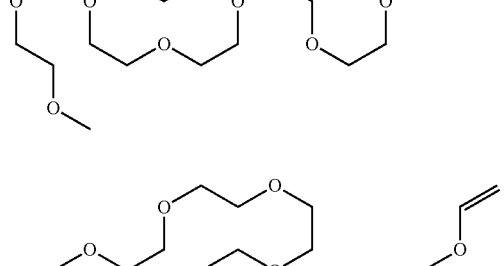
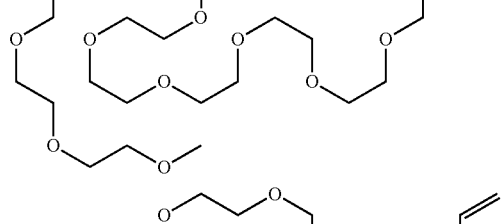
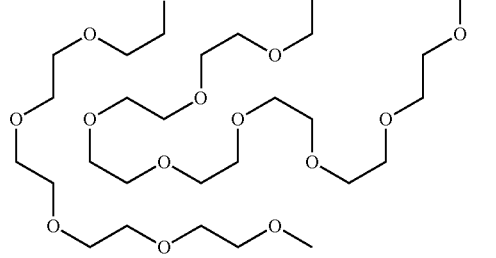

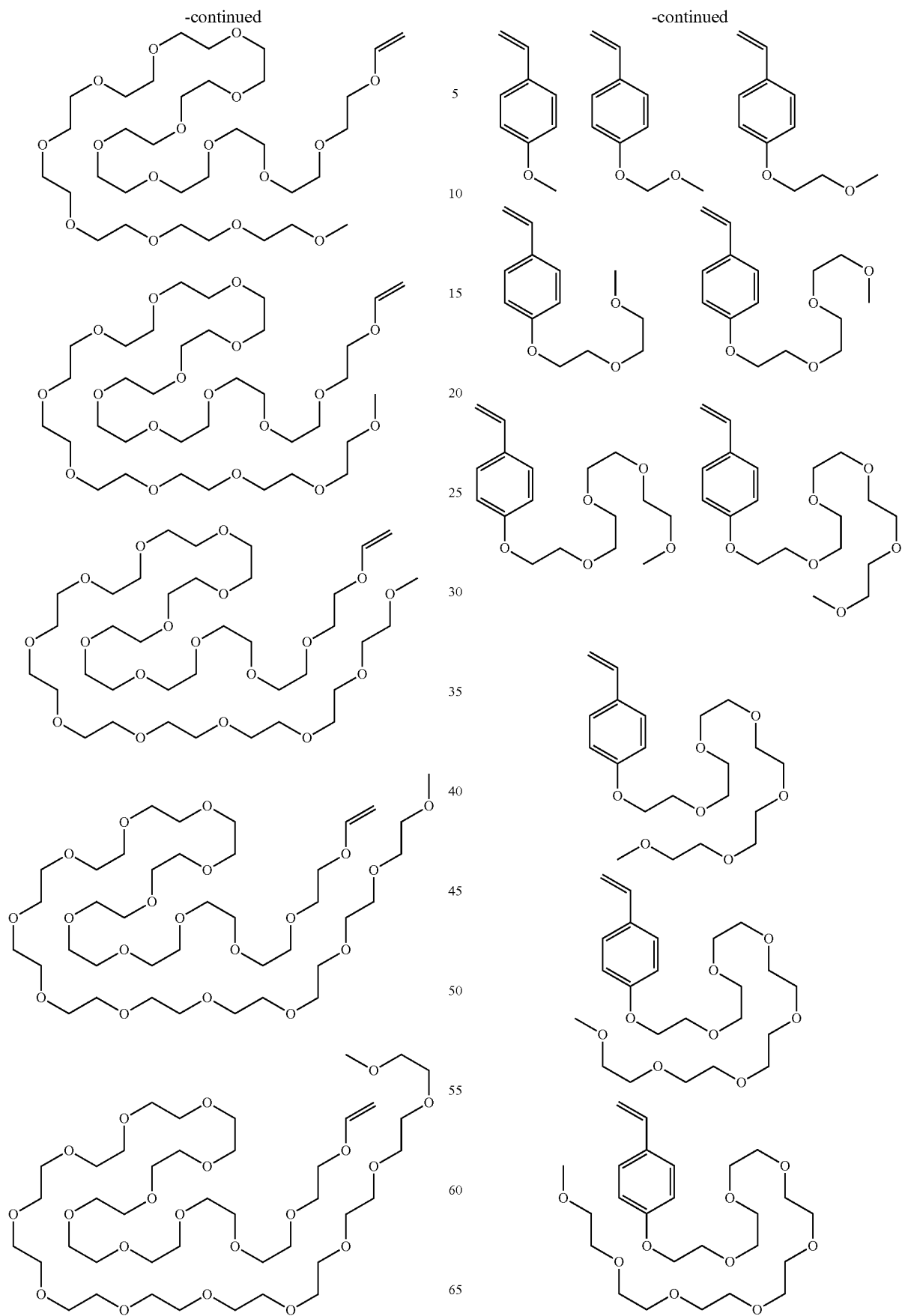

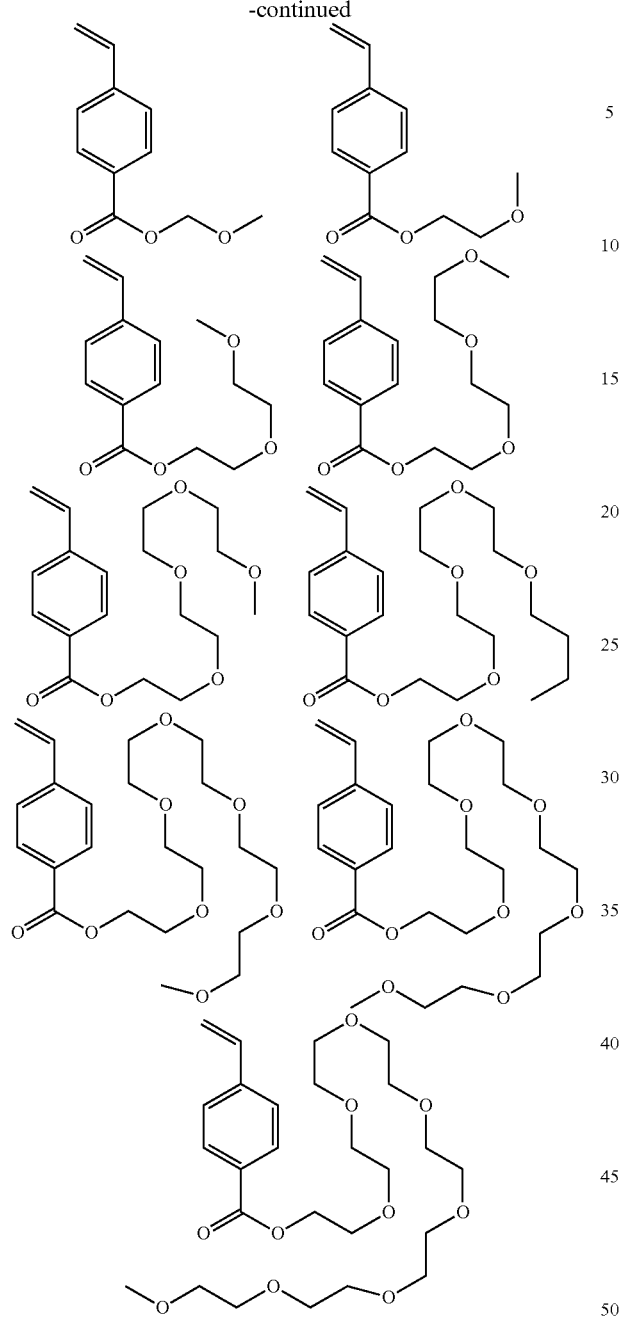

In the above formulae, R represents a hydrogen atom or a methyl group.

(Repeating Unit-c)

In order to improve the electric conductivity, the polymer compound (A) (component (A)) of the inventive bio-electrode composition can also be copolymerized with, in addition to the repeating units-a1 to -a7 and the optional repeating unit-b, a hydrophilic repeating unit-c having a hydrophilic group such as a hydroxy group, a carboxyl group, an ammonium salt, a betaine, an amide group, pyrrolidone, a lactone ring, a lactam ring, a sultone ring, a sulfonic acid sodium salt, and a sulfonic acid potassium salt. Specific examples of a monomer to give the hydrophilic repeating unit-c include the following. The copolymerization with repeating units containing such hydrophilic groups can increase the sensitivity of the bio-electrode (dry electrode) by increasing the sensitivity to ions released from skin.

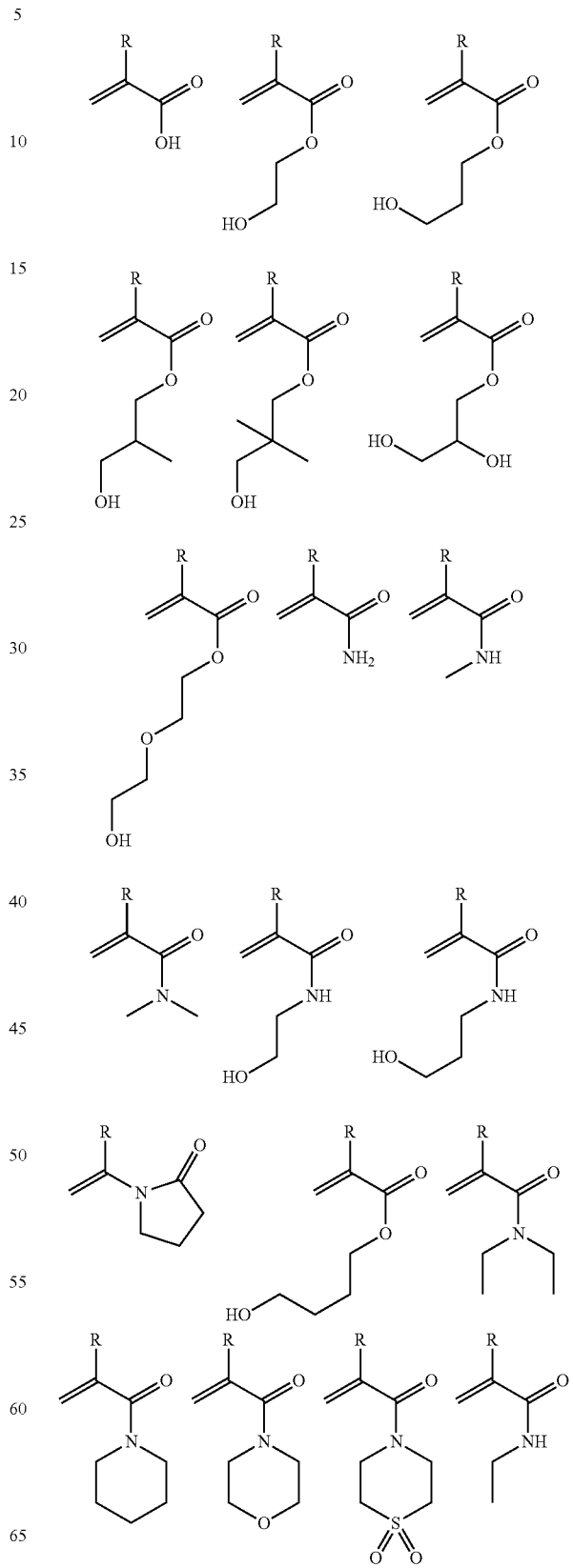

-continued
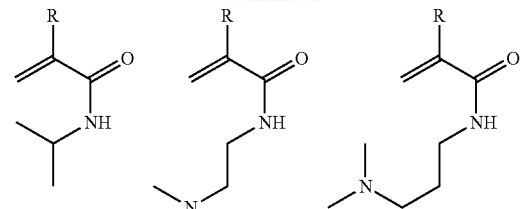
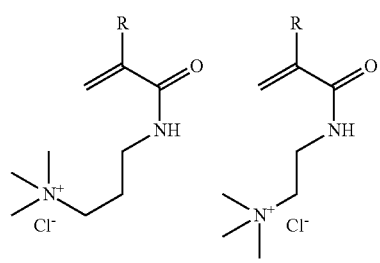
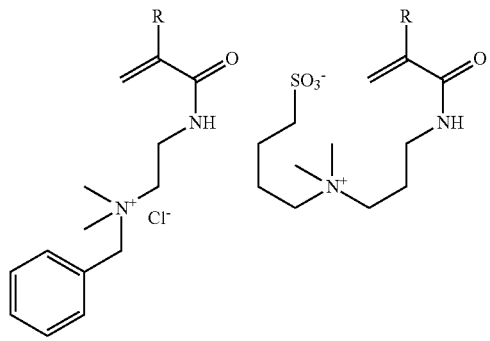
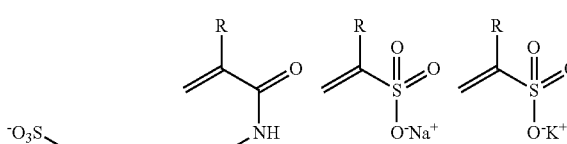
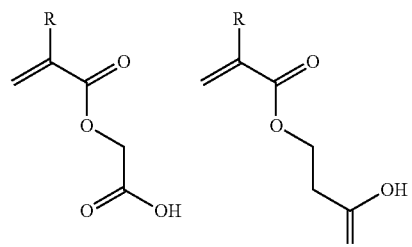
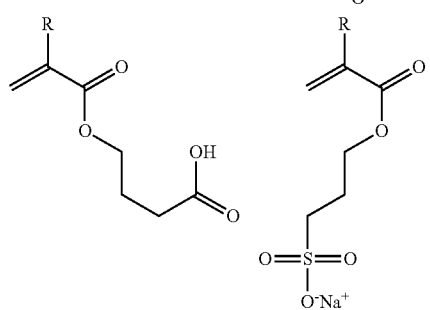
-continued
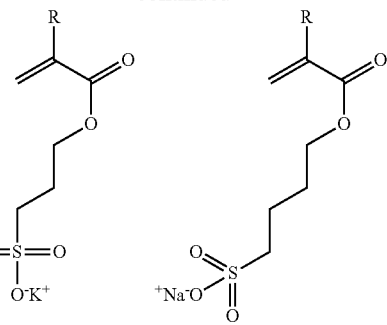
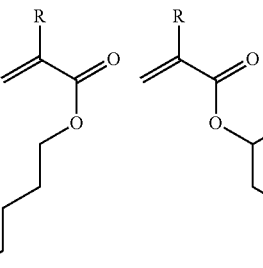
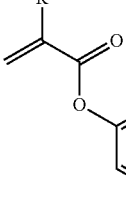
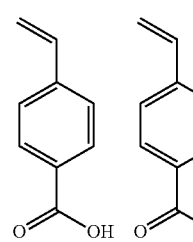
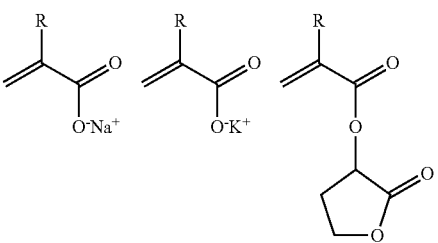
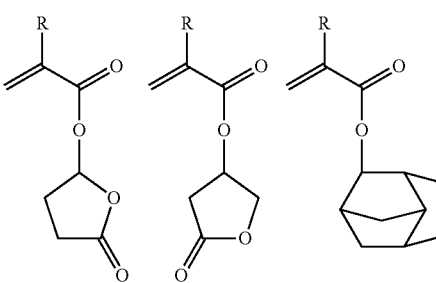

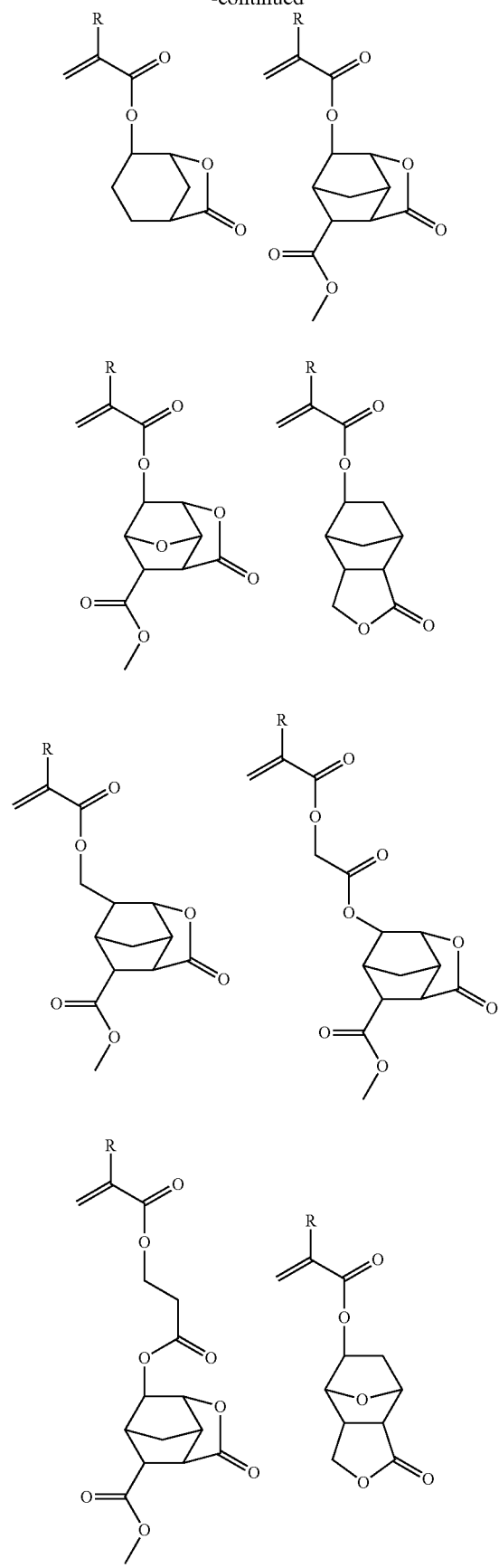
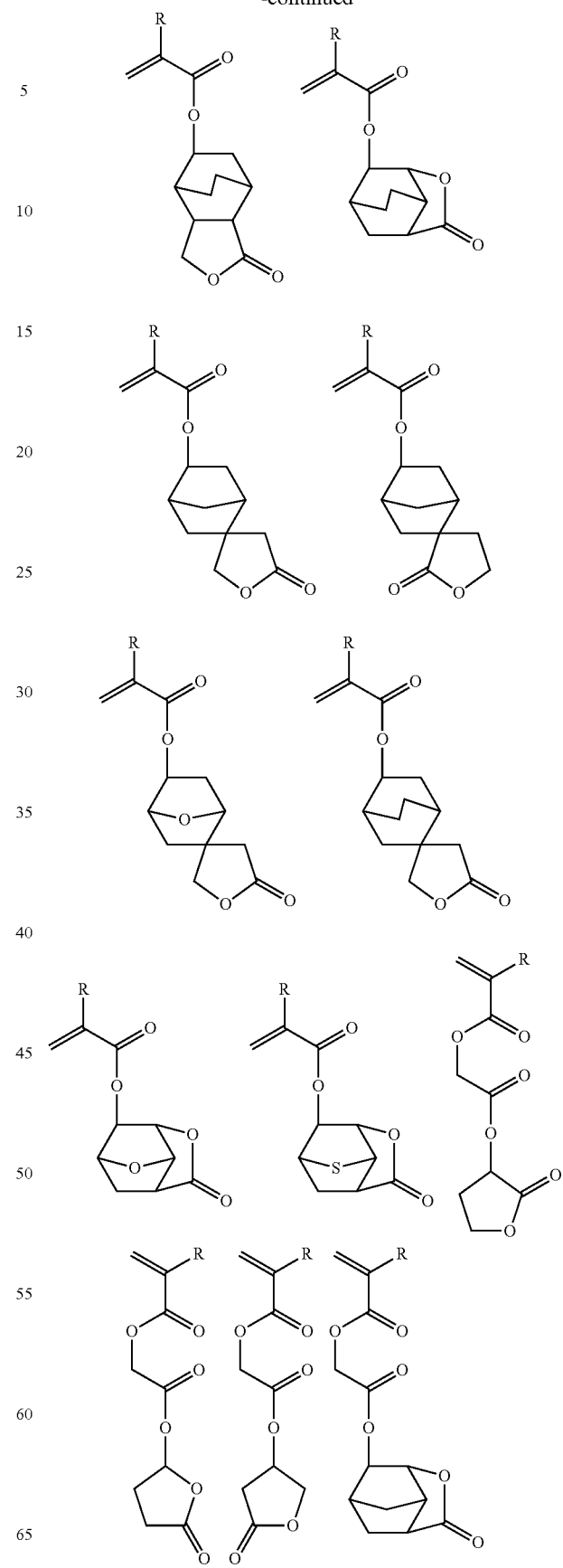

-continued
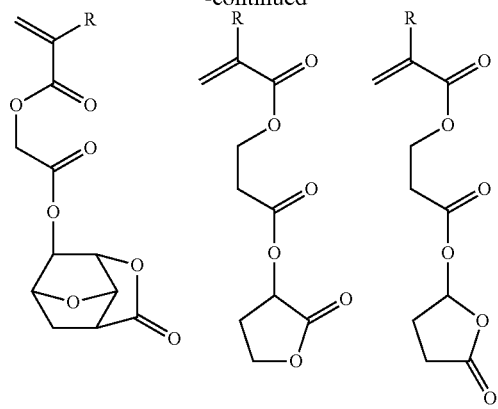
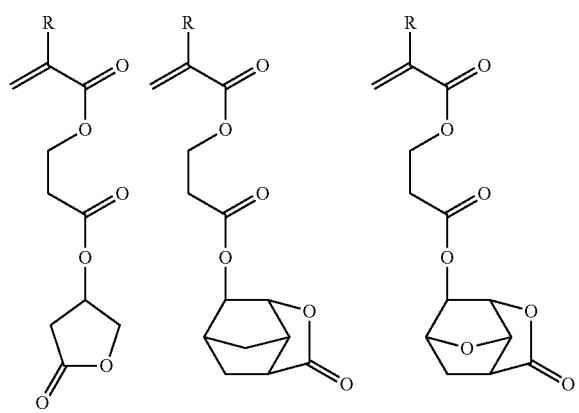
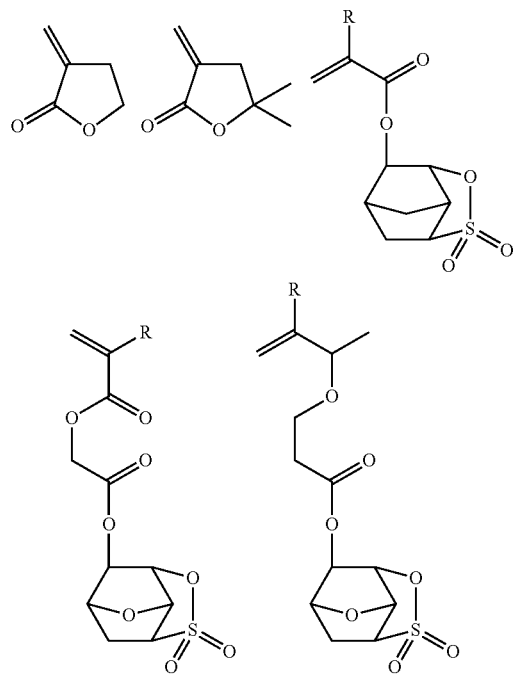
-continued
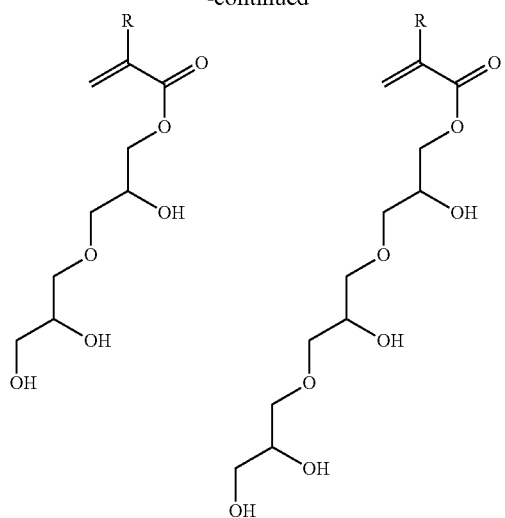
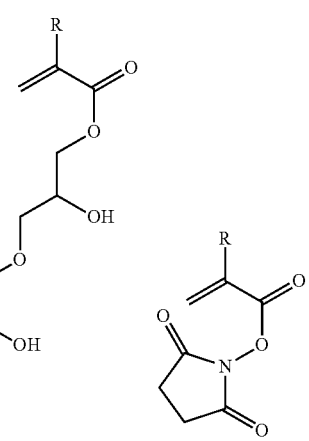
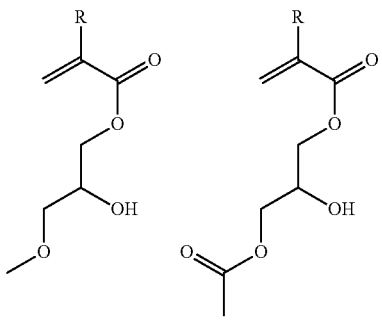

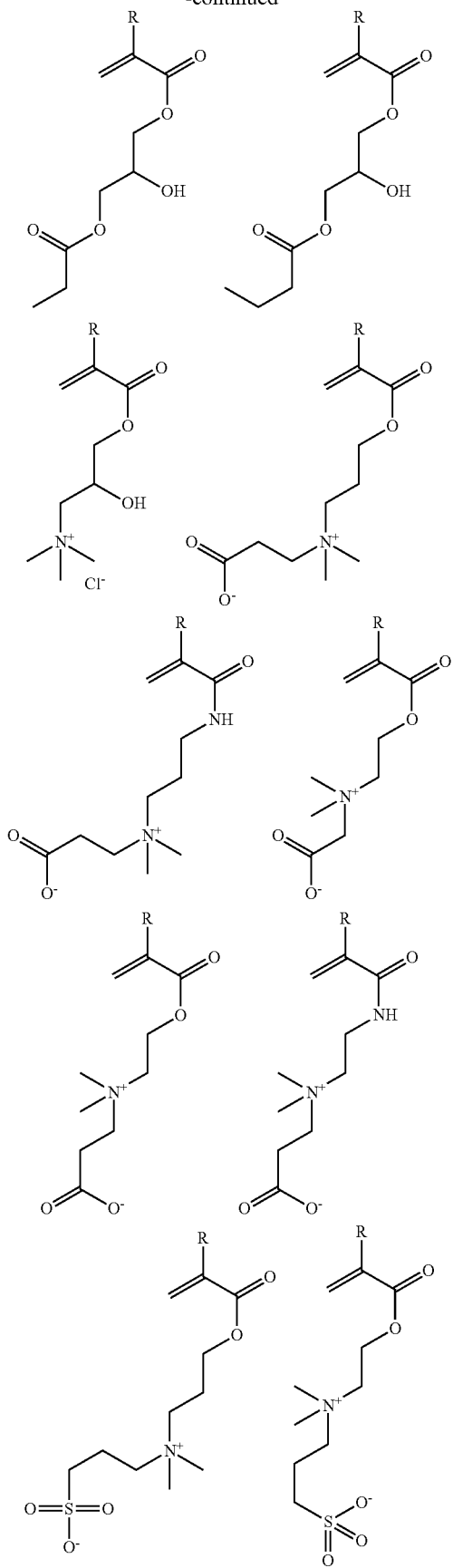
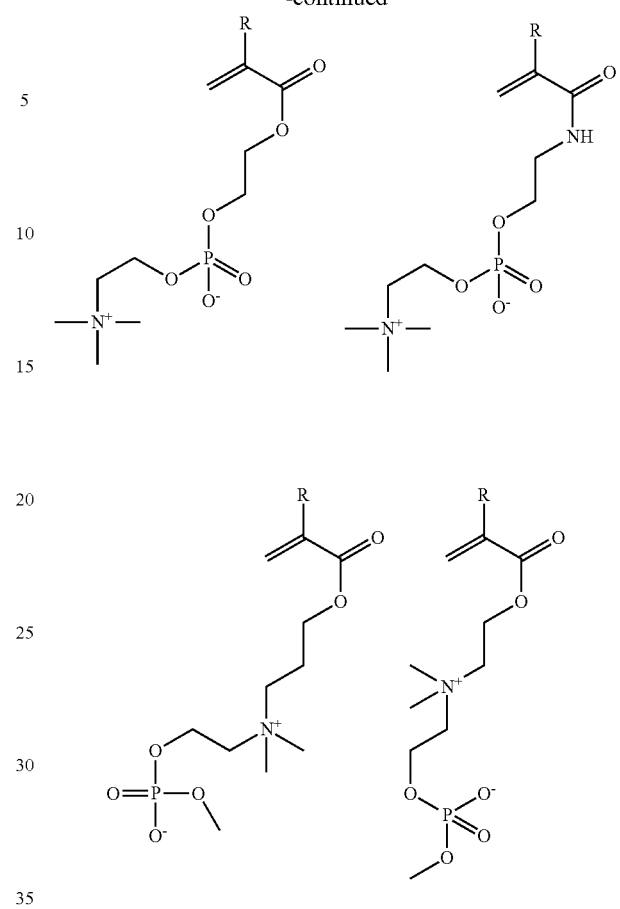
In the above formulae, R represents a hydrogen atom or a methyl group.
(Repeating Unit-d)
The polymer compound (A) in the inventive bio-electrode composition can contain a repeating unit-d to give adhesion properties.
Specific examples of a monomer to give the repeating unit-d include the following.
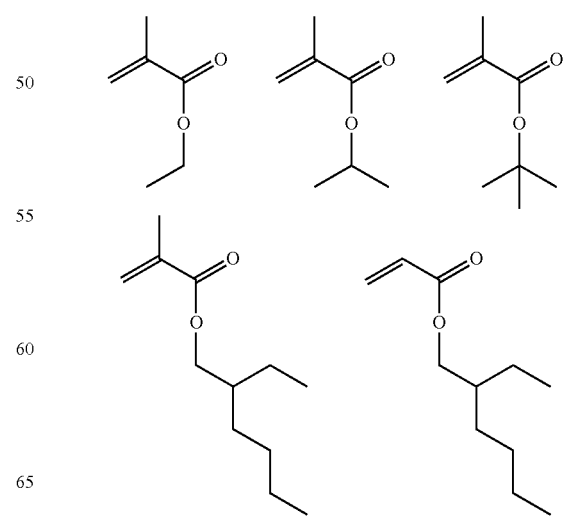

151
-continued
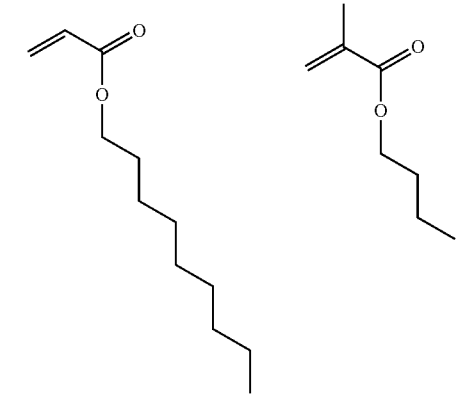
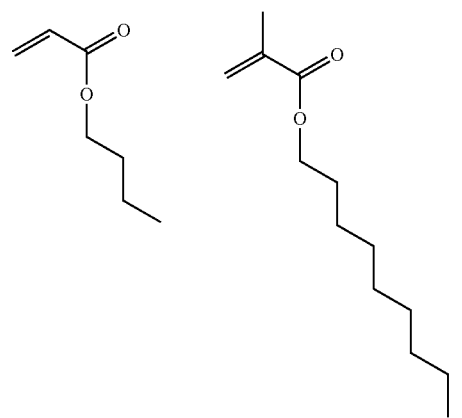
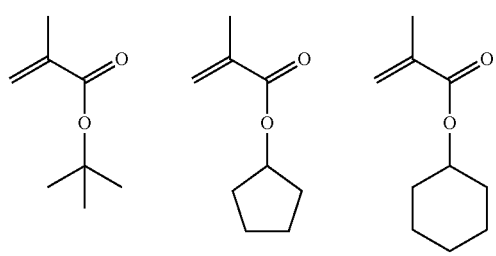
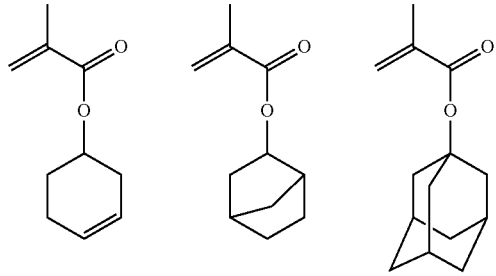
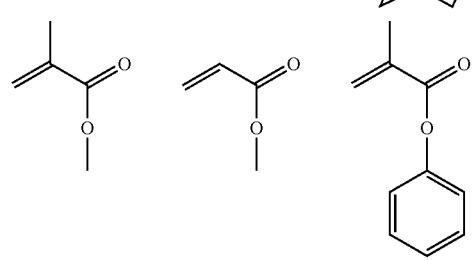
152
-continued
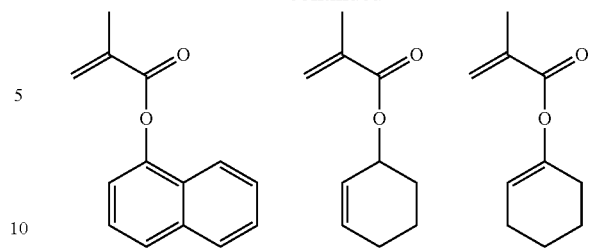
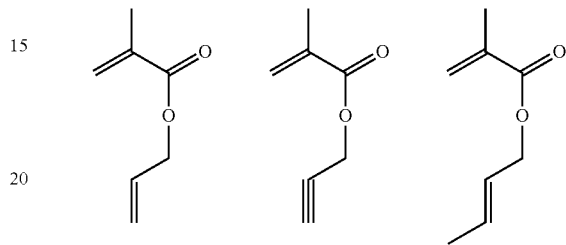
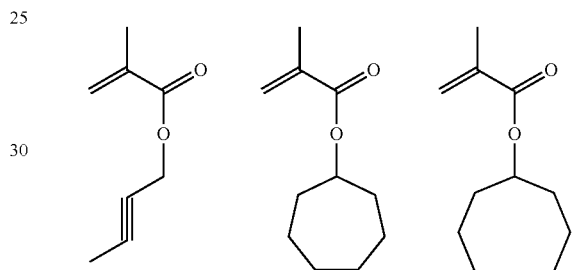
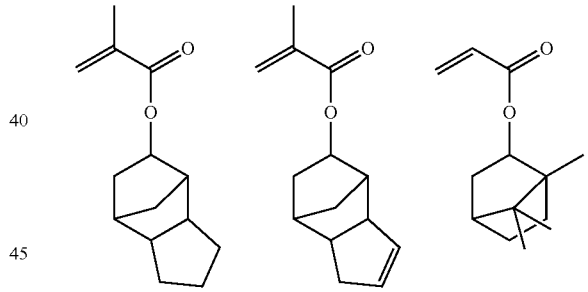
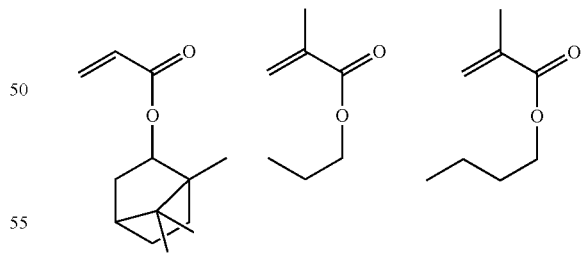
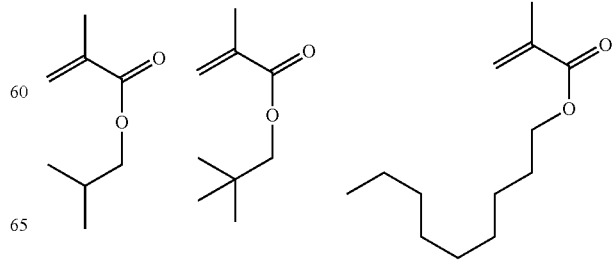

153
-continued
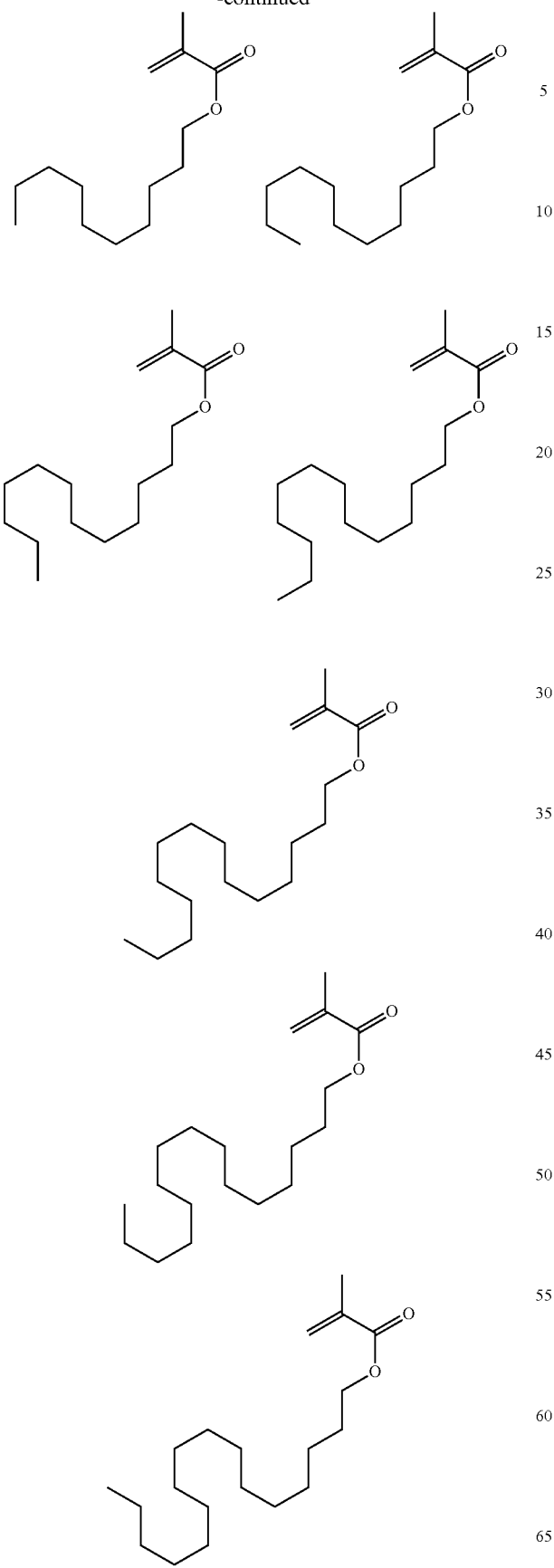
154
-continued
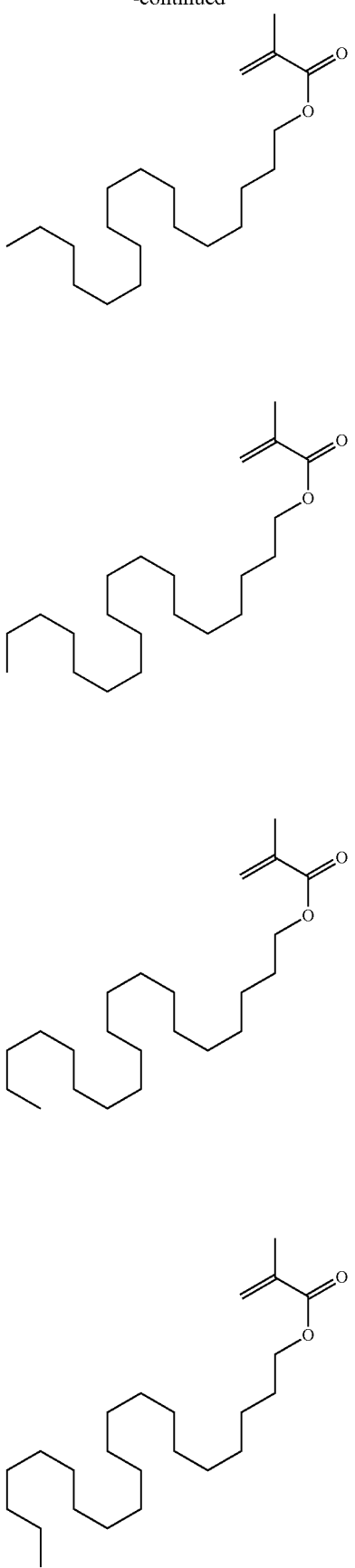

155 -continued
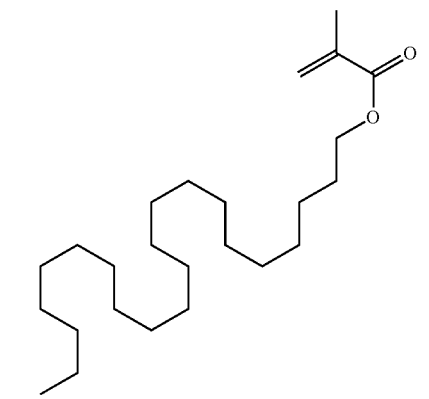
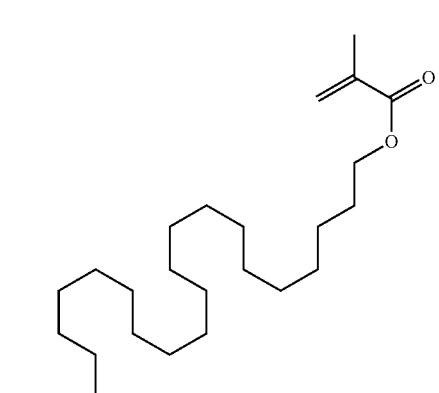
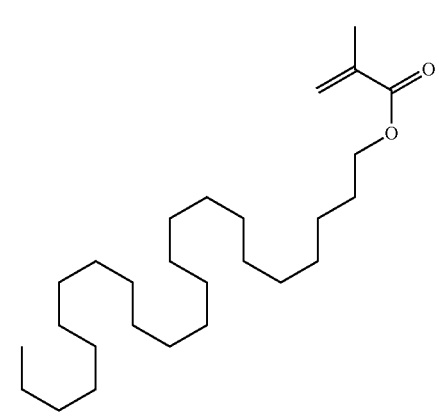
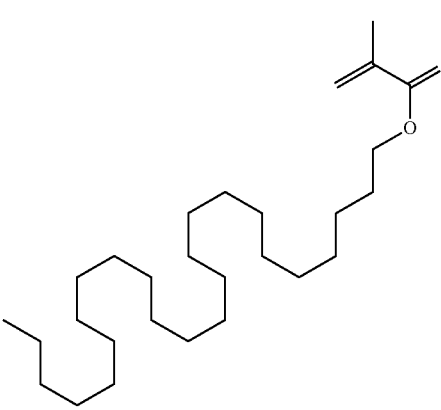
156 -continued
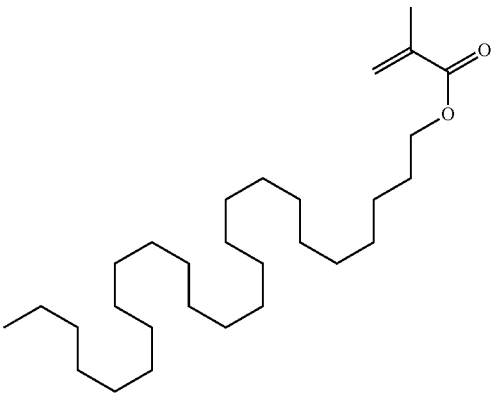
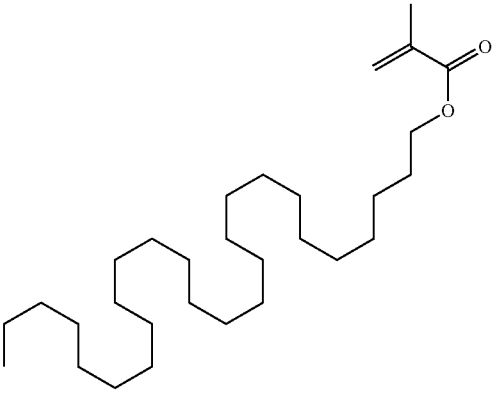
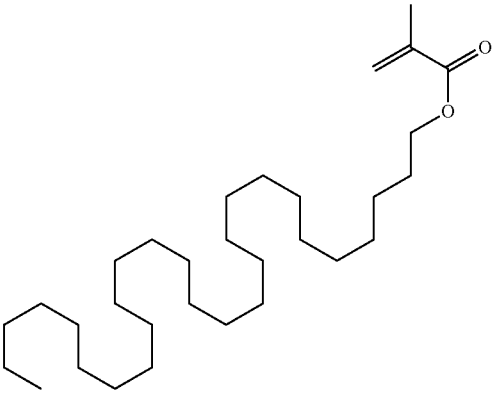
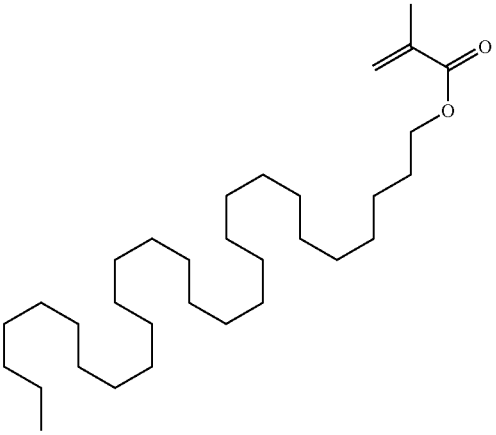

157
-continued
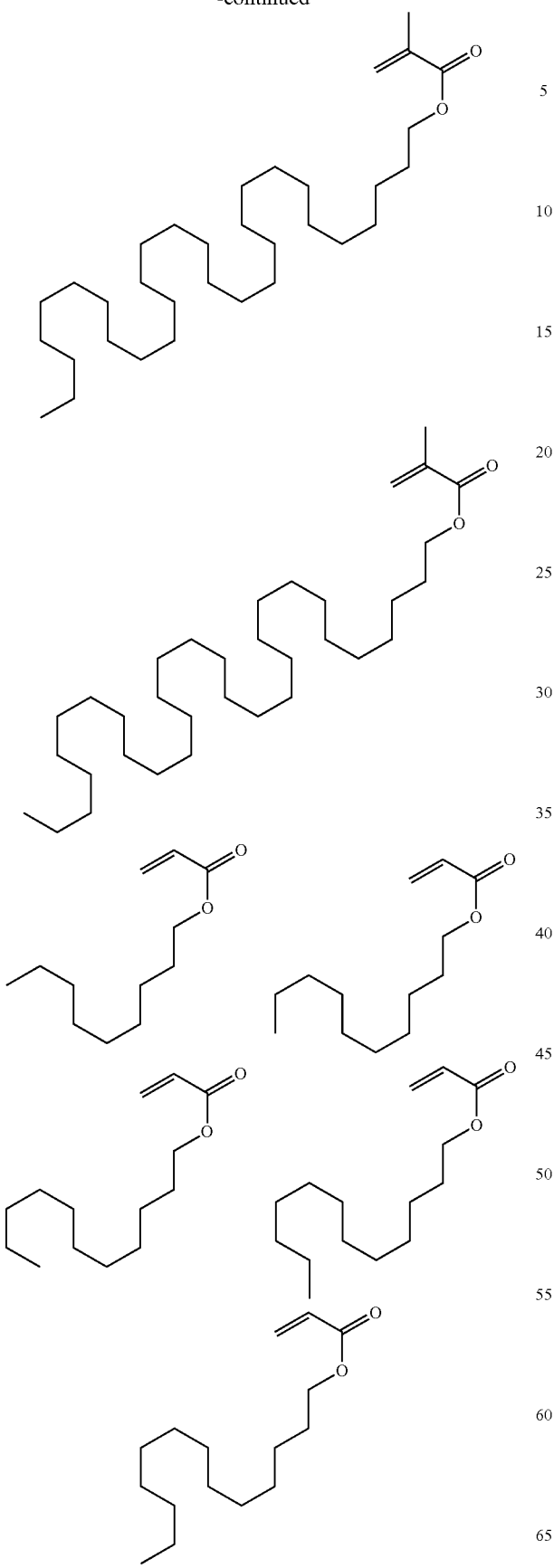
158
-continued
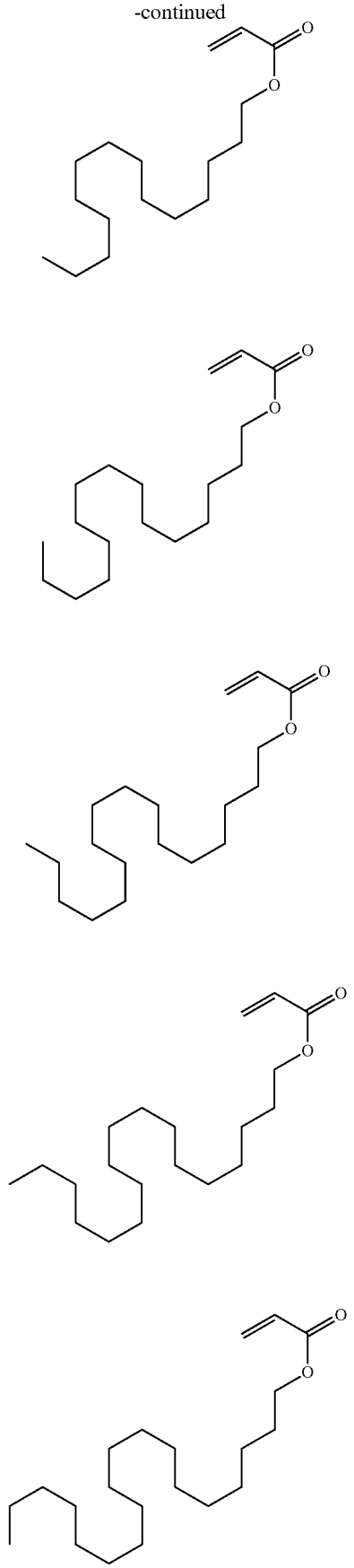

159
-continued
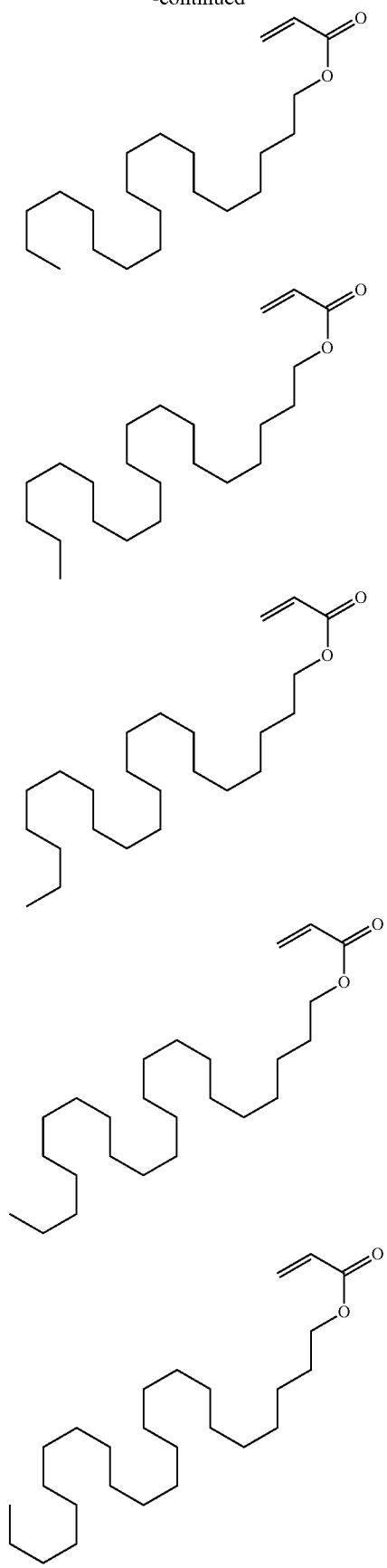
160
-continued
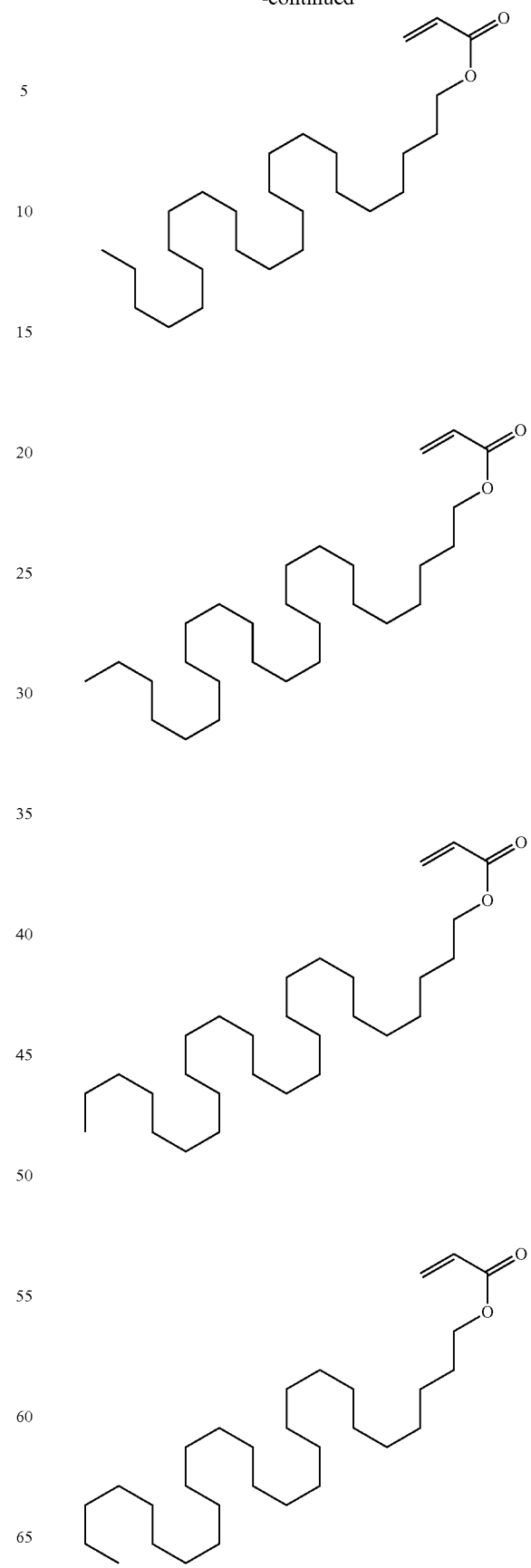

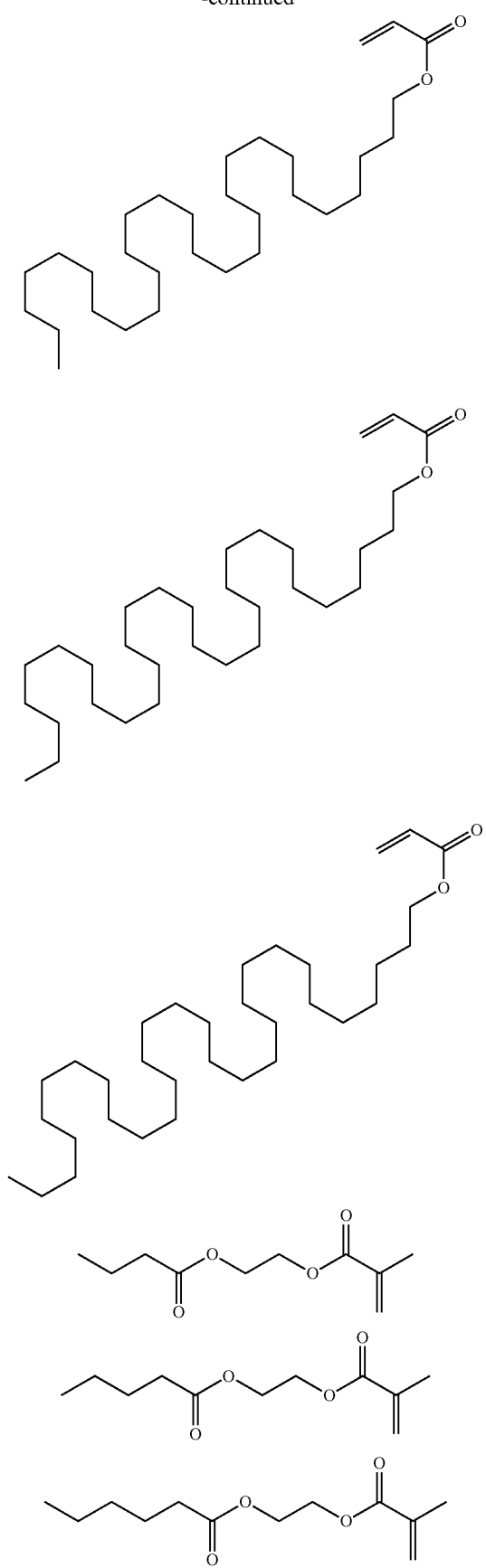
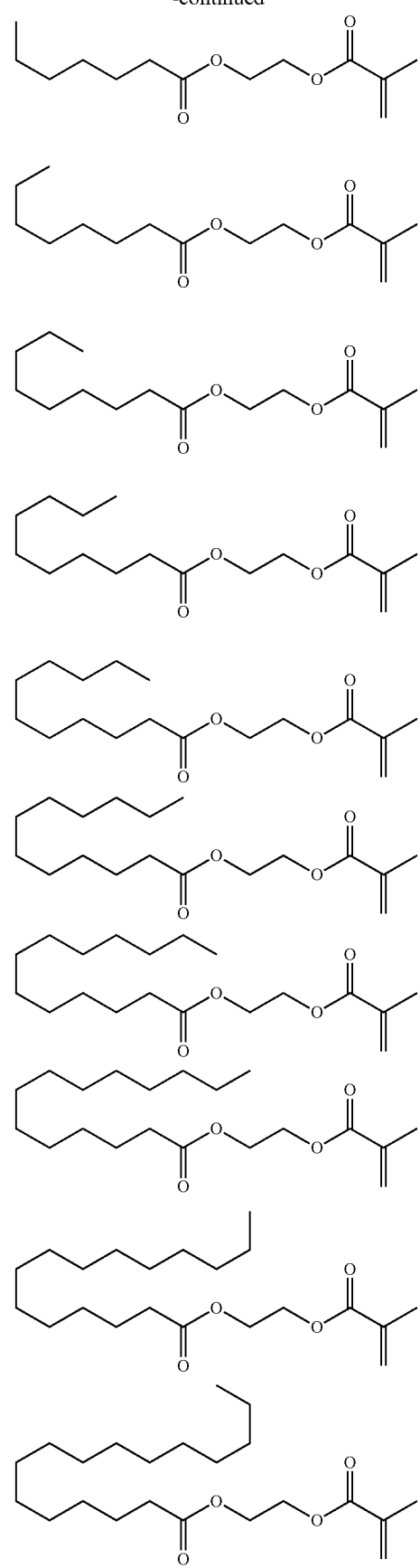

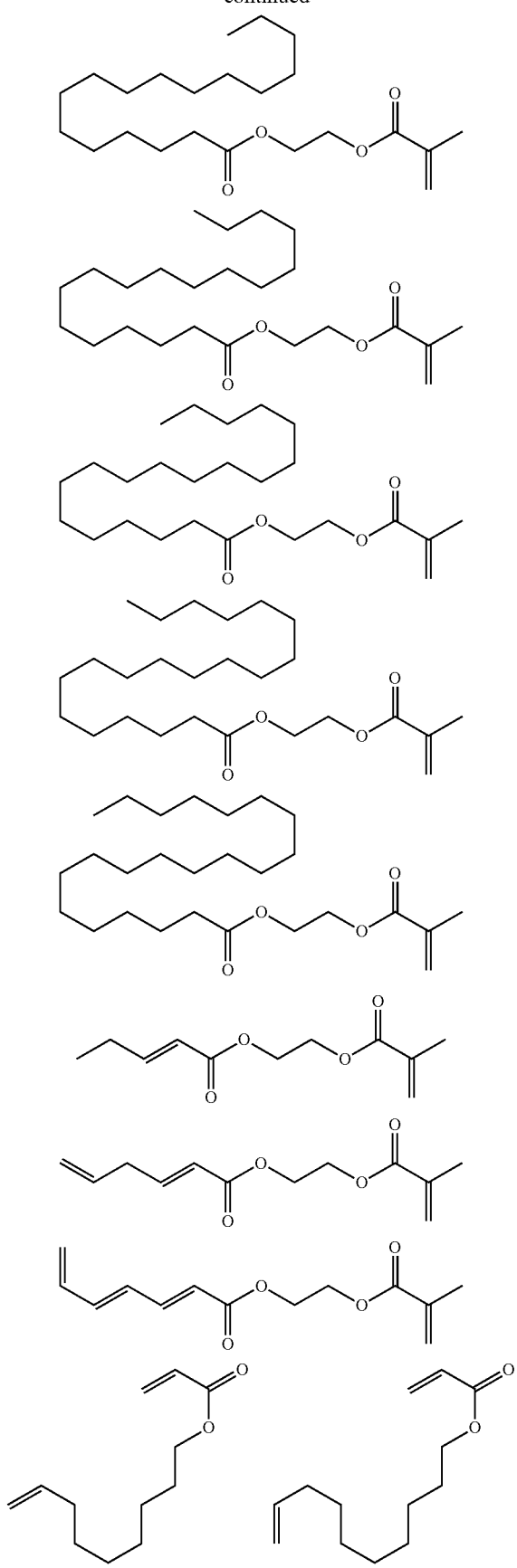
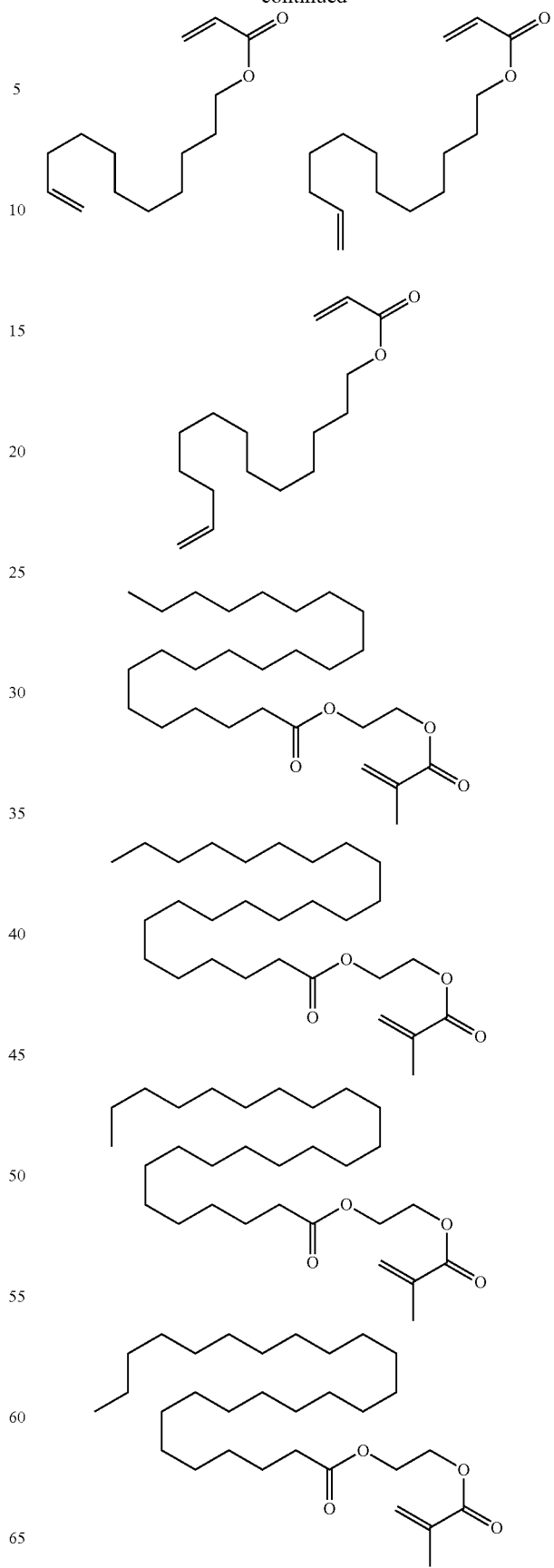

165
-continued
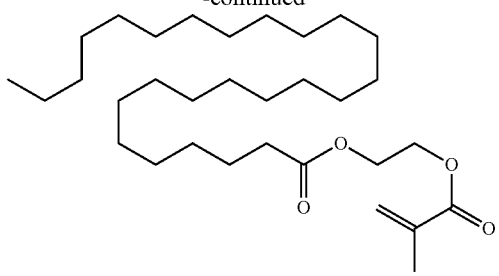
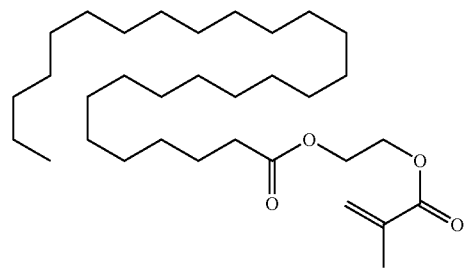
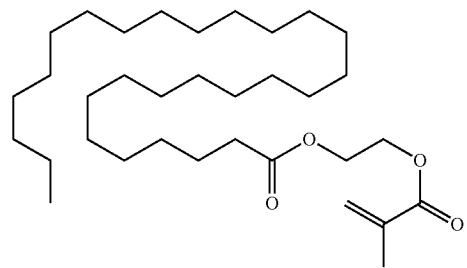
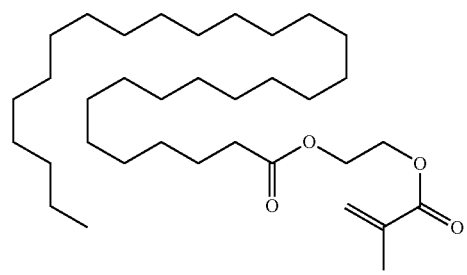
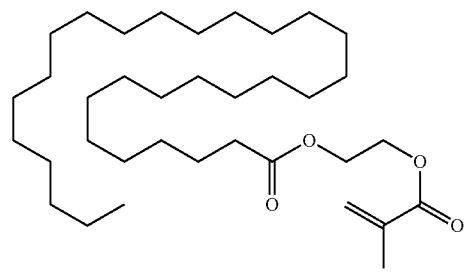
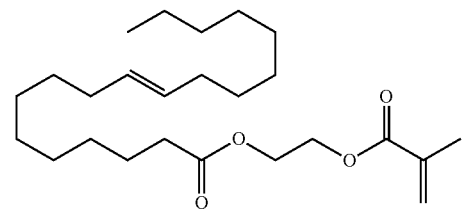
166
-continued
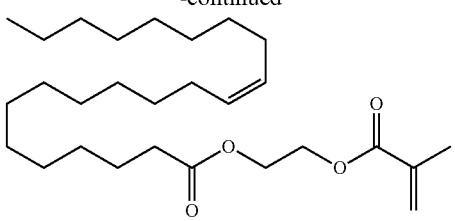
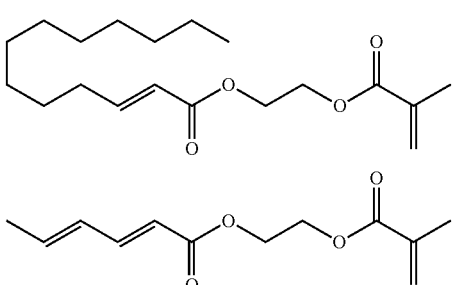
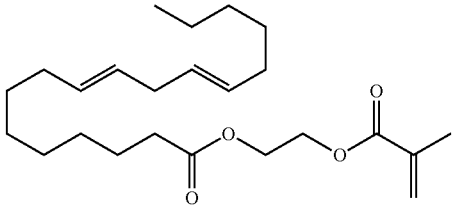
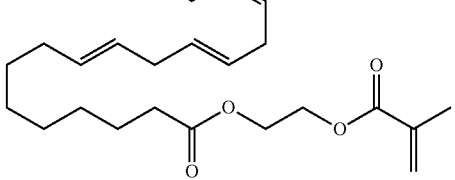
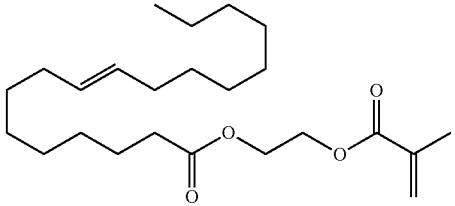
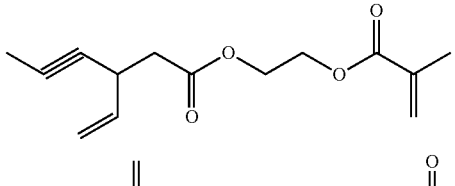
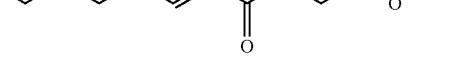
(Repeating Unit-e)
Further, it is also possible to copolymerize a crosslinkable repeating unit-e. Examples of the crosslinkable repeating unit-e include repeating units having an oxirane ring or an oxetane ring.
Specific examples of monomers to give the repeating unit-e having an oxirane ring or an oxetane ring include the following.

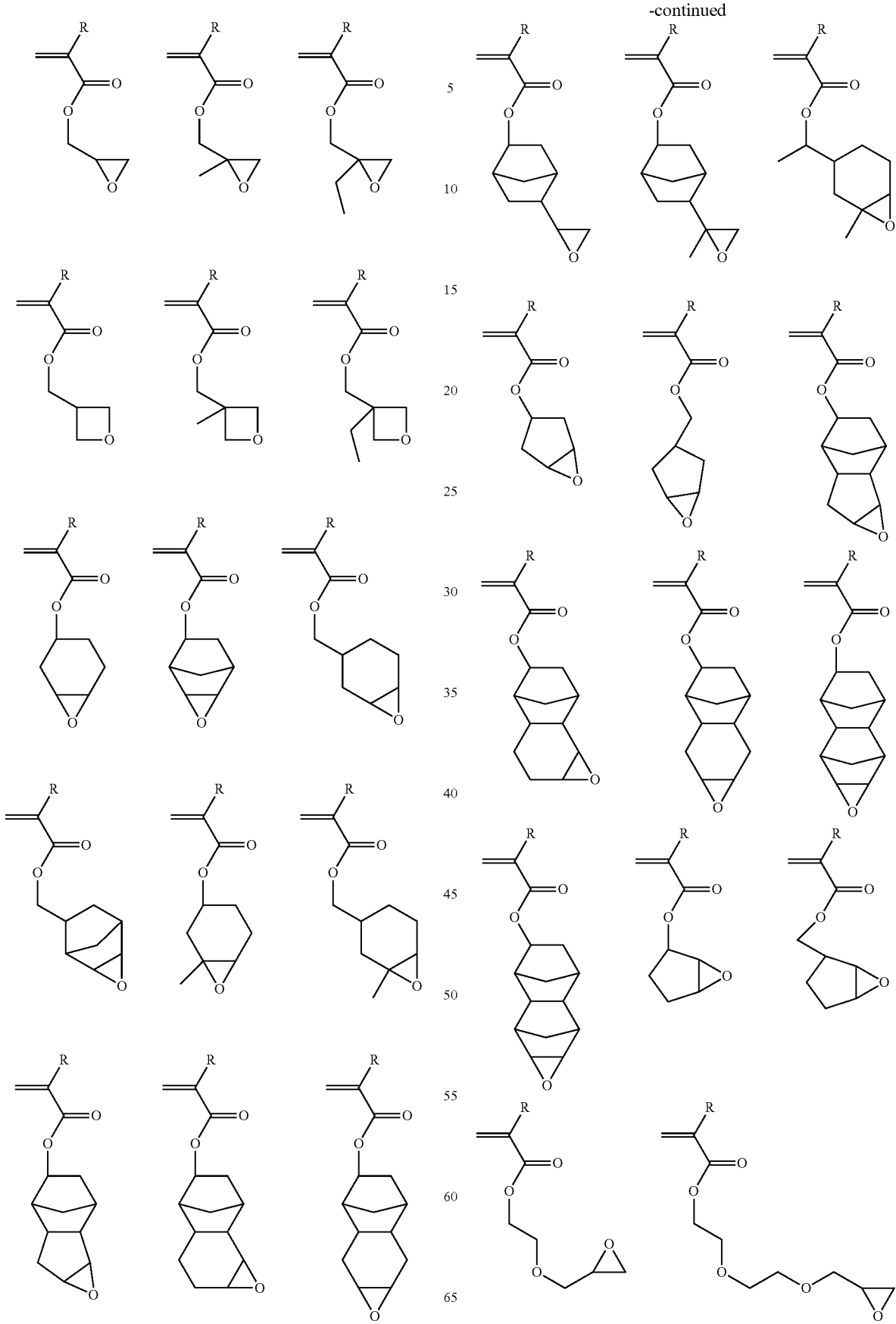

-continued

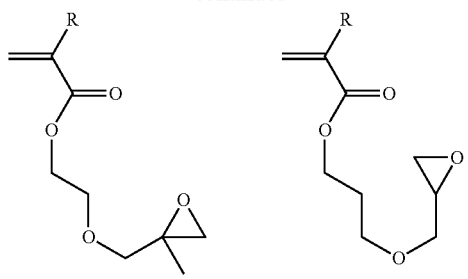

In these formulae, R represents a methyl group or a hydrogen atom.

(Repeating Unit-f)

The polymer compound (A) (component (A)) of the inventive bio-electrode composition can contain a repeating unit-f having silicon, in addition to the repeating units-a1 to -a7 and the optional repeating unit(s) selected from the group consisting of the repeating units-b to -e. Specific examples of a monomer to give the repeating unit-f include the following. In the following, "n" is 0 to 100.

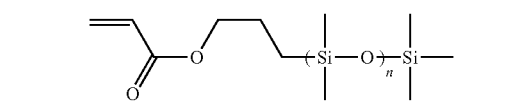
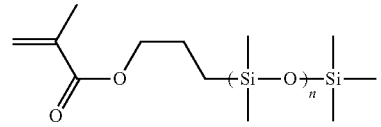
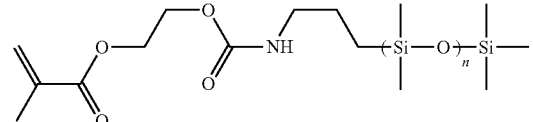
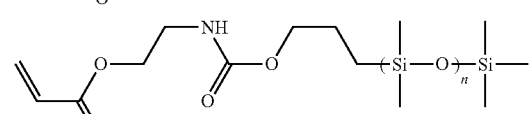
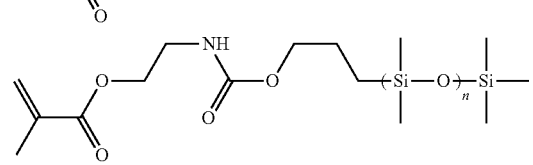
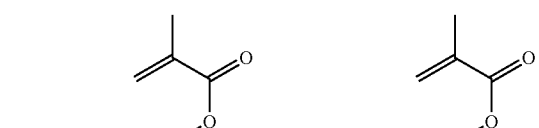
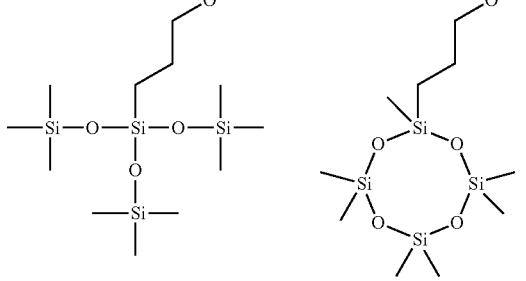

-continued

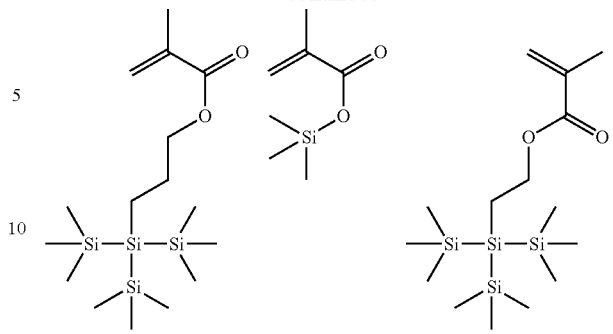
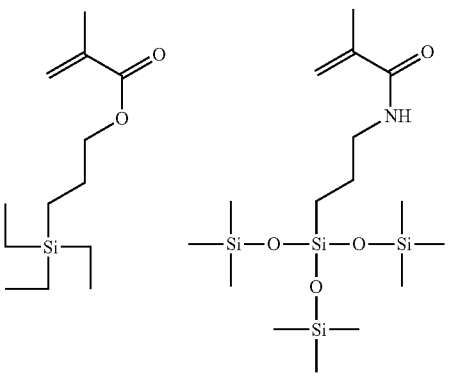
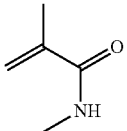
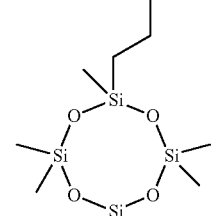
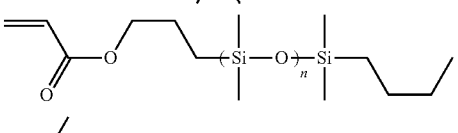
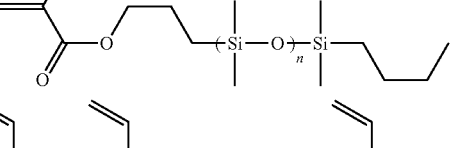
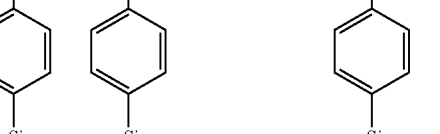
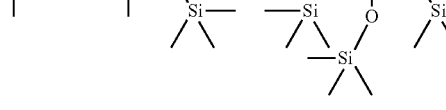

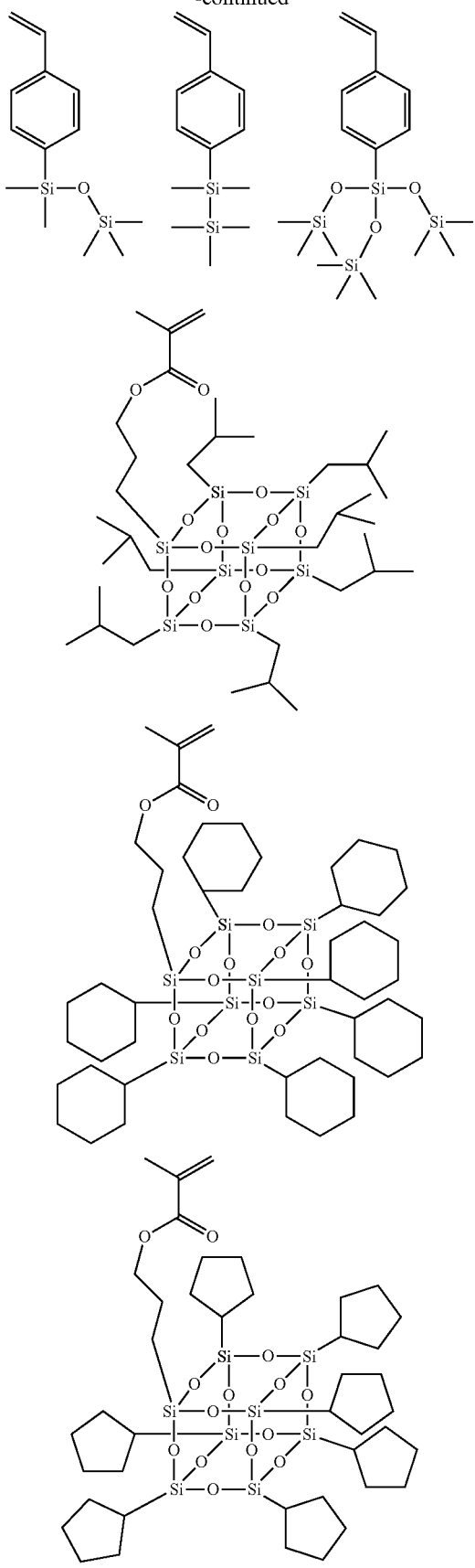

(Repeating Unit-g)

The polymer compound (A) (component (A)) of the inventive bio-electrode composition can contain a repeating unit-g having fluorine, in addition to the repeating units-a1 to -a7 and the optional repeating unit(s) selected from the group consisting of the repeating units-b to -f.

Specific examples of a monomer to give the repeating unit-g having fluorine include the following.

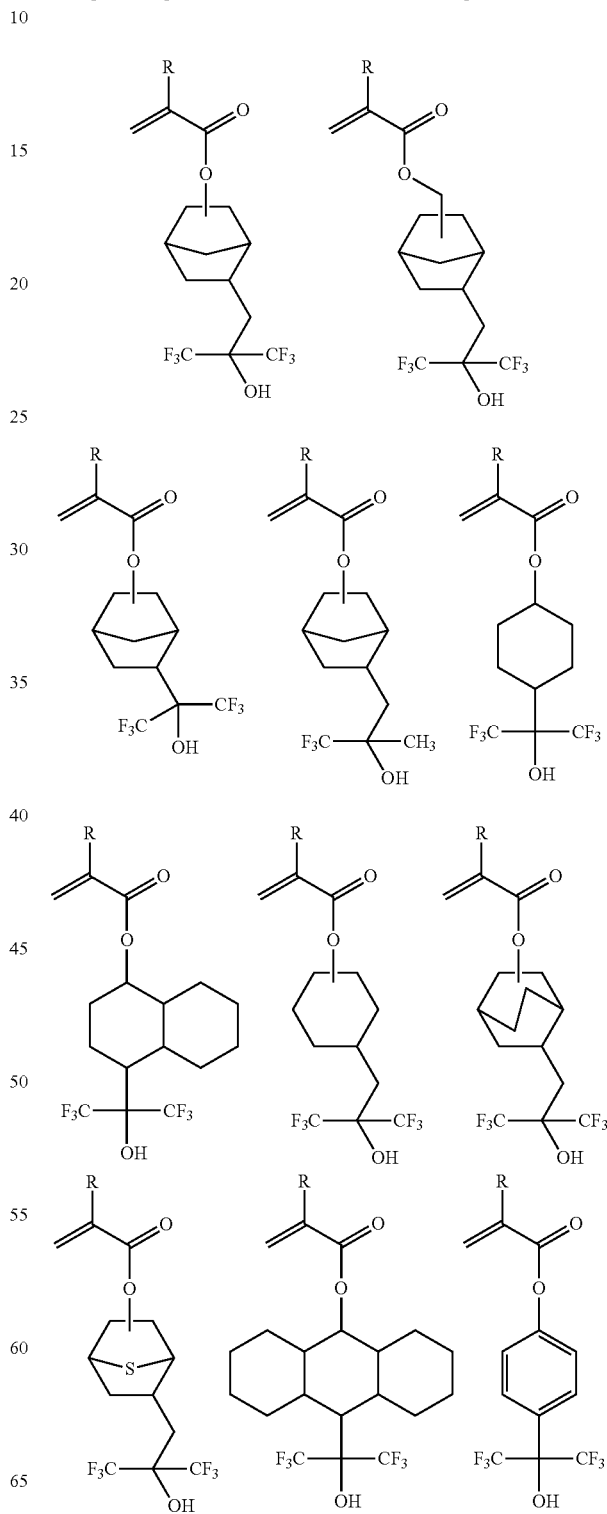

-continued
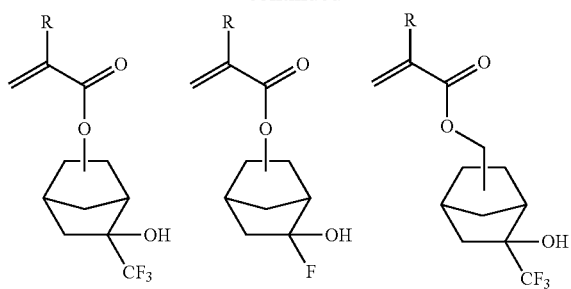
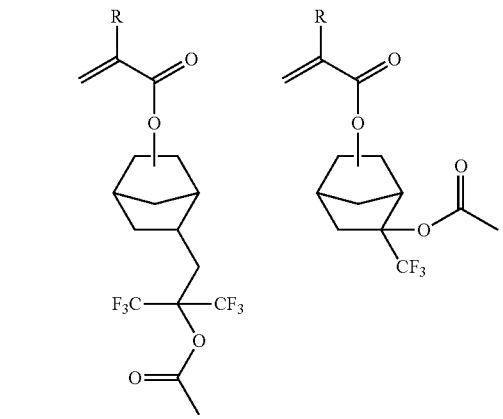
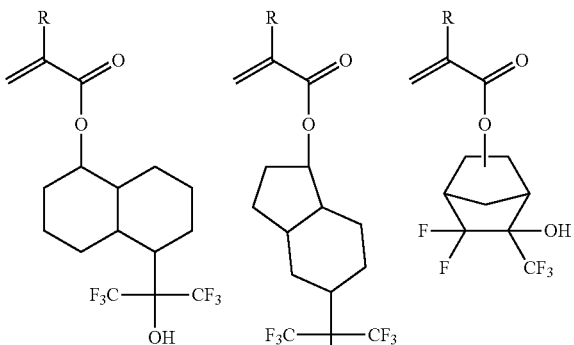
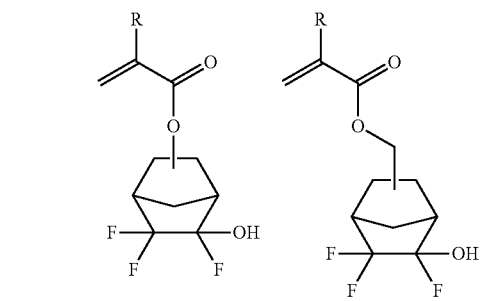
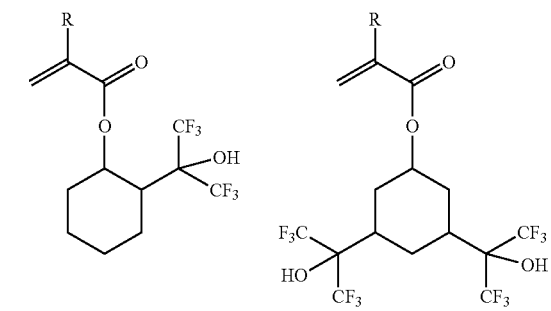
-continued
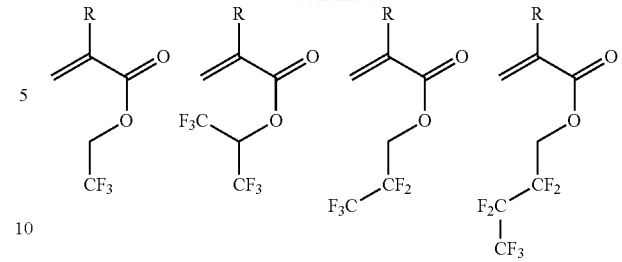
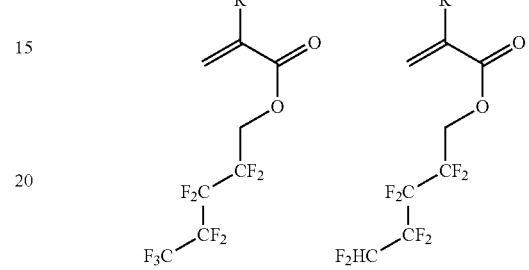
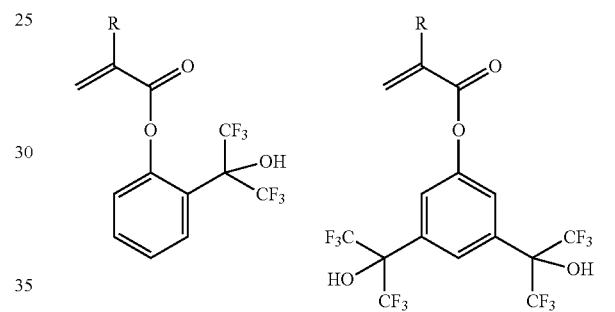
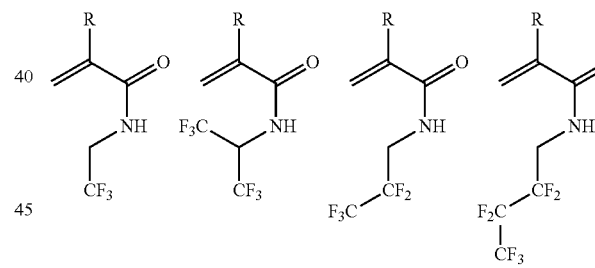
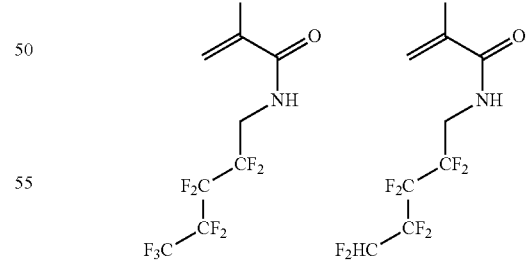
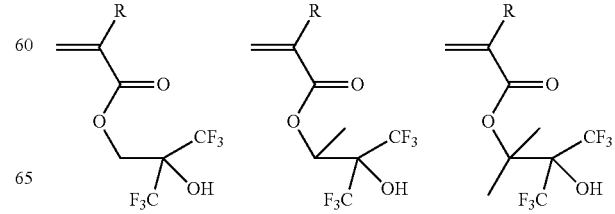

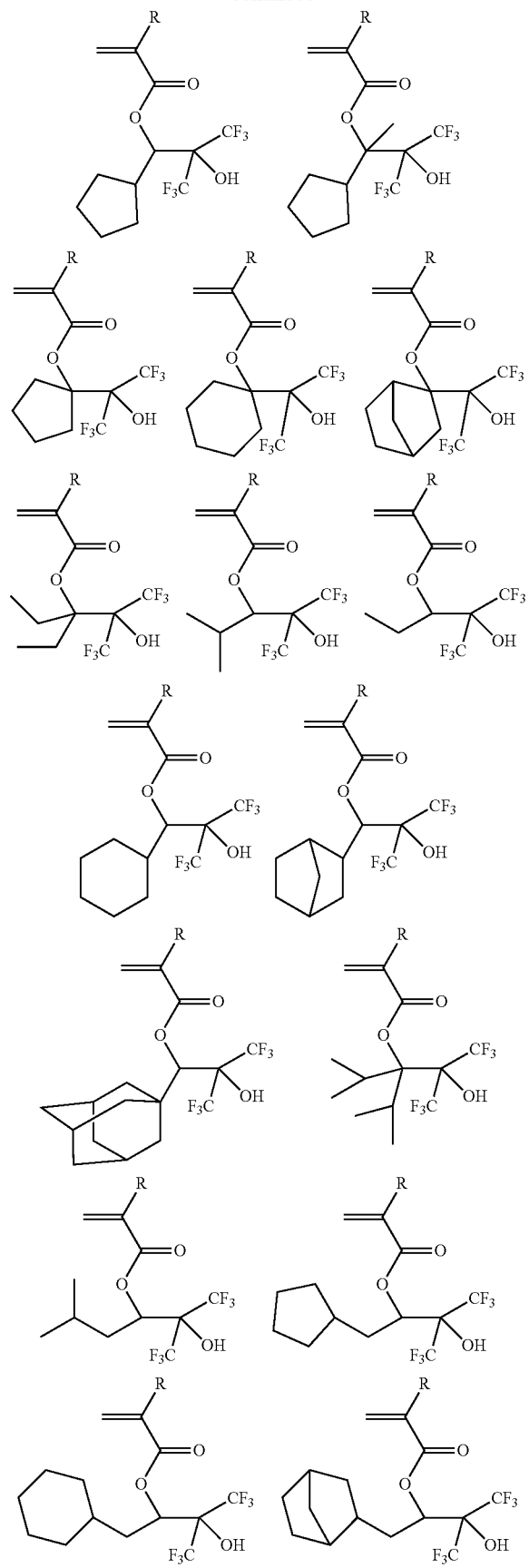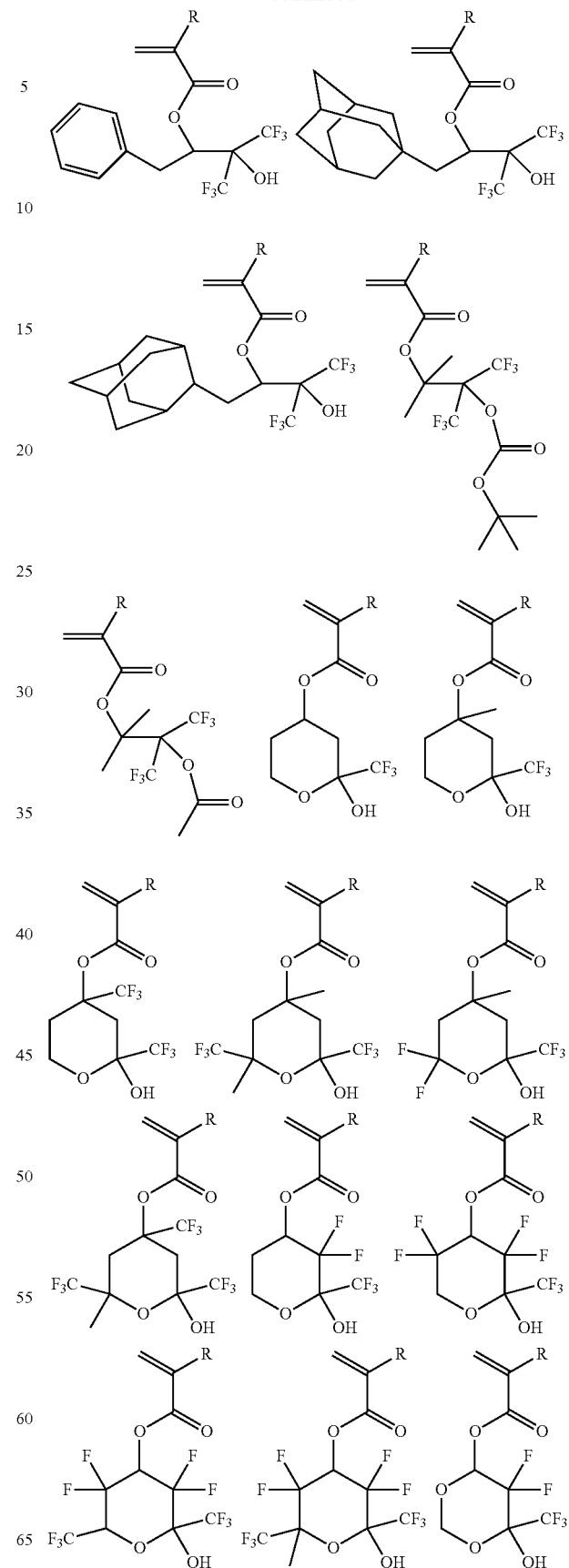

-continued
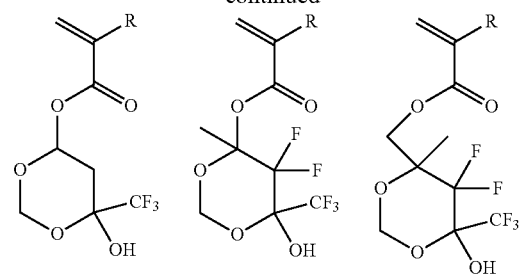
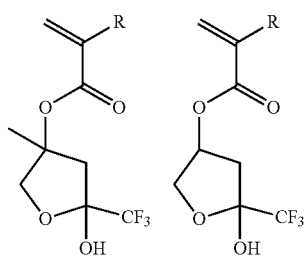
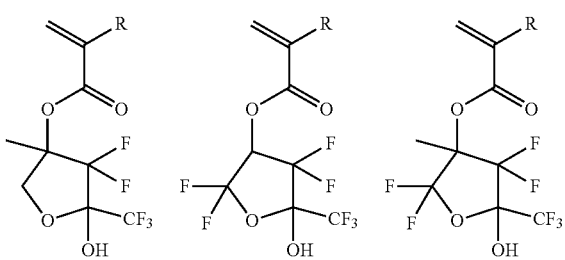
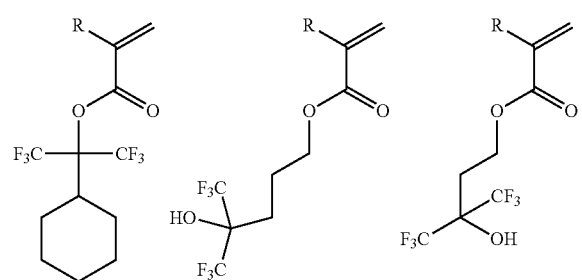
-continued
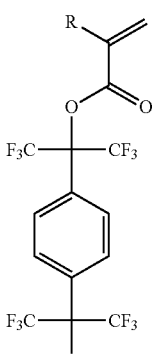
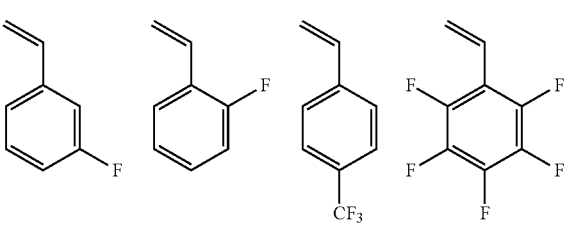
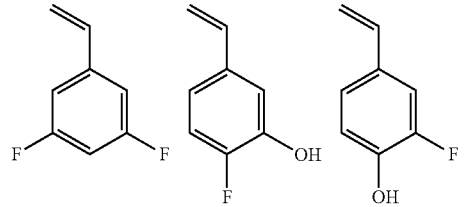
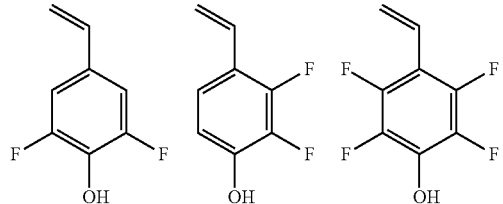
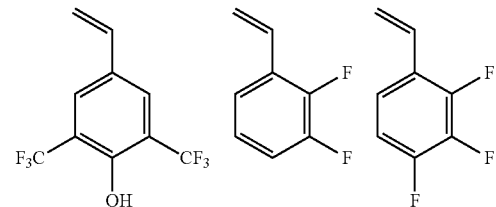

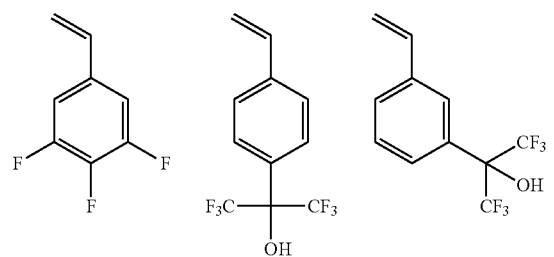
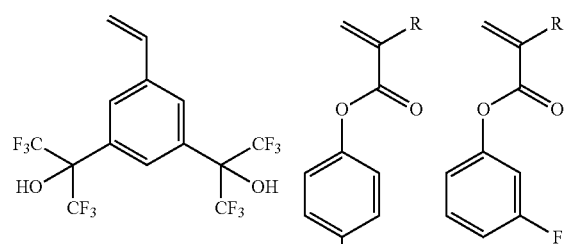
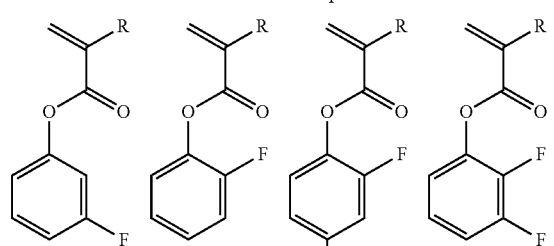
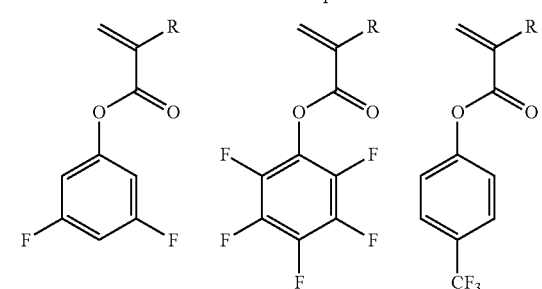
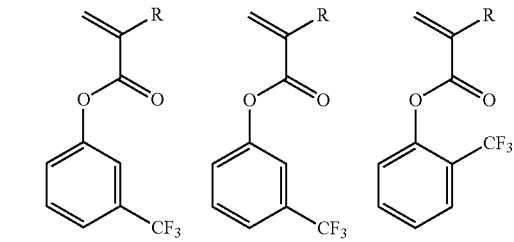
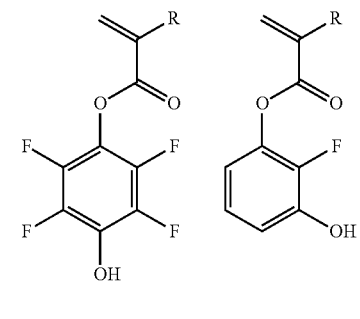
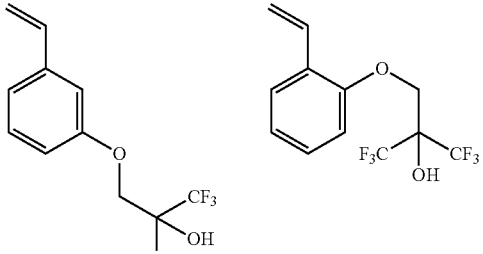
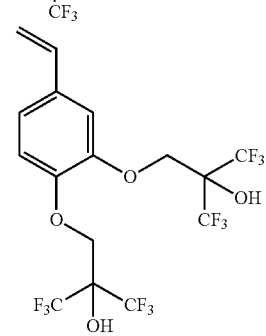
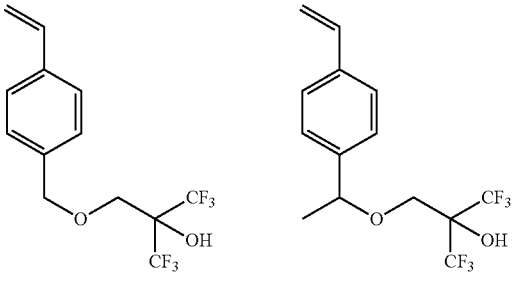
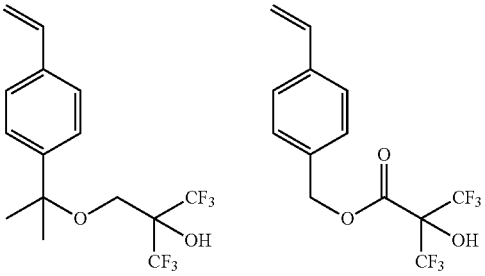
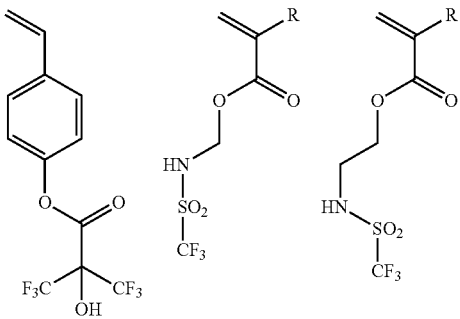

-continued

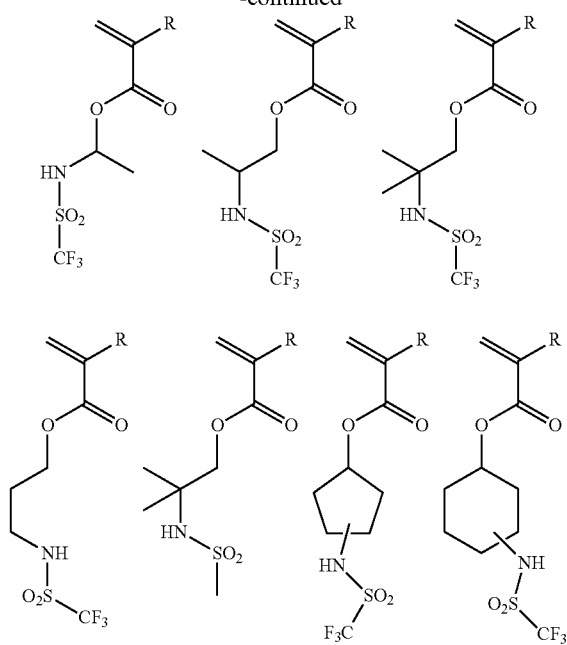

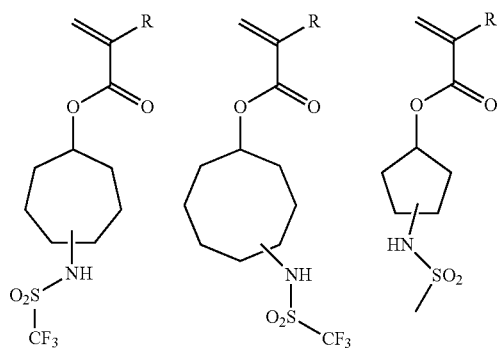

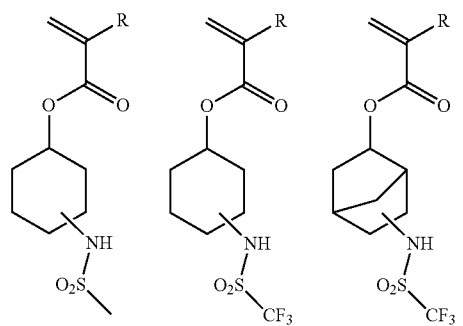

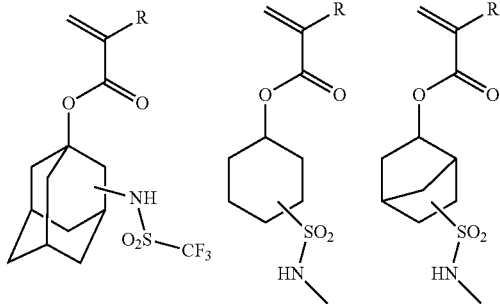

-continued

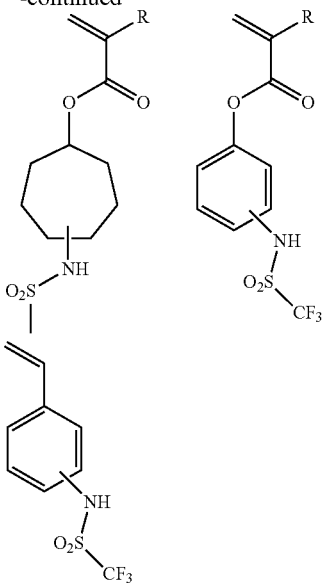

In these formulae, R represents a hydrogen atom or a methyl group.

As one of the method for synthesizing the component (A) that is the polymer compound (A), a copolymer compound can be obtained, for example, by a method in which desired monomer(s) among the monomers to give the repeating units-a1 to -a7, -b, -c, -d, -e, -f, and -g undergo heat polymerization in an organic solvent to which a radical polymerization initiator is added.

Examples of the organic solvent used in the polymerization include toluene, benzene, tetrahydrofuran, diethyl ether, dioxane, etc. Examples of the polymerization initiator include 2,2'-azobisisobutyronitrile (AIBN), 2,2'-azobis(2,4-dimethylvaleronitrile), dimethyl 2,2-azobis(2-methylpropionate), benzoyl peroxide, lauroyl peroxide, etc. The heating temperature is preferably 50 to 80° C., and the reaction time is preferably 2 to 100 hours, more preferably 5 to 20 hours.

Here, the ratios of the repeating units-a1 to -a7, -b, -c, -d, -e, -f, and -g in the polymer compound (A) (polymer (A)) may be $0 \le a1 \le 1.0$, $0 \le a2 \le 1.0$, $0 \le a3 \le 1.0$, $0 \le a4 \le 1.0$, $0 \le a5 \le 1.0$, $0 \le a6 \le 1.0$, $0 \le a7 \le 1.0$, $0 < a1+a2+a3+a4+a5+a6+a7 \le 1.0$, $0 \le b < 1.0$, $0 \le c < 1.0$, $0 \le d < 1.0$, $0 \le e < 0.9$, $0 \le f < 0.9$, and $0 \le g < 0.9$; preferably $0 \le a1 \le 0.9$, $0 \le a2 \le 0.9$, $0 \le a3 \le 0.9$, $0 \le a4 \le 0.9$, $0 \le a5 \le 0.9$, $0 \le a6 \le 0.9$, $0 \le a7 \le 0.9$, $0.01 \le a1+a2+a3+a4+a5+a6+a7 \le 0.9$, $0.03 \le b \le 0.9$, $0 \le c \le 0.8$, $0 \le d \le 0.8$, $0 \le e < 0.8$, $0 \le f < 0.8$, and $0 \le g < 0.8$; more preferably $0 \le a1 \le 0.8$, $0 \le a2 \le 0.8$, $0 \le a3 \le 0.8$, $0 \le a4 \le 0.8$, $0 \le a5 \le 0.8$, $0 \le a6 \le 0.8$, $0 \le a7 \le 0.8$, $0.02 \le a1+a2+a3+a4+a5+a6+a7 \le 0.8$, $0.05 \le b \le 0.9$, $0 \le c \le 0.7$, $0 \le d \le 0.5$, $0 \le e \le 0.3$, $0 \le f < 0.7$, and $0 \le g < 0.7$.

Incidentally, for example, a1+a2+a3+a4+a5+a6+a7+b+c+d+e+f+g=1 means that the total amount of the repeating units-a1, -a2, -a3, -a4, -a5, -a6, -a7, -b, -c, -d, -e, -f, and -g is 100 mol % on the basis of the total amount of the whole repeating units in the polymer compound (A) containing the repeating units-a1, -a2, -a3, -a4, -a5, -a6, -a7, -b, -c, -d, -e, -f, and -g; and a1+a2+a3+a4+a5+a6+a7+b+c+d+e+f+g<1 means that the total amount of the repeating units-a1, -a2, -a3, -a4, -a5, -a6, -a7, -b, -c, -d, -e, -f, and -g is less than 100 mol % on the basis of the total amount of the whole repeating units, which indicates that the polymer compound (A) contains another repeating unit(s) besides the repeating units-a1, -a2, -a3, -a4, -a5, -a6, -a7, -b, -c, -d, -e, -f, and -g.

Regarding the molecular weight of the polymer compound (A) (component (A)), the weight-average molecular weight is preferably 500 or more, more preferably 1,000 or more and 1,000,000 or less, further preferably 2,000 or more and 500,000 or less. Regarding the ionic monomer (residual monomer) that is not incorporated into the component (A) after polymerization, if the amount is small, the residual monomer can be prevented from permeating to skin in a biocompatibility test to cause allergy. Accordingly, it is preferable to decrease the amount of residual monomer(s). The amount of residual monomer(s) is preferably 10 parts by mass or less on the basis of 100 parts by mass of the whole component (A). As the component (A), one kind of the polymer compound may be used singly or in admixture of two or more kinds which differ in molecular weight, dispersity, and constitutive polymerizable monomer.

The weight-average molecular weight of the polymer compound (A) can be determined by gel permeation chromatography (GPC) using tetrahydrofuran (THF) as a solvent.

[(B) Silicone Compound]

The inventive bio-electrode composition is also characterized by containing the silicone compound (B) (component (B)) having a polyglycerin structure. The component (B) is blended in an amount of preferably 0.01 to 100 parts by mass, more preferably 0.5 to 60 parts by mass, on the basis of 100 parts by mass of the component (A). One kind of the component (B) may be used singly or in admixture of two or more kinds.

The silicone compound (B) having the polyglycerin structure is preferably shown by the following general formula (4) or (5).

identical to or different from each other and independently represents the $R^{1\prime}$ group, the $R^{2\prime}$ group, or an oxygen atom. When $R^{4\prime}$ represents an oxygen atom, the $R^{4\prime}$ moieties bond to each other and optionally constitute an ether group to form a ring together with silicon atoms. In the formulae (4), (5), and (6), each a' is identical to or different from each other and represents 0 to 100, b' represents 0 to 100, and a'+b' is 0 to 200. Nevertheless, in the formula (4), when b' is 0, at least one $R^{3\prime}$ is the $R^{2\prime}$ group. In the formulae (4)-1, (4)-2, and (5), $R^{5\prime}$ represents an alkylene group having 2 to 10 carbon atoms or an aralkylene group having 7 to 10 carbon atoms. c' represents 0 to 20. d' represents 1 to 20. In the formulae (4)-1, (5), and (6), $R^{6\prime}$ and $R^{7\prime}$ each represent an alkylene group having 2 to 6 carbon atoms. $R^{8\prime}$ represents an alkylene group having 2 to 6 carbon atoms, or an ether group. $R^{9\prime}$ represents a hydrogen atom, a linear or branched alkyl group having 1 to 50 carbon atoms and optionally containing an ether group, or a phenyl group.

In one embodiment, the silicone compound (B) having the polyglycerin structure is shown by the general formula (4). In this formula (4), each $R^{1\prime}$ is identical to or different from each other and independently represents a linear or branched alkyl group having 1 to 10 carbon atoms, or a phenyl group. $R^{2\prime}$ represents a group having a polyglycerin group structure shown by a formula (4)-1 or (4)-2. Each $R^{3\prime}$ is identical to or different from each other and independently represents the $R^{1\prime}$ group or the $R^{2\prime}$ group. Each $R^{4\prime}$ is identical to or different from each other and independently represents the $R^{1\prime}$ group, the $R^{2\prime}$ group, or an oxygen atom. When $R^{4\prime}$ is an oxygen atom, the $R^{4\prime}$ moieties bond to each other and may constitute a single ether group to form a ring together with

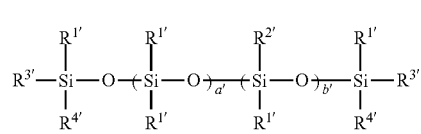

(4)

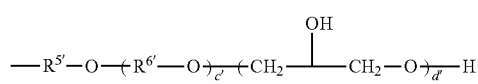

(4)-1

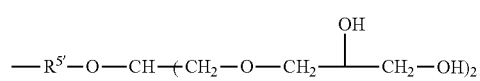

(4)-2

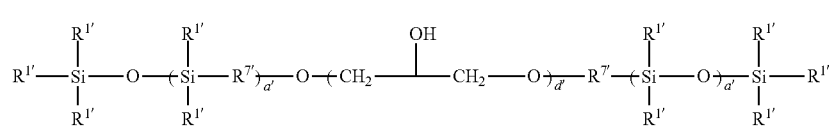

(5)

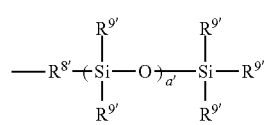

(6)

In the formulae (4) and (5), each $R^{1\prime}$ is identical to or different from each other and independently represents a hydrogen atom, a linear or branched alkyl group having 1 to 50 carbon atoms and optionally containing an ether group, a phenyl group, or a silicone chain shown by a general formula (6). $R^{2\prime}$ represents a group having a polyglycerin group structure shown by a formula (4)-1 or (4)-2. Each $R^{3\prime}$ is identical to or different from each other and independently represents the $R^{1\prime}$ group or the $R^{2\prime}$ group. Each $R^{4\prime}$ is silicon atoms. a' represents 0 to 6 and b' represents 0 to 4 such that a'+b' is 0 to 10. Nevertheless, when b' is 0, at least one $R^{3\prime}$ is the $R^{2\prime}$ group. In the formulae (4)-1 and (4)-2, $R^{5\prime}$ represents an alkylene group having 2 to 10 carbon atoms or an aralkylene group having 7 to 10 carbon atoms. c' represents 0 to 10. d' represents 2 to 6. In the formula (4)-1, $R^{6\prime}$ represents $-C_2H_4-$.

Examples of the silicone compound (B) having such a polyglycerin structure include the following.

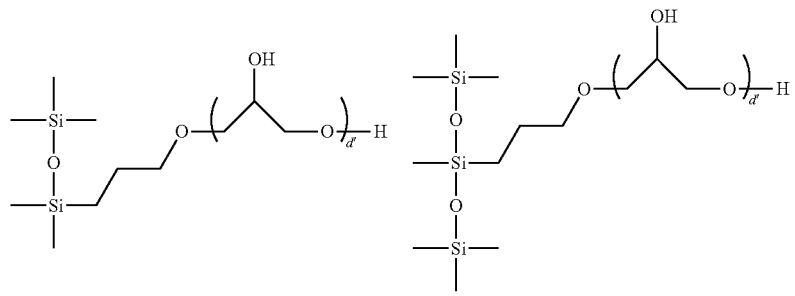
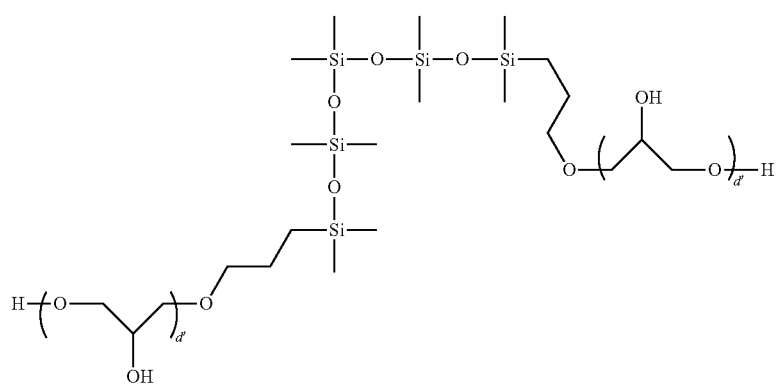
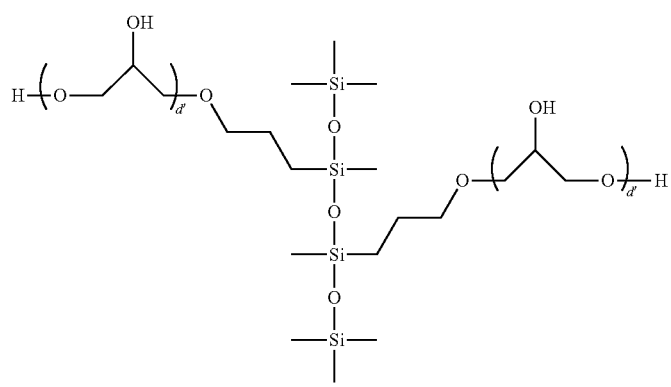
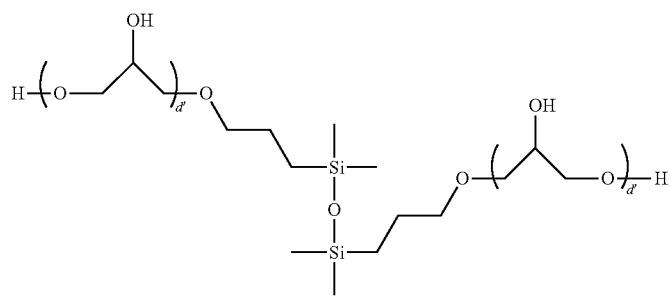

-continued
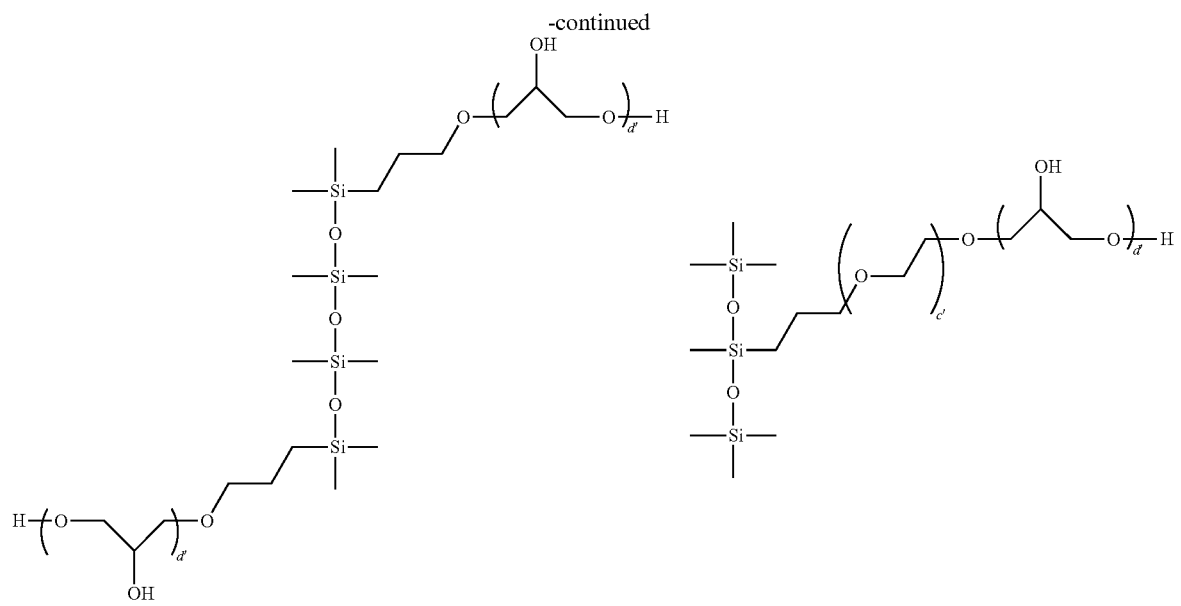
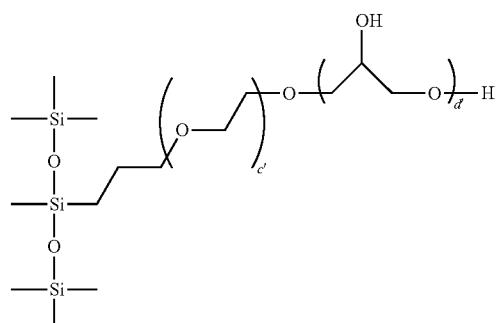
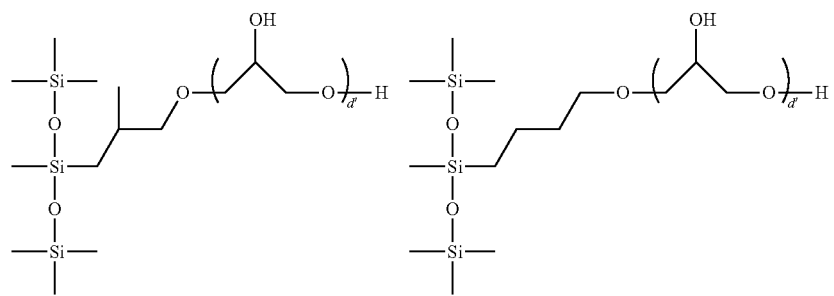
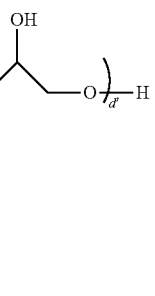
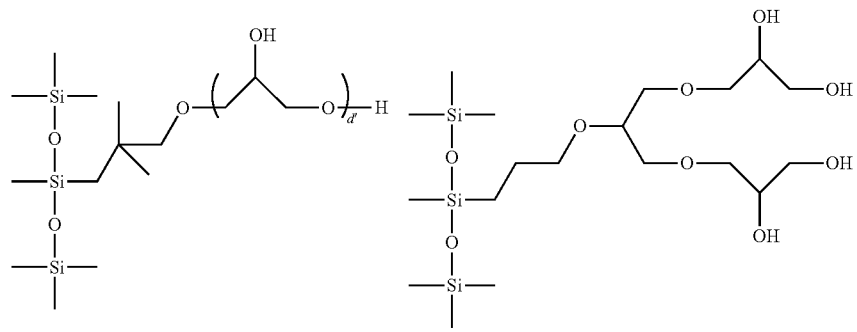
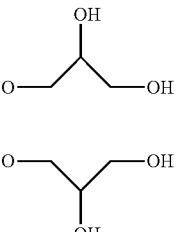
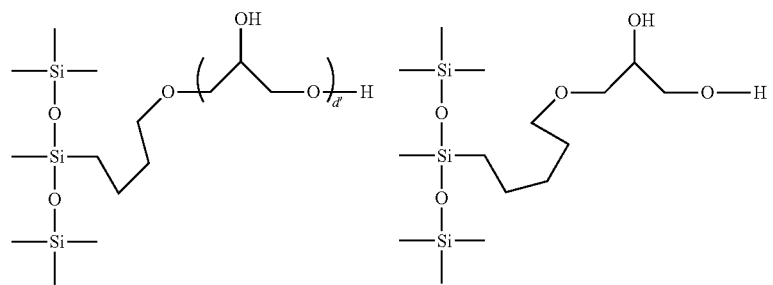
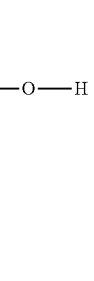

-continued
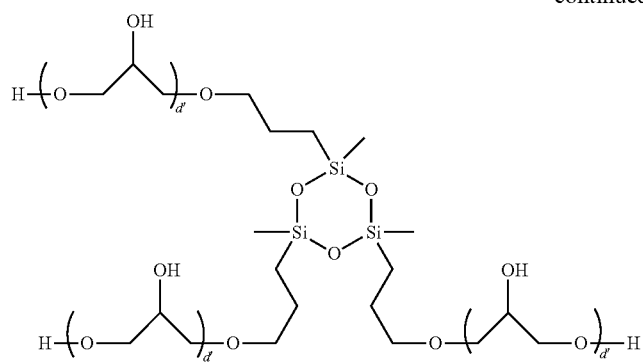
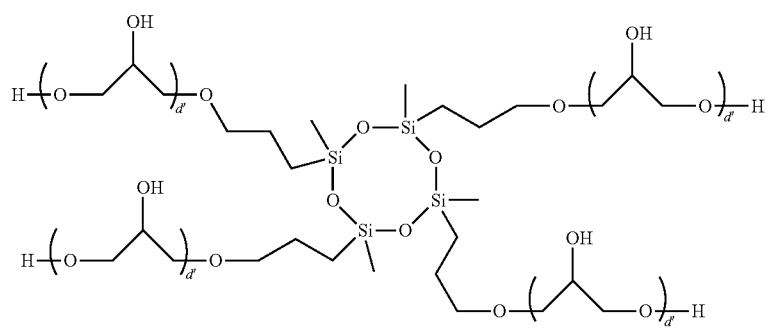
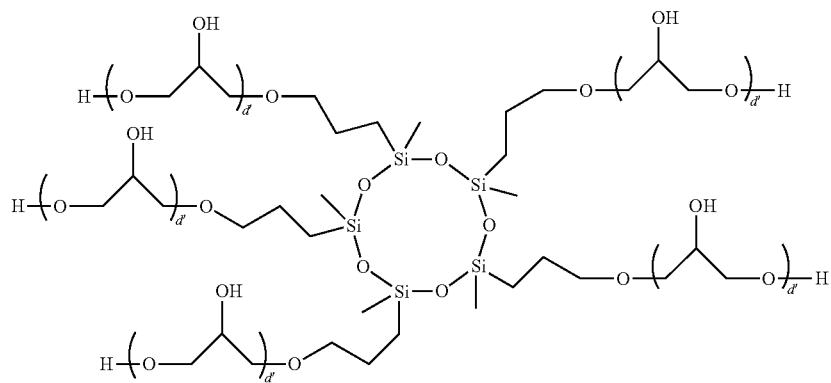
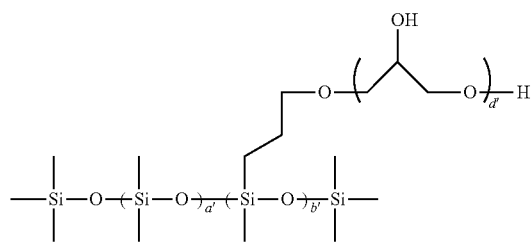
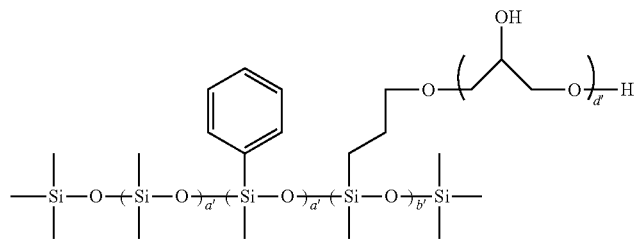

-continued
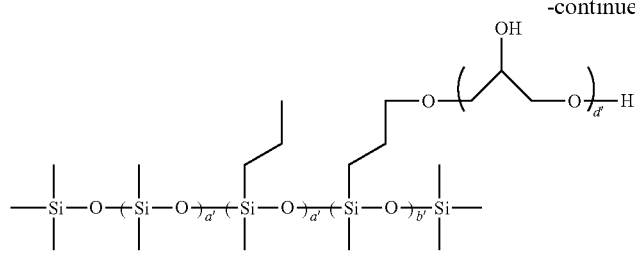
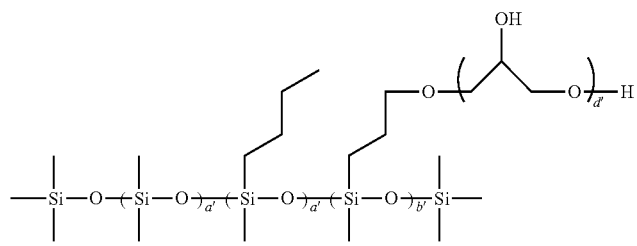
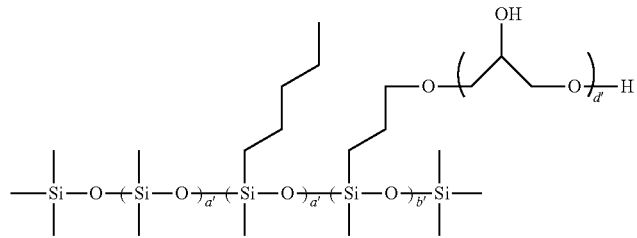
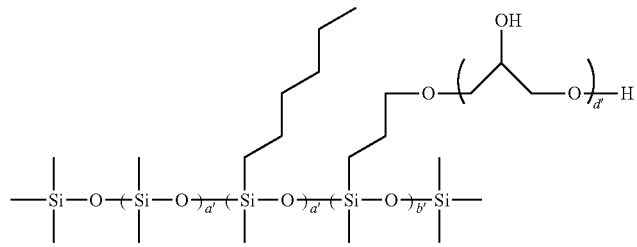
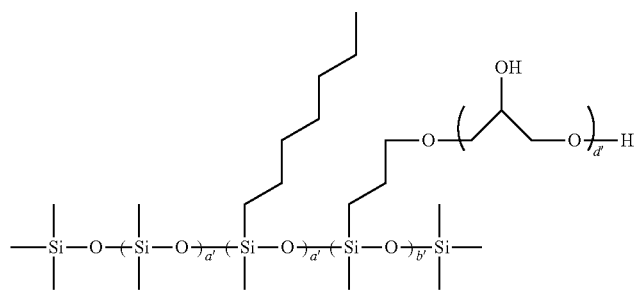
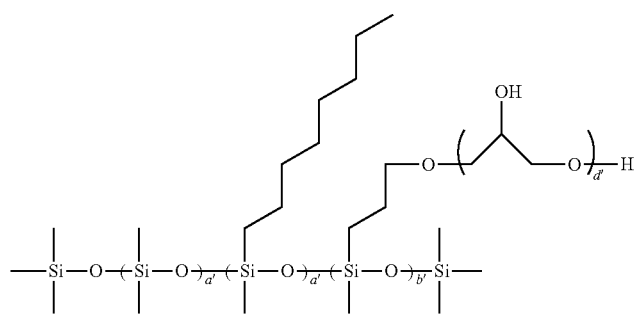

-continued
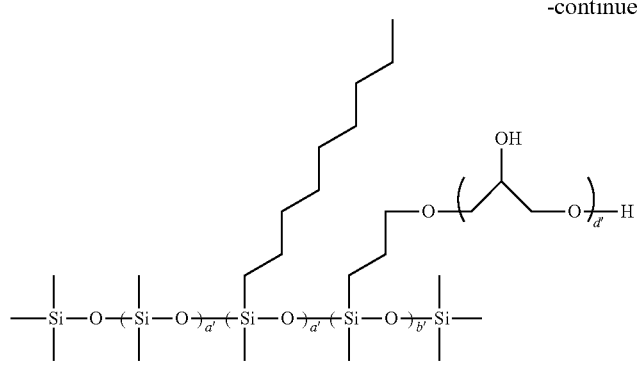
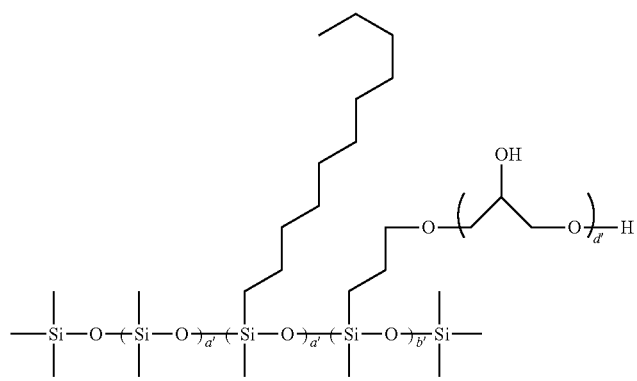
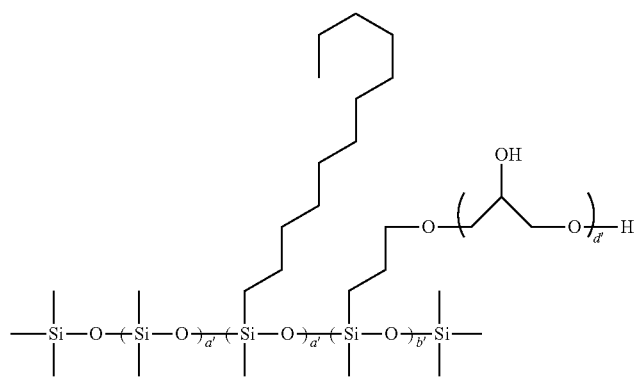
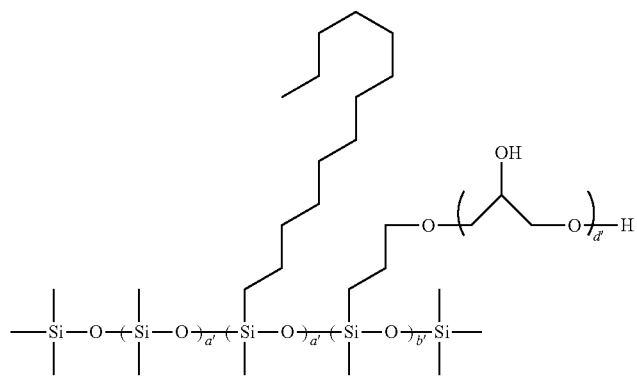

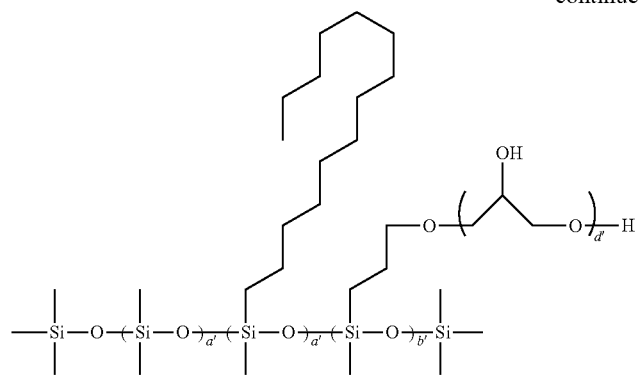
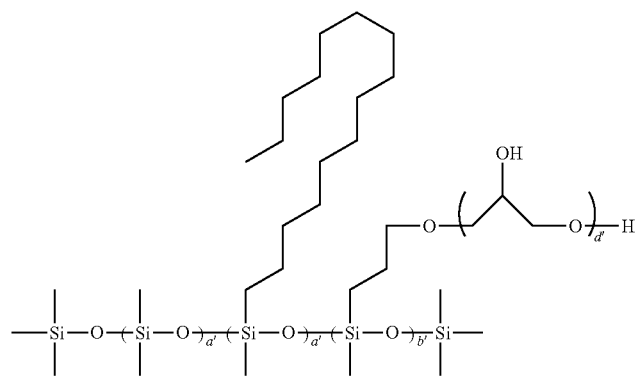
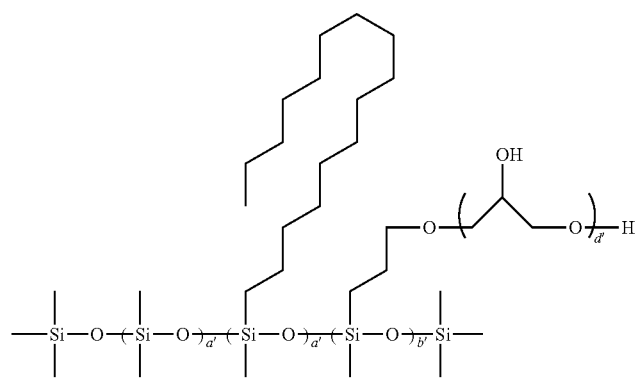
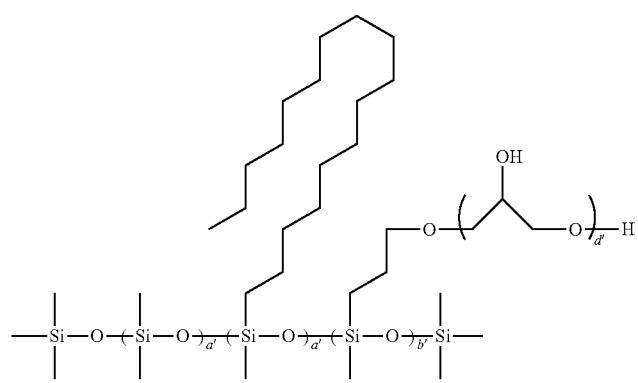

-continued
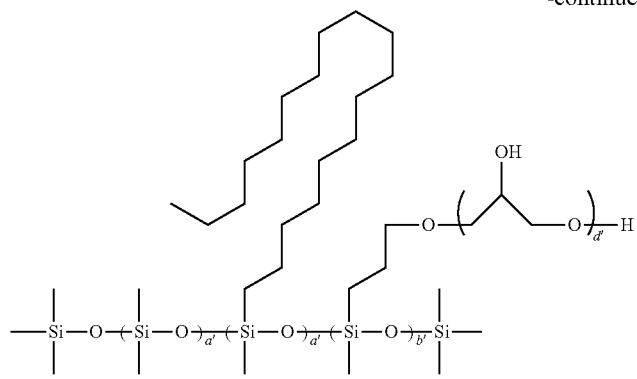
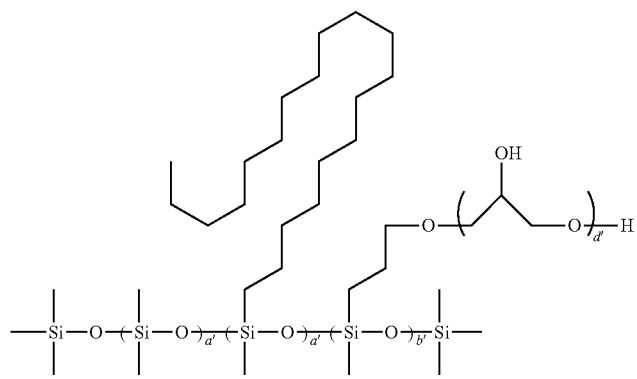
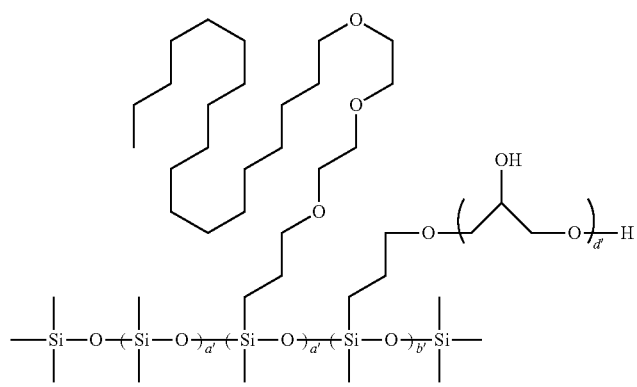
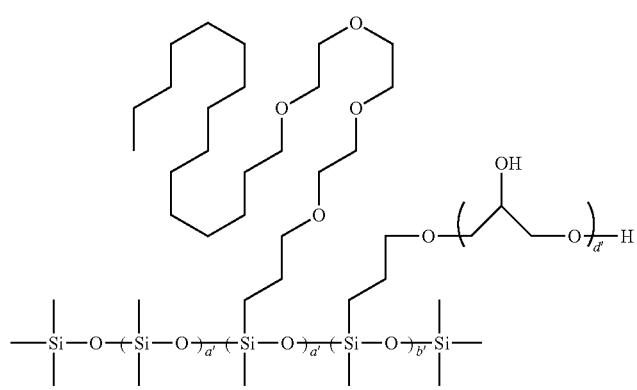

-continued
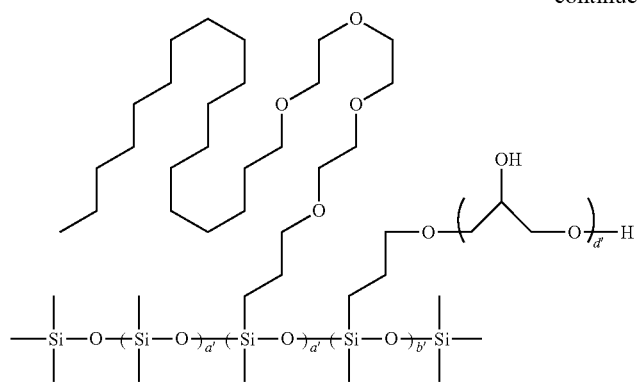
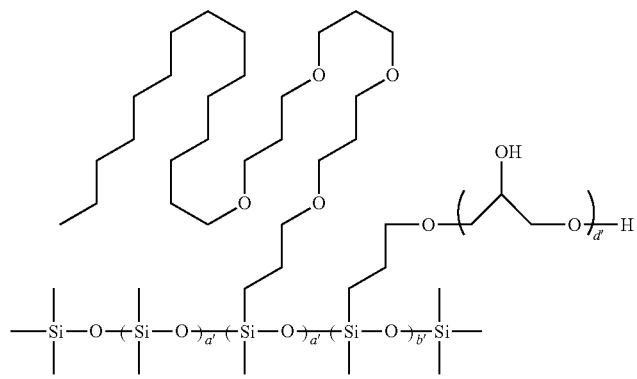
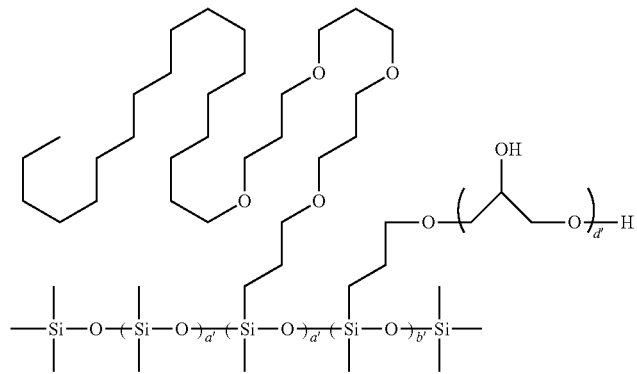
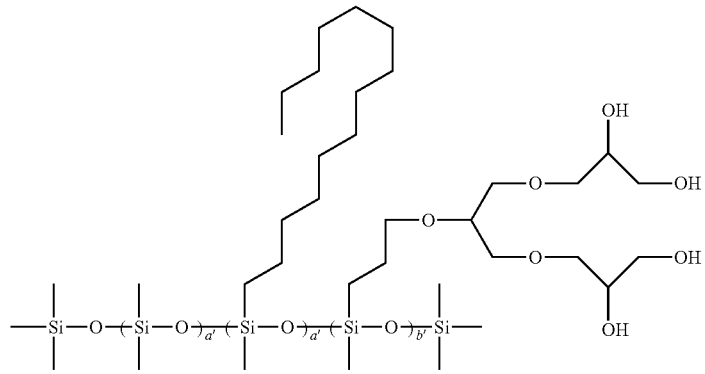

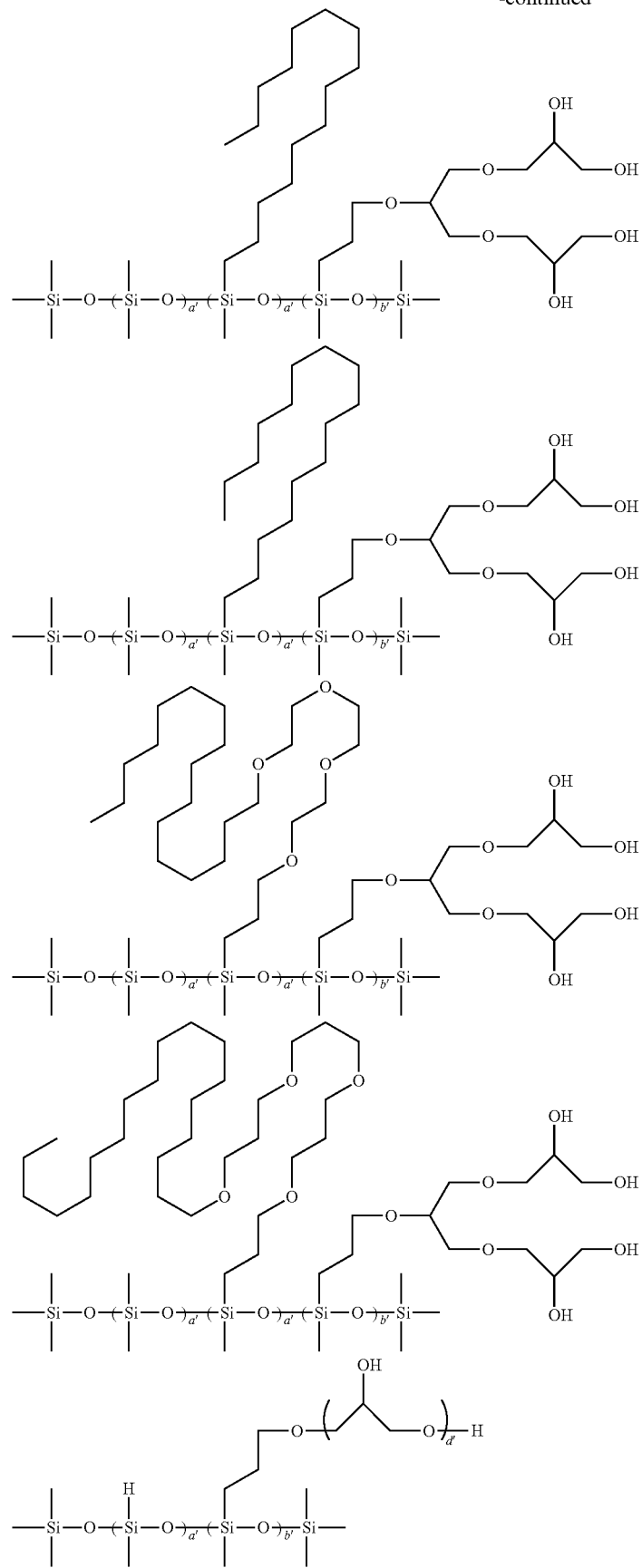

-continued
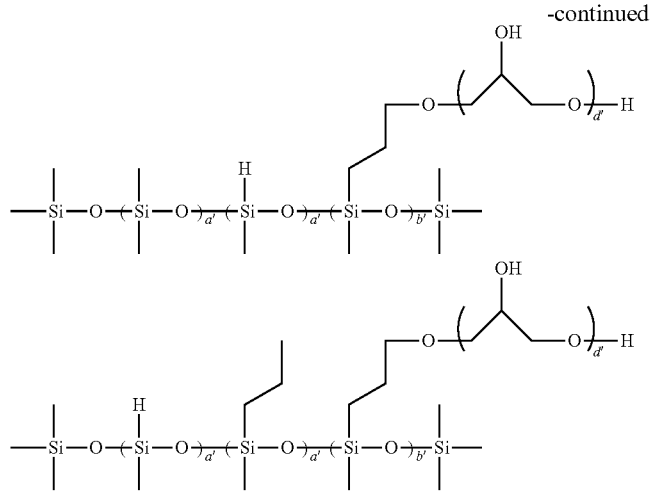
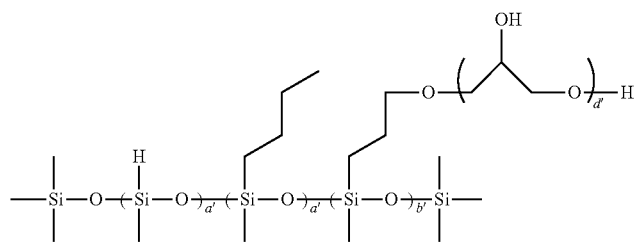
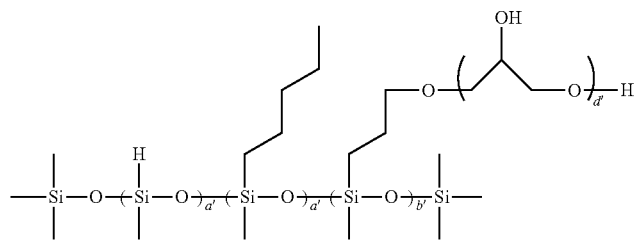
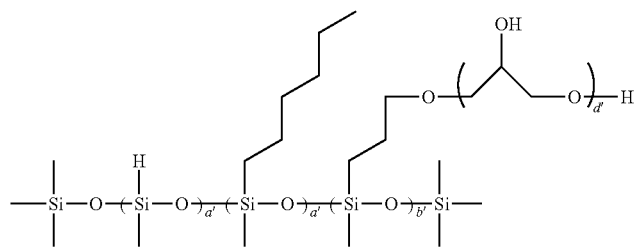
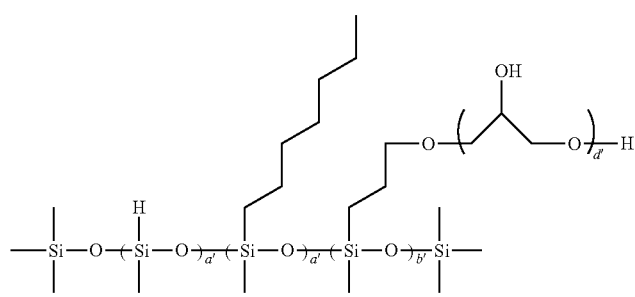

-continued
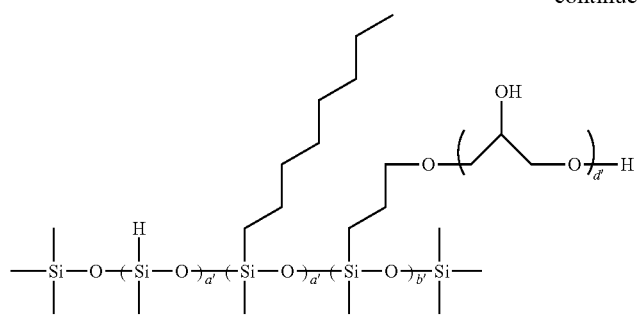
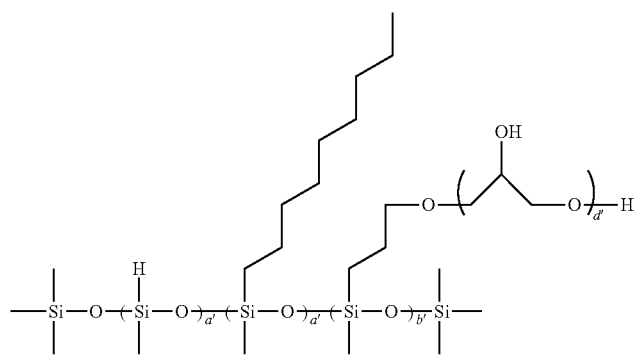
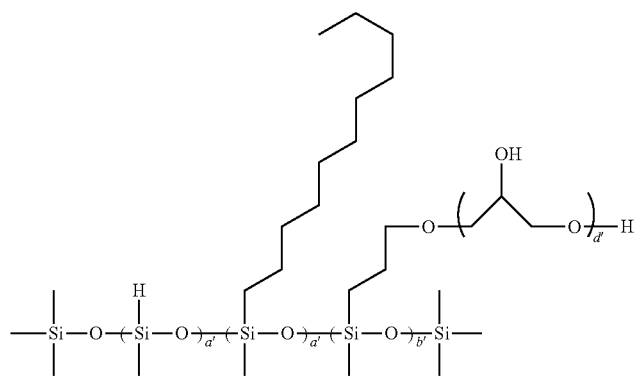
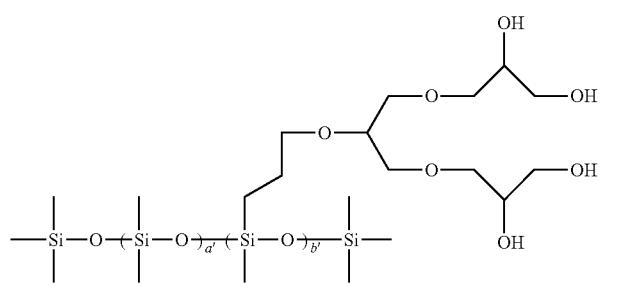
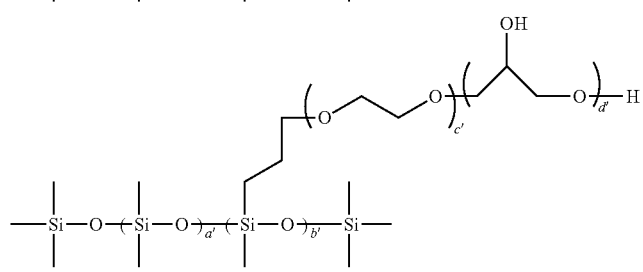

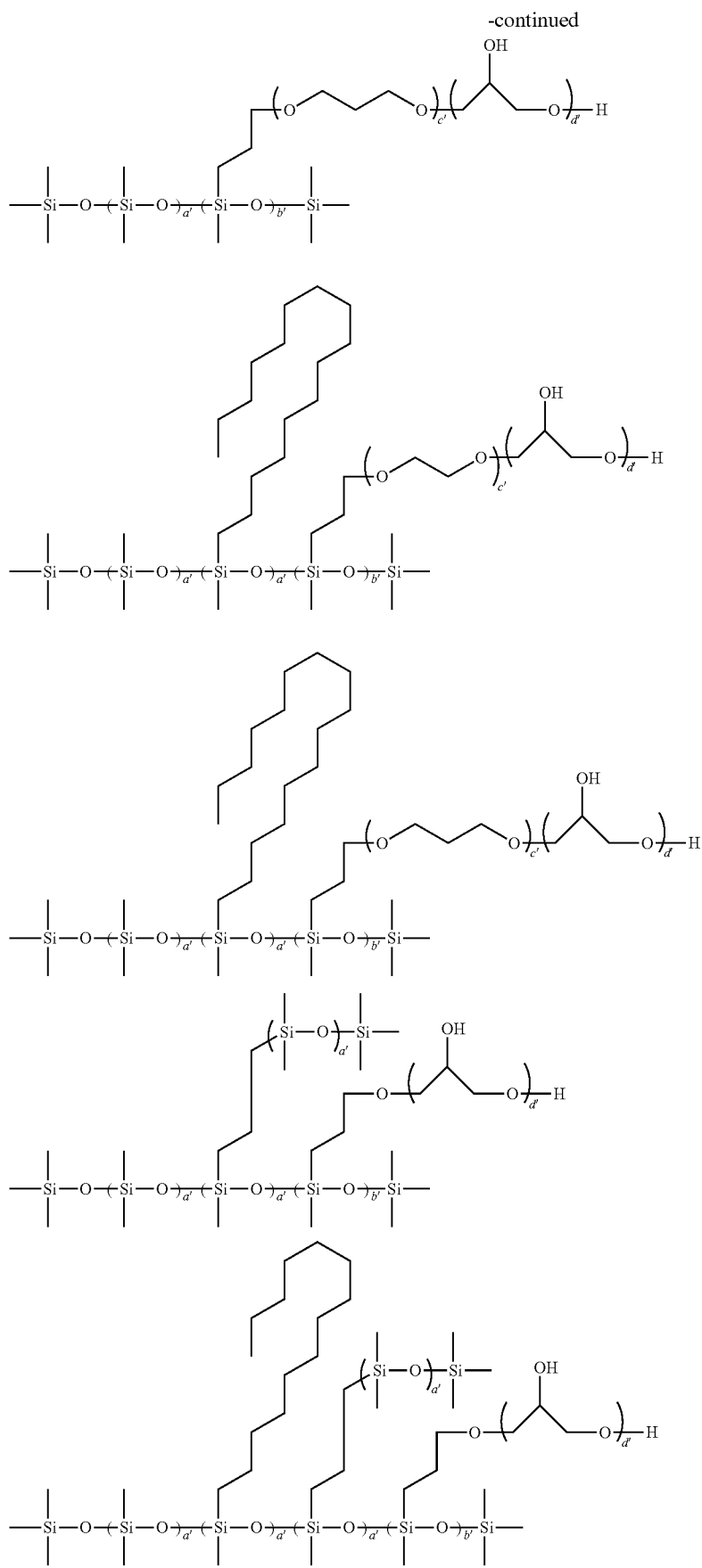

-continued
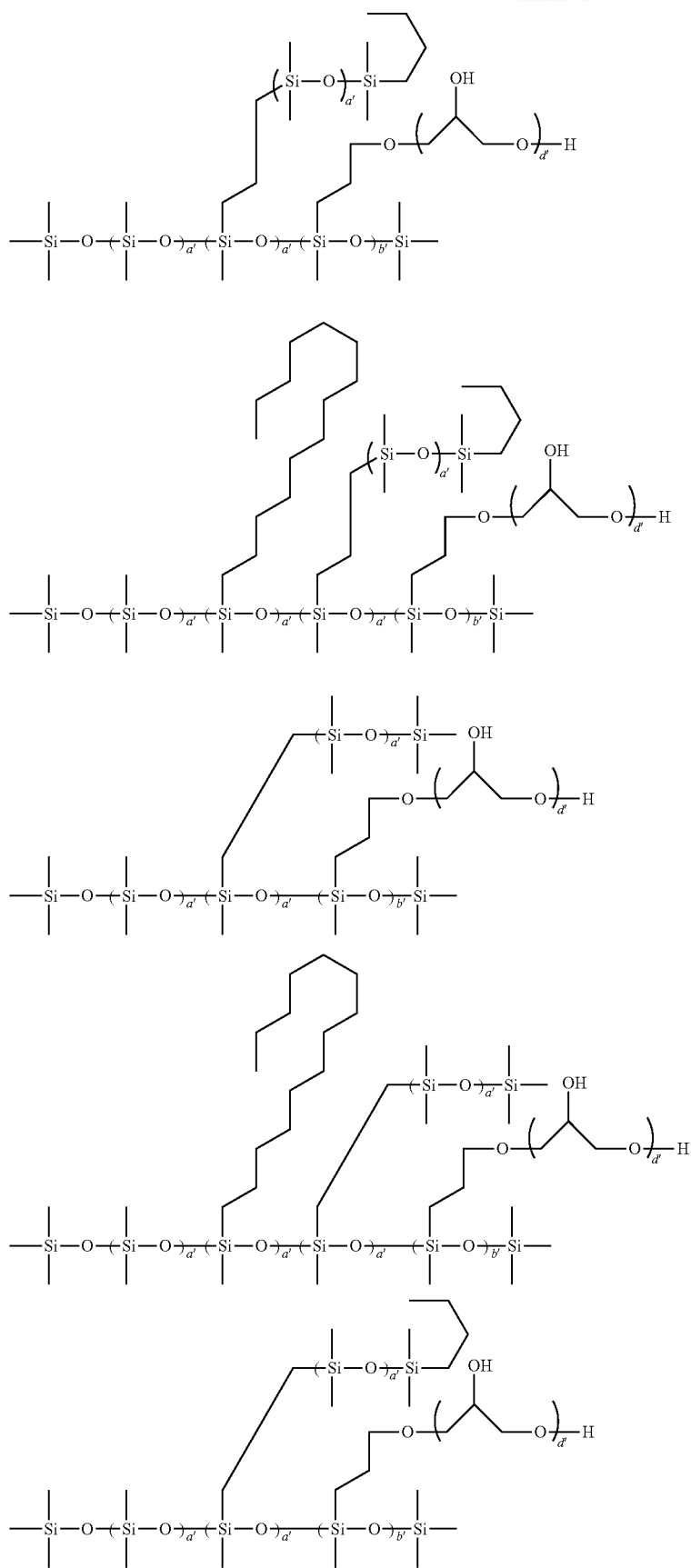

-continued
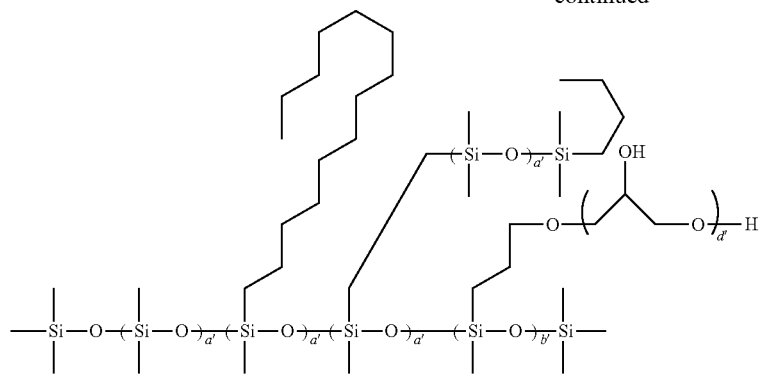
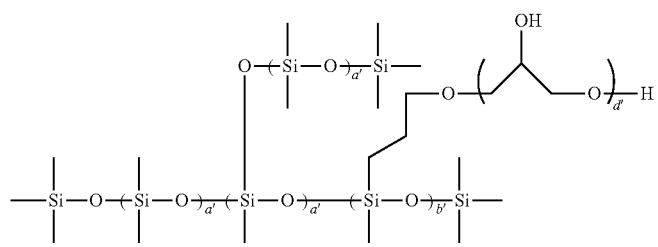
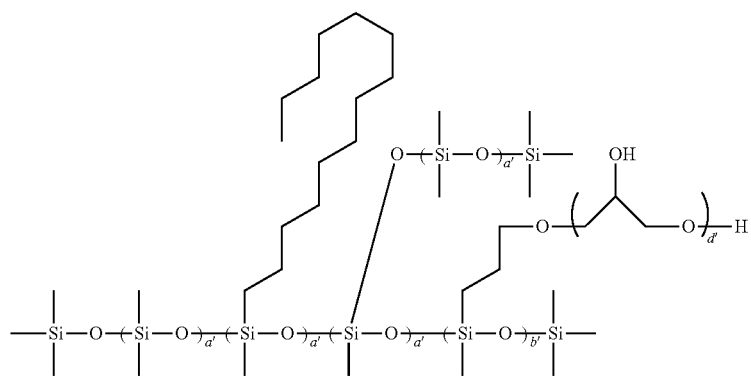
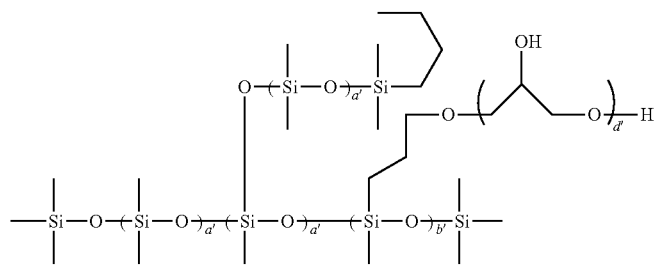
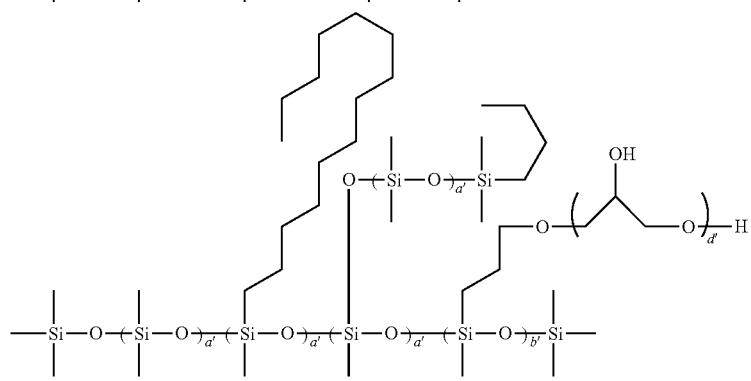

-continued

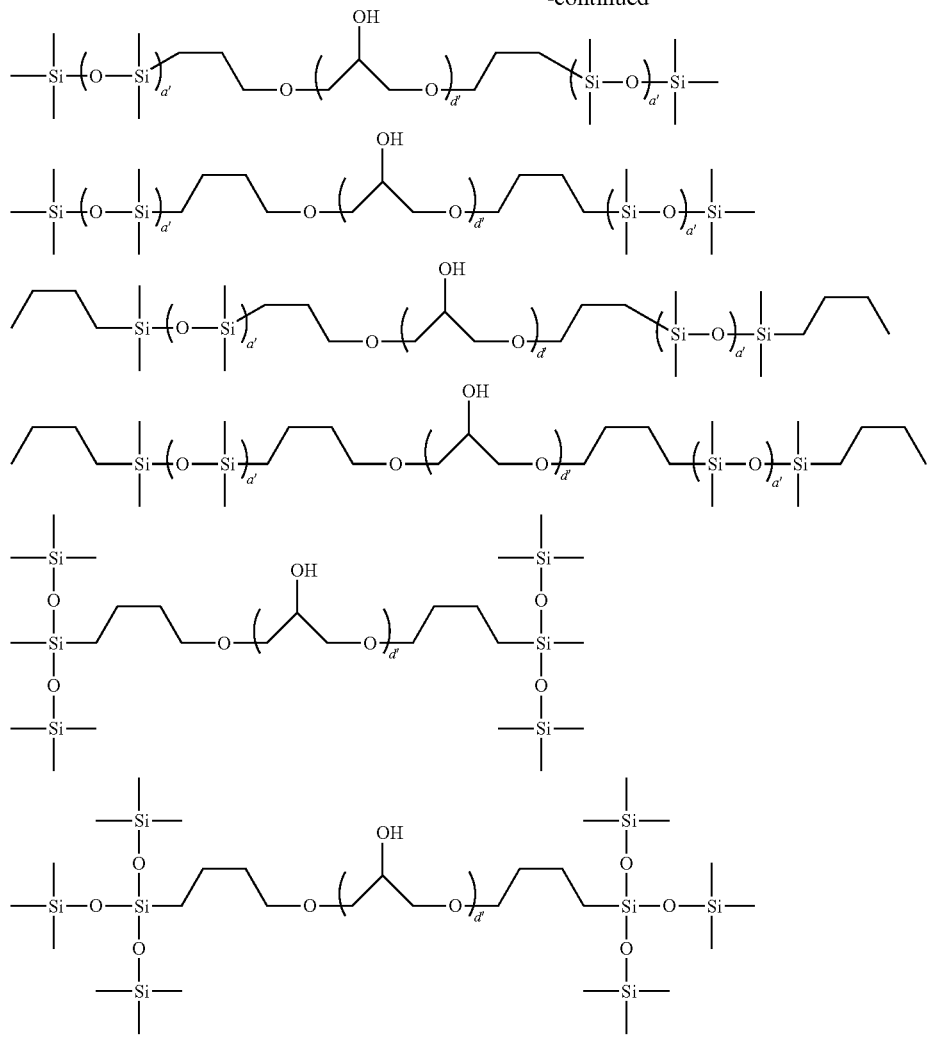

In the formulae, a', b', c', and d' are as defined above.

When such a silicone compound (B) is incorporated, the resulting bio-electrode composition is capable of forming a living body contact layer that can exhibit more excellent moisture-holding property and consequently more excellent sensitivity to ions released from skin.

[(C) Resin Component]

The inventive bio-electrode composition can further contain (C) a resin component, in addition to the polymer compound (A) and the silicone compound (B). For example, the inventive bio-electrode composition may further contain (C) a resin component which is one or more selected from the group consisting of silicone base resins other than the silicone compound (B), acrylic base resins, and urethane base resins. Incorporating one or more resins selected from the group consisting of silicone type, acrylic type, and urethane type resins makes it possible to provide a bio-electrode that includes a living body contact layer excellent in stretchability.

The resin component (C) blendable in the inventive bio-electrode composition can be, for example, a component for preventing elution of the polymer compound (A) (ionic material (salt)) by being compatibilized with the salt, and for achieving adhesion. When the bio-electrode composition contains a metal powder, a carbon powder, a silicon powder, a lithium titanate powder, or the like as described later, the resin component (C) can hold these powders. When the polymer compound (A) has adhesion, the resin (C) is not necessarily essential. It is to be noted that the resin component (C) may be any resin other than the component (A), and is preferably either or both of a thermosetting resin and a photo-curable resin, particularly preferably one or more resins selected from the group consisting of silicone base resins other than the silicone compound (B), acrylic base resins, and urethane base resins.

The adherent (adhesive) silicone base resin include an addition-curable (addition reaction-curable) type and a radical curable (radical crosslinking reaction-curable) type. As the addition-curable type, it is possible to use one that contains diorganosiloxane having an alkenyl group(s), an MQ resin having $R_3SiO_{0.5}$ and $SiO_2$ units, organohydrogenpolysiloxane having a plurality of SiH groups, a platinum catalyst, an addition reaction inhibitor, and an organic solvent, for example, described in JP 2015-193803A. As the radical curable type, it is possible to use one that contains diorganopolysiloxane with or without an alkenyl group, an MQ resin having $R_3SiO_{0.5}$ and $SiO_2$ units, organic peroxide, and an organic solvent, for example, described in JP 2015-

193803A. Here, R represents a substituted or unsubstituted monovalent hydrocarbon group having 1 to 10 carbon atoms.

It is also possible to use a polysiloxane-resin integrated compound that is formed by condensation reaction of an MQ resin and polysiloxane having silanol at the terminal or the side chain of the polymer. The MQ resin contains many silanols and improves adhesion by addition of it, but does not bind to the polysiloxane in molecular level because it is not crosslinkable. The adhesion can be increased by integrating the polysiloxane and the resin as described above.

The silicone resin may contain modified siloxane that has a group selected from the group consisting of an amino group, an oxirane group, an oxetane group, a polyether group, a hydroxy group, a carboxyl group, a mercapto group, a methacryl group, an acryl group, a phenol group, a silanol group, a carboxylic anhydride group, an aryl group, an aralkyl group, an amide group, an ester group, and a lactone ring. The addition of the modified siloxane improves dispersibility of the component (A) in the silicone resin. The modified siloxane may be modified at any part such as one terminal, both terminals, or a side chain of the siloxane.

As the adherent acrylic base resin, it is possible to use one having hydrophilic (meth)acrylic ester and hydrophobic long chain (meth)acrylic ester as the repeating units described in JP 2016-011338A, for example. In some cases, it is also possible to copolymerize (meth)acrylic ester having a functional group or (meth)acrylic ester having a siloxane bond.

As the adherent urethane base resin, it is possible to use one having a urethane bond with a polyether bond, a polyester bond, a polycarbonate bond, or a siloxane bond described in JP 2016-065238A, for example.

In the inventive bio-electrode composition, the resin component (C) preferably has high compatibility with the component (A) to prevent lowering of the electric conductivity due to elution of the component (A) from the living body contact layer. In the inventive bio-electrode composition, the resin component (C) preferably has high adhesion to the electro-conductive base material (substrate) to prevent peeling of the living body contact layer from the electro-conductive base material. In order to increase the compatibility of the resin with the electro-conductive base material and the salt, the use of a resin with high polarity is effective. Examples of such a resin include resin having one or more moieties selected from an ether bond, an ester bond, an amide bond, an imide bond, a urethane bond, a thiourethane bond, and a thiol group; a polyacrylic resin, a polyamide resin, a polyimide resin, a polyurethane resin, a polythiourethane resin, etc. On the other hand, the living body contact layer comes into contact with a living body, thereby being susceptible to perspiration. Accordingly, in the inventive bio-electrode composition, the resin component (C) preferably has high repellency and is hardly hydrolyzed. To make the resin be highly repellent and hardly hydrolyzed, the use of a silicon-containing resin is effective.

The silicon atom-containing polyacrylic resin includes a polymer that has a silicone main chain and a polymer that has a silicon atom(s) on the side chain, either of which can be suitably used. As the polymer that has a silicone main chain, silsesquioxane, siloxane, or the like, having a (meth)acrylpropyl group can be used. In this case, an addition of a photoradical generator allows the (meth)acryl moiety to polymerize to cure.

As the silicon atom-containing polyamide resin, it is possible to suitably use polyamide silicone resins described in JP 2011-079946A and U.S. Pat. No. 5,981,680B, for example. Such polyamide silicone resins can be synthesized by combining, for example, a silicone or non-silicone compound having amino groups at both terminals and a non-silicone or silicone compound having carboxyl groups at both terminals.

It is also possible to use polyamic acid before cyclization thereof, which is obtained by reacting carboxylic anhydride and amine. The carboxyl group of the polyamic acid may be crosslinked by using a crosslinking agent such as an epoxy type and an oxetane type. It is also possible to esterify the carboxyl group with hydroxyethyl (meth)acrylate to perform photoradical crosslinking of the (meth)acrylate moiety.

As the silicon atom-containing polyimide resin, it is possible to suitably use polyimide silicone resins described in JP 2002-332305A, for example. Although polyimide resins have very high viscosity, the viscosity can be decreased by blending a (meth)acrylic monomer as a solvent and a crosslinking agent.

Examples of the silicon atom-containing polyurethane resin include polyurethane silicone resins. Such polyurethane silicone resins can be crosslinked through urethane bond by blending a compound having isocyanate groups at both terminals and a compound having a hydroxy group(s) at the terminal(s), followed by heating thereof. In this case, a silicon atom(s) (siloxane bond) have to be contained in either or both of the compound having isocyanate groups at both terminals and the compound having a hydroxy group(s) at the terminal(s). Alternatively, polysiloxane and a urethane (meth)acrylate monomer can be blended and photo-crosslinked, as described in JP 2005-320418A. It is also possible to photo-crosslink a polymer having both of a siloxane bond(s) and a urethane bond(s), with the terminal having a (meth)acrylate group(s). Particularly, a polyurethane main chain having a silicone chain on a side chain as described in JP 2018-123304 A and JP 2019-70109A is preferable because of the properties of high strength and high stretchability.

The silicon atom-containing polythiourethane resin can be obtained by reaction of a compound having a thiol group(s) and a compound having an isocyanate group(s), provided that either of them contains a silicon atom(s). It can also be photo-cured if (meth)acrylate groups are contained at the terminals.

The silicone base resin can be improved in compatibility with the foregoing salt by adding modified siloxane that has a functional group selected from the group consisting of an amino group, an oxirane group, an oxetane group, a polyether group, a hydroxy group, a carboxyl group, a mercapto group, a methacryl group, an acryl group, a phenol group, a silanol group, a carboxylic anhydride group, an aryl group, an aralkyl group, an amide group, an ester group, and a lactone ring, in addition to the diorganosiloxane having an alkenyl group(s), the MQ resin having $R_3SiO_{0.5}$ and $SiO_2$ units, and the organohydrogenpolysiloxane having multiple SiH groups.

In the inventive bio-electrode composition, the amount of the resin component (C) blended is preferably 0 to 2000 parts by mass, more preferably 10 to 1000 parts by mass, on the basis of 100 parts by mass of the ion polymer (A). One kind of the resin component (C) may be used singly or in admixture of two or more kinds.

As will be described later, the living body contact layer of the inventive bio-electrode is a cured material (cured product) of the inventive bio-electrode composition. The curing improves the adhesion of the living body contact layer to both of skin and the electro-conductive base material. The curing means is not particularly limited, and common means can be used, including crosslinking reaction by either or both of heat and light, or with an acid catalyst or a base catalyst, for example. The crosslinking reaction can be performed, for example, by appropriately selecting methods described in "Kakyou han-nou handbook (handbook of crosslinking reaction)", Chapter 2, pages 51-371, Yasuharu Nakayama, Maruzen shuppan Publishing Co., Ltd (2013).

The diorganosiloxane having an alkenyl group(s) and the organohydrogenpolysiloxane having multiple SiH groups can be crosslinked through an addition reaction with a platinum catalyst.

Examples of the platinum catalyst include platinum-based catalysts such as platinic chloride, alcohol solution of platinic chloride, reaction product of platinic chloride and alcohol, reaction product of platinic chloride and an olefin compound, reaction product of platinic chloride and vinyl group-containing siloxane, a platinum-olefin complex, and a complex of platinum and vinyl group-containing siloxane; platinum group metal-based catalysts such as a rhodium complex and a ruthenium complex; etc. These catalysts may be used after dissolved or dispersed in alcohol solvent, hydrocarbon solvent, or siloxane solvent.

The amount of the platinum catalyst added is preferably in a range of 5 to 2,000 ppm, particularly preferably 10 to 500 ppm, on the basis of 100 parts by mass of the resin including the polymer compound (A) and the resin component (C).

When the addition curable silicone resin is used, an addition reaction inhibitor may be added. This addition reaction inhibitor is added as a quencher to prevent the action of the platinum catalyst in the solution and under a low temperature circumstance after forming the coating film and before heat curing. Specific examples of the addition reaction inhibitor include 3-methyl-1-butyn-3-ol, 3-methyl-1-pentyn-3-ol, 3,5-dimethyl-1-hexyn-3-ol, 1-ethynylcyclohexanol, 3-methyl-3-trimethylsiloxy-1-butyne, 3-methyl-3-trimethylsiloxy-1-pentyne, 3,5-dimethyl-3-trimethylsiloxy-1-hexyne, 1-ethynyl-1-trimethylsiloxycyclohexane, bis(2,2-dimethyl-3-butynoxy)dimethylsilane, 1,3,5,7-tetramethyl-1,3,5,7-tetravinylcyclotetrasiloxane, 1,1,3,3-tetramethyl-1,3-divinyldisiloxane, etc.

The amount of the addition reaction inhibitor added is preferably in a range of 0 to 10 parts by mass, particularly preferably 0.05 to 3 parts by mass, on the basis of 100 parts by mass of the resin.

Examples of the photo-curing method include a method of adding a photoradical generator to generate radical by light, together with a resin having a (meth)acrylate terminal(s) or an olefin terminal(s), or a crosslinking agent with the terminal(s) being (meth)acrylate, olefin, or a thiol group(s); and a method of adding a photo-acid generator to generate acid by light, together with a resin or a crosslinking agent having an oxirane group(s), an oxetane group(s), or a vinyl ether group(s).

Examples of the photoradical generator include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoate, 2-(1,3-benzodioxole-5-yl)-4,6-bis(trichloromethyl)-1,3,5-triazine, 2-benzyl-2-(dimethylamino)-4'-morpholinobutyrophenone, 4,4'-dichlorobenzophenone, 2,2-diethoxyacetophenone, 2,2-dimethoxy-2-phenylacetophenone, 2,4-diethylthioxanthene-9-one, diphenyl(2,4,6-trimethylbenzoyl)phosphine oxide (BAPO), 1,4-dibenzoylbenzene, 2-ethylanthraquinone, 1-hydroxycyclohexyl phenyl ketone, 2-hydroxy-2-methyl-propiophenone, 2-hydroxy-4'-(2-hydroxyethoxy)-2-methyl-propiophenone, 2-isonitrosopropiophenone, and 2-phenyl-2-(p-toluenesulfonyloxy)acetophenone.

The curing can also be performed by adding a radical generator of a heat decomposition type. Examples of the thermal radical generator include 2,2'-azobis(isobutyronitrile), 2,2'-azobis(2,4-dimethylvaleronitrile), 2,2'-azobis(2-methylbutyronitrile), 2,2'-azobis(methylpropionamidine) hydrochloride, 2,2'-azobis[2-(2-imidazolin-2-yl)propane] hydrochloride, 2,2'-azobis(4-methoxy-2,4-dimethylvaleronitrile), 2,2'-azobis(cyclohexane-1-carbonitrile), 1[(1-cyano-1-methylethyl)azo]formamide, 2,2'-azobis[2-methyl-N-(2-hydroxyethyl)propionamide], 2,2'-azobis[N-(2-propenyl)-2-methylpropionamide], 2,2'-azobis(N-butyl-2-methylpropionamide), dimethyl-2,2'-azobis(isobutylate), 4,4'-azobis(4-cyanopentanoic acid), dimethyl-2,2'-azobis(2-methylpropionate), benzoyl peroxide, tert-butyl hydroperoxide, cumene hydroperoxide, di-tert-butyl peroxide, di-tert-amyl peroxide, di-n-butyl peroxide, dicumyl peroxide, etc.

Examples of the photo-acid generator include sulfonium salt, iodonium salt, sulfonyldiazomethane, N-sulfonyloxy-imide, oxime-O-sulfonate type acid generators, etc. Specific examples of the photo-acid generator include ones described in paragraphs [0122] to [0142] of JP 2008-111103A, and in JP 2009-080474A.

The amount of radical generator or photo-acid generator added is preferably in a range of 0.1 to 50 parts by mass on the basis of 100 parts by mass of the resin.

Among them, particularly preferable resin of the component (C) contains any of: a silicone resin having an $SiO_2$ unit and an $R_xSiO_{(4-x)/2}$ unit, where R represents a substituted or unsubstituted monovalent hydrocarbon group having 1 to 10 carbon atoms, and "x" is a number in a range of 2.5 to 3.5; diorganosiloxane having an alkenyl group; and organohydrogenpolysiloxane having an SiH group. Such a resin component (C) is compatibilized with the polymer compound (A), and can prevent the salt elution and can also impart higher adhesion to the bio-electrode composition.

[Metal Powder]

The inventive bio-electrode composition can also contain a metal powder selected from the group consisting of gold, silver, platinum, copper, tin, titanium, nickel, aluminum, tungsten, molybdenum, ruthenium, chromium, and indium in order to improve electron conductivity. The amount of the metal powder added is preferably in a range of 1 to 50 parts by mass on the basis of 100 parts by mass of the resin.

As the kind of the metal powder, gold, silver, and platinum are preferable in view of electric conductivity; and silver, copper, tin, titanium, nickel, aluminum, tungsten, molybdenum, ruthenium, and chromium are preferable in view of cost. In view of biocompatibility, noble metals are preferable. On the whole of these viewpoints, silver is most preferable.

The metal powder may have any shape, such as a spherical shape, a disk shape, a flaky shape, and a needle shape. The addition of flaky powder brings highest electric conductivity and is preferable thereby. The metal powder is preferably a flake having relatively lower density and larger specific surface area with a size of 100 μm or less, a tapped density of not more than 5 $g/cm^3$, and a specific surface area of not less than 0.5 $m^2/g$.

[Carbon Material]

A carbon material can be added as an electric conductivity improver. Examples of the carbon powder (carbon material)

include carbon black, graphite, carbon nanotube, carbon fiber, etc. The carbon nanotube may be either single layer or multilayer, and the surface may be modified with an organic group(s). The amount of the carbon material added is preferably in a range of 1 to 50 parts by mass on the basis of 100 parts by mass of the resin.

[Silicon Powder]

The inventive bio-electrode composition may contain a silicon powder to enhance ion reception sensitivity. Examples of the silicon powder include powders of silicon, silicon monoxide, or silicon carbide. The particle diameter of the powder is preferably smaller than 100 μm, more preferably 1 μm or less. Since finer particles have a larger surface area, the resulting bio-electrode can receive a larger amount of ions and has higher sensitivity. The amount of the silicon powder added is preferably in a range of 1 to 50 parts by mass on the basis of 100 parts by mass of the resin.

[Lithium Titanate Powder]

The inventive bio-electrode composition may contain a lithium titanate powder to enhance ion reception sensitivity. Examples of the lithium titanate powder include powders containing materials shown by molecular formulae $Li_2TiO_3$, $LiTiO_2$, and $Li_4Ti_5O_{12}$ with a spinel structure. A lithium titanate powder having a spinel structure is preferable. It is also possible to use carbon-incorporated lithium titanate particles. The particle diameter of the powder is preferably smaller than 100 μm, more preferably 1 μm or less. Since finer particles have a larger surface area, the bio-electrode can receive a larger amount of ions, and has higher sensitivity. The aforementioned powders may be composite powders with carbon. The amount of the lithium titanate powder added is preferably in a range of 1 to 50 parts by mass on the basis of 100 parts by mass of the resin.

[Tackifier]

The inventive bio-electrode composition may also contain a tackifier in order to have adhesion to a living body. Examples of such a tackifier include silicone resin, non-crosslinkable siloxane, non-crosslinkable poly(meth)acrylate, non-crosslinkable polyether, etc.

[Crosslinking Agent]

The inventive bio-electrode composition may contain an epoxy-type crosslinking agent. This crosslinking agent is a compound having multiple epoxy groups or oxetane groups in one molecule. The amount of the crosslinking agent added is preferably 1 to 30 parts by mass on the basis of 100 parts by mass of the resin.

[Crosslinking Catalyst]

The inventive bio-electrode composition may also contain a catalyst for crosslinking the epoxy groups or the oxetane groups. As this catalyst, ones described in paragraphs 0027 to 0029 of JP 2019-503406A can be used. The amount of the catalyst added is preferably 0.01 to 10 parts by mass on the basis of 100 parts by mass of the resin.

[Ionic Additive]

The inventive bio-electrode composition may contain an ionic additive to increase ionic conductivity. In consideration of biocompatibility, examples of the ionic additive include sodium chloride, potassium chloride, calcium chloride, saccharin, acesulfame K, and salts disclosed in JP 2018-44147A, JP 2018-59050A, JP 2018-59052A, and JP 2018-130534A.

[Organic Solvent]

Further, the inventive bio-electrode composition may contain an organic solvent. Specific examples of the organic solvent include aromatic hydrocarbon solvent such as toluene, xylene, cumene, 1,2,3-trimethylbenzene, 1,2,4-trimethylbenzene, 1,3,5-trimethylbenzene, styrene, α-methyl styrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, pentamethylbenzene, hexamethylbenzene, hexylbenzene, and 1,3,5-triethylbenzene; aliphatic hydrocarbon solvent such as n-heptane, isoheptane, 3-methylhexane, 2,3-dimethylpentane, 3-ethylpentane, 1,6-heptadiene, 5-methyl-1-hexyne, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, dicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[$6.2.1.0^{2,7}$]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, and isoparaffin; ketone solvent such as cyclohexanone, cyclopentanone, 2-octanone, 2-nonanone, 2-heptanone, 3-heptanone, 4-heptanone, 2-hexanone, 3-hexanone, diisobutyl ketone, methylcyclohexanone, and methyl n-pentyl ketone; alcohol solvent such as 3-methoxybutanol, 3-methyl-3-methoxybutanol, 1-methoxy-2-propanol, and 1-ethoxy-2-propanol; ether solvent such as propylene glycol monomethyl ether, ethylene glycol monomethyl ether, propylene glycol monoethyl ether, ethylene glycol monoethyl ether, propylene glycol dimethyl ether, diethylene glycol monomethyl ether, diethylene glycol monoethyl ether, diethylene glycol monopropyl ether, diethylene glycol monobutyl ether, diethylene glycol monopentyl ether, diethylene glycol monoheptyl ether, diethylene glycol diethyl ether, diethylene glycol dipropyl ether, diethylene glycol dibutyl ether, diisopropyl ether, diisobutyl ether, diisopentyl ether, di-n-pentyl ether, methyl cyclopentyl ether, methyl cyclohexyl ether, di-n-butyl ether, di-sec-butyl ether, di-sec-pentyl ether, di-tert-amyl ether, di-n-hexyl ether, and anisole; ester solvent such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactone solvent such as γ-butyrolactone; water; etc.

The amount of the organic solvent added is preferably in a range of 10 to 50,000 parts by mass on the basis of 100 parts by mass of the resin.

[Other Additives]

The inventive bio-electrode composition can be mixed with at least one kind selected from the group consisting of silica particles, alumina particles, titania particles, and zirconia particles. These silica particles, alumina particles, titania particles, and zirconia particles have hydrophilic surfaces and favorable compatibility with the hydrophilic ion polymer and polyglycerin silicone, and can improve the dispersibility of the ion polymer in the hydrophobic silicone adhesive and that of the polyglycerin silicone in the silicone adhesive. The silica particles, alumina particles, titania particles, and zirconia particles may be either dry type or wet type both of which are preferably usable. The shape of the silica particles, alumina particles, titania particles, and zirconia particles may be any of spherical, elliptical, amorphous, hollow, and porous shapes.

As has been described above, the inventive bio-electrode composition makes it possible to form a living body contact layer for a bio-electrode that is excellent in electric conductivity and biocompatibility, light-weight, manufacturable at low cost, and capable of preventing significant reduction in the electric conductivity even when wetted with water or dried, and capable of quick signal collection after attachment to skin. The living body contact layer for a bio-electrode formed using the inventive bio-electrode composition is capable of exhibiting excellent electric conductivity, and thus capable of transmitting electric signals from a living body, for example, skin, to a device efficiently. Moreover, this living body contact layer is capable of exhibiting excellent biocompatibility, thereby preventing allergy even when the bio-electrode is worn on skin for a long time. It is also possible to further improve the electric conductivity by adding an electric conductivity improver such as a carbon material. In addition, it is possible to manufacture a bio-electrode with particularly high adhesion and stretchability by combining the inventive bio-electrode composition with a resin having adhesion and stretchability. Further, the stretchability and adhesion to skin can be improved by adding an additive and so forth to the inventive bio-electrode composition. Furthermore, the stretchability and adhesion can be controlled by appropriately adjusting the composition of the polymer compound (A) and/or the silicone compound of the inventive bio-electrode composition, or the thickness of the living body contact layer.

A bio-electrode composition according to another embodiment of the present invention comprises a silicone compound having a polyglycerin structure.

The silicone compound having a polyglycerin structure is high in hygroscopicity and capable of exhibiting excellent moisture-holding property, as described previously. The bio-electrode composition of this embodiment makes it possible to prevent electric conductivity from significantly lowering, which would otherwise occur by wetting with water or drying. Moreover, this bio-electrode composition can demonstrate excellent ionic conductivity by further incorporating a material with ionic conductivity. Thus, this bio-electrode composition can form a living body contact layer for a bio-electrode, the living body contact layer being capable of preventing significant reduction in electric conductivity regardless of wetting with water or drying, and also capable of quickly collecting signals after attachment to skin.

As the silicone compound having a polyglycerin structure, the bio-electrode composition of this embodiment can contain, for example, the silicone compound (B) having the polyglycerin structure exemplified above.

The bio-electrode composition of this embodiment can further contain another component(s). Examples of the other component(s) include the polymer compound (A), the resin component (C), metal powders, carbon materials, silicon powders, lithium titanate powders, tackifiers, crosslinking agents, crosslinking catalysts, ionic additives, organic solvents, silica particles, alumina particles, titania particles, and zirconia particles as exemplified above.

<Bio-Electrode>

The present invention also provides a bio-electrode comprising an electro-conductive base material and a living body contact layer formed on the electro-conductive base material, wherein the living body contact layer is a cured material of the inventive bio-electrode composition described above.

Hereinafter, the inventive bio-electrode will be described in detail with reference to the drawings, but the present invention is not limited thereto.

FIG. 1 is a schematic sectional view showing an example of the inventive bio-electrode. In FIG. 1, a bio-electrode 1 has an electro-conductive base material 2 and a living body contact layer 3 formed on the electro-conductive base material 2. The living body contact layer 3 is a layer in which an ionic polymer (ionic material) 4 and a metal powder 5 are dispersed in a resin 6. The ionic polymer 4 is an example of the polymer compound (A) described above. The resin 6 corresponds to the resin components (B) and (C) described above. The living body contact layer 3 is a cured material of the bio-electrode composition according to an example of the present invention.

When the bio-electrode 1 as shown in FIG. 1 is used, the living body contact layer 3 (i.e., the layer in which the ionic polymer 4 and the metal powder 5 are dispersed in the resin 6) is brought into contact with a living body 7 as shown in FIG. 2. Electric signals are picked from the living body 7 through the ionic polymer 4 and the metal powder 5, and then conducted to a sensor device etc. (not shown) via the electro-conductive base material 2. As described above, the inventive bio-electrode is capable of coping with both electric conductivity and biocompatibility due to the ionic polymer (ionic material) described above, and obtaining electric signals from skin stably in high sensitivity because the contact area with skin is kept constant due to the adhesion thereof. Particularly, as described above, the inventive bio-electrode composition is capable of forming a living body contact layer that enables quick signal collection after attachment to skin. Accordingly, the bio-electrode 1 of FIG. 1 is capable of quickly collecting signals after the attachment to the living body 7.

Hereinafter, each component composing the inventive bio-electrode will be described more specifically.

[Electro-Conductive Base Material]

The inventive bio-electrode has an electro-conductive base material. This electro-conductive base material is usually connected electrically with a sensor device and so on, and conducts electrical signals picked from a living body through the living body contact layer to the sensor device and so on.

As the electro-conductive base material, any electro-conductive material can be used without being limited to particular ones. However, it is preferable to comprise one or more selected from the group consisting of gold, silver, silver chloride, platinum, aluminum, magnesium, tin, tungsten, iron, copper, nickel, stainless steel, chromium, titanium, and carbon, for example.

The electro-conductive base material may be a hard electro-conductive substrate, an electro-conductive film having flexibility, a substrate having a stretchable film coated with electro-conductive paste, a cloth with the surface being coated with electro-conductive paste, a cloth into which electro-conductive polymer is kneaded, or the like without being limited to particular substrates. The electro-conductive base material may be flat, uneven, or mesh-form of woven metal wires, which can be appropriately selected in accordance with the use of the bio-electrode, and so forth. Among these, in consideration of the use of the bio-electrode that is attached onto skin, preferable is a substrate having a stretchable film or cloth coated with electro-conductive paste. Examples of the stretchable film include polyurethane and polyester. The electro-conductive paste to be used can be obtained by mixing an electro-conductive powder of carbon, silver, gold, copper, or the like with a solvent in a stretchable resin such as polyurethane, polyester, silicone, or nitrile resin.

[Living Body Contact Layer]

The inventive bio-electrode includes a living body contact layer formed on the electro-conductive base material. This living body contact layer is a part to be actually in contact with a living body when using the bio-electrode, and has electric conductivity and adhesion. The living body contact layer is a cured material of the inventive bio-electrode composition described above; that is, an adherent resin layer containing: (A) the polymer compound (ionic material (salt)), (B) the silicone compound having a polyglycerin structure, and optionally (C) additives such as the resin component (C).

The living body contact layer preferably has adhesion in a range of 0.5 N/25 mm or more and 20 N/25 mm or less. The adhesion is commonly measured by the method shown in JIS Z 0237, in which a metal substrate such as a stainless steel (SUS) substrate or a polyethylene terephthalate (PET) substrate can be used as a base material. Alternatively, human skin can be used for measuring. Human skin has lower surface energy than metals and various plastics, and as low as that of Teflon (registered trade mark). Hence, human skin is hard to adhere.

The living body contact layer of the bio-electrode has a thickness of preferably 1 μm or more and 5 mm or less, more preferably 2 μm or more and 3 mm or less. As the living body contact layer is thinner, the adhesion lowers, but the flexibility is improved, the weight decreases, and the compatibility with skin is improved. The thickness of the living body contact layer can be selected based on the balance of adhesion and texture to the skin.

The living body contact layer of the inventive bio-electrode is preferably humidified. The bio-electrode including such a living body contact layer can more quickly collect signals when attached to skin.

The inventive bio-electrode may be provided with an adherent film separately on the living body contact layer as in conventional bio-electrodes (e.g., the bio-electrode described in JP 2004-033468A) in order to prevent peeling off of the bio-electrode from a living body during the use. When the adherent film is prepared separately, the adherent film may be formed by using a raw material for the adherent film such as an acrylic type, a urethane type, and a silicone type. Particularly, the silicone type is suitable because of: the high oxygen permeability, which enables dermal respiration while pasting the same, the high water repellency, which decreases lowering of adhesion due to perspiration, and the low irritation to skin. It is to be noted that the inventive bio-electrode does not necessarily require this adherent film that is prepared separately, because peeling off from a living body can be prevented by adding a tackifier to the bio-electrode composition or using a resin having good adhesion to a living body as described above.

When the inventive bio-electrode is used as a wearable device, wiring between the bio-electrode and a sensor device, and other components are not limited to particular ones. For example, it is possible to apply the ones described in JP 2004-033468A.

As described above, since the inventive bio-electrode includes the living body contact layer formed from the cured material of the aforementioned inventive bio-electrode composition, the inventive bio-electrode is excellent in electric conductivity and biocompatibility, light-weight, manufacturable at low cost, capable of preventing significant reduction in the electric conductivity even when wetted with water or dried, and capable of quickly collecting signals after attachment to skin. The living body contact layer of the inventive bio-electrode is capable of exhibiting excellent electric conductivity, and thus capable of conducting electric signals from a living body, for example, skin, to a device efficiently. Moreover, this living body contact layer is capable of exhibiting excellent biocompatibility, thereby preventing allergy even when the bio-electrode is attached to skin for a long time. It is also possible to further improve the electric conductivity by adding a metal powder to the living body contact layer of the inventive bio-electrode. In addition, it is possible to manufacture a bio-electrode with particularly high adhesion and stretchability by combining the inventive bio-electrode composition with a resin having adhesion and stretchability. Further, the stretchability and adhesion to skin of the living body contact layer can be improved by adding an additive and so forth to the living body contact layer. Furthermore, the stretchability and adhesion can be controlled by appropriately adjusting the composition of the polymer compound (A) and/or the silicone compound (B) of the inventive bio-electrode composition, and the thickness of the living body contact layer. Accordingly, the inventive bio-electrode described above is particularly suitable as a bio-electrode used for a medical wearable device.

<Method for Manufacturing Bio-Electrode>

The present invention also provides a method for manufacturing a bio-electrode having an electro-conductive base material and a living body contact layer formed on the electro-conductive base material, the method including:

applying the above-described inventive bio-electrode composition onto the electro-conductive base material to obtain a coating film; and curing the coating film to form the living body contact layer.

The electro-conductive base material, the bio-electrode composition, etc. used for the inventive method for manufacturing a bio-electrode may be the same as those described above.

The method for applying the bio-electrode composition onto the electro-conductive base material is not limited to particular ones. Examples of the suitable method include dip coating, spray coating, spin coating, roll coating, flow coating, doctor coating, screen printing, flexographic printing, gravure printing, stencil printing, inkjet printing, etc.

The method for curing the resin can be appropriately selected based on the kind of the polyglycerin silicone component (B) and the resin (C) used for the bio-electrode composition without being limited to particular methods. For example, the bio-electrode composition is preferably cured by either or both of heat and light. The foregoing bio-electrode composition can also be cured by adding a catalyst in advance to generate acid or base to the bio-electrode composition, which causes a crosslinking reaction.

The heating temperature is not particularly limited and may be appropriately selected based on the kind of the polyglycerin silicone component (B) and the resin (C) used for the bio-electrode composition, but is preferably about 50 to 250° C., for example.

When the heating and light irradiation are combined, it is possible to perform the heating and the light irradiation simultaneously, to perform the light irradiation and then the heating, or to perform the heating and then the light irradiation. It is also possible to perform air-drying to evaporate the solvent before heating the film coating.

The cured film, that is, the formed living body contact layer, may be immersed in water; alternatively, the surface of the cured film may be wiped with a water-containing absorbent cotton, gauze, or nonwoven fabric, or may be sprayed with water droplets, water vapor, or mist. Performing these humidification treatments improves the compatibility with skin, and can obtain biological signals quickly. Water mixed with alcohol can be used to prepare water vapor, mist, or water droplets with minute sizes.

Before the inventive bio-electrode is attached to skin, the sensitivity to biological signals can be improved by wiping the skin with a gauze, absorbent cotton, nonwoven fabric, or the like containing water or alcohol to remove the oily substance on the skin and moisturize the skin. If the skin is dry, this suppresses ion release from the skin. Moisturizing the skin and the bio-electrode promotes the ion release from the skin, and improves the sensitivity to the biological signals. The absorbent cotton, nonwoven fabric, gauze, and so forth preferably contain water, or water-containing water-soluble alcohols such as ethanol, glycerin, ethylene glycol, and diethylene glycol.

As has been described above, the inventive method for manufacturing a bio-electrode makes it possible to manufacture the inventive bio-electrode easily and at low cost, with the bio-electrode being excellent in electric conductivity and biocompatibility, light-weight, capable of preventing significant reduction in the electric conductivity even when wetted with water or dried, and capable of collecting signals quickly after attachment to skin.

EXAMPLE

Hereinafter, the present invention will be specifically described by giving Examples and Comparative Examples, but the present invention is not limited thereto. Incidentally, "Me" represents a methyl group, and "Vi" represents a vinyl group.

[Polymer Compound (A)]

Ionic polymers 1 to 19, which were blended to bio-electrode composition solutions of Examples as the polymer compound (A) (ionic material (conductive material)), and Comparative ionic polymer 1, which was blended to bio-electrode composition solutions of Example and Comparative Examples, were synthesized as follows. Each 30 mass % monomer solution in cyclopentanone was introduced into a reaction vessel and mixed. The reaction vessel was cooled to −70° C. under a nitrogen atmosphere, and subjected to vacuum degassing and nitrogen blowing, which were repeated three times. After raising the temperature to room temperature, azobisisobutyronitrile (AIBN) was added thereto as a polymerization initiator in an amount of 0.01 mole per 1 mole of the whole monomers. This was warmed to a temperature of 60° C. and then allowed to react for 15 hours. The composition of obtained polymer was identified by $^1$H-NMR after drying the solvent. The molecular weight (Mw) and the dispersity (Mw/Mn) of the obtained polymer were determined by gel permeation chromatography (GPC) using tetrahydrofuran (THF) as a solvent. Thus synthesized Ionic polymers 1 to 19 and Comparative ionic polymer 1 are shown below.

Ionic Polymer 1
Mw=38,100
Mw/Mn=1.91

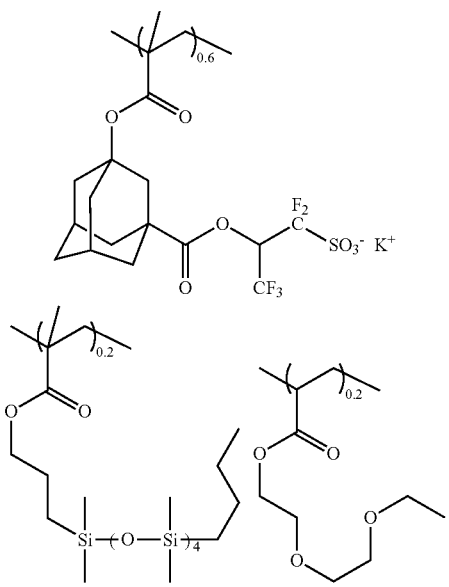

The repeating number in each formula shows the average value.

Ionic Polymer 2
Mw=36,100
Mw/Mn=1.93

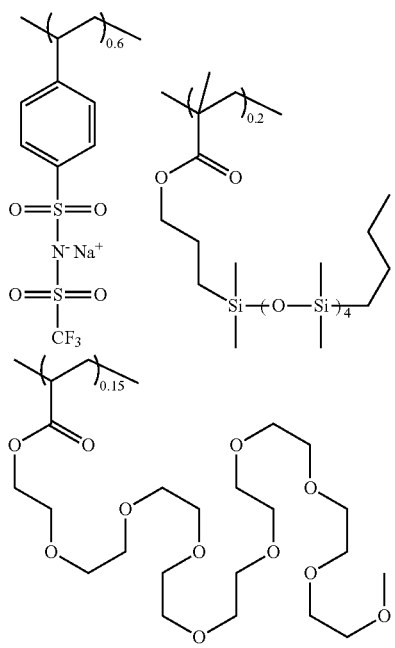

The repeating number in each formula shows the average value.
Ionic Polymer 3
Mw=150,600
Mw/Mn=1.85

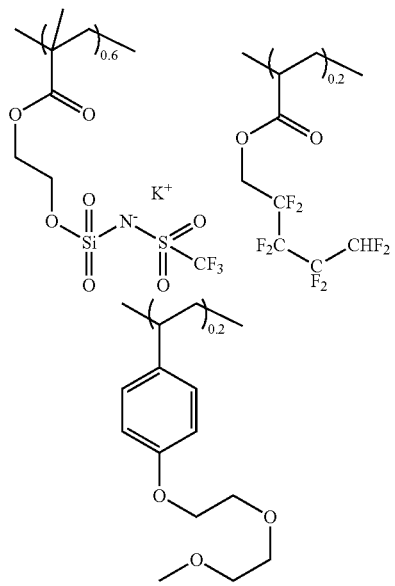

The repeating number in each formula shows the average value.
Ionic Polymer 4
Mw=44,400
Mw/Mn=1.94

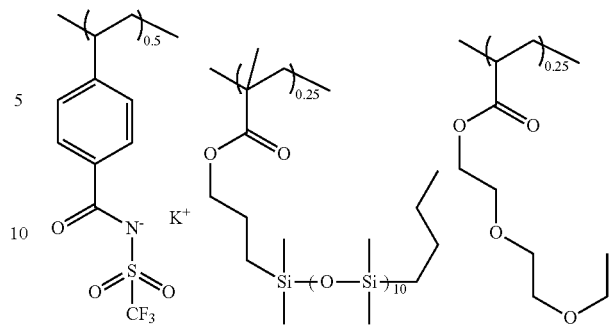

The repeating number in each formula shows the average value.
Ionic Polymer 5
Mw=43,100
Mw/Mn=1.88

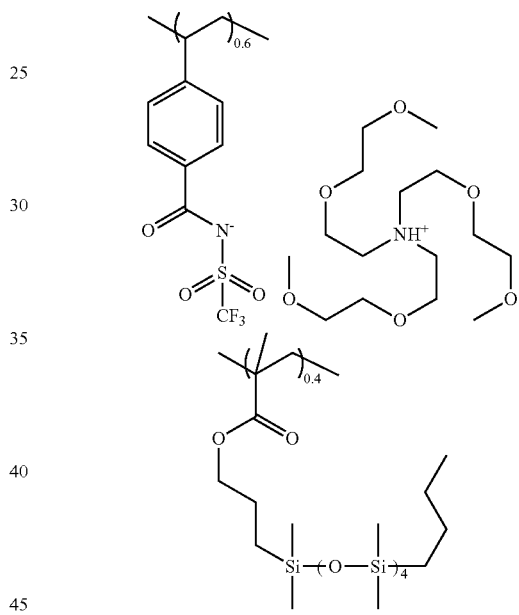

The repeating number in each formula shows the average value.
Ionic Polymer 6
Mw=41,200
Mw/Mn=1.72

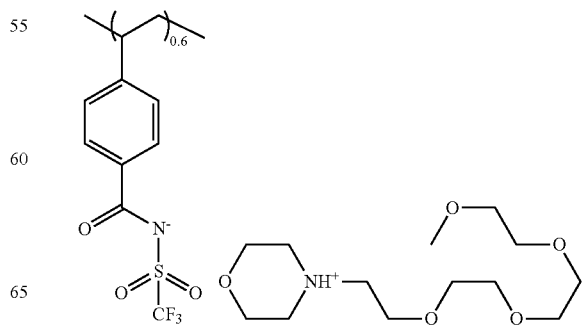

-continued

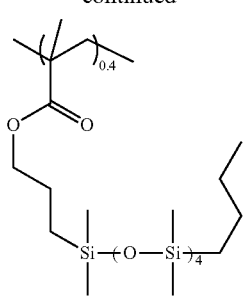

The repeating number in each formula shows the average value.
Ionic Polymer 7
Mw=43,600
Mw/Mn=1.93

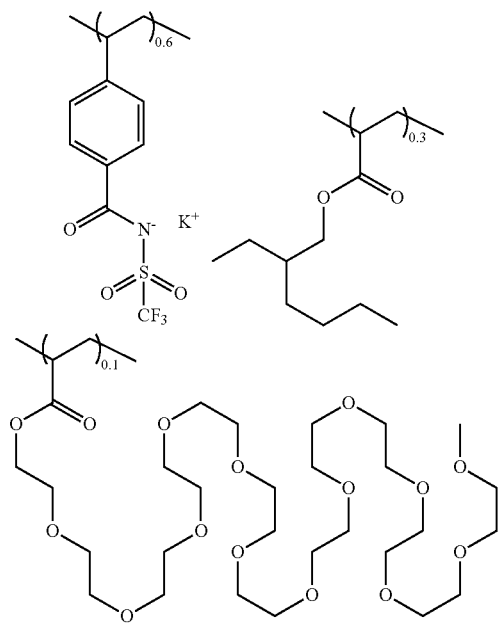

The repeating number in each formula shows the average value.
Ionic Polymer 8
Mw=31,600
Mw/Mn=2.10

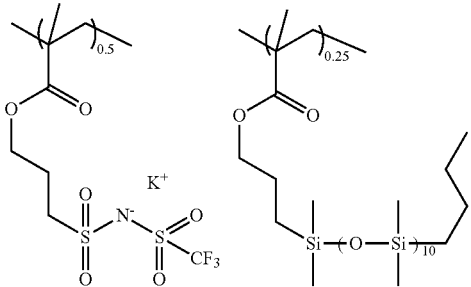

-continued

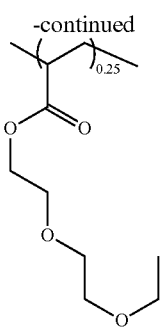

The repeating number in each formula shows the average value.
Ionic Polymer 9
Mw=55,100
Mw/Mn=2.02

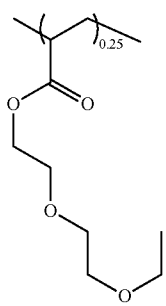

The repeating number in each formula shows the average value.
Ionic Polymer 10
Mw=87,500
Mw/Mn=2.01

231
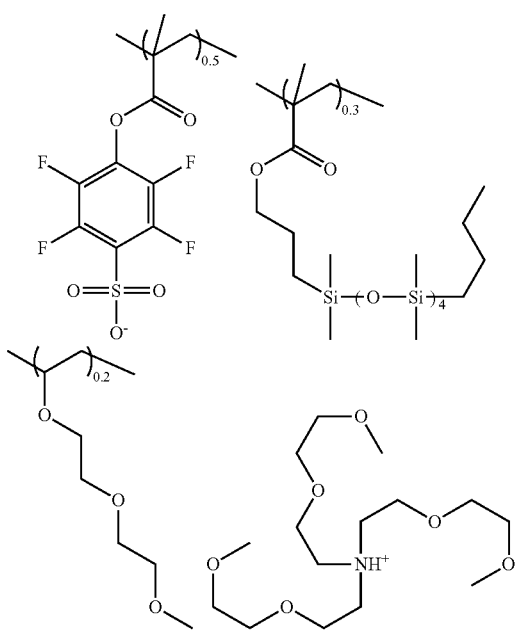
The repeating number in each formula shows the average value.
Ionic Polymer 11
Mw=43,600
Mw/Mn=1.91
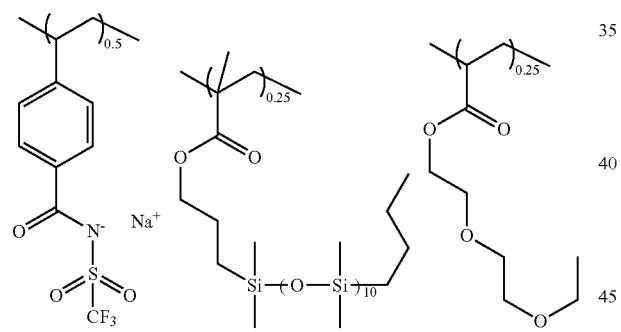
The repeating number in each formula shows the average value.
Ionic Polymer 12
Mw=97,100
Mw/Mn=2.20
232
-continued
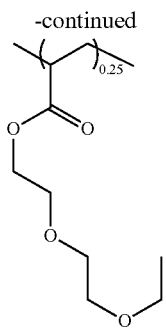
The repeating number in each formula shows the average value.
Ionic Polymer 13
Mw=98,300
Mw/Mn=2.05
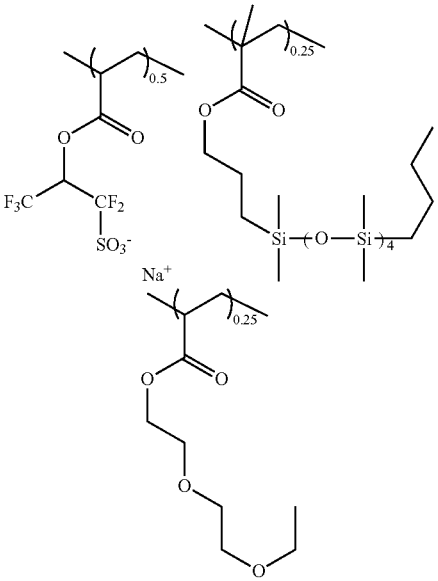
The repeating number in each formula shows the average value.
Ionic Polymer 14
Mw=68,900
Mw/Mn=2.26

-continued
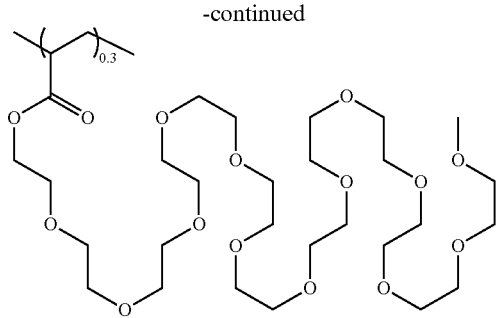
Ionic Polymer 15
Mw=67,100
Mw/Mn=1.89
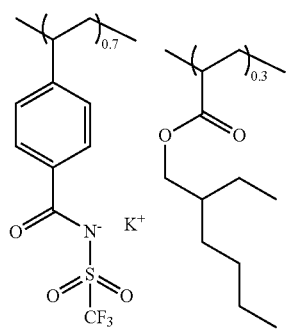
Ionic Polymer 16
Mw=23,400
Mw/Mn=1.77
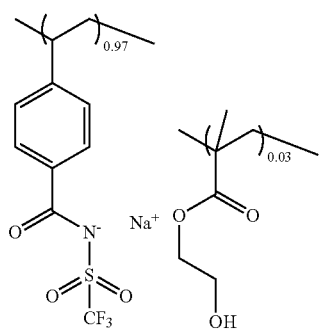
Ionic Polymer 17
Mw=34,300
Mw/Mn=1.75
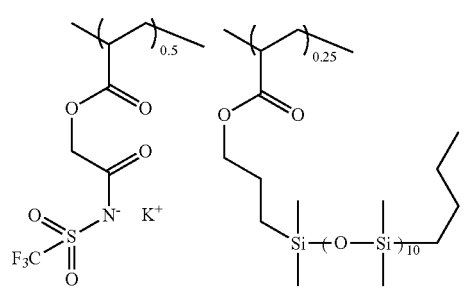
-continued
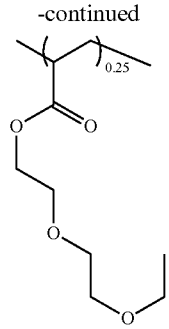
Ionic Polymer 18
Mw=37,700
Mw/Mn=1.79
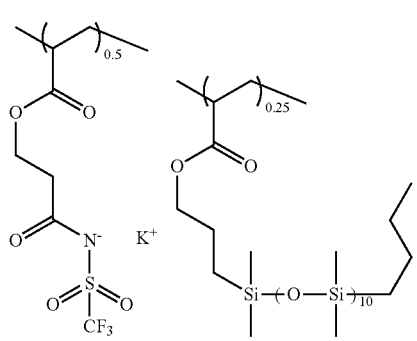
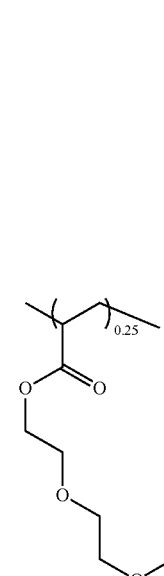
Ionic Polymer 19
Mw=46,300
Mw/Mn=2.21

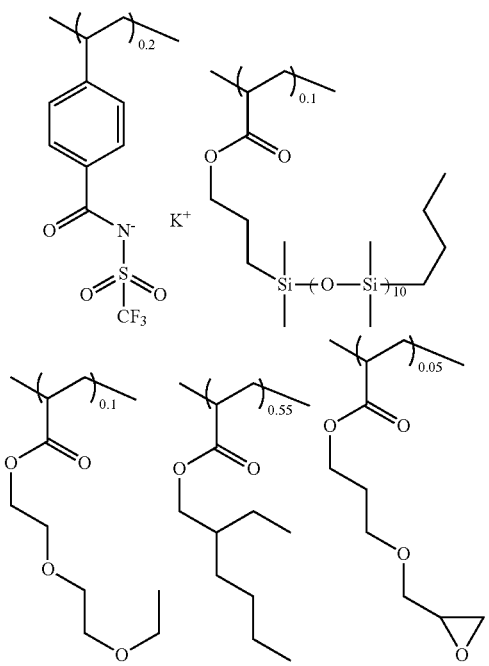

Comparative Ionic Polymer 1
Mw=46,700
Mw/Mn=2.25

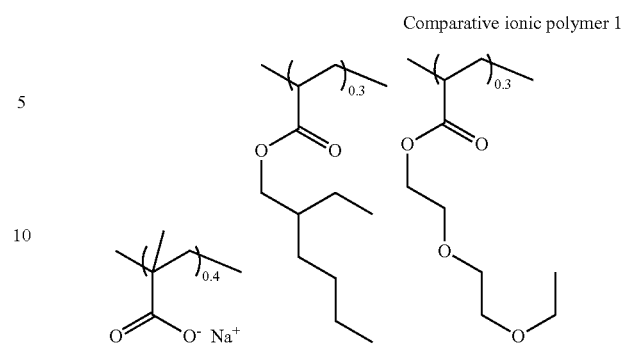

Comparative ionic polymer 1

[Silicone Compound (B) Having Polyglycerin Structure]

Polyglycerin-silicone compounds 1 to 22, which were blended to the bio-electrode composition solutions of Examples as the silicone compound (B) having a polyglycerin structure, and Comparative polyether-silicone compound 1, which was blended to the bio-electrode composition solution of Comparative Example, are shown below. As the method for synthesizing these compounds, the synthesis was carried out through hydrosilylation reaction using a silicone compound having an SiH group described in JP 2019-99469A, a polyglycerin compound having a double bond, a compound having an alkylene group, and a polyether compound having a double bond in the presence of a platinum catalyst.

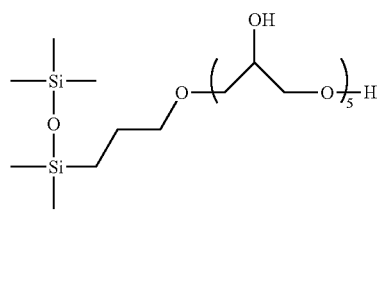

Polyglycerin-silicone compound 1

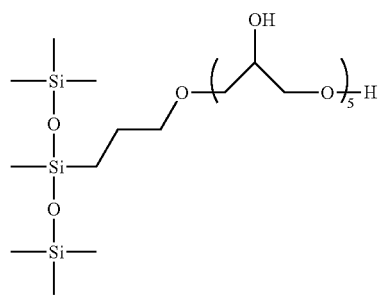

Polyglycerin-silicone compound 2

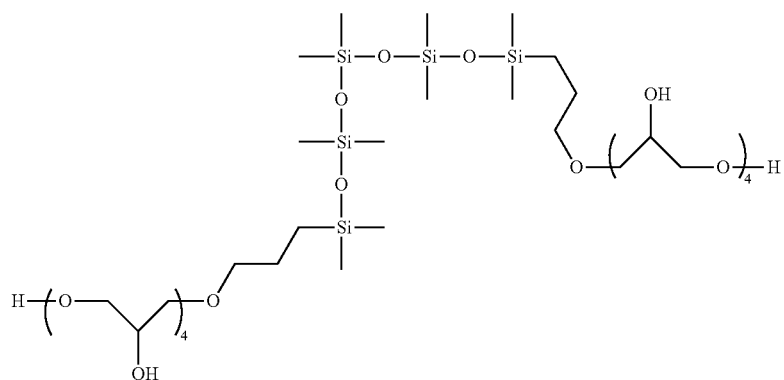

Polyglycerin-silicone compound 3

-continued
Polyglycerin-silicone compound 4
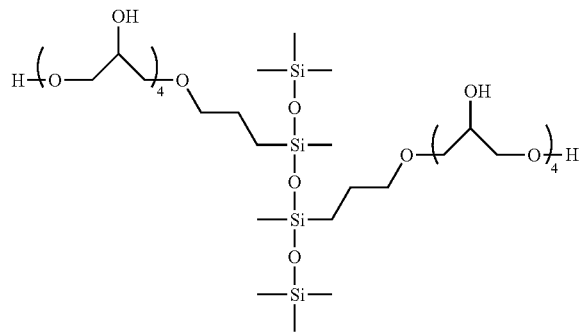
Polyglycerin-silicone compound 5
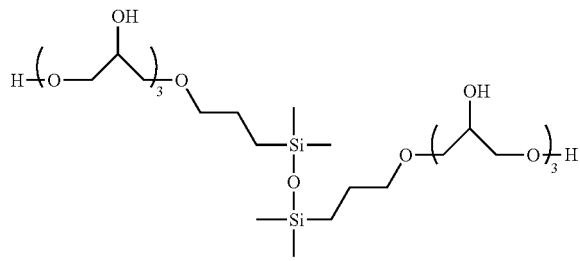
Polyglycerin-silicone compound 6
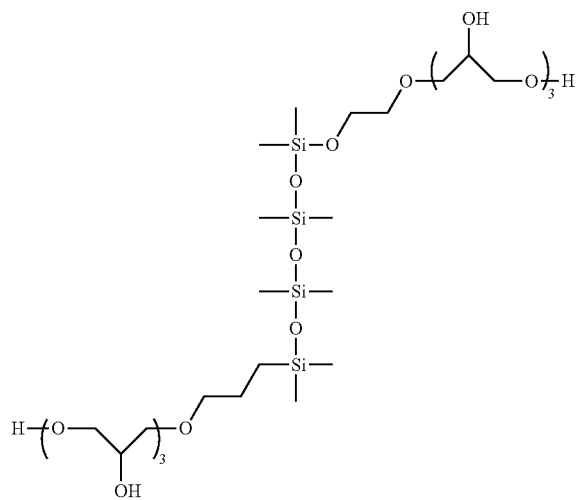
Polyglycerin-silicone compound 7
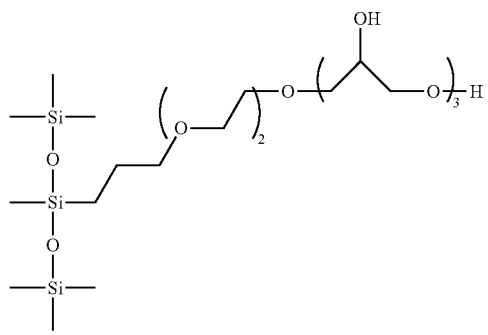
Polyglycerin-silicone compound 8
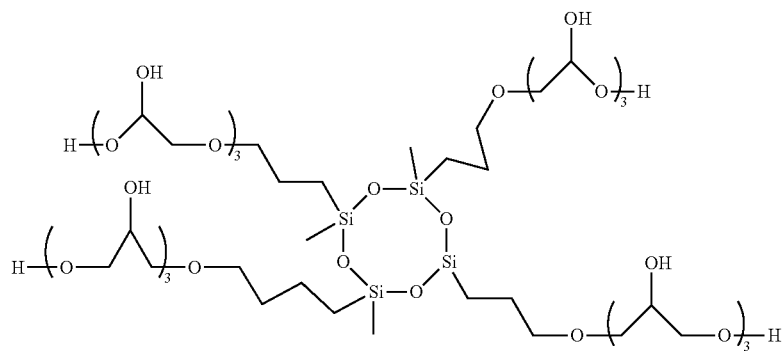
Polyglycerin-silicone compound 9
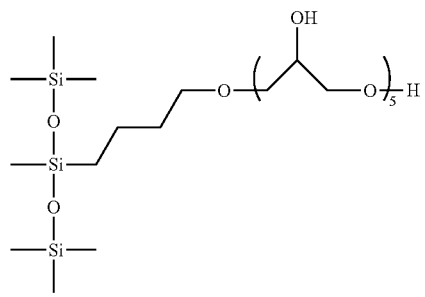
Polyglycerin-silicone compound 10
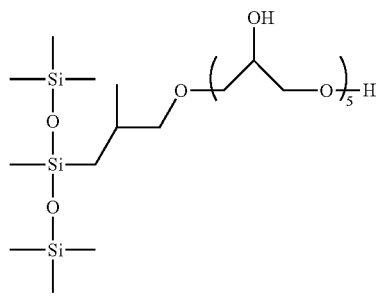

-continued
Polyglycerin-silicone compound 11
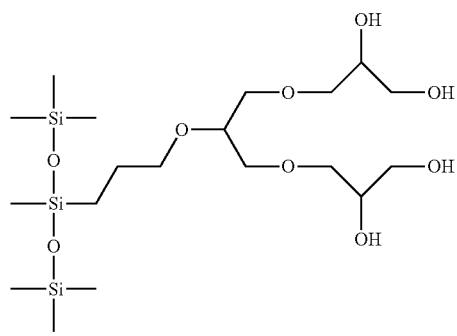
Comparative polyether-silicone compound 1
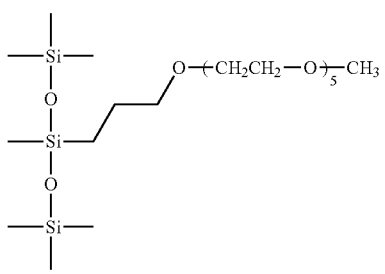
Polyglycerin-silicone compound 12
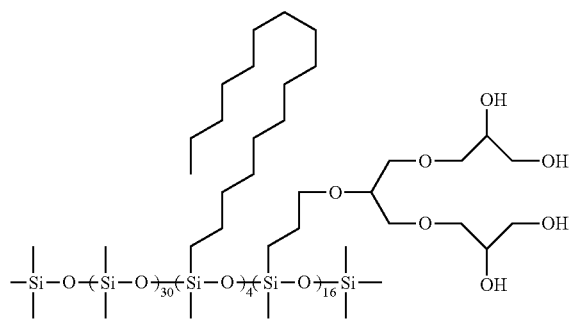
Polyglycerin-silicone compound 13
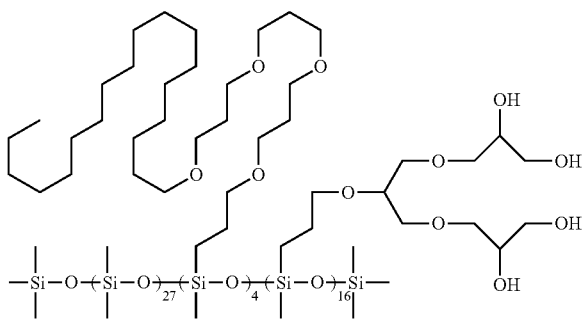
Polyglycerin-silicone compound 14
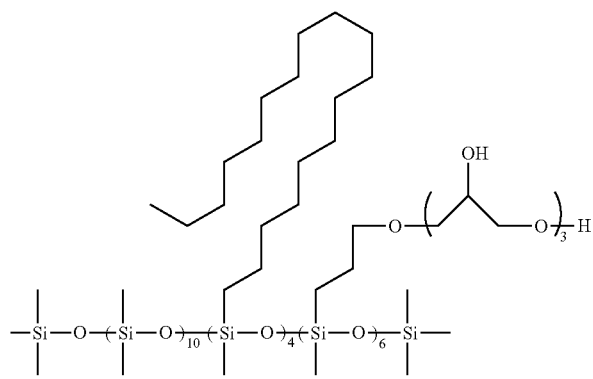
Polyglycerin-silicone compound 15
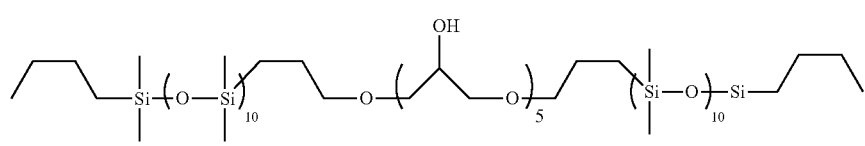
Polyglycerin-silicone compound 16
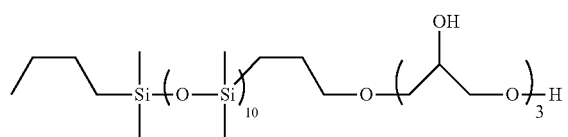
Polyglycerin-silicone compound 17
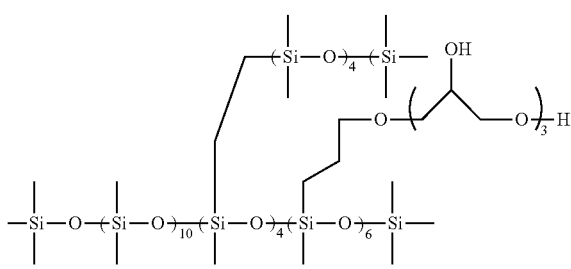

Polyglycerin-silicone compound 18

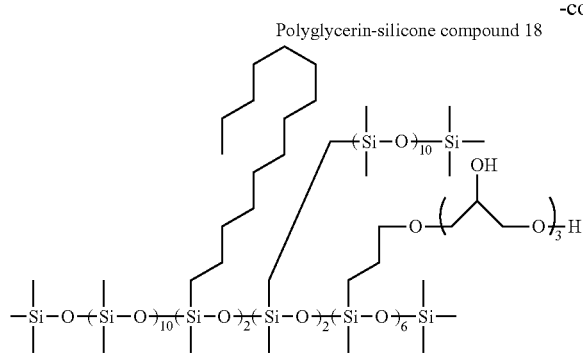

Polyglycerin-silicone compound 19

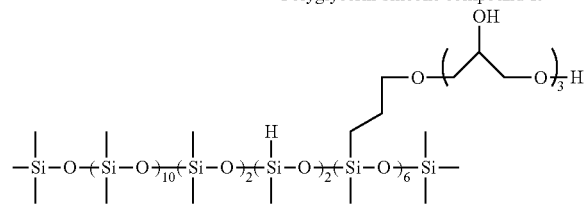

Polyglycerin-silicone compound 20

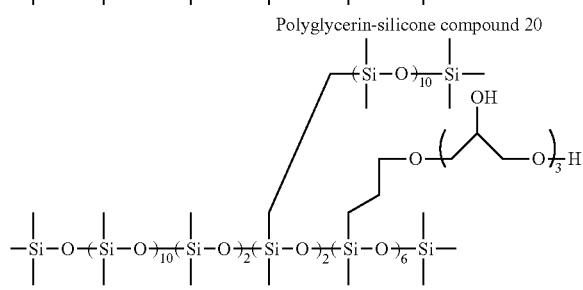

Polyglycerin-silicone compound 21

Polyglycerin-silicone compound 22

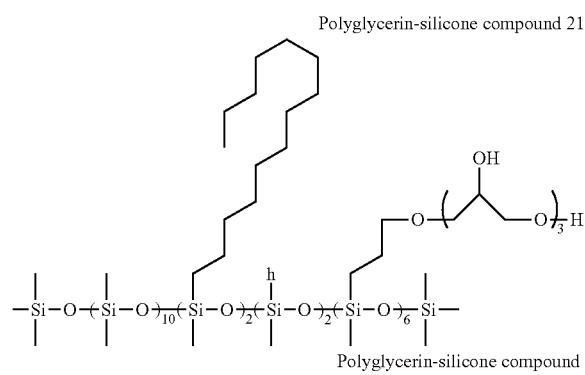

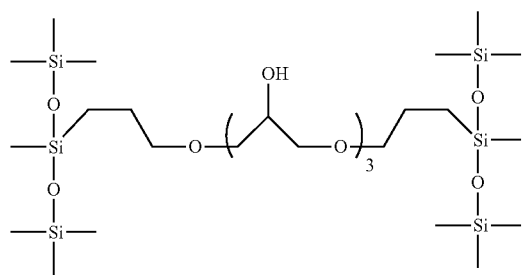

[Resin Component (C)]

Siloxane compounds 1 to 4, which were blended to the bio-electrode composition solutions of Examples and Comparative Examples as a silicone base resin, are shown below.

(Siloxane Compound 1)

Siloxane compound 1 was vinyl group-containing polydimethylsiloxane having an alkenyl group-content of 0.007 mol/100 g in which the terminals of molecular chain were blocked with $SiMe_2Vi$ groups, with the 30% toluene solution thereof having a viscosity of 27,000 mPa·s.

(Siloxane Compound 2)

Siloxane compound 2 was a 60% toluene solution of polysiloxane of MQ resin composed of an $Me_3SiO_{0.5}$ unit and an $SiO_2$ unit ($Me_3SiO_{05}$ unit/$SiO_2$ unit=0.8).

(Siloxane Compound 3)

Siloxane compound 3 was polydimethylsiloxane-bonded MQ resin obtained by heating a solution (composed of 40 parts by mass of vinyl group-containing polydimethylsiloxane having an alkenyl group-content of 0.007 mol/100 g in which the terminals of molecular chain were blocked with OH groups, with the 30% toluene solution thereof having a viscosity of 42,000 mPa·s; 100 parts by mass of 60% toluene solution of polysiloxane of MQ resin composed of an $Me_3SiO_{05}$ unit and an $SiO_2$ unit ($Me_3SiO_{0.5}$ unit/$SiO_2$ unit=0.8); and 26.7 parts by mass of toluene) with refluxing for 4 hours, followed by cooling.

(Siloxane Compound 4)

As methylhydrogensilicone oil, KF-99 manufactured by Shin-Etsu Chemical Co., Ltd. was used.

Acrylic polymer blended as an acrylic base resin in the bio-electrode composition solutions is shown below.

Acrylic Polymer 1

Mw=108,000

Mw/Mn=2.32

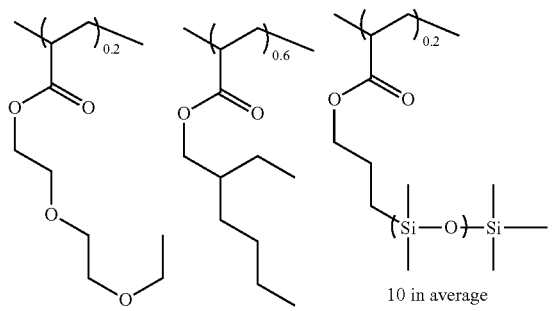

The repeating number in each formula shows the average value.

Silicone pendant urethane (meth)acrylates 1 to 3 and Urethane (meth)acrylate 4, which were blended to the bio-electrode composition solutions of Examples and Comparative Examples as silicone, acrylic, or urethane base resins, are shown below.

Silicone pendent urethane (meth)acrylate 1

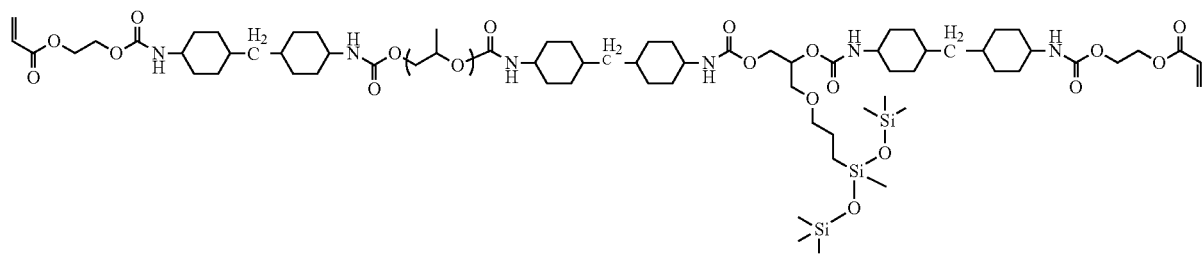

130 in average
Mw 24800 Mw/Mn 2.65

Silicone pendent urethane (meth)acrylate 2

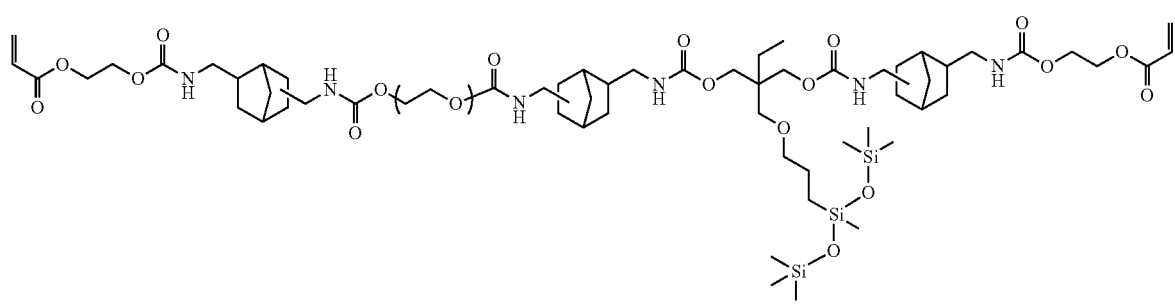

16 in average
Mw 8900 Mw/Mn 2.67

Silicone pendent urethane (meth)acrylate 3

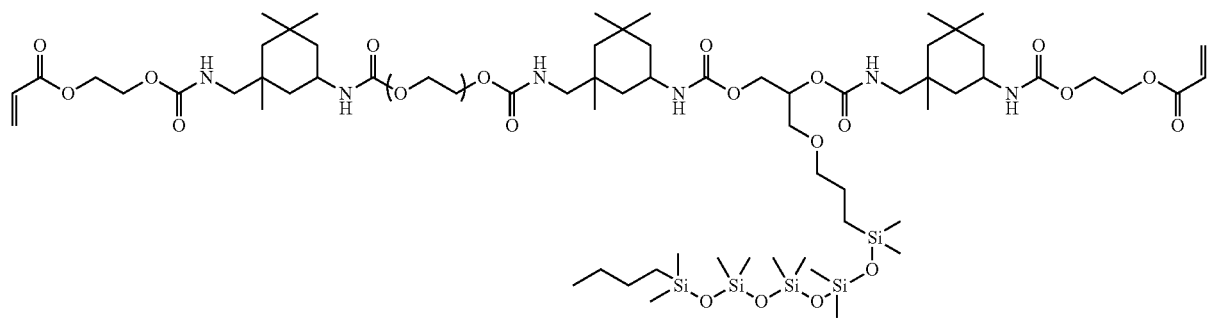

20 in average
Mw 8100 Mw/Mn 2.69

Urethane (meth)acrylate 4

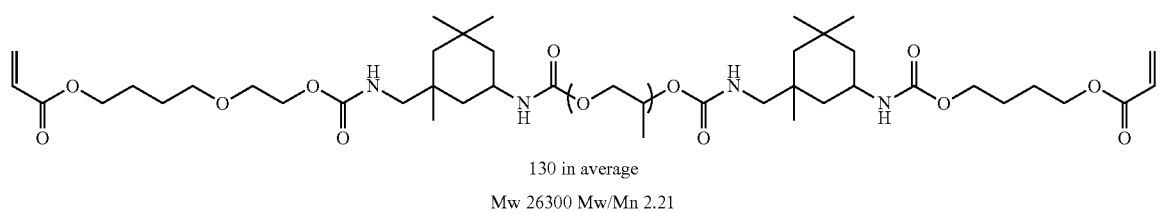

130 in average
Mw 26300 Mw/Mn 2.21

The repeating number in each formula shows the average value.

[Crosslinking Agent]

A crosslinking agent, which was blended to the bioelectrode composition solutions of Examples and Comparative Examples, is shown below.

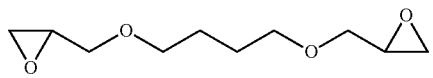

Crosslinking agent

[Organic Solvent]

Organic solvents, which were blended to the bio-electrode composition solutions of Examples and Comparative Examples, are shown below.
EDE: diethylene glycol diethyl ether
BE: diethylene glycol butyl ether
ISOPAR G (manufactured by Exxon Mobile Corporation): isoparaffin

[Others]

A lithium titanate powder, silver flakes, a radical generator, a platinum catalyst, and electric conductivity improvers (carbon black, carbon nanotube), which were blended to the bio-electrode composition solutions of Examples and Comparative Examples as additives, are shown below.
Lithium titanate powder, spinel: manufactured by Sigma-Aldrich Co. LLC., with the size of 200 nm or less
Silver flakes: manufactured by Sigma-Aldrich Co. LLC., with the average size of 10 μm
Radical generator: IRGACURE TPO manufactured by BASF SE
Platinum catalyst: CAT-PL-50T manufactured by Shin-Etsu Chemical Co., Ltd.
Carbon black: DENKA BLACK Li-400 manufactured by Denka Co., Ltd.
Multilayer carbon nanotube: manufactured by Sigma-Aldrich Co. LLC., with the diameter of 110 to 170 nm and length of 5 to 9 μm Examples 1 to 33, Comparative Examples 1 to 3

On the basis of the compositions shown in Tables 1 to 4, the ionic material (salt), the resin, the organic solvent, the additives (radical generator, platinum catalyst, electric conductivity improver, lithium titanate powder, ionic additive), and the crosslinking agent were blended to prepare bio-electrode composition solutions (Bio-electrode composition solutions 1 to 31, Comparative bio-electrode composition solutions 1 to 3).

TABLE 1

| Bio-electrode composition solution | Ionic material (parts by mass) | Polyglycerin-silicone compound (parts by mass) | Resin (parts by mass) | Organic solvent (parts by mass) | Additive (parts by mass) |
|---|---|---|---|---|---|
| Bio-electrode composition solution 1 | Ionic polymer 1(30) | Polyglycerin-silicone compound 1(5) | Siloxane compound 1(40) Siloxane compound 2(100) Siloxane compound 4(3) | ISOPAR G(60) cyclopentanone(70) | CAT-PL-50T(1.5) carbon black(14) |
| Bio-electrode composition solution 2 | Ionic polymer 2(30) | Polyglycerin-silicone compound 2(10) | Siloxane compound 3(126) Siloxane compound 4(3) | ISOPAR G(60) cyclopentanone(70) | CAT-PL-50T(1.5) carbon black(14) |
| Bio-electrode composition solution 3 | Ionic polymer 3(25.0) | Polyglycerin-silicone compound 3(10) | Siloxane compound 1(40) Siloxane compound 2(100) Siloxane compound 4(3) | ISOPAR G(60) cyclopentanone(70) | CAT-PL-50T(1.5) carbon black(14) |
| Bio-electrode composition solution 4 | Ionic polymer 4(30) | Polyglycerin-silicone compound 4(10) | Siloxane compound 1(40) Siloxane compound 2(100) Siloxane compound 4(3) | ISOPAR G(60) cyclopentanone(70) | CAT-PL-50T(0.7) lithium titanate powder(12) silver flake(8) |
| Bio-electrode composition solution 5 | Ionic polymer 5(30) | Polyglycerin-silicone compound 5(10) | Siloxane compound 3(126) Siloxane compound 4(3) | n-octane(60) cyclopentanone(70) | CAT-PL-50T(1.5) carbon black(14) |
| Bio-electrode composition solution 6 | Ionic polymer 6(30) | Polyglycerin-silicone compound 6(10) | Siloxane compound 3(126) Siloxane compound 4(3) | n-nonane(60) 2-heptanone(14) | CAT-PL-50T(1.5) lithium titanate powder(5) carbon black(5) |
| Bio-electrode composition solution 7 | Ionic polymer 7(30) | Polyglycerin-silicone compound 7(10) | Siloxane compound 3(126) Siloxane compound 4(3) | ISOPAR G(60) cyclopentanone(60) | CAT-PL-50T(1.5) carbon black(14) |
| Bio-electrode composition solution 8 | Ionic polymer 8(30) | Polyglycerin-silicone compound 8(10) | Siloxane compound 3(126) Siloxane compound 4(3) | n-decane(30) n-octane(30) 2-heptanone(14) | CAT-PL-50T(1.5) lithium titanate powder(5) carbon black(5) |
| Bio-electrode composition solution 9 | Ionic polymer 9(30) | Polyglycerin-silicone compound 9(10) | Siloxane compound 3(126) Siloxane compound 4(3) | ISOPAR G(60) cyclopentanone70) | CAT-PL-50T(1.5) lithium titanate powder(5) multilayer carbon nanotube(3) |

TABLE 2

| Bio-electrode composition solution | Ionic material (parts by mass) | Polyglycerin-silicone compound (parts by mass) | Resin (parts by mass) | Organic solvent (parts by mass) | Additive (parts by mass) |
|---|---|---|---|---|---|
| Bio-electrode composition solution 10 | Ionic polymer 10(40) | Polyglycerin-silicone compound 10(10) | Silicone urethane acrylate 1(80) | EDE(60) cyclopentanone(70) | IRGACURE TPO(1) |

TABLE 2-continued

| Bio-electrode composition solution | Ionic material (parts by mass) | Polyglycerin-silicone compound (parts by mass) | Resin (parts by mass) | Organic solvent (parts by mass) | Additive (parts by mass) |
|---|---|---|---|---|---|
| Bio-electrode composition solution 11 | Ionic polymer 11(20) | Polyglycerin-silicone compound 11(10) | Acrylic polymer 1(55) Silicone urethane acrylate 1(25) | EDE(60) cyclopentanone(70) | IRGACURE TPO(1) |
| Bio-electrode composition solution 12 | Ionic polymer 12(20) | Polyglycerin-silicone compound 1(10) | Acrylic polymer 1(20) Silicone urethane acrylate 2(60) | EDE(60) cyclopentanone(70) | IRGACURE TPO(1) |
| Bio-electrode composition solution 13 | Ionic polymer 13(25) | Polyglycerin-silicone compound 1(10) | Acrylic polymer 1(20) Silicone urethane acrylate 3(60) | EDE(60) cyclopentanone(70) | IRGACURE TPO(1) |
| Bio-electrode composition solution 14 | Ionic polymer 14(25) | Polyglycerin-silicone compound 5(10) | Silicone urethane acrylate 1(80) | BE(120) water(10) | IRGACURE TPO(1) sodium chloride(2) |
| Bio-cloctrodo composition solution 15 | Ionic polymer 15(26) | Polyglycerin-silicone compound 5(10) | Silicone urethane acrylate 1(80) | BE(120) water(10) | IRGACURE TPO(1) potassium chloride(2) |
| Bio-electrode composition solution 16 | Ionic polymer 16(16) | Polyglycerin-silicone compound 5(10) | Silicone urethane acrylate 1(80) | BE(120) water(10) | IRGACURE TPO(1) crosslinking agent(2) |
| Bio-electrode composition solution 17 | Ionic polymer 11(20) | Polyglycerin-silicone compound 11(10) | Urethane acrylate 4(80) | EDE(60) cyclopentanone(70) | IPGACURE TPO(1) |

TABLE 3

| Bio-electrode composition solution | Ionic material (parts by mass) | Polyglycerin-silicone compound (parts by mass) | Resin (parts by mass) | Organic solvent (parts by mass) | Additive (parts by mass) |
|---|---|---|---|---|---|
| Bio-electrode composition solution 18 | Ionic polymer 1(30) | Polyglycerin-silicone compound 12(15) | Siloxane compound 1(40) Siloxane compound 2(100) Siloxane compound 4(3) | ISOPAR G(60) cyclopentanone(70) | CAT-PL-50T(1.5) carbon black(14) |
| Bio-electrode composition solution 19 | Ionic polymer 1(30) | Polyglycerin-silicone compound 13(15) | Siloxane compound 1(40) Siloxane compound 2(100) Siloxane compound 4(3) | ISOPAR G(60) cyclopentanone(70) | CAT-PL-50T(1.5) carbon black(14) |
| Bio-electrode composition solution 20 | Ionic polymer 1(30) | Polyglycerin-silicone compound 14(15) | Siloxane compound 1(40) Siloxane compound 2(100) Siloxane compound 4(3) | ISOPAR G(60) cyclopentanone(70) | CAT-PL-50T(1.5) carbon black(14) |
| Bio-electrode composition solution 21 | Ionic polymer 1(30) | Polyglycerin-silicone compound 15(15) | Siloxane compound 1(40) Siloxane compound 2(100) Siloxane compound 4(3) | ISOPAR G(60) cyclopentanone(70) | CAT-PL-50T(1.5) carbon black(14) |
| Bio-electrode composition solution 22 | Ionic polymer 1(30) | Polyglycerin-silicone compound 16(8) | Siloxane compound 1(40) Siloxane compound 2(100) Siloxane compound 4(3) | ISOPAR G(60) cyclopentanone(70) | CAT-PL-50T(1.5) carbon black(14) |
| Bio-electrode composition solution 23 | Ionic polymer 1(30) | Polyglycerin-silicone compound 17(15) | Siloxane compound 1(40) Siloxane compound 2(100) Siloxane compound 4(3) | ISOPAR G(60) cyclopentanone(70) | CAT-PL-50T(1.5) carbon black(14) |
| Bio-electrode composition solution 24 | Ionic polymer 1(30) | Polyglycerin-silicone compound 18(8) | Siloxane compound 1(40) Siloxane compound 2(100) Siloxane compound 4(3) | ISOPAR G(60) cyclopentanone(70) | CAT-PL-50T(1.5) carbon black(14) |
| Bio-electrode composition solution 25 | Ionic polymer 17(30) | Polyglycerin-silicone compound 19(8) | Siloxane compound 1(40) Siloxane compound 2(100) Siloxane compound 4(3) | ISOPAR G(60) cyclopentanone(70) | CAT-PL-50T(1.5) carbon black(14) |
| Bio-electrode composition solution 26 | Ionic polymer 18(30) | Polyglycerin-silicone compound 20(5) | Siloxane compound 1(40) Siloxane compound 2(100) Siloxane compound 4(3) | ISOPAR G(60) cyclopentanone(70) | CAT-PL-50T(1.5) carbon black(14) |
| Bio-electrode composition solution 27 | Ionic polymer 19(100) | Polyglycerin-silicone compound 19(8) | — | cyclopentanone(150) | — |
| Bio-electrode composition solution 28 | Ionic polymer 1(30) | Polyglycerin-silicone compound 20(5) | Siloxane compound 1(40) Siloxane compound 2(100) | ISOPAR G(60) cyclopentanone(70) | CAT-PL-50T(1.5) carbon black(14) |
| Bio-electrode composition solution 29 | Ionic polymer 1(30) | Polyglycerin-silicone compound 21(5) | Siloxane compound 1(40) Siloxane compound 2(100) | ISOPAR G(60) cyclopentanone(70) | CAT-PL-50T(1.5) carbon black(14) |
| Bio-electrode composition solution 30 | Ionic polymer 1(30) | Polyglycerin-silicone compound 22(5) | Siloxane compound 1(40) Siloxane compound 2(100) Siloxane compound 4(2) | ISOPAR G(60) cyclopentanone(70) | CAT-PL-50T(1.5) carbon black(14) |

TABLE 4

| Bio-electrode composition solution | Ionic material (parts by mass) | Polyglycerin-silicone compound (parts by mass) | Resin (parts by mass) | Organic solvent (parts by mass) | Additive (parts by mass) |
|---|---|---|---|---|---|
| Comparative bio-electrode composition solution 1 | Ionic polymer 1(30) | — | Siloxane compound 1(40) Siloxane compound 2(100) Siloxane compound 4(3) | ISOPAR G(60) cyclcpentanone(70) | CAT-PL-50T(1.5) carbon black(14) |
| Bio-electrode composition solution 31 | Comparative ionic polymer 1(30) | Polyglycerin-silicone compound 1(10) | Siloxane compound 3(126) Siloxane compound 4(3) | ISOPAR G(60) cyclcpentanone(70) | CAT-PL-50T(1.5) carbon black(14) |
| Comparative bio-electrode composition solution 2 | Ionic polymer 1(30) | Comparative polyether-silicone compound 1(10) | Siloxane compound 1(40) Siloxane compound 2(100) Siloxane compound 4(3) | ISOPAR G(60) cyclcpentanone(70) | CAT-PL-50T(1.5) carbon black(14) |
| Comparative bio-electrode composition solution 3 | Comparative Ionic polymer 1(30) | — | Siloxane compound 1(40) Siloxane compound 2(100) Siloxane compound 4(3) | ISOPAR G(60) cyclcpentanone(70) | CAT-PL-50T(1.5) carbon black(14) |

(Preparation of Samples for Biological Signal Evaluation)

A thermoplastic urethane (TPU) film ST-604 (manufactured by Bemis Associates Inc.) was coated with an electro-conductive paste DOTITE FA-333 (manufactured by Fujikura Kasei Co., Ltd.) by screen printing. The coating film was baked in an oven at 120° C. for 10 minutes to print a keyhole-shaped electro-conductive pattern including a circular portion with a diameter of 2 cm and a rectangular portion. Then, one of the bio-electrode composition solutions shown in Tables 1 to 4 was applied onto the circular portion of the printed electro-conductive pattern by screen printing. After air-dried at room temperature for 10 minutes, the coating film was baked using an oven at 125° C. for 10 minutes to evaporate the solvent and cure the film. In Examples 10 to 17, the films were further cured by irradiation with a xenon lamp at a radiant exposure level of 200 mJ/cm$^2$ under a nitrogen atmosphere. By the curing, cured materials of the bio-electrode compositions were obtained as living body contact layers. In Examples 18 and 19, the cured bio-electrodes respectively prepared in Examples 15 and 16 were left standing in a 30° C. and 90%-humidity environment for 30 minutes to perform humidification treatment.

FIG. 3 is a schematic view of the printed bio-electrodes prepared in each Example. As shown in FIG. 3, multiple bio-electrodes 1 were prepared on the thermoplastic urethane film 20. The bio-electrodes 1 each include the keyhole-shaped electro-conductive pattern 2 as the electro-conductive base material, and the living body contact layer 3 formed to cover the circular portion of the electro-conductive pattern 2.

Then, as shown in FIG. 4, the urethane film 20 with the printed bio-electrode 1 was cut out and pasted on a double-sided tape 21. In this manner, three bio-electrode samples 10 (samples for biological signal evaluation) were prepared for each of the composition solutions.

(Thickness Measurement of Living Body Contact Layer)

The thickness of the living body contact layer of each bio-electrode sample prepared as described above was measured with a micrometer. Tables 5 and 6 show the result.

(Biological Signal Measurement)

The electro-conductive wiring pattern formed from the electro-conductive paste of each bio-electrode was connected to a portable electrocardiograph HCG-901 (manufactured by OMRON HEALTHCARE Co., Ltd.) through an electro-conductive wire. A positive electrode of the electrocardiograph was attached to a location LA in FIG. 5 on a human body, a negative electrode was attached to a location LL, and an earth was attached to a location RA. Immediately before the attachments, the skin was wiped with a gauze impregnated with a solution containing 70% ethanol and 30% water. Immediately after the attachments, the electrocardiogram measurement was started to measure the time until an electrocardiogram waveform including P, Q, R, S, and T waves appeared as shown in FIG. 6. Tables 5 and 6 show the result.

TABLE 5

| Example | Bio-electrode composition solution | Resin thickness (μm) | Time (min.) until ECG signal appeared |
|---|---|---|---|
| Example 1 | Bio-electrode composition solution 1 | 20 | 3.5 |
| Example 2 | Bio-electrode composition solution 2 | 18 | 2 |
| Example 3 | Bio-electrode composition solution 3 | 22 | 2 |
| Example 4 | Bio-electrode composition solution 4 | 28 | 2 |
| Example 5 | Bio-electrode composition solution 5 | 27 | 1.5 |
| Example 6 | Bio-electrode composition solution 6 | 31 | 2 |
| Example 7 | Bio-electrode composition solution 7 | 33 | 2 |
| Example 8 | Bio-electrode composition solution 8 | 29 | 1.8 |
| Example 9 | Bio-electrode composition solution 9 | 28 | 2.2 |
| Example 10 | Bio-electrode composition solution 10 | 31 | 3 |
| Example 11 | Bio-electrode composition solution 11 | 41 | 4 |
| Example 12 | Bio-electrode composition solution 12 | 33 | 3 |
| Example 13 | Bio-electrode composition solution 13 | 25 | 2 |
| Example 14 | Bio-electrode composition solution 14 | 21 | 2 |
| Example 15 | Bio-electrode composition solution 15 | 26 | 2 |
| Example 16 | Bio-electrode composition solution 16 | 20 | 2 |
| Example 17 | Bio-electrode composition solution 17 | 23 | 1.8 |
| Example 18 | Bio-electrode composition solution 15 | 26 | 0.5 |
| Example 19 | Bio-electrode composition solution 16 | 20 | 0.5 |

TABLE 5-continued

| Example | Bio-electrode composition solution | Resin thickness (μm) | Time (min.) until ECG signal appeared |
|---|---|---|---|
| Comparative Example 1 | Comparative bio-electrode composition solution 1 | 20 | 30 |
| Example 33 | Bio-electrode composition solution 31 | 21 | 7 |
| Comparative Example 2 | Comparative bio-electrode composition solution 2 | 29 | 20 |
| Comparative Example 3 | Comparative bio-electrode composition solution 3 | 30 | N/A |

TABLE 6

| Example | Bio-electrode composition solution | Resin thickness (μm) | Time (min.) until ECG signal appeared |
|---|---|---|---|
| Example 20 | Bio-electrode composition solution 18 | 23 | 2 |
| Example 21 | Bio-electrode composition solution 19 | 24 | 2 |
| Example 22 | Bio-electrode composition solution 20 | 24 | 1.5 |
| Example 23 | Bio-electrode composition solution 21 | 20 | 1 |
| Example 24 | Bio-electrode composition solution 22 | 20 | 1.5 |
| Example 25 | Bio-electrode composition solution 23 | 22 | 1.5 |
| Example 26 | Bio-electrode composition solution 24 | 23 | 1.5 |
| Example 27 | Bio-electrode composition solution 25 | 21 | 1.5 |
| Example 28 | Bio-electrode composition solution 26 | 23 | 1.5 |
| Example 29 | Bio-electrode composition solution 27 | 24 | 1.2 |
| Example 30 | Bio-electrode composition solution 28 | 26 | 1.0 |
| Example 31 | Bio-electrode composition solution 29 | 25 | 1.5 |
| Example 32 | Bio-electrode composition solution 30 | 27 | 1.5 |

As shown in Tables 5 and 6, in Examples 1 to 32 in each of which the living body contact layer was formed using the inventive bio-electrode composition containing the polymer compound (A) (salt (ionic material)) having a particular structure and the silicone compound (B) having a polyglycerin structure as described above, biological signals (ECG signals) were detected within short times after the attachment to the body. In contrast, in Comparative Example 1 not containing the silicone compound (B) having a polyglycerin structure, the living body contact layer presumably failed to keep sufficient water content in comparison with Examples 1 to 32. This is presumably the reason that in Comparative Example 1, the polymer compound (A) of the living body contact layer was inferior in ion sensitivity to those in Examples, and it took longer time to obtain a biological signal. Meanwhile, the living body contact layer of Example 33 contained the silicone compound (B) having a polyglycerin structure, but did not contain the polymer compound (A). This is presumably the reason that the living body contact layer of Example 33 exhibited higher ion sensitivity than the living body contact layer of Comparative Example 1, and that the time to obtain a biological signal was shorter than that in Comparative Example 1. On the other hand, the living body contact layers of Examples 1 to 32 exhibited further higher ion sensitivity than the living body contact layer of Example 33. This is presumably the reason the time to obtain a biological signal was shorter than that in Example 33. Meanwhile, the living body contact layer of Comparative Example 2 did not contain the silicone compound (B) having a polyglycerin structure, but instead contained Comparative polyether-silicone compound 1. Such a bio-electrode of Comparative Example 2 had to spend longer time to obtain a biological signal than those in Examples 1 to 33. Further, the living body contact layer of Comparative Example 3 did not contain both of the polymer compound (A) having a particular structure described above and the silicone compound (B) having a polyglycerin structure. Such a bio-electrode of Comparative Example 3 cannot obtain any biological signal.

The above results have revealed the bio-electrode including the living body contact layer formed using the inventive bio-electrode composition is capable of obtaining a biological signal quickly. Further, the inventive bio-electrode composition can demonstrate a synergistic effect by the polymer compound (A) and the silicone compound (B) having a polyglycerin structure having been described above, and thus provides a bio-electrode which enables quick biological signal detection when attached to a living body.

In addition, the bio-electrodes of Examples 18 and 19 are respectively the bio-electrodes of Examples 1 and 11 which were further humidified as described above. As apparent from the result shown in Table 5, the bio-electrodes of Examples 18 and 19 were able to obtain biological signals in much shorter time than those by the bio-electrodes of Examples 15 and 16. This indicates that increasing the water content in the bio-electrode film obtained from the inventive bio-electrode composition can provide a bio-electrode capable of obtaining biological signals from skin more quickly.

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:
1. A bio-electrode composition comprising:
   (A) a polymer compound comprising a repeating unit-a having a structure selected from the group consisting of salts of ammonium, sodium, potassium, and silver formed with any of fluorosulfonic acid, fluorosulfonimide, and N-carbonyl-fluorosulfonamide; and
   (B) a silicone compound having a polyglycerin structure.
2. The bio-electrode composition according to claim 1, wherein the repeating unit-a is shown by any of the following general formulae (1)-1 to (1)-4,

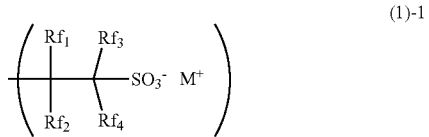

(1)-1

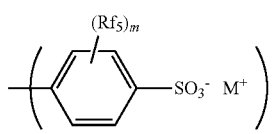

(1)-2

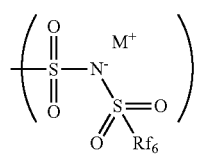

(1)-3

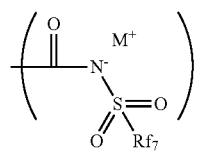

(1)-4 wherein $Rf_1$ and $Rf_2$ each represent a hydrogen atom, a fluorine atom, an oxygen atom, a methyl group, or a trifluoromethyl group, provided that when $Rf_1$ and $Rf_2$ represent an oxygen atom, the single oxygen atom represented by $Rf_1$ and $Rf_2$ bonds to a single carbon atom to form a carbonyl group; and $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group;

$Rf_5$, $Rf_6$, and $Rf_7$ each represent a fluorine atom, or a linear or branched alkyl group having 1 to 4 carbon atoms and at least one or more fluorine atoms;

$M^+$ represents an ion selected from the group consisting of an ammonium ion, a sodium ion, a potassium ion, and a silver ion; and "m" represents an integer of 1 to 4.

3. The bio-electrode composition according to claim 1, wherein the repeating unit-a comprises at least one repeating unit selected from the group consisting of repeating units-a1 to -a7 shown by the following general formula (2), (2)

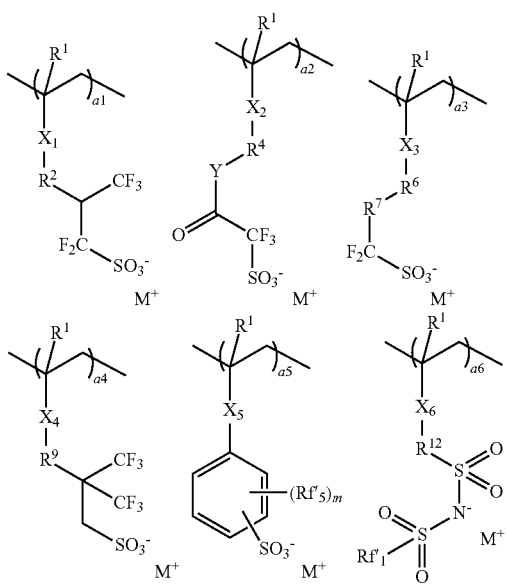

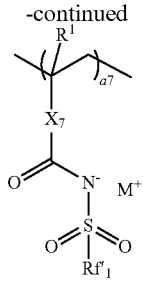

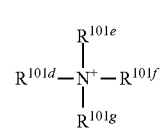

wherein $R^1$, $R^3$, $R^5$, $R^8$, $R^{10}$, $R^{11}$, and $R^{13}$ each independently represent a hydrogen atom or a methyl group; $R^2$, $R^9$, $R^4$, $R^6$, and $R^{12}$ each independently represent a single bond, or a linear, branched, or cyclic hydrocarbon group having 1 to 12 carbon atoms, the hydrocarbon group optionally having either or both of an ester group and an ether group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_5$ represents any of a single bond, an ether group, and an ester group; Y represents an oxygen atom or a $-NR^{19}-$ group; $R^{19}$ represents a hydrogen atom, or a linear or branched alkyl group having 1 to 4 carbon atoms; $Rf_1'$ represents a fluorine atom or a trifluoromethyl group; $Rf_5'$ represents a fluorine atom, or a linear or branched alkyl group having 1 to 4 carbon atoms and at least one or more fluorine atoms; "m" represents an integer of 1 to 4; a1, a2, a3, a4, a5, a6, and a7 satisfy $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, and $0 \leq a1+a2+a3+a4+a5+a6+a7 \leq 1.0$; and $M^+$ represents an ion selected from the group consisting of an ammonium ion, a sodium ion, a potassium ion, and a silver ion.

4. The bio-electrode composition according to claim 2, wherein the polymer compound (A) comprises an ammonium ion shown by the following general formula (3) as the $M^+$, (3)

$$R^{101d}-\underset{\underset{R^{101g}}{|}}{\overset{\overset{R^{101e}}{|}}{N^+}}-R^{101f}$$

wherein $R^{101d}$, $R^{101e}$, $R^{101f}$, and $R^{101g}$ each represent a hydrogen atom, a linear, branched, or cyclic alkyl group having 1 to 12 carbon atoms, a linear, branched, or cyclic alkenyl group or alkynyl group having 2 to 12 carbon atoms, or an aromatic group having 4 to 20 carbon atoms, and optionally have one or more selected from the group consisting of an ether group, a carbonyl group, an ester group, a hydroxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$ are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the formula (3) within the ring.

5. The bio-electrode composition according to claim 1, wherein the silicone compound (B) having the polyglycerin structure is shown by the following general formula (4) or (5),

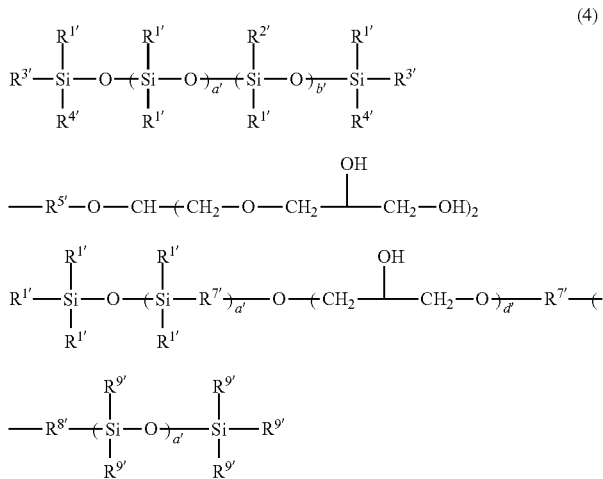

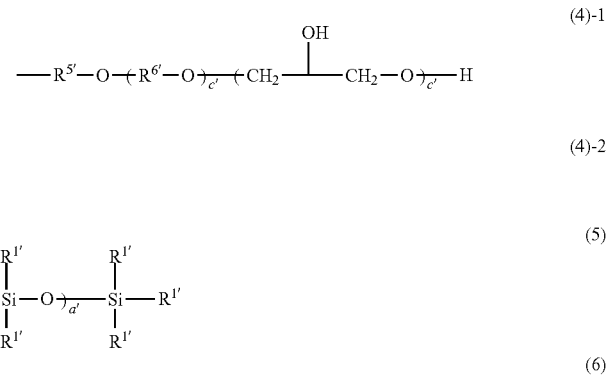

wherein each $R^{1\prime}$ is identical to or different from each other and independently represents a hydrogen atom, a linear or branched alkyl group having 1 to 50 carbon atoms and optionally containing an ether group, a phenyl group, or a silicone chain shown by a general formula (6); $R^{2\prime}$ represents a group having a polyglycerin group structure shown by a formula (4)-1 or (4)-2; each $R^{3\prime}$ is identical to or different from each other and independently represents the $R^{1\prime}$ group or the $R^{2\prime}$ group; and each $R^{4\prime}$ identical to or different from each other and independently represents the $R^{1\prime}$ group, the $R^{2\prime}$ group, or an oxygen atom, provided that when $R^{4\prime}$ represents an oxygen atom, the $R^{4\prime}$ moieties bond to each other and optionally constitute an ether group to form a ring together with silicon atoms;

each a' is identical to or different from each other and represents 0 to 100, b' represents 0 to 100, and a'+b' is 0 to 200, provided that when b' is 0, at least one $R^{3\prime}$ is the $R^{2\prime}$ group;

$R^{5\prime}$ represents an alkylene group having 2 to 10 carbon atoms or an aralkylene group having 7 to 10 carbon atoms; c' represents 0 to 20; and d' represents 1 to 20; and $R^{6\prime}$ and $R^{7\prime}$ each represent an alkylene group having 2 to 6 carbon atoms; $R^{8\prime}$ represents an alkylene group having 2 to 6 carbon atoms, or an ether group; and $R^{9\prime}$ represents a hydrogen atom, a linear or branched alkyl group having 1 to 50 carbon atoms and optionally containing an ether group, or a phenyl group.

6. The bio-electrode composition according to claim 2, wherein the silicone compound (B) having the polyglycerin structure is shown by the following general formula (4) or (5),

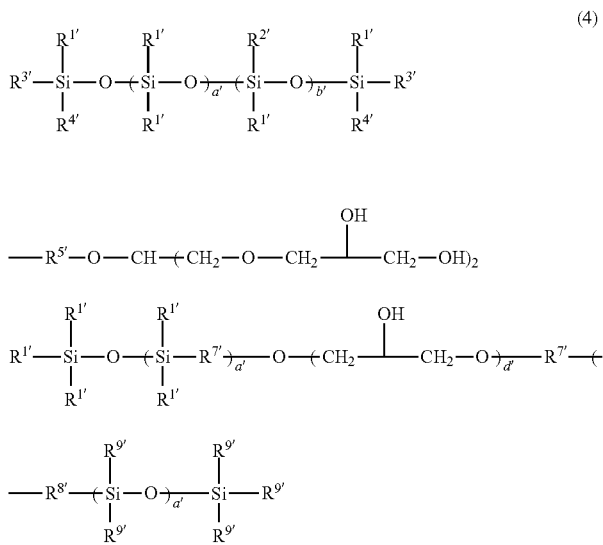

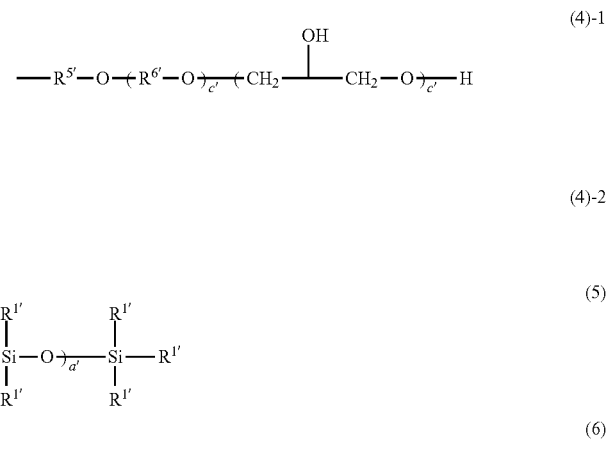

wherein each $R^{1'}$ is identical to or different from each other and independently represents a hydrogen atom, a linear or branched alkyl group having 1 to 50 carbon atoms and optionally containing an ether group, a phenyl group, or a silicone chain shown by a general formula (6); $R^{2'}$ represents a group having a polyglycerin group structure shown by a formula (4)-1 or (4)-2; each $R^{3'}$ is identical to or different from each other and independently represents the $R^{1'}$ group or the $R^{2'}$ group; and each $R^{4'}$ identical to or different from each other and independently represents the $R^{1'}$ group, the $R^{2'}$ group, or an oxygen atom, provided that when $R^{4'}$ represents an oxygen atom, the $R^{4'}$ moieties bond to each other and optionally constitute an ether group to form a ring together with silicon atoms;

each a' is identical to or different from each other and represents 0 to 100, b' represents 0 to 100, and a'+b' is 0 to 200, provided that when b' is 0, at least one $R^{3'}$ is the $R^{2'}$ group;

$R^{5'}$ represents an alkylene group having 2 to 10 carbon atoms or an aralkylene group having 7 to 10 carbon atoms; c' represents 0 to 20; and d' represents 1 to 20; and $R^{6'}$ and $R^{7'}$ each represent an alkylene group having 2 to 6 carbon atoms; $R^{8'}$ represents an alkylene group having 2 to 6 carbon atoms, or an ether group; and $R^{9'}$ represents a hydrogen atom, a linear or branched alkyl group having 1 to 50 carbon atoms and optionally containing an ether group, or a phenyl group.

7. The bio-electrode composition according to claim 3, wherein the silicone compound (B) having the polyglycerin structure is shown by the following general formula (4) or (5), 8. The bio-electrode composition according to claim 4, wherein the silicone compound (B) having the polyglycerin structure is shown by the following general formula (4) or (5),

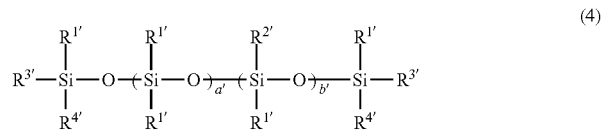

(4)

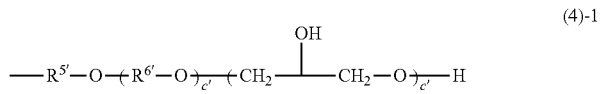

(4)-1

(4)-2

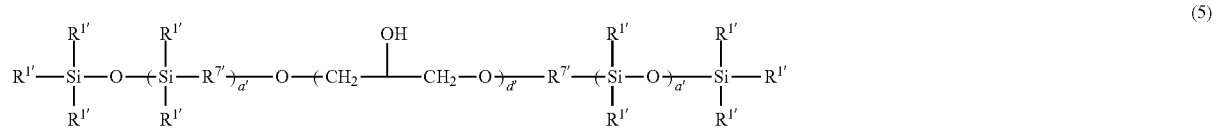

(5)

(6)

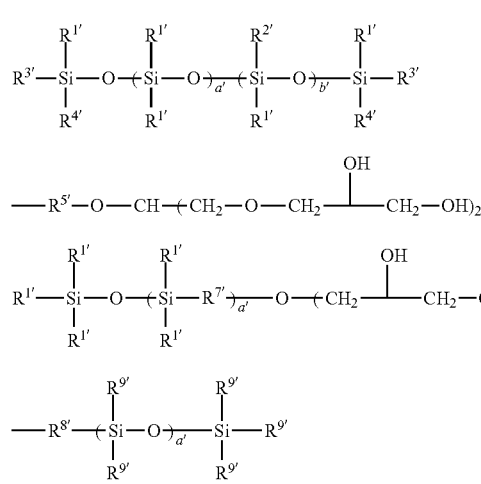
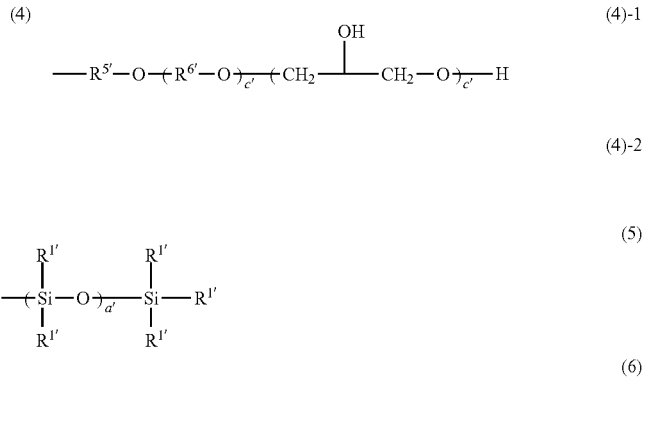

wherein each $R^{1\prime}$ is identical to or different from each other and independently represents a hydrogen atom, a linear or branched alkyl group having 1 to 50 carbon atoms and optionally containing an ether group, a phenyl group, or a silicone chain shown by a general formula (6); $R^{2\prime}$ represents a group having a polyglycerin group structure shown by a formula (4)-1 or (4)-2; each $R^{3\prime}$ is identical to or different from each other and independently represents the $R^{1\prime}$ group or the $R^{2\prime}$ group; and each $R^{4\prime}$ identical to or different from each other and independently represents the $R^{1\prime}$ group, the $R^{2\prime}$ group, or an oxygen atom, provided that when $R^{4\prime}$ represents an oxygen atom, the $R^{4\prime}$ moieties bond to each other and optionally constitute an ether group to form a ring together with silicon atoms;

each a' is identical to or different from each other and represents 0 to 100, b' represents 0 to 100, and a'+b' is 0 to 200, provided that when b' is 0, at least one $R^{3\prime}$ is the $R^{2\prime}$ group;

$R^{5\prime}$ represents an alkylene group having 2 to 10 carbon atoms or an aralkylene group having 7 to 10 carbon atoms; c' represents 0 to 20; and d' represents 1 to 20; and $R^{6\prime}$ and $R^{7\prime}$ each represent an alkylene group having 2 to 6 carbon atoms; $R^{8\prime}$ represents an alkylene group having 2 to 6 carbon atoms, or an ether group; and $R^{9\prime}$ represents a hydrogen atom, a linear or branched alkyl group having 1 to 50 carbon atoms and optionally containing an ether group, or a phenyl group.

9. The bio-electrode composition according to claim 1, further comprising (C) a resin component which is one or more selected from the group consisting of silicone base resins other than the silicone compound (B), acrylic base resins, and urethane base resins.

10. The bio-electrode composition according to claim 9, wherein the resin component (C) comprises any of:
a silicone resin having an SiO2 unit and an $R_xSiO_{(4-x)/2}$ unit, wherein R represents a substituted or unsubstituted monovalent hydrocarbon group having 1 to 10 carbon atoms, and "x" is a number in a range of 2.5 to 3.5;
diorganosiloxane having an alkenyl group; and
organohydrogenpolysiloxane having an SiH group.

11. The bio-electrode composition according to claim 1, further comprising an organic solvent.

12. The bio-electrode composition according to claim 1, further comprising a carbon powder, a silver powder, a silicon powder, and/or a lithium titanate powder.

13. The bio-electrode composition according to claim 12, wherein the carbon powder is one or both of carbon black and carbon nanotube.

14. A bio-electrode comprising:
an electro-conductive base material; and
a living body contact layer formed on the electro-conductive base material,
wherein the living body contact layer comprises a cured material of the bio-electrode composition according to claim 1.

15. The bio-electrode according to claim 14, wherein the electro-conductive base material comprises one or more selected from the group consisting of gold, silver, silver chloride, platinum, aluminum, magnesium, tin, tungsten, iron, copper, nickel, stainless steel, chromium, titanium, and carbon.

16. The bio-electrode according to claim 14, wherein the living body contact layer is humidified.

17. A method for manufacturing a bio-electrode having an electro-conductive base material and a living body contact layer formed on the electro-conductive base material, comprising:
applying the bio-electrode composition according to claim 1 onto the electro-conductive base material; and
curing the bio-electrode composition to form the living body contact layer.

18. The method for manufacturing a bio-electrode according to claim 17, wherein the electro-conductive base material comprises one or more selected from the group consisting of gold, silver, silver chloride, platinum, aluminum, magnesium, tin, tungsten, iron, copper, nickel, stainless steel, chromium, titanium, and carbon.

19. The method for manufacturing a bio-electrode according to claim 17, wherein after the living body contact layer is formed, the living body contact layer is immersed in water, or the living body contact layer is humidified.

* * * * *